US008524894B2

(12) United States Patent
Catena Ruiz et al.

(10) Patent No.: US 8,524,894 B2
(45) Date of Patent: Sep. 3, 2013

(54) INHIBITOR COMPOUNDS OF 11-BETA-HYDROXYSTEROID DEHYDROGENASE TYPE 1

(75) Inventors: Juan Lorenzo Catena Ruiz, Barcelona (ES); Carme Serra Comas, Barcelona (ES); Oscar Rey Puiggros, Barcelona (ES); Albert Antolin Hernandez, Barcelona (ES); Esther Monlleo Mas, Barcelona (ES)

(73) Assignee: Laboratorios Salvat, S.A., Barcelona (ES)

( * ) Notice: Subject to any disclaimer, the term of this patent is extended or adjusted under 35 U.S.C. 154(b) by 0 days.

(21) Appl. No.: 13/375,389

(22) PCT Filed: Jun. 4, 2010

(86) PCT No.: PCT/ES2010/000258
§ 371 (c)(1),
(2), (4) Date: Nov. 30, 2011

(87) PCT Pub. No.: WO2010/139827
PCT Pub. Date: Dec. 9, 2010

(65) Prior Publication Data
US 2012/0071466 A1 Mar. 22, 2012

(30) Foreign Application Priority Data
Jun. 4, 2009 (ES) .................. P200901402

(51) Int. Cl.
| C07D 215/14 | (2006.01) |
| C07D 217/04 | (2006.01) |
| C07D 217/06 | (2006.01) |
| C07D 217/08 | (2006.01) |
| C07D 401/06 | (2006.01) |
| C07D 401/12 | (2006.01) |
| C07D 405/12 | (2006.01) |
| C07D 409/12 | (2006.01) |
| C07D 409/14 | (2006.01) |
| C07D 413/06 | (2006.01) |

(52) U.S. Cl.
USPC ........... 540/481; 540/597; 544/128; 544/363; 548/140; 548/141; 548/146; 548/153; 548/156; 548/164

(58) Field of Classification Search
None
See application file for complete search history.

(56) References Cited

U.S. PATENT DOCUMENTS

| 3,936,458 | A | 2/1976 | Sturm et al. | |
| 7,229,986 | B2 * | 6/2007 | Ishihara et al. | ......... 514/217.01 |
| 2004/0133011 | A1 | 7/2004 | Waddell et al. | |

FOREIGN PATENT DOCUMENTS

| EP | 1 918 285 A1 | 5/2008 |
| WO | WO 01/90090 A1 | 11/2001 |
| WO | WO 01/90092 A1 | 11/2001 |
| WO | WO 02/072084 A2 | 9/2002 |
| WO | WO 03/045367 A1 | 6/2003 |
| WO | WO 03/075660 A1 | 9/2003 |
| WO | WO 03/104207 A2 | 12/2003 |
| WO | WO 2004/033427 A1 | 4/2004 |
| WO | WO 2004/056745 A2 | 7/2004 |
| WO | WO 2004/065351 A1 | 8/2004 |
| WO | WO 2004/089380 A2 | 10/2004 |
| WO | WO 2004/089471 A2 | 10/2004 |
| WO | WO 2004/089896 A1 | 10/2004 |
| WO | WO 2004/106294 A2 | 12/2004 |
| WO | WO 2005/016877 A2 | 2/2005 |
| WO | WO 2005/042513 A1 | 5/2005 |
| WO | WO 2005/046685 A1 | 5/2005 |
| WO | WO 2005/060963 A1 | 7/2005 |
| WO | WO 2005/063247 A1 | 7/2005 |
| WO | WO 2005/103023 A1 | 11/2005 |
| WO | WO 2005/108359 A1 | 11/2005 |
| WO | WO 2005/108360 A1 | 11/2005 |
| WO | WO 2005/108361 A1 | 11/2005 |
| WO | WO 2005/108368 A1 | 11/2005 |
| WO | WO 2005/110980 A2 | 11/2005 |
| WO | WO 2005/110992 A1 | 11/2005 |
| WO | WO 2005/116002 A2 | 12/2005 |
| WO | WO 2005/118538 A2 | 12/2005 |
| WO | WO 2006/002349 A1 | 1/2006 |
| WO | WO 2006/002350 A1 | 1/2006 |
| WO | WO 2006/002361 A2 | 1/2006 |
| WO | WO 2006/012173 A1 | 2/2006 |
| WO | WO 2006/012226 A2 | 2/2006 |
| WO | WO 2006/012227 A2 | 2/2006 |
| WO | WO 2006/017542 A1 | 2/2006 |
| WO | WO 2006/024627 A2 | 3/2006 |
| WO | WO 2006/024628 A2 | 3/2006 |
| WO | WO 2006/040329 A1 | 4/2006 |
| WO | WO 2006/048330 A1 | 5/2006 |

(Continued)

OTHER PUBLICATIONS

Wu et al., Discovery of 3-Hydroxy-4-Cyano-Isoquinolines as Novel, Potent, and Selective Inhibitors of Human 11-Beta-Hydroxydehydrogenase 1 (11Beta-HSD1), 21 Bioorg. & Med. Chem. Letts 6693-6698 (2011).*

Agarwal et al., "Cloning and Expression of Rat cDNA Encoding Corticosteroid 11β-Dehydrogenase" J. Riot Chem. 1989, 264(32): 18939-43.

Arampatzis et al., "Comparative Enzymology of 11β-Hydroxysteroid Dehydrogenase Type 1 From Six Species", J. Mol Endocrinol. 2005:35(1):89-101.

(Continued)

*Primary Examiner* — Janet Andres
*Assistant Examiner* — Timothy R Rozof
(74) *Attorney, Agent, or Firm* — Gary J. Gershik; Cooper & Dunham

(57) ABSTRACT

The compounds of formula (I) are derived from perhydroquinoline and perhydroisoquinoline and are useful as active pharmaceutical ingredients for the prophylaxis or treatment of diseases caused by 11-beta-hydroxysteroid dehydrogenase type 1 (11-beta-HSD1) enzyme-associated disorders, such as glaucoma, elevated ocular pressure, metabolic disorders, obesity, metabolic syndrome, dyslipidemia, hypertension, diabetes, atherosclerosis, Cushing's syndrome, psoriasis, rheumatoid arthritis, cognitive disorders, Alzheimer's disease or neurodegeneration.

20 Claims, No Drawings

(56) References Cited

FOREIGN PATENT DOCUMENTS

| | | |
|---|---|---|
| WO | WO 2006/048750 A2 | 5/2006 |
| WO | WO 2006/049952 A1 | 5/2006 |
| WO | WO 2006/055752 A2 | 5/2006 |
| WO | WO 2006/105127 A2 | 5/2006 |
| WO | WO 2006/068991 A1 | 6/2006 |
| WO | WO 2006/068992 A1 | 6/2006 |
| WO | WO 2006/074244 A2 | 7/2006 |
| WO | WO 2006/094633 A1 | 9/2006 |
| WO | WO 2006/100502 A1 | 9/2006 |
| WO | WO 2006/106423 A2 | 10/2006 |
| WO | WO 2006/135795 A1 | 12/2006 |
| WO | WO 2006/138508 A2 | 12/2006 |
| WO | WO 2007/003521 A2 | 1/2007 |
| WO | WO 2007/026920 A2 | 3/2007 |
| WO | WO 2007/029021 A1 | 3/2007 |
| WO | WO 2007/047625 A2 | 4/2007 |
| WO | WO 2007/051810 A2 | 5/2007 |
| WO | WO 2007/051811 A2 | 5/2007 |
| WO | WO 2007/057768 A2 | 5/2007 |
| WO | WO 2007/061661 A2 | 5/2007 |
| WO | WO 2007/068330 A1 | 6/2007 |
| WO | WO 2007/082808 A2 | 7/2007 |
| WO | WO 2007/101270 A1 | 9/2007 |
| WO | WO 2007/115935 A1 | 10/2007 |
| WO | WO 2008/000950 A2 | 1/2008 |
| WO | WO 2008/000951 A2 | 1/2008 |
| WO | WO 2008/006702 A1 | 1/2008 |
| WO | WO 2008/052638 A1 | 5/2008 |
| WO | WO 2008/074384 A1 | 6/2008 |
| WO | WO 2008/101885 A1 | 8/2008 |
| WO | WO 2008/101886 A1 | 8/2008 |
| WO | WO 2008/101907 A2 | 8/2008 |
| WO | WO 2008/101914 A2 | 8/2008 |
| WO | WO 2008/110196 A1 | 9/2008 |
| WO | WO 2008/119017 A1 | 10/2008 |
| WO | WO 2008/127924 A1 | 10/2008 |
| WO | WO 2008/134221 A1 | 11/2008 |
| WO | WO 2010/046445 A2 | 4/2010 |
| WO | WO 2010/059618 A1 | 5/2010 |
| WO | WO 2010/091067 A2 | 8/2010 |
| WO | WO 2010/100139 A1 | 9/2010 |
| WO | WO 2010/139673 A1 | 12/2010 |
| WO | WO 2010/141424 A1 | 12/2010 |
| WO | WO 2010/141550 A2 | 12/2010 |
| WO | WO 2010/146338 A1 | 12/2010 |
| WO | WO 2011/011123 A1 | 1/2011 |
| WO | WO 2011/012800 A1 | 2/2011 |
| WO | WO 2011/012801 A1 | 2/2011 |

OTHER PUBLICATIONS

Barf & Williams, "Recent Progress in 11β-Hydroxysteroid Dehydrogenase Type 1 (11-β-HSD1) Inhibitor Development", Drugs Fut 2006 31(3):231-243.
Chang et al., "Association of Intraocular Pressure With the Metabolic Syndrome and Novel Cardiometabolic Risk Factors", Eye (Lond). 2010:24(6):1037-43.
Draper & Stewart, "11β-Hydroxysteroid Dehydrogenase and the Pre-Receptor Regulation of Corticosteroid Hormone Action", J. Endocrinol. 2005 186(2):251-271.
Gu et al., "Discovery of 4-Heteroarylbicyclo [2.2.2] Octyltriazoles As Potent and Selective Inhibitors of 11β-HSD1: Novel Therapeutic Agents for the Treatment of Metabolic Syndrome", Bioorg. Med Chem Lett. 2005:15(23):5266-9.
Hale & Wang, "Development of 11β-HSD1 Inhibitors for the Treatment of Type 2 Diabetes", Mini Rev Med Chem. 2008 8(7):702-10.
Hughes et al., "11 Beta-Hydroxysteroid Dehydrogenase Type 1 (11β-HSD1) Inhibitors in Type 2 Diabetes Mellitus and Obesity", Expert Opin. Investig Drugs. 2008: 17(4):481-96.
Hult et al., "Selective Inhibition of Human Type 1 11β-Hydroxysteroid Dehydrogenase by Synthetic Steroids and Xenobiotics", FEBS Lett. 1998 441(1) 25-8.
Hult et al., "Active Site Variability of Type 1 11β-Hydroxysteroid Dehydrogenase Revealed by Selective Inhibitors and Cross-Species Comparisons", Mol Cell Endocrinol. 2006 248(1-2) 26-33.
Jean et al., "2-(S)-Phenethylarninothiazolones As Potent, Orally Efficacious Inhibitors of 11β-Hydroxysteroid Dehydrogenase Type 1", J Med Chem. 2007 50(3) 429-32.
Kotelevtsev et al., "11β-Hydroxysteroid Dehydrogenase Type 1 Knockout Mice Show Attenuated Glucocorticoid-Inducible Responses and Resist Hyperglycemia on Obesity or Stress", Proc Natl Acad Sci USA. 1997 94(26):14924-9.
Masuzaki et al., "Transgenic Amplification of Glucocorticoid Action in Adipose Tissue Causes High Blood Pressure in Mice", J Clin Invest. 2003 112(1) 83-90.
Onyimba et al., "Characterisation of the Prereceptor Regulation of Glucocorticoids in the Anterior Segment of the Rabbit Eye", J Endocrinol. 2006 190(2) 483-93.
Patel et al., "Discovery of Adamantane Ethers As Inhibitors of 11β-HSD-1: Synthesis and Biological Evaluation", Bioorg Med Chem Lett. 2007 17(3) 750-5.
Rauz et al., "Expression and Putative Role of 11β-Hydroxysteroid Dehydrogenase Isozymes Within the Human Eye", Invest Ophthalmol Vis Sci. 2001 42(9) 2037:42.
Rauz at al., "Inhibition of 11β-Hydroxysteroid Dehydrogenase Type 1 Lowers Intraocular Pressure in Patients With Ocular Hypertension", QJM 2003 96(7):481-90.
Rohde et al., "Discovery and Metabolic Stabilization of Potent and Selective 2-Amino-N-(adamant-2~yl) Acetamide 11β-Hydroxysteroid Dehydrogenase Type 1 inhibitors", J Med Chem 2007 50(1): 149-64.
Saiah, "The Role of 11β-Hydroxysteroid Dehydrogenase in Metabolic Disease and Therapeutic Potential of 11β-HSD1 Inhibitors", Curr Med Chem. 2008 15(7):642-9.
Sandeep et al., "11β-Hydroxysteroid Dehydrogenase Inhibition Improves Cognitive Function in Healthy Elderly Men and Type 2 Diabetics", Proc Natl Acad Sci USA. 2004 101(17):6734-9.
Schuster et al., "The Discovery of New 11β-Hydroxysteroid Dehydrogenase Type 1 Inhibitors by Common Feature Pharmacophore Modeling and Virtual Screening",J Med Chem 2006 49(12):3454-66.
Schweizer et al., "A Rapid Screening Assay for Inhibitors of 11β-Hydroxysteroid. Dehydrogenase (11β-HSD): Elavanone Selectively Inhibits 11β-HSD1 Reductase Activity", Mol Cell Endocrinol. 2003 212(1-2) 41-9.
Stokes at al., "Distribution of Glucocorticoid and Mineralocorticoid Receptors and 11β-Hydroxysteroid Dehydrogenases in Human and Rat Ocular Tissues", Invest Ophthalmol Vis Sci 2000. 41(7) 1629-38.
Stokes et al., "Altered Peripheral Sensitivity to Glucocorticoids in Primary Open-Angle Glaucoma", Invest Ophthalmol Vis Sci 2003 44(12) 5163-7.
Su et al., "Benzothiazole Derivatives As Novel Inhibitors of Human 11β- Hydroxysteroid Dehydrogenase Type 1", Mol Cell Endocrinol., 2006 248 (1-2):214-7.
Su at al., "Discovery of Adamantyl Ethanone Derivatives As Potent 11β-Hydroxysteroid Dehydrogenase Type 1 (11β-HSD1) Inhibitors", Chem Med Chem., 2010 5(7):1026-44.
Suzuki at al., "Immunohistochemical Distribution of 11β-Hydroxysteroid Dehydrogenase in Human Eye", Mol Cell Endocrinol., 2001 173 (1-2) :121-5.
Tomlinson et al., "11β-Hydroxysteroid Dehydrogenase Type 1: A Tissue Specific Regulator of Glucocorticoid Response", Endocr Rev., 2004 25(5):831-66.
Veniant et al. "Discovery of a Potent, Orally Active 11β-Hydroxysteroid Dehydrogenase Type 1 Inhibitor for Clinical Study: Identification of (S)-2-((1S, 2S, 4R) -Bicyclo [2.2.1] heptan-2-ylamino)-f-isopropyl-5-methylthiazol-4(5H)-one (AMG 221)", J Med Chem 2010 53 (11) :4481-7.
Webster et al. "Discovery and Biological Evaluation of Adamantyl Amide 11β-HSD1 Inhibitors", Bioorg Med Chem Lett, 2007 17(10):2838-43.
Webster & Pallin "11β-hydroxysteroid Dehydrogenase Type 1 Inhibitors As Therapeutic Agents", Expert Opin Ther Patents, 2007 17 (12) :1407-1422.
Weinreb et al. "Acute Effects of Dexamethasone on Intraocular Pressure in Glaucoma", Invest Ophthalmol Vis Sci. 1985 26(2):170-5.

Xiang et al. "Synthesis and Biological Evaluation of Sulfonamidooxazoles and β-Kato Sulfones: Selective Inhibitors of 11β-Hydroxysteroid Dehydrogenase Type 1", Bioorg Med Chem Lett, 2005 15(11):2865-9.

Xu et al. "Cell-Based Assay for Screening 11β-Hydroxysteroid Dehydrogenase Inhibitors Using Liquid Chromatography/tandem Mass Spectrometry Detection", Rapid Commun Mass Spectrom, 2006 20(11):1643-7.

Yeh et al. "Discovery of Orally Active Butyrolactam 11β-HSD1 Inhibitors", Bioorg Med Chem Lett, 2006 16(21):5555-60.

Yuan et al. "The Discovery of 2-anilinothiazolones as 11β-HSD1 Inhibitors", Bioorg Med Chem Lett, 2007 17(22):6506-61.

PCT International Application Publication No. WO 2007/144394 A2 (Novo Nordisk); published Dec. 21, 2007, of PCT International Application No. PCT/EP2007/055865, filed Jun. 14, 2007.

PCT International Application Publication No. WO 2007/111921 A1 (Amgen Inc.) published Oct. 4, 2007, of PCT International Application No. PCT/US2007/007077, filed Mar. 22, 2007.

International Search Report issued by the International Searching Authority (ISA/O.E.P.M.) on Aug. 9, 2010 in connection with International Application No. PCT/ES2010/000258.

Roche, D. et al., "Discovery and structure-activity relationships of pentanedioic acid diamides as potent inhibitors of 11β-hydroxysteroid dehydrogenase type I", Bioorganic & Medicinal Chemistry Letters, 2009, vol. 19, pp. 2674-2678.

Supplementary European Search Report issued by the International Searching Authority (ISA/O.E.P.M.) on Nov. 2, 2012 in connection with European Application No. EP 10 783 009.3.

\* cited by examiner

INHIBITOR COMPOUNDS OF 11-BETA-HYDROXYSTEROID DEHYDROGENASE TYPE 1

This application is a §371 national stage application of PCT International Application No. PCT International Application No. PCT/ES2010/000,258, filed Jun. 4, 2010, claiming priority of Spanish Patent Application No. P200901402, filed Jun. 4, 2009, the contents of all of which are hereby incorporated by reference into this application.

The present invention relates to perhydroquinoline and perhydroisoquinoline derivatives and methods of treating certain diseases using such compounds.

STATE OF THE ART

Glucocorticoids (cortisol in humans, corticosterone in mice and rats) are an important adrenocorticosteroid group regulating many metabolic and homeostatic processes and form a key element of stress response. Glucocorticoids act through the intracellular glucocorticoid receptors and, in some tissues, through mineralocorticoid receptors, both being nuclear transcription factors. The action of glucocorticoids on the target tissues depends not only on circulating steroid concentrations and the cellular expression of the receptors, but also on the intracellular enzymes which critically determine up to what point the glucocorticoids will have active access to the receptors. The 11-beta-hydroxysteroid dehydrogenases (11-beta-HSD) catalyze the interconversion between the main active 11-hydroxy-glucocorticoid (cortisol in man) and its inactive 11-keto metabolites (cortisone in man).

The 11-beta-hydroxysteroid dehydrogenase type 1 (11-beta-HSD1) enzyme reconverts inactive glucocorticoids into active ones, thus playing an important role in modulating cellular agonist concentration and, therefore, in activating corticosteroid receptors in the target tissues. It has been described that the overexpression of 11-beta-HSD1 in mice adipocytes leads to visceral obesity and to the phenotype similar to that of the metabolic syndrome. Collectively, these data significantly confirm the important role of 11-beta-HSD1 in inducing obesity and the disequilibrium of glucose homeostasis and lipid parameters. Therefore, the selective inhibition of this enzyme could reduce the levels of blood glucose in type 2 diabetes patients, normalize the elevated lipid parameters and/or reduce the weight of obese subjects.

The first pharmacological indication that the inhibition of 11-beta-HSD1 in man could have beneficial effects has been achieved by using carbenoxolone, an anti-ulcer drug which inhibits both 11-beta-HSD1 and the similar 11-beta-HSD2 enzyme. Treatment with carbenoxolone increases the sensitivity to insulin, which indicates that the inhibition of 11-beta-HSD1 can reduce the levels of cortisol in the cells and therefore minimize some of its damaging effects.

Studies conducted with the non-specific carbenoxolone inhibitor clearly show the importance of developing 11-beta-HSD1 specific inhibitors. Inhibition of the 11-beta-HSD2 enzyme is poorly tolerated and increases blood pressure. In contrast, inhibition of 11-beta-HSD1 would be well tolerated because it has been observed that the 11-beta-HSD1 knockout mice are healthy and resist hyperglycemia caused by obesity or stress (cf. Kotelevtsev et al., Proc. Natl. Acad. Sci. USA 1997, vol. 94, pp. 14924-14929). Other studies indicate that 11-beta-HSD1 inhibitors can also be beneficial for reducing high blood pressure (cf. Masuzaki et al., J. Clin. Invest. 2003, vol. 112, pp. 83-90), for reducing intraocular pressure (cf. Rauz et al., Q J Med 2003, vol. 96, pp. 481-490), for improving cognitive capacity (cf. Sandeep et al., Proc Natl Acad Sci. USA 2004, vol. 101, pp. 6734-6739) or for improving deficiencies associated with Alzheimer's disease. Overall, inhibition of 11-beta-HSD1 can be a safe and effective strategy for treating symptoms of glaucoma, diabetes, obesity and other diseases.

Glucocorticoids increase the risk of glaucoma by increasing intraocular pressure when they are exogenously administered and in certain conditions of increased production such as Cushing's syndrome. The increase of intraocular pressure induced by corticosteroids is caused by an increased resistance to the aqueous efflux due to changes induced by glucocorticoids.

11-beta-HSD1 is expressed in corneal epithelium basal cells and non-pigmented epithelial cells. The mRNA of the glucocorticoid receptor has been detected in the trabecular reticulum, whereas mRNA for the glucocorticoid receptor, the mineralocorticoid receptor and 1-beta-HSD1 was present in non-pigmented epithelial cells. The administration of carbenoxolone to patients resulted in a significant reduction in intraocular pressure (cf. Rauz et al., Invest. Ophtalmol. Vis. Sci. 2001, vol. 42, pp. 2037-2042), which suggests a role for HSD1 inhibitors in the treatment of glaucoma.

The expression of 11-beta-HSD isoenzymes in human and rodent eyes has been described (cf. Stokes et al., Invest Ophthalmol Vis Sci. 2000, vol. 41, pp. 1629-1638), particularly 11-beta-HSD1 in ciliary epithelial cells, which suggests the possibility of a role in producing aqueous humor and in regulating intraocular pressure. In aqueous humor, cortisol concentrations are approximately 14 times greater than those of cortisone. This suggests to a large extent predominant 11-beta-reductase HSD1 activity. In a double blinded controlled study with glaucoma patients it was observed that treatment with carbenoxolone significantly reduces intraocular pressure therefore 11-beta-HSD1 inhibitors can represent a therapeutic strategy suitable for treating glaucoma.

Document WO2007026920 describes N-arylamide compounds and related compounds as Rho kinase (ROCK) inhibitors, as well as pharmaceutical compositions and the use thereof in treating diseases related to ROCK.

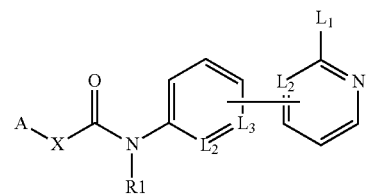

Document WO2006106423 describes N-pyridyl heterocyclylsulfonamide compounds and the use thereof as 11-beta-HSD1 modulators.

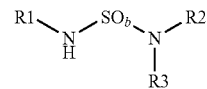

Document WO2006048330 describes N-benzylsulfonamide compounds and related derivatives as 11-beta-HSD1 inhibitors, pharmaceutical compositions and the use thereof in therapy.

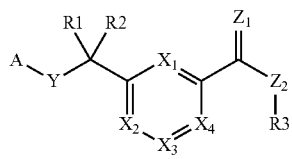

Document WO2003045367 describes compounds derived from pyridylalkylurea, some of which are structurally similar to those of the present invention but with a different use.

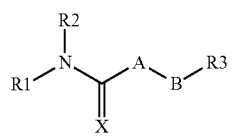

Nevertheless, providing new 11-beta-HSD1 inhibitor compounds is desirable.

DESCRIPTION OF THE INVENTION

The present invention provides new compounds derived from perhydroquinoline and perhydroisoquinoline of formula (I) which are effective as 11-beta-HSD1 inhibitors and have selectivity for 11-beta-HSD1 with respect to 11-beta-HSD2.

Thus, a first aspect of the invention refers to compounds of formula (I)

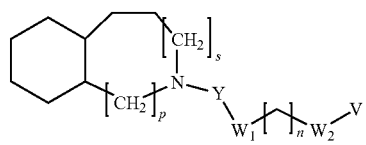

(I)

and pharmaceutically acceptable salts thereof, wherein:

s and p are an integer selected in an opposite manner between 0 and 1, such that when s is 1, p is 0 (to form a perhydroquinoline) and when s is 0, p is 1 (to form a perhydroisoquinoline).

Y is a biradical selected from CO, CS and $SO_2$,

W1 and W2 can be independently a bond or a biradical selected from O, S and NR1, wherein R1 is optionally H, $C_{1-4}$ alkyl or $C_{3-10}$ cycloalkyl, n is an integer selected from 0, 1, 2, 3 and 4, V is a radical selected from —CO-T, —CS-T and —$SO_2$-T or a radical selected from:

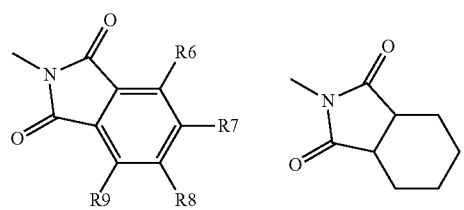

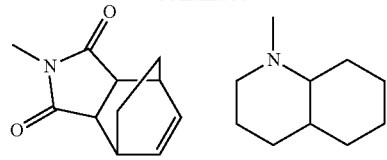

T is a group selected from NR2R3, R2, OR2 and SR2; or a group selected from

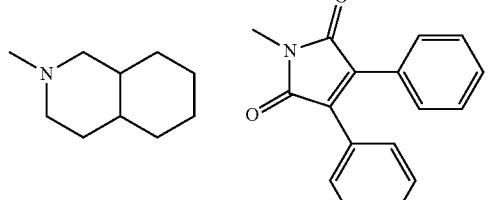

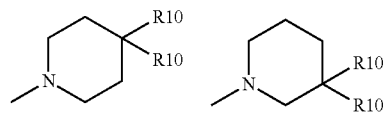

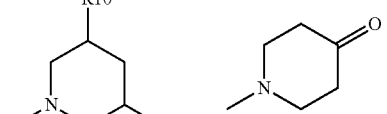

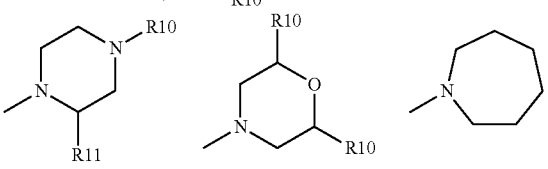

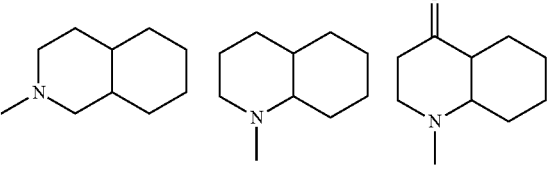

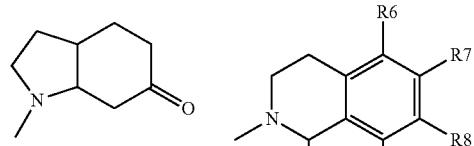

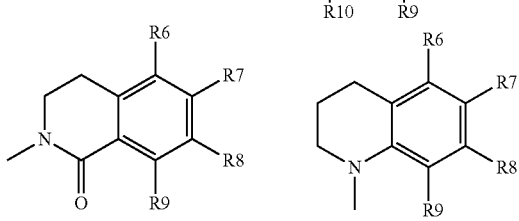

wherein R2 and R3 are independently selected from H, COR4, $SO_2$R4, $C_{1-4}$ alkyl, aryl, benzyl, phenethyl, $C_{2-4}$ alkenyl, $C_{2-4}$ alkynyl, $C_{3-10}$ cycloalkyl or heterocycle wherein when R2 or R3 is an alkyl or an alkenyl these can be optionally substituted with one or several substituents independently selected from F, OR4, NR4R5, COOR4, CONR4R5, $C_{3-10}$ cycloalkyl, aryl and heterocycle;

wherein when R2 or R3 is an aryl, a benzyl, a phenethyl, a cycloalkyl or a heterocycle, these can be optionally substituted with one or several substituents independently selected from $NH_2$, F, Cl, CN, $NO_2$, COOH, R4, COOR4, OR4, $OCF_3$, SH, SR4, CONR4R5, $SO_2NR4R5$, COR4, NR1COR4, OCOR4, SOR4, $SO_2R4$ and heterocycle, wherein when R2 or R3 is a cycloalkyl this can be optionally substituted with one or several benzene rings fused with the cycloalkyl, the benzene could be optionally substituted with one or several substituents independently selected from alkyl, alkoxide or halogen, wherein R4 and R5 are independently selected from H, $C_{1-4}$ alkyl, aryl, benzyl, phenethyl, $C_{2-4}$ alkenyl, $C_{2-4}$ alkynyl, $C_{3-10}$ cycloalkyl and heterocycle wherein optionally R4 and R5 can be bound to one another forming a 3 to 8 membered cycle.

R6, R7, R8 and R9 are independently selected from H, OR4, F and Cl,

R10 is independently selected from H, OH, F, $C_{1-4}$ alkyl, COOR11, COR11, phenyl, benzyl, benzhydryl, $C_{2-4}$ alkenyl, $C_{2-4}$ alkynyl, $C_{3-10}$ cycloalkyl and heterocycle, and wherein the alkyl, phenyl, benzyl, benzhydryl, cycloalkyl or heterocycle can be optionally substituted with one or several substituents independently selected from $NH_2$, F, Cl, $NO_2$, COOH, COOR4, OR4, $CF_3$, SH, SR4, CONR4R5, $SO_2NR4R5$, COR4, NR1COR4, OCOR4, SOR4, $SO_2R4$ and $C_{1-4}$ alkyl;

and R11 is selected from H, $C_{1-4}$ alkyl, aryl and $C_{3-10}$ cycloalkyl.

In a particular embodiment of the invention, s is 0 and p is 1. In another particular embodiment of the invention, s is 1 and p is 0.

In another particular embodiment of the invention, Y is selected from CO and $SO_2$.

In another particular embodiment of the invention, W1 and W2 are independently selected from a bond, S and NR1. In another particular embodiment of the invention, R1 is H.

In another particular embodiment of the invention, V is selected from —CO-T, —CS-T and —$SO_2$-T.

In another particular embodiment of the invention, V is selected from

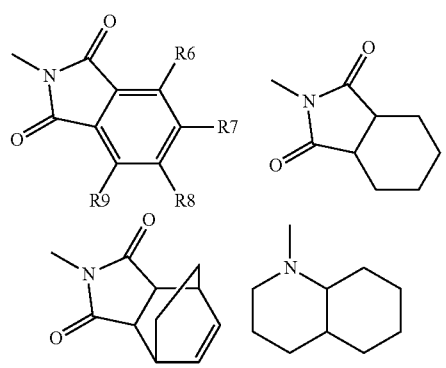

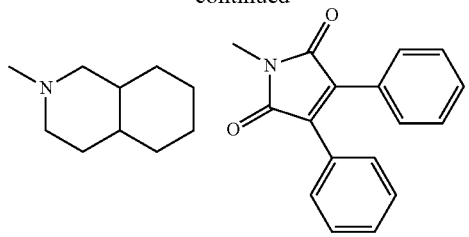

In another particular embodiment of the invention, R2 and R3 are independently selected from H, COR4, $SO_2R4$, $C_{1-4}$ alkyl, phenyl, naphthyl, benzyl, phenethyl, $C_{2-4}$ alkenyl, $C_{3-10}$ cycloalkyl, and heterocycle, particularly, 2-furanyl, 2-thiophenyl, 2-(1-methylindole), quinoline, isoquinoline, 2-benzofuranyl.

In another particular embodiment of the invention, when R2 or R3 are independently $C_{1-4}$ alkyl or $C_{2-4}$ alkenyl, R2 or R3 can be optionally substituted with one or several substituents independently selected from F, OR4, NR4R5, COOR4, CONR4R5, phenyl, $C_{3-10}$ cycloalkyl, hexenyl, naphthyl and heterocycle, particularly pyridine, 3-(1-methylindole), 3-thiophenyl and 2-furanyl.

In another particular embodiment of the invention, when R2 or R3 are independently phenyl, benzyl, phenethyl or $C_{3-10}$ cycloalkyl, R2 or R3 can be optionally substituted with one or several substituents independently selected from F, Cl and OR4.

In another particular embodiment of the invention, when R2 or R3 is a cycloalkyl this can be optionally substituted with one or several benzene rings fused with the cycloalkyl, the benzene could be optionally substituted with one or several substituents independently selected from alkyl, alkoxide or halogen.

In another particular embodiment of the invention, R4 and R5 are independently selected from $C_{1-4}$ alkyl, benzyl, phenethyl and phenyl.

In another particular embodiment of the invention, R4 and R5 can be optionally bound to one another forming a 3 to 8 membered cycle.

In another particular embodiment of the invention, R6, R7, R8 and R9 are independently selected from H, OR4, F and Cl.

In another particular embodiment of the invention, R10 is selected from H, OH, F, $C_{1-4}$ alkyl, COOR11, COR11, phenyl, benzyl and benzhydryl.

In another particular embodiment of the invention, R10 is selected from phenyl, benzyl and benzhydryl, all of them optionally substituted with one or several substituents, independently selected from F, OR4, $CF_3$, COR4 and $C_{1-4}$ alkyl.

In another particular embodiment of the invention, R11 is selected from H and $C_{3-10}$ cycloalkyl.

In another particular embodiment, T is selected from NR2R3, R2, OR2 and SR2.

In another particular embodiment, T is selected from

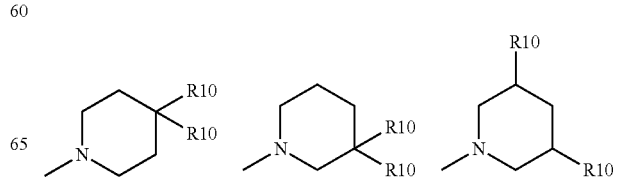

-continued

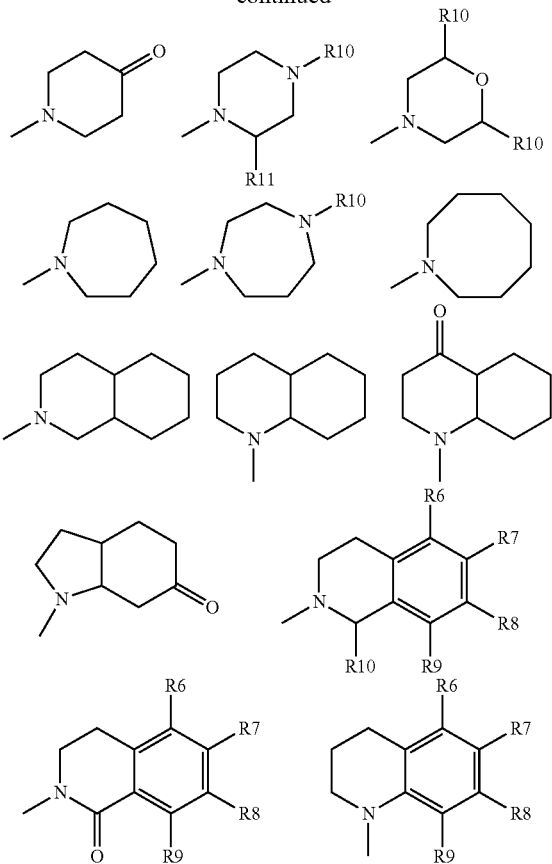

A second aspect of the present invention refers to a compound of formula (I) or a pharmaceutically acceptable salt thereof for use as a medicament, particularly for the prophylaxis or treatment of diseases caused by 11-beta-HSD1-associated disorders, particularly glaucoma, elevated ocular pressure, metabolic disorders, obesity, metabolic syndrome, dyslipidemia, hypertension, diabetes, particularly type II diabetes, atherosclerosis, Cushing's syndrome, psoriasis, rheumatoid arthritis, cognitive disorders, Alzheimer's disease or neurodegeneration, preferably for the prophylaxis or treatment of glaucoma or metabolic syndrome.

Another aspect of the present invention refers to the use of a compound of formula (I) or a pharmaceutically acceptable salt thereof in the manufacture of a medicaments intended for the prophylaxis or treatment of diseases caused by 11-beta-HSD1-associated disorders, particularly one of the disorders mentioned above.

Another aspect of the present invention refers to a method of prophylaxis or treatment of an individual who is suffering or is susceptible to suffering a disease caused by 11-beta-HSD1-associated disorders, particularly one of the disorders mentioned above, which comprises administrating to said individual a therapeutically effective amount of a compound of formula (I) or a pharmaceutically acceptable salt thereof together with one or more pharmaceutically acceptable excipients.

The compounds of formula (I) and the pharmaceutically acceptable salts thereof, particularly the compounds of formula (I) described as examples or as intermediates are preferred.

The compounds of the present invention can be used alone or in combination with one or more compounds which are useful for the prophylaxis or treatment of diseases such as glaucoma, elevated ocular pressure, metabolic disorders, such as obesity, metabolic syndrome, dyslipidemia, hypertension and/or diabetes, particularly type II diabetes, atherosclerosis, Cushing's syndrome, psoriasis, rheumatoid arthritis, cognitive disorders, Alzheimer's disease and/or neurodegeneration.

The term "$C_{1-4}$ alkyl", alone or in combination, means a linear- or branched-chain alkyl group having 1 to 4 carbon atoms.

The terms "$C_{2-4}$ alkenyl", and "$C_{2-4}$ alkynyl", alone or in combination, mean a linear- or branched chain radical having 2 to 4 carbon atoms and having one or more unsaturated bonds.

The term "$C_{3-10}$ cycloalkyl", alone or in combination, refers to a stable monocyclic, bicyclic or tricyclic radical of 3 to 10 members, which is saturated or partially saturated, and which only consists of carbon and hydrogen atoms. Examples of $C_{3-10}$ cycloalkyl are the following: cyclopropyl, cyclopentyl, cyclohexyl, 1-cyclohexenyl, cycloheptyl, cyclooctyl, 1-tricyclo[3.3.1.1$^{3,7}$]decanyl, 2-tricyclo[3.3.1.1$^{3,7}$]decanyl and 2-bicyclo[2.2.1]heptanyl. Unless otherwise specifically established in the specification, the term "cycloalkyl" refers to that including cycloalkyl radicals which are optionally substituted with one or more substituents such as alkyl, halogen, hydroxyl, amino, cyano, nitro, alkoxyl, carboxyl, alkoxycarbonyl, phenyl, etc.

The term "aryl", alone or in combination refers to radicals of a single ring and multiple rings, including radicals of multiple rings containing separated and/or condensed aryl groups. The typical aryl groups contain 1 to 3 separated or condensed rings and from 6 to 18 carbon ring atoms, such as phenyl or naphthyl radicals, preferably a phenyl group optionally having one or several substituents, preferably from one to three, chosen independently from one another from halogen, trifluoromethyl, trifluoromethoxy, amino, alkyl, alkoxy, alkylcarbonyl, cyano, carbamoyl, alkoxycarbamoyl, methylenedioxy, carboxy, alkoxycarbonyl, aminocarbonyl, alkylaminocarbonyl, dialkylaminocarbonyl, hydroxy, nitro, alkyl-SO$_2$—, amino-SO$_2$—, cycloalkyl and the like. Phenyl or naphthyl is preferred, particularly phenyl optionally substituted from one to three times, preferably one or two times by substituents chosen independently from one another from alkyl, halogen, alkoxy, trifluoromethoxy, nitro and trifluoromethyl. Phenyl is particularly preferred.

The terms "benzyl" and "phenethyl", can optionally have one or several substituents, chosen independently from one another from halogen, trifluoromethyl, trifluoromethoxy, amino, alkyl, alkoxy, alkylcarbonyl, cyano, carbamoyl, alkoxycarbamoyl, methylenedioxy, carboxy, alkoxycarbonyl, aminocarbonyl, alkylaminocarbonyl, dialkylaminocarbonyl, hydroxy, nitro, alkyl-SO$_2$—, amino-SO$_2$—, cycloalkyl and the like.

The term "heterocycle", alone or in combination, means a saturated, partially unsaturated or aromatic, 5 to 10 membered heterocycle, containing one or several heteroatoms chosen between nitrogen, oxygen and sulfur. For the purposes of this invention, the heterocycle can be a monocyclic, bicyclic or tricyclic ring system which can include condensed ring systems. The heterocycle can be substituted on one or several carbon atoms e.g. by halogen, alkyl, phenyl, alkoxy, oxo, etc. and/or on a secondary nitrogen atom (i.e., —NH—) by alkyl, cycloalkyl, aralkoxycarbonyl, alcanoyl, phenyl or phenylalkyl or on a tertiary nitrogen atom (i.e., =N—) by oxide, being especially preferred halogen, alkyl, cycloalkyl and alkoxy. Examples of heterocycle groups are pyrrolidinyl, piperidinyl, piperazinyl, azepine, morpholinyl, thiomorpholinyl, imidazolyl (e.g. imidazol-4-yl and 1-benzyloxycarbonylimidazol-4-yl), pyrazolyl, pyridyl, pyrazinyl, pyrimidinyl, hexahydropyrimidinyl, furyl, thienyl, thiazolyl, oxazolyl, indolyl (e.g. 2-indolyl), quinolyl (e.g. 2-quinolyl, 3-quinolyl and 1-oxide-2-quinolyl), isoquinolyl (e.g. 1-isoquinolyl and 3-isoquinolyl), tetrahydroquinolyl (e.g. 1,2,3,4-tetrahydro-2-quinolyl), 1,2,3,4-tetrahydroisoquinolyl (e.g. 1,2,3,4-tetrahydro-1-oxoisoquinolyl)benzimidazoyl, benzothiazoyl and quinoxalinyl. Preferred examples are thiophenyl, quinolyl, piperidyl, morpholyl, thiomorpholyl, oxazolyl, pyridinyl, pyrimidinyl, pyrazolyl, imidazolyl and thiazolyl.

The term "pharmaceutically acceptable salts" means those salts which conserve the efficiency and the biological properties of the free bases or of the free acids and which are not disturbing in a biological sense or in any other sense.

According to the invention, the compounds of formula I and their pharmaceutically acceptable salts are useful for the prophylaxis or treatment of diseases caused by 11-beta-HSD1 enzyme-associated disorders.

Unless defined otherwise, all the technical and scientific terms used herein have the same meaning as those commonly understood by a person skilled in the field of the invention. Methods and materials which are similar or equivalent to those described herein can be used in practicing the present invention. Throughout the description and claims the word "comprises" and its variants do not aim to exclude other technical features, additives, components, steps or stereoisomers of the compounds involved. For the persons skilled in the art, other objects, advantages and features of the invention will be inferred partially from the description and partially from practicing the invention.

The compounds of formula (I) can be prepared following different methods known by any person skilled in the field of organic synthesis, particularly through the general processes shown in the following schemes. The starting materials for the preparative methods are commercially available or they can be prepared by means of methods of the literature. All of them started with perhydroquinoline but they are analogous for perhydroisoquinoline.

Scheme 1

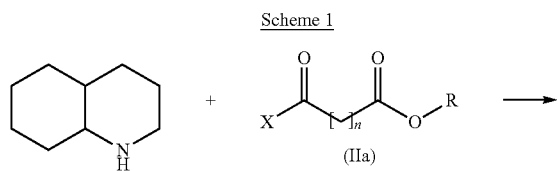

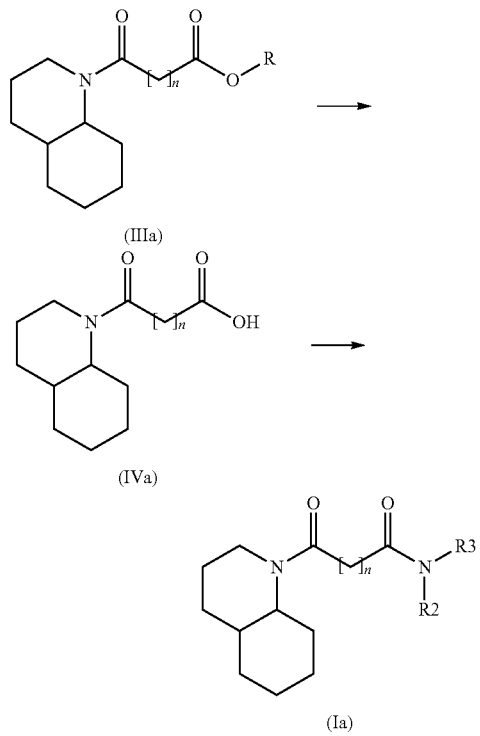

X = OH o Cl

According to this method an acid-ester (IIa) is treated with decahydroquinoline in the presence of a suitable coupling agent, such as for example the combination of 1-(3-dimethylaminopropyl)-3-ethylcarbodiimide (EDC) and 1-hydroxybenzotriazole (HOST), or by means of converting the acid to the corresponding acyl halide with a large variety of reagents such as thionyl chloride, sulfuryl chloride, oxalyl chloride, etc. In the presence of a tertiary base such as Et$_3$N (Elmore, Amino Acids Pep. Proteins 2001, vol. 32, pp. 107-162) for obtaining the amide-ester intermediate (IIIa). The diamide (Ia) is obtained by means of a prior saponification of the compound (IIIa) in aqueous medium with bases of the LiOH type, NaOH type, etc. and subsequent formation of the diamide with any of the methods previously described for the intermediate (IIIa).

Scheme 2

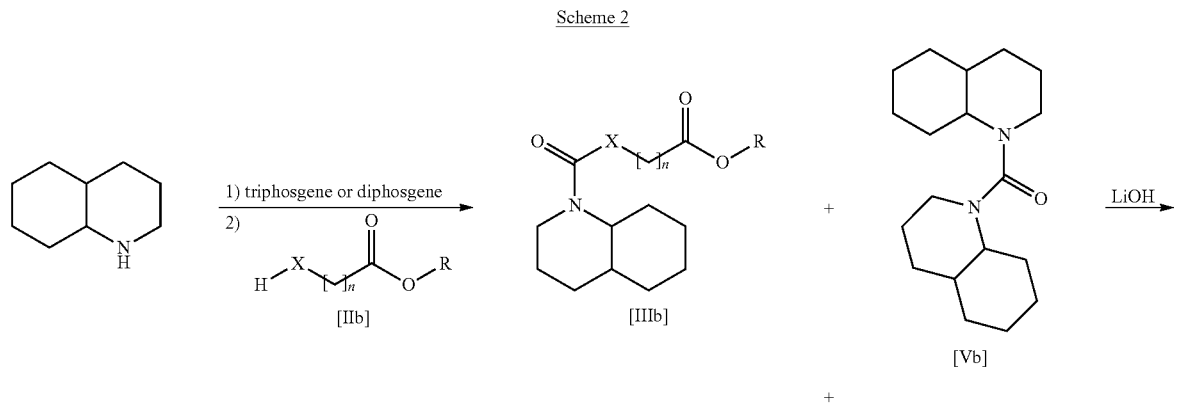

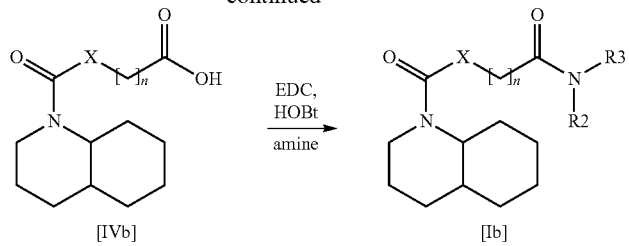

X: NR1, S or O

Scheme 2 shows the reaction of the decahydroquinoline with diphosgene or triphosgene and subsequent addition of amino-ester, hydroxy-ester or mercapto-ester type derivatives respectively providing the urea-ester, carbamate-ester or thiocarbamate-ester type intermediates. Subsequently a deprotection and coupling treatment similar to that described in scheme 1 for obtaining the amide derivatives is performed.

Scheme 3:

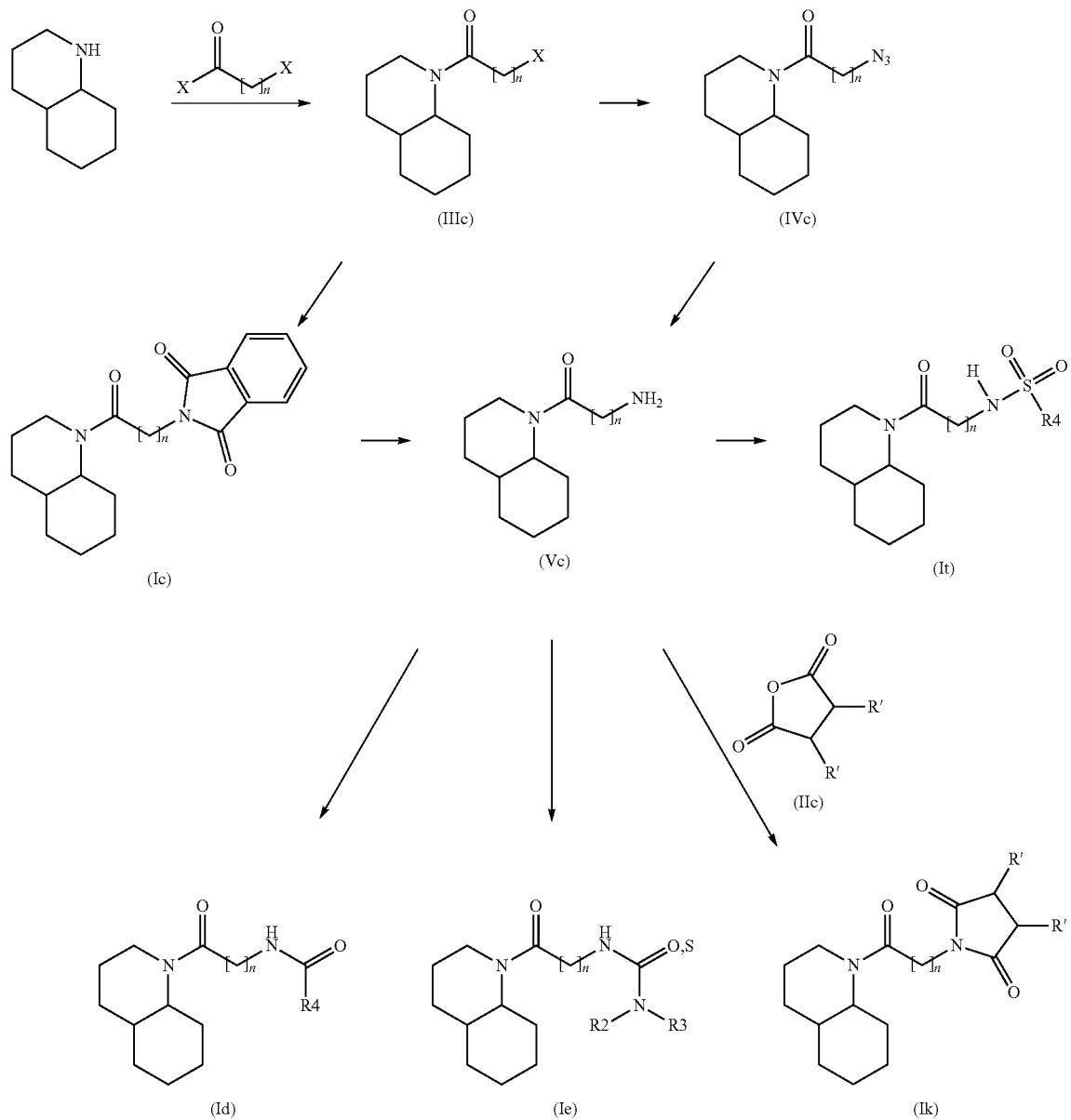

X = Br, Cl

Scheme 3 shows a method for preparing the compounds amido-succinimide (Ic and Ik), amido-amide (Id), amido-sulfonamide (It) and amido-urea or amido-thiourea (Ie) of the present invention. The intermediate amine (Vc) can be prepared by means of two alternative methods: on one hand Gabriel synthesis with potassium phthalimide from the intermediate (IIIc) providing the compound (Ic) and subsequent treatment of this compound with hydrazine under EtOH reflux yielding the mentioned amine (Vc), optionally the intermediate (IIIc) is reacted with sodium azide generating alkyl azide (IVc) which provides the amine (Vc) by reduction.

The intermediate amine (Vc) can be converted both into amide (Id) and into sulfamide (It) by any of the methods previously described or into urea or thiourea (Ie) by means of reaction with an isocyanate or thioisocyanate, respectively. The compound of formula (Ik) can easily be prepared by condensing an anhydride of a 1,2-dicarboxylic acid of general formula (IIc) and the intermediate amine (Vc) previously described.

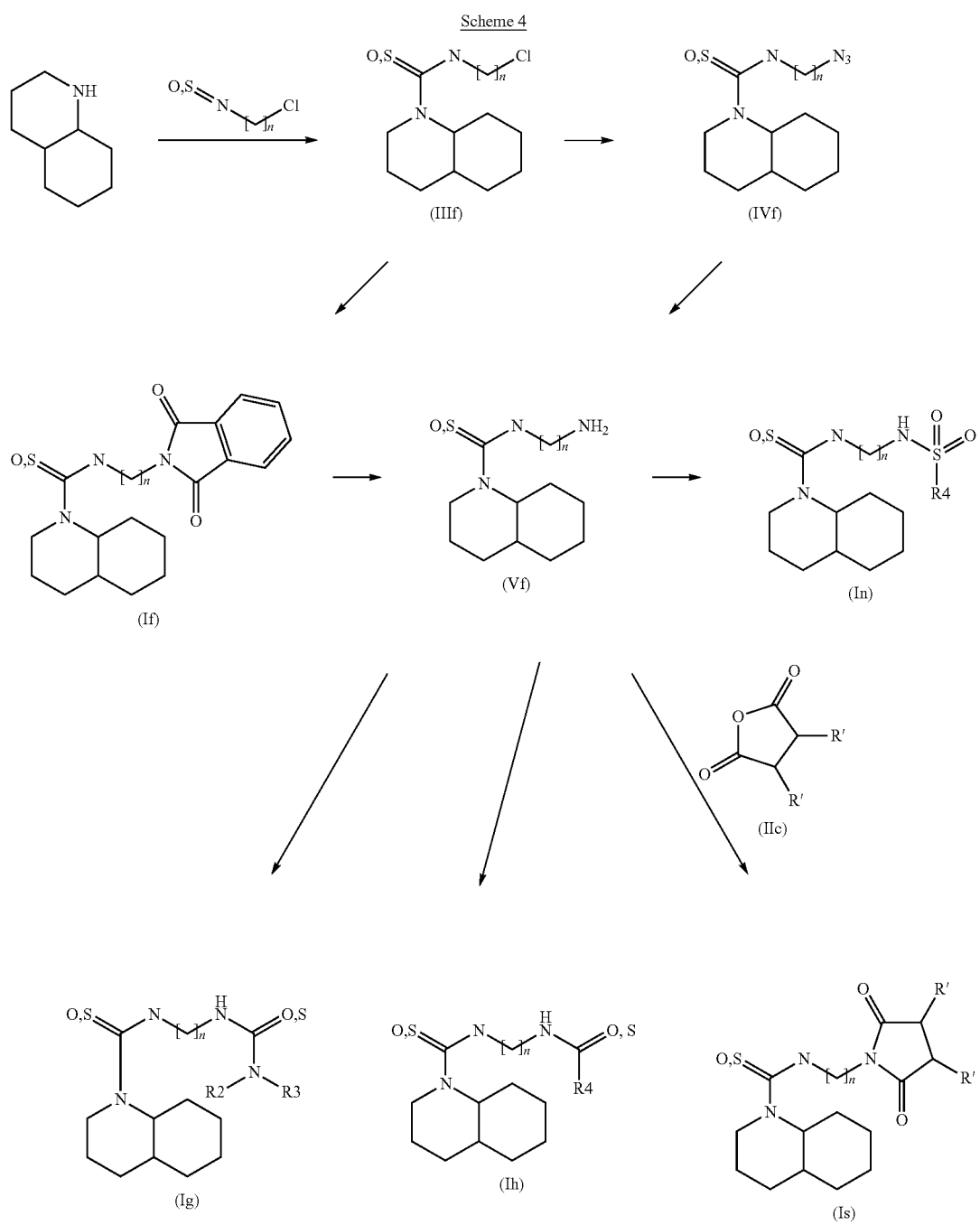

Scheme 4 shows a method for preparing the compounds of the present invention applying a combination of methods previously described in the schemes above to provide ureas and thioureas from decahydroquinoline with different terminal functionalities already described previously in scheme 3.

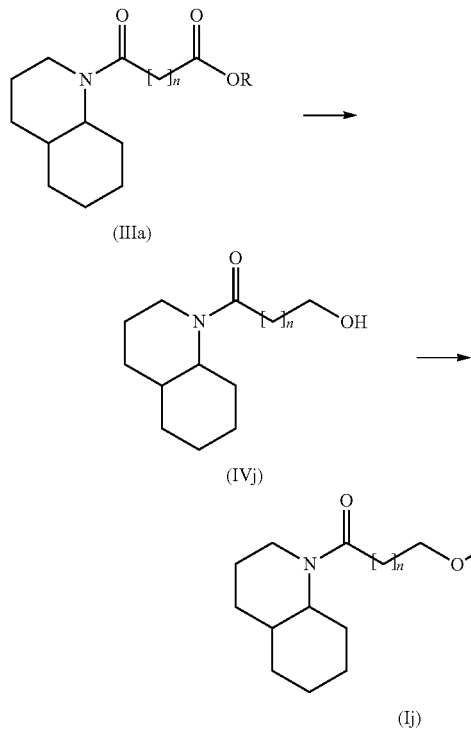

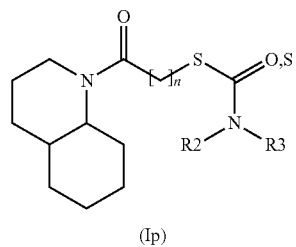

Scheme 6 shows a method for preparing the compounds of the present invention of amido-S-thiocarbamate and amido-dithiocarbamate type. After the formation of the intermediate amide (IVp) by methods previously described and its subsequent reaction with isocyanate, thiocyanate, carbamoyl chloride or thiocarbamoyl chloride provides S-thiocarbamate or dithiocarbamate (Ip).

Scheme 5 shows a method for preparing the compounds of the present invention of amido-carbamate and amido-O-thiocarbamate type. The reduction of the intermediate ester (IIIa) to alcohol (IVj) by means of saponification of the ester, formation of a mixed anhydride and subsequent reduction thereof with sodium borohydride. The reaction of the alcohol (IVj) with isocyanate, thiocyanate, carbamoyl chloride or thiocarbamoyl chloride provides the carbamate or O-thiocarbamate (Ij).

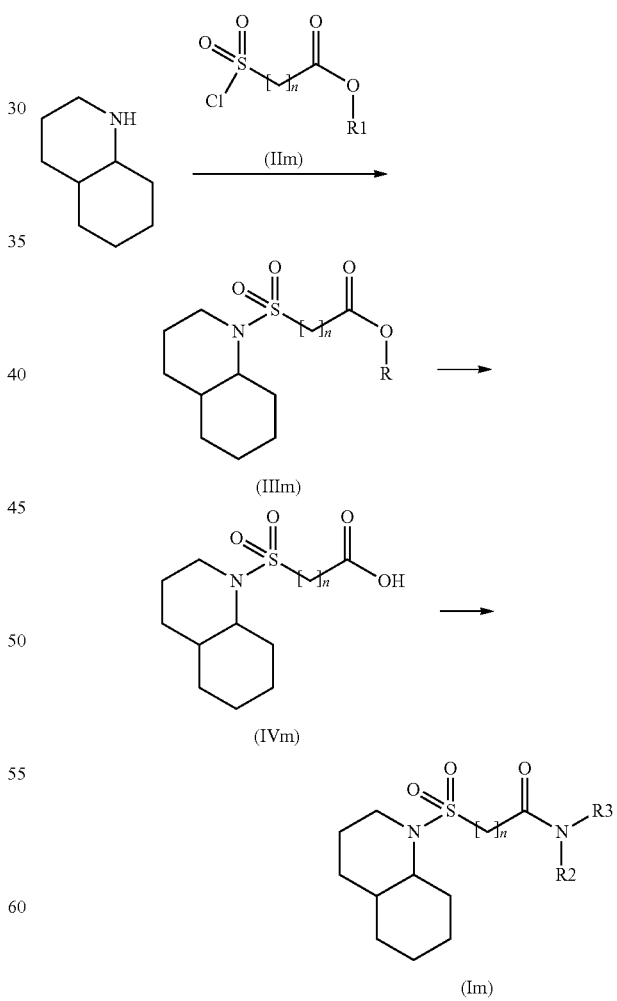

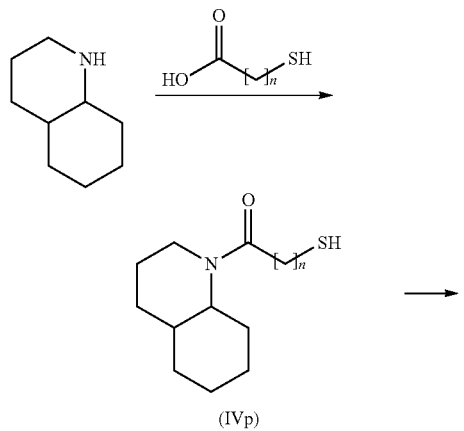

Scheme 7 shows a method for preparing the sulfonamide (Im) in which decahydroquinoline is reacted with the sulfonyl ester chloride (IIm). The deprotection and coupling treatment previously described in scheme 1 provides the sulfonamides (Im),

EXAMPLES

The following examples serve to better illustrate the invention but they must not be considered as limiting the same.

The nomenclature used in the present document is based on the Beilstein-Institut computer program known as AUTONOM (Automatic Nomenclature), which uses the systematic nomenclature of the IUPAC Abbreviations:

AcOEt ethyl acetate

Brine saturated NaCl solution

DCM dichloromethane

DMF dimethylformamide

DMSO dimethylsulfoxide

EDC 1-(3-dimethylaminopropyl)-3-ethylcarbodiimide $Et_3N$ triethylamine

EtOH ethanol

HOBT 1-hydroxybenzotriazole

HPLC High performance liquid chromatography

MeOH methanol

MS Mass spectrometry m/z Mass/charge ratio rt Room temperature

THF tetrahydrofuran

TLC Thin layer chromatography tr Retention time

UV Ultraviolet

General Data:

The products were analyzed using Agilent HPLC-UV-MS equipment provided with a UV detector of variable wavelength and a mass spectrometer model 1100 VL. The wavelength used for detecting UV was 210 nm, whereas the MS detector has been operated in a positive electrospray ionization mode and a 100 to 700 m/z scan has been performed. Concerning chromatographic separation, the column used was a Kromasil 100 C18, 40×4.0 mm, 3.5 μm, and 2-5 μl have been injected. For the elution one of the two solvent gradients described below was followed:

Method A: 5-90% B, 0-8 min; 90% B, 8-11 min; 5% B, 9-11 min. The flow rate of the mobile phase is 0.7 ml/min.

Method B: 5-90% B, 0-4.5 min; 90% B, 45-6 min; 5% B, 6-7 min. The flow rate of the mobile phase is 1.4 ml/min.

In both cases, the solvent A consists of 0.2% formic acid in water, whereas B is 0.2% formic acid in acetonitrile.

Alternatively, the analysis was conducted by means of Waters HPLC-UV-MS equipment provided with a detector having diodes in series and a mass spectrometer model EMDI000. The wavelength used for detecting UV was 210 nm, whereas the MS detector has been operated in a positive electrospray ionization mode and a 100 to 700 m/z scan has been performed. Concerning chromatographic separation, the column used was a Kromasil C18 2.1×50 mm, 3.5 μm and 2 μl have been injected. For the elution, the following gradient was followed:

The flow rate of the mobile phase is 0.5 ml/min.

Intermediate IIIa.1 ethyl 3-(octahydroquinolin-1-yl)-3-oxopropionate

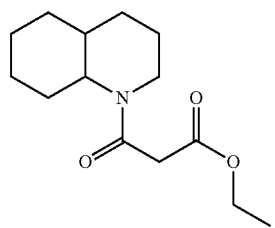 [SMILES: CCOC(=O)CC(=O)N1CCCC2CCCCC21]

3.38 mL of $Et_3N$ and 1.44 mL (11 mmol) of ethyl 3-chloro-3-oxopropionate are added to a solution of 1.5 mL (10 mmol) of decahydroquinoline in 100 mL of AcOEt. The resulting solution is kept under stirring at reflux for 10 h. Then water is added and the organic phase is separated, the aqueous phase is extracted once again with AcOEt. The organic phases are pooled and they are first washed with 5% solution of $NaHCO_3$ and subsequently with brine, they are dried over anhydrous $Na_2SO_4$, they are filtered and the solvent is evaporated under reduced pressure. 2.0 g of a yellow oil are obtained. It is identified as intermediate IIIa.1. Method A: tr: 6.76 min; m/z: 268.

Intermediate IIIa.2

6-(octahydroisoquinolin-2-yl)-6-oxohexanoic acid methyl ester

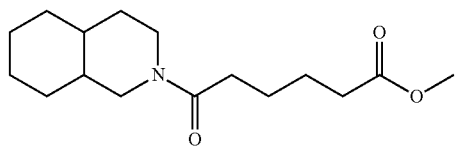 [SMILES: COC(=O)CCCCC(=O)N1CCC2CCCCC2C1]

80 mL of AcOEt and, then, 3 mL (22 mmol) of $Et_3N$ are added to a mixture formed by 1.1 mL (8.32 mmol) of decahydroisoquinoline, 1.5 mL (10 mmol) of monomethyl adipate, 2 g (15 mmol) of HOBT and 2.9 g (15 mmol) of EDC. The solution formed is kept under stirring for 18 h. Then, it is treated with water and AcOEt, the organic phase is separated and the aqueous phase is extracted once more with AcOEt. The organic phases are pooled and they are washed successively with saturated $NaHCO_3$ solution, 1N HCl and brine. It is then dried over anhydrous $Na_2SO_4$, it is filtered and the solvent is evaporated under reduced pressure. 1.5 g of an oil identified as intermediate IIIa.2 are obtained.

Method B: tr: 3.66 min/3.78 min; m/z: 282/282

The following intermediates were prepared in a manner similar to intermediates IIIa.1 or IIIa.2:

| Int. | structure | name | method | tr (min) | m/z |
|---|---|---|---|---|---|
| IIIa.3 | 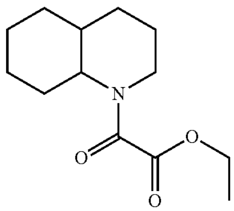 [SMILES: CCOC(=O)C(=O)N1CCCC2CCCCC21] | (Octahydroquinolin-1-yl)oxoacetic acid ethyl ester | A | 6.83 | 240 |
| IIIa.4 | 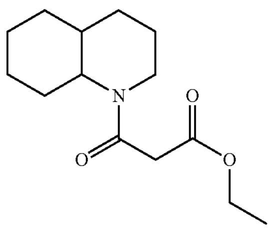 [SMILES: CCOC(=O)CC(=O)N1CCCC2CCCCC21] | 3-(octahydroquinolin-1-yl)-3-oxopropionic acid ethyl ester | A | 6.37 | 254 |
| IIIa.5 | 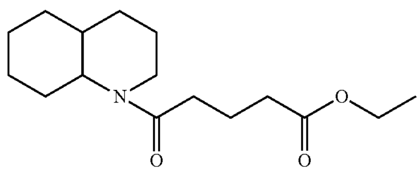 [SMILES: CCOC(=O)CCCC(=O)N1CCCC2CCCCC21] | 5-(octahydroquinolin-1-yl)-5-oxopentanoic acid ethyl ester | A | 6.96 | 282 |
| IIIa.6 | 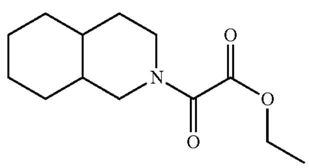 [SMILES: CCOC(=O)C(=O)N1CCC2CCCCC2C1] | (Octahydroisoquinolin-2-yl)oxoacetic acid ethyl ester | A | 6.83<br>7.05 | 240<br>240 |
| IIIa.7 | 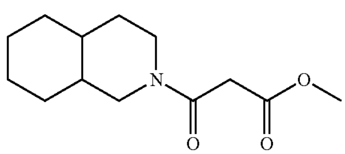 [SMILES: COC(=O)CC(=O)N1CCC2CCCCC2C1] | 3-(octahydroisoquinolin-2-yl)-3-oxopropionic acid methyl ester | A | 5.86<br>6.09 | 240<br>240 |
| IIIa.8 | 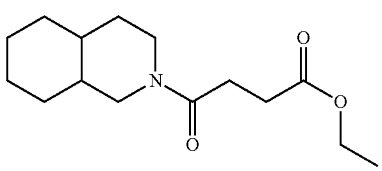 [SMILES: CCOC(=O)CCC(=O)N1CCC2CCCCC2C1] | 4-(octahydroisoquinolin-2-yl)-4-oxobutyric acid ethyl ester | A | 6.72<br>6.92 | 268<br>268 |
| IIIa.9 | 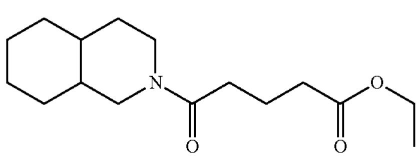 [SMILES: CCOC(=O)CCCC(=O)N1CCC2CCCCC2C1] | 5-(octahydroisoquinolin-2-yl)-5-oxopentanoic acid ethyl ester | A | 7.13<br>7.55 | 282<br>282 |
| IIIa.10 | 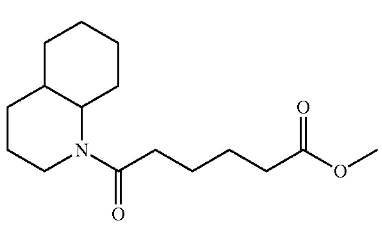 [SMILES: COC(=O)CCCCC(=O)N1CCCC2CCCCC21] | 6-(octahydroquinolin-1-yl)-6-oxohexanoic acid methyl ester | B | 3.67 | 282 |

Intermediate IIIb.1

3-[(octahydroquinoline-1-carbonyl)amino]propionic acid methyl ester

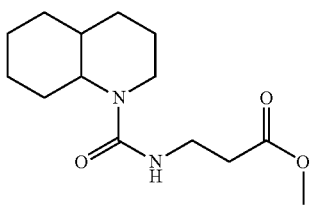 [SMILES: COC(=O)CCNC(=O)N1CCCC2CCCCC21]

Step 1:

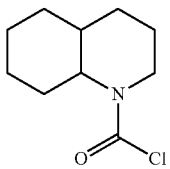 [SMILES: O=C(Cl)N1CCCC2CCCCC21]

2.5 g (18 mmol) of decahydroquinoline are dissolved in 150 mL of DCM and 2.7 g (9 mmol) of triphosgene are slowly added to the solution formed, preventing the temperature from exceeding 25° C. The resulting mixture is then refluxed for 18 h. It is then evaporated to dryness and the residue obtained is purified by means of silica gel filtration using AcOEt as eluent, obtaining 2 g of a yellowish oil identified as 1-chlorocarbonyloctahydroquinoline.

IR: 1729.

Step 2:

0.5 g (3.5 mmol) of the 3-aminopropionic acid methyl ester hydrochloride are dissolved in 5 mL of anhydrous THF and 0.9 mL of Et$_3$N. Once dissolved, 650 mg of 1-chlorocarbonyloctahydroquinoline are slowly added and it is refluxed for 18 h. AcOEt is then added and the resulting solution is sequentially washed with water, 1N HCl and brine. The organic phase is dried over anhydrous Na$_2$SO$_4$, it is filtered and the solvent is evaporated under reduced pressure yielding 580 mg of intermediate IIIb.1.

Method B: tr: 3.17 min; m/z: 269.

The following intermediates were prepared in a manner similar to intermediate IIIb.1:

Intermediate IIIb.5

3-(octahydroisoquinoline-2-carbonylsulfenyl)propionic acid methyl ester

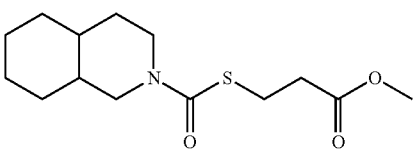

Step 1:

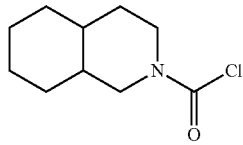

2-chlorocarbonyloctahydroisoquinoline: it was prepared in a manner similar to that described for step 1 of intermediate IIIb.1. IR: 1737.

Step 2:

1 g (5 mmol) of 2-chlorocarbonyloctahydroisoquinoline is added to a 0° C. solution of 0.55 mL (5 mmol) of 3-mercaptopropionic acid methyl ester in 10 mL of pyridine. Once added, it is left under stirring at rt for 18 h. AcOEt is then added to the reaction mixture and it is sequentially washed with a 5% solution of NaHCO$_3$, 1N HCl and brine. The organic phase is dried over anhydrous Na$_2$SO$_4$, it is filtered and the solvent is evaporated under reduced pressure being purified by means of silica gel column chromatography, using a (1:1) mixture of hexane:AcOEt as eluent, yielding 1.17 g of a residue identified as intermediate IIIb.5. and 210 mg of a solid identified as his-(octahydroisoquinolin-2-yl)methanone (Vb.1)

| Int. | structure | name | method | tr (min) | m/z |
|---|---|---|---|---|---|
| IIIb.2 | 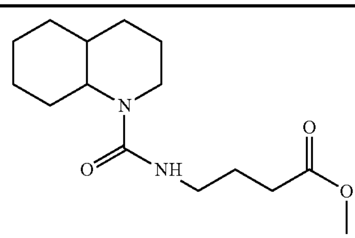 | 4-[(octahydroquinoline-1-carbonyl)amino]butyric acid methyl ester | B | 3.29 | 283 |
| IIIb.3 | 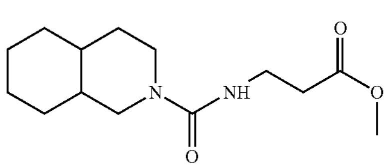 [SMILES: COC(=O)CCNC(=O)N1CCC2CCCCC2C1] | 3-(octahydroisoquinoline-2-carbonyl)amino]propionic acid methyl ester | B | 3.29 | 269 |
| IIIb.4 | 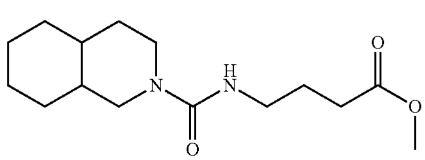 [SMILES: COC(=O)CCCNC(=O)N1CCC2CCCCC2C1] | 4-[(octahydroisoquinoline-2-carbonyl)amino]butyric acid methyl ester | B | 3.40 | 283 |

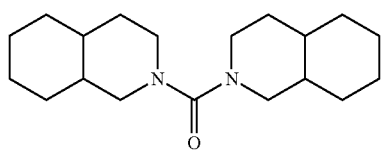 [SMILES: O=C(N1CCC2CCCCC2C1)N1CCC2CCCCC2C1]

Method B: for IIIb.5 tr: 4.35 min; m/z: 286.
for Vb.1: tr: 5.34 min; m/z: 305,

The following intermediates were prepared in a manner similar to intermediate IIIb.5:

| Int. | structure | name | method | tr (min) | m/z |
|---|---|---|---|---|---|
| IIIb.6 | 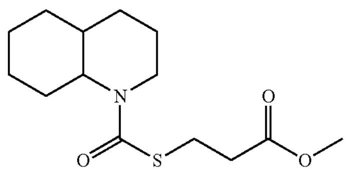 [SMILES: COC(=O)CCSC(=O)N1CCCC2CCCCC21] | 3-(octahydroquinoline-1-carbonylsulfenyl)propionic acid methyl ester | B | 4.23 | 286 |
| IIIb.7 | 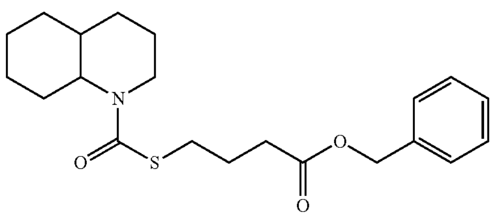 [SMILES: O=C(CCCSC(=O)N1CCCC2CCCCC21)OCc1ccccc1] | 4-(octahydroquinoline-1-carbonylsulfenyl)butyric acid benzyl ester | B | 5.04 | 376 |
| IIIb.8 | 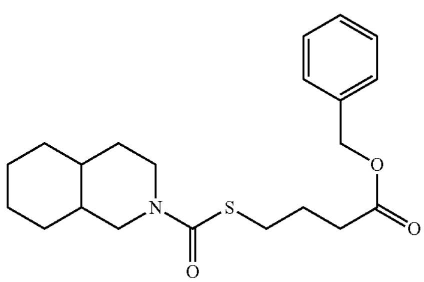 [SMILES: O=C(CCCSC(=O)N1CCC2CCCCC2C1)OCc1ccccc1] | 4-(octahydroisoquinoline-2-carbonylsulfenyl)butyric acid benzyl ester | B | 5.14 | 377 |

Intermediate IIIm.1

3-(octahydroquinoline-1-sulfonyl)propionic acid methyl ester

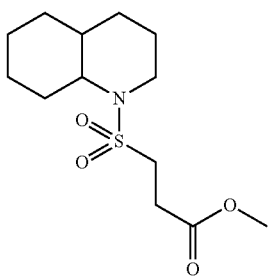 [SMILES: COC(=O)CCS(=O)(=O)N1CCCC2CCCCC21]

Step 1

4.48 mL (55.9 mmol) of sulfuryl chloride are added dropwise to a mixture formed by 2.47 mL (22.4 mmol) of methyl 3-mercaptopropionate and 5.64 g (55.9 mmol) of potassium nitrate cooled to 0° C. Once added it is left to reach rt keeping the stirring for 10 h. Saturated NaHCO$_3$ solution is added and the organic phase is separated, which is subsequently washed again with NaHCO$_3$ and then with brine. The organic phase is dried over anhydrous Na$_2$SO$_4$, it is filtered and the solvent is evaporated under reduced pressure yielding 2.6 g of an oil identified as the 3-chlorosulfonylpropionic acid methyl ester.

Method B: tr: 2.05 min; m/z: non ionizable.

Step 2

2.1 mL of Et$_3$N (15.3 mmol) and subsequently, dropwise, 1.3 g (7 mmol) of the 3-chlorosulfonylpropionic acid methyl ester are added to a solution formed by 1.1 mL (7.6 mmol) of decahydroquinoline in 70 mL of AcOEt. The mixture is heated to 70° C. and that temperature is maintained for 12 h. It is then left to cool and water is added, the organic phase is separated and it is sequentially washed with 5% solution of sodium bicarbonate, 2N HCl and brine. The organic phase is dried over anhydrous Na$_2$SO$_4$, it is filtered and the solvent is evaporated under reduced pressure yielding 1.32 g of a reddish oil identified as intermediate IIIm.1.

Method B: tr: 3.36 min: m/z: 290

The following intermediates were prepared in a manner similar to intermediate IIIm.1:

| Int. | structure | name | method | tr (min) | m/z |
|---|---|---|---|---|---|
| IIIm.2 | 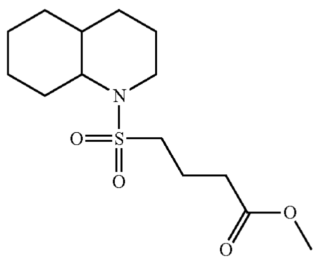 [SMILES: COC(=O)CCCS(=O)(=O)N1CCCC2CCCCC21] | 4-(octahydroquinoline-1-sulfonyl)butyric acid methyl ester | B | 3.73 | 304 |
| IIIm.3 | 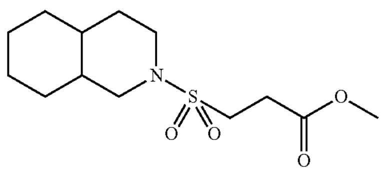 [SMILES: COC(=O)CCS(=O)(=O)N1CCC2CCCCC2C1] | 3-(octahydroisoquinoline-2-sulfonyl)propionic acid methyl ester | B | 3.79 | 290 |
| IIIm.4 | 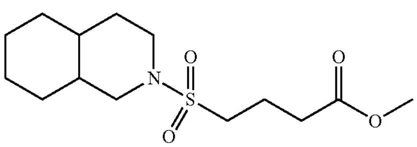 [SMILES: COC(=O)CCCS(=O)(=O)N1CCC2CCCCC2C1] | 4-(octahydroisoquinoline-2-sulfonyl)butyric acid methyl ester | B | 3.83<br>3.91 | 304<br>304 |

Intermediate IVb.1

4-[(octahydroisoquinoline-2-carbonyl)amino]butyric acid

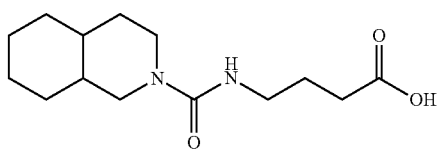 [SMILES: O=C(O)CCCNC(=O)N1CCC2CCCCC2C1]

1.2 g (4.21 mmol) of intermediate IIIb.4 are dissolved in a mixture formed by 37.5 mL of THF and 12.5 mL of MeOH, and 5.1 mL of a 1M LiOH solution in water are added to the solution formed. The resulting mixture is kept under stirring at rt for 18 h. Then it is diluted in AcOEt and washed with water, the aqueous phase is acidified with a 1N solution of HCl until pH=3 and it is extracted with AcOEt. Finally, the organic phases are pooled, they are dried over anhydrous Na$_2$SO$_4$, they are filtered and the solvent is evaporated under reduced pressure. 570 mg of a white solid are obtained.

Method B: tr: 2.85 min/2.96 min; m/z: 269/269

The following intermediates were prepared in a manner similar to intermediate IVb.1:

| Int. | structure | name | method | tr (min) | m/z |
|---|---|---|---|---|---|
| IVa.1 | 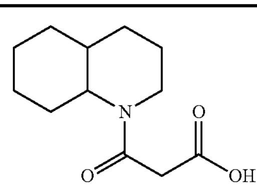 | 3-(octahydroquinolin-1-yl)-3-oxopropionic acid | A | 5.18 | 226 |
| IVa.2 | 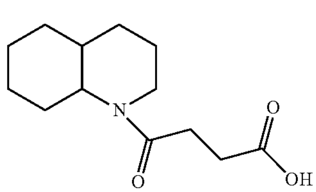 [SMILES: O=C(O)CCC(=O)N1CCCC2CCCCC21] | 4-(octahydroquinolin-1-yl)-4-oxobutyric acid | A | 5.32 | 240 |

| Int. | structure | name | method | tr (min) | m/z |
|---|---|---|---|---|---|
| IVa.3 | 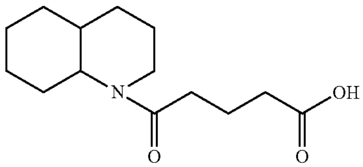 [SMILES: O=C(O)CCCC(=O)N1CCCC2CCCCC21] | 5-(octahydroquinolin-1-yl)-5-oxopentanoic acid | A | 5.42 | 254 |
| IVa.4 | 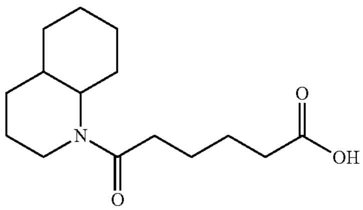 [SMILES: O=C(O)CCCCC(=O)N1CCCC2CCCCC21] | 6-(octahydroisoquinolin-2-yl)-6-oxobutyric acid | B | 3.08 | 268 |
| IVa.5 | 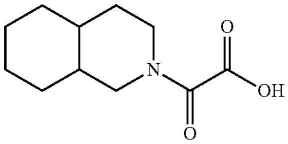 [SMILES: O=C(O)C(=O)N1CCC2CCCCC2C1] | (octahydroisoquinolin-2-yl)oxoacetic acid | A | 4.25<br>4.40 | 212<br>212 |
| IVa.6 | 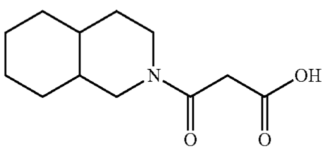 [SMILES: O=C(O)CC(=O)N1CCC2CCCCC2C1] | 3-(octahydroisoquinolin-2-yl)-3-oxopropionic acid | A | 5.19<br>5.40 | 226<br>226 |
| IVa.7 | 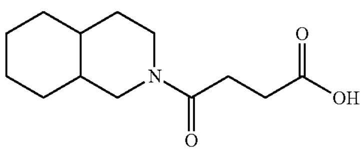 [SMILES: O=C(O)CCC(=O)N1CCC2CCCCC2C1] | 4-(octahydroisoquinolin-2-yl)-4-oxobutyric acid | A | 5.30<br>5.51 | 240<br>240 |
| IVa.8 | 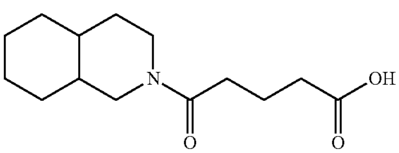 [SMILES: O=C(O)CCCC(=O)N1CCC2CCCCC2C1] | 5-(octahydroisoquinolin-2-yl)-5-oxopentanoic acid | A | 5.44<br>5.64 | 254<br>254 |
| IVa.9 | 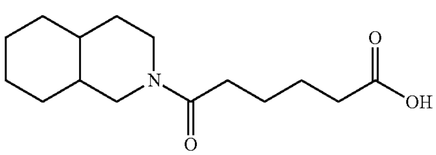 [SMILES: O=C(O)CCCCC(=O)N1CCC2CCCCC2C1] | 6-(octahydroisoquinolin-2-yl)-6-oxohexanoic acid | B | 3.09<br>3.20 | 268<br>268 |
| IVb.2 | 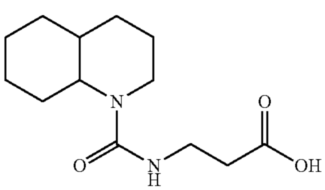 [SMILES: O=C(O)CCNC(=O)N1CCCC2CCCCC21] | 3-[(octahydroquinoline-1-carbonyl)amino]propionic acid | B | 2.75 | 255 |
| IVb.3 | 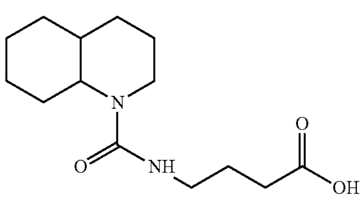 [SMILES: O=C(O)CCCNC(=O)N1CCCC2CCCCC21] | 4-[(octahydroquinoline-1-arbonyl)amino]butyric acid | B | 2.85 | 269 |

-continued

| Int. | structure | name | method | tr (min) | m/z |
|---|---|---|---|---|---|
| IVb.4 | 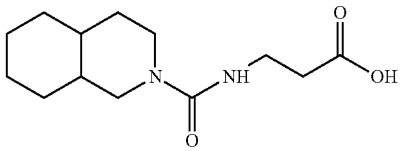 [SMILES: O=C(O)CCNC(=O)N1CCC2CCCCC2C1] | 3-[(octahydroisoquinoline-2-carbonyl)amino]propionic acid | B | 2.87 | 255 |
| IVb.5 | 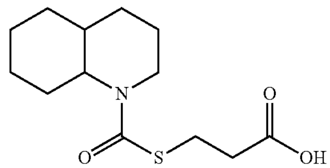 [SMILES: O=C(O)CCSC(=O)N1CCCC2CCCCC21] | 3-(octahydroquinoline-1-carbonylsulfenyl)propionic acid | B | 3.53 | 272 |
| IVb.6 | 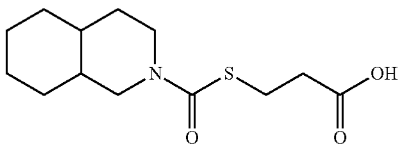 [SMILES: O=C(O)CCSC(=O)N1CCC2CCCCC2C1] | 3-(octahydroisoquinoline-2-carbonylsulfenyl)propionic acid | B | 3.66 | 272 |
| IVb.7 | 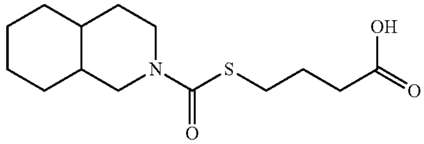 [SMILES: O=C(O)CCCSC(=O)N1CCC2CCCCC2C1] | 4-(octahydroisoquinoline-2-carbonylsulfenyl)butyric acid | B | 3.81 | 286 |
| IVm.1 | 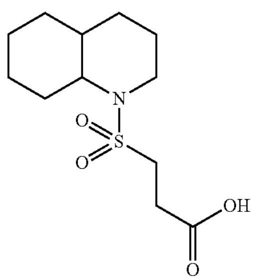 [SMILES: O=C(O)CCS(=O)(=O)N1CCCC2CCCCC21] | 3-(octahydroquinoline-1-sulfonyl)propionic acid | B | 3.10 | 276 |
| IVm.2 | 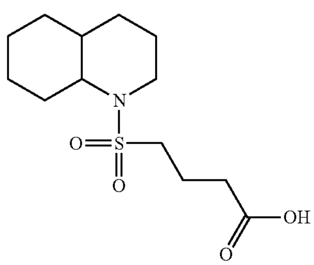 [SMILES: O=C(O)CCCS(=O)(=O)N1CCCC2CCCCC21] | 4-(octahydroquinoline-1-sulfonyl)butyric acid | B | 3.18 | 290 |
| IVm.3 | 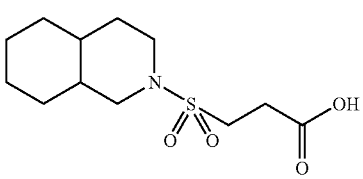 [SMILES: O=C(O)CCS(=O)(=O)N1CCC2CCCCC2C1] | 3-(octahydroisoquinoline-2-sulfonyl)propionic acid | B | 3.18<br>3.27 | 276<br>276 |
| IVm.4 | 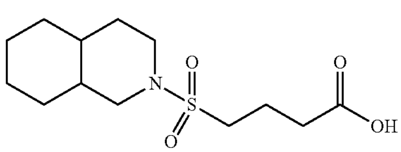 [SMILES: O=C(O)CCCS(=O)(=O)N1CCC2CCCCC2C1] | 4-(octahydroisoquinoline-2-sulfonyl)butyric acid | B | 3.25<br>3.34 | 290<br>290 |

Intermediate IIIc.1

4-bromo-1-(octahydroquinolin-1-yl)butan-1-one

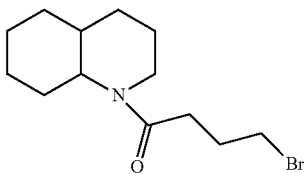 [SMILES: O=C(CCCBr)N1CCCC2CCCCC21]

1.37 mL (9.9 mmol) of Et₃N and 0.5 mL (4.5 mmol) of 5-bromovaleric acid chloride are added to a solution of 1 mL (4.0 mmol) of the decahydroquinoline in AcOEt. The resulting solution is kept under stirring for 18 h at rt. The solution is then washed with water, and the water re-extracted twice with AcOEt. The pooled organic phases are sequentially washed with 5% solution of NaHCO₃, 1N HCl and saturated ammonium chloride solution. Finally the organic phase is dried over anhydrous Na₂SO₄, it is filtered and the solvent is evaporated under reduced pressure. 1.2 g of a yellow oil, which was used without subsequent purification, are obtained.

The following intermediates were prepared in a manner similar to intermediate IIIc.1:

| Int. | structure | name | method | tr (min) | m/z |
|---|---|---|---|---|---|
| IIIc.2 | 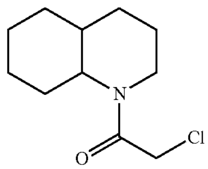 [SMILES: O=C(CCl)N1CCCC2CCCCC21] | 2-chloro-1-(octahydroquinolin-1-yl)ethanone | A | 6.45 | 216, 218 |
| IIIc.3 | 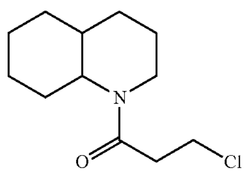 [SMILES: O=C(CCCl)N1CCCC2CCCCC21] | 3-chloro-1-(octahydroquinolin-1-yl)propan-1-one | A | 7.02 | 230, 232 |
| IIIc.4 | 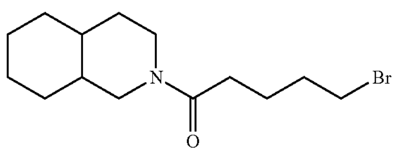 [SMILES: O=C(CCCCBr)N1CCC2CCCCC2C1] | 5-bromo-1-(octahydroisoquinolin-2-yl)-pentan-1-one | A | 7.60<br>7.78 | (302, 304)<br>(302, 304) |
| IIIc.5 | 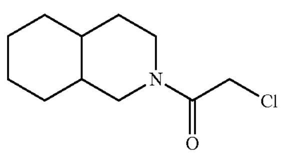 [SMILES: O=C(CCl)N1CCC2CCCCC2C1] | 2-chloro-1-(octahydroisoquinolin-2-yl)ethanone | A | 6.44<br>6.68 | (216, 218)<br>(216, 218) |
| IIIc.6 | 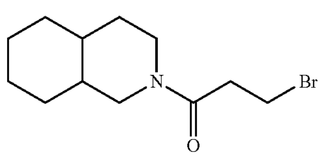 [SMILES: O=C(CCBr)N1CCC2CCCCC2C1] | 3-bromo-1-(octahydroisoquinolin-2-yl)propan-1-one | A | 7.00<br>7.21 | (274, 276)<br>(274, 276) |
| IIIc.7 | 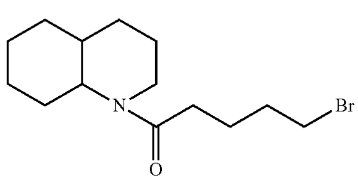 [SMILES: O=C(CCCCBr)N1CCCC2CCCCC21] | 5-bromo-1-(octahydroquinolin-1-yl)-pentan-1-one | A | — | — |

Intermediate IIIf.1

Octahydroquinoline-1-carboxylic acid 3-chloropropylamide

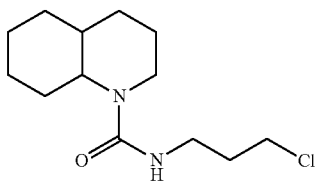 [SMILES: O=C(NCCCCl)N1CCCC2CCCCC21]

2.5 g (21 mmol) of 3-chloropropylisocyanate are dissolved in 150 mL of anhydrous THF and 6.4 mL (46 mmol) of Et₃N. Once dissolved 3.4 mL (23 mmol) of decahydroquinoline are slowly added and it is refluxed for 18 h. AcOEt is then added and the resulting solution is sequentially washed with water, 1N HCl and brine. The organic phase is dried over anhydrous Na₂SO₄, it is filtered and the solvent is evaporated under reduced pressure yielding 4.6 g of intermediate IIIf.1. Method B: tr: 3.58 min; m/z: 259

Intermediate IIIf.2

Octahydroisoquinoline-2-carboxylic acid 3-(chloropropyl)amide

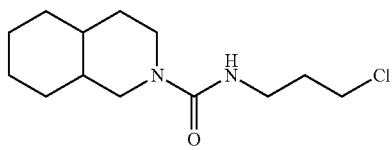 [SMILES: O=C(NCCCCl)N1CCC2CCCCC2C1]

It was prepared in a manner similar to that described for intermediate IIIf.1. Method B: tr: 357 min/3.68 min; m/z: 259, 259

Intermediate IVc.1

4-azido-1-(octahydroquinolin-1-yl)butan-1-one 710 mg (10.8 mmol) of sodium azide are added to a solution of 1.1 g (3.6 mmol) of intermediate IIIc.1 in 35 mL of anhydrous DMF. The resulting solution is kept under stirring for 18 h at a temperature of 90° C. The solution is then cooled and water is added, extracting three times with AcOEt. The pooled organic phases are washed with brine. Finally the organic phase is dried over anhydrous Na₂SO₄, it is filtered and the solvent is evaporated under reduced pressure. 830 mg of a yellow oil, which was used without subsequent purification, are obtained. Method A: tr: 7.07 min; m/z: 251.

The following intermediates were prepared in a manner similar to intermediate IVc.1:

| Int. | structure | name | method | tr (min) | m/z |
|---|---|---|---|---|---|
| IVc.2 | 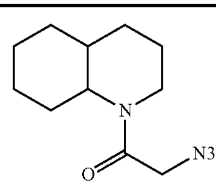 | 2-azido-1-(octahydroquinolin-1-yl)ethanone | A | 6.48 | 223 |
| IVc.3 | 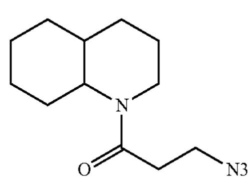 [SMILES: [N-]=[N+]=NCCC(=O)N1CCCC2CCCCC21] | 3-azido-1-(octahydroquinon-1-yl)propan-1-one | A | 6.79 | 237 |
| IVc.4 | 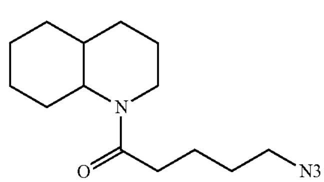 [SMILES: [N-]=[N+]=NCCCCC(=O)N1CCCC2CCCCC21] | 5-azido-1-(octahydroquinolin-1-yl)pentan-1-one | A | 7.33 | 265 |

| Int. | structure | name | method | tr (min) | m/z |
| --- | --- | --- | --- | --- | --- |
| IVc.5 | 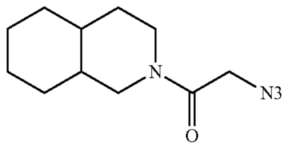 [SMILES: [N-]=[N+]=NCC(=O)N1CCC2CCCCC2C1] | 2-azido-1-(octahydroisoquinolin-2-yl)ethanone | A | 6.46<br>6.70 | 223<br>223 |
| IVc.6 | 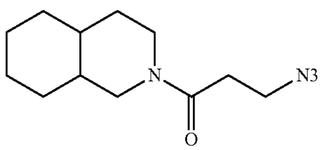 [SMILES: [N-]=[N+]=NCCC(=O)N1CCC2CCCCC2C1] | 3-azido-1-(octahydroisoquinolin-2-yl)propan-1-one | A | 6.77<br>6.99 | 237<br>237 |
| IVc.7 | 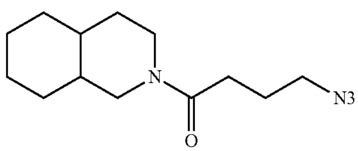 [SMILES: [N-]=[N+]=NCCCC(=O)N1CCC2CCCCC2C1] | 4-azido-1-(octahydroisoquinolin-2-yl)butan-1-one | A | 7.07<br>7.27 | 251<br>251 |
| IVc.8 | 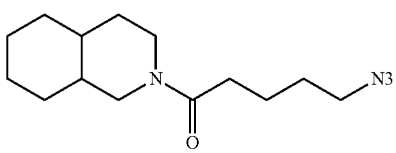 [SMILES: [N-]=[N+]=NCCCCC(=O)N1CCC2CCCCC2C1] | 5-azido-1-(octahydroisoquinolin-2-yl)pentan-1-one | A | 7.33<br>7.51 | 265<br>265 |
| IVf.1 | 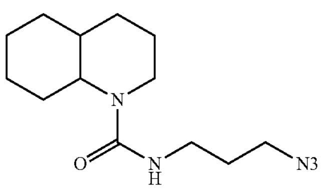 [SMILES: [N-]=[N+]=NCCCNC(=O)N1CCCC2CCCCC21] | Octahydroquinoline-1-carboxylic acid (3-azidopropyl)amide | B | 3.56 | 266 |
| IVf.2 | 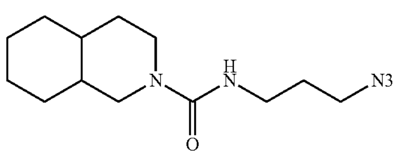 [SMILES: [N-]=[N+]=NCCCNC(=O)N1CCC2CCCCC2C1] | Octahydroisoquinoline-2-carboxylic acid (3-azidopropyl)amide | B | 3.55<br>3.66 | 266<br>266 |

Intermediate Ic.1

2-[4-(octahydroquinolin-1-yl)-4-oxobutyl]isoindole-1,3-dione

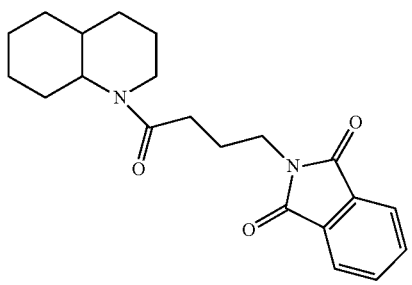 [SMILES: O=C1c2ccccc2C(=O)N1CCCC(=O)N1CCCC2CCCCC21]

200 mg (1.1 mmol) of potassium phthalimide are added to a solution of 307 mg (1.1 mmol) of intermediate IIIc.1 in 10 mL of anhydrous DMF. The resulting solution is kept under stirring for 18 h at a temperature of 90° C. The solution is then cooled and water is added, extracting it with AcOEt. The pooled organic phases are washed with brine. Finally the organic phase is dried over anhydrous $Na_2SO_4$, it is filtered and the solvent is evaporated under reduced pressure. 360 mg of a paste, which was purified by means of silica gel column chromatography using a (1:1) mixture of hexane:AcOEt as eluent, yielding 180 mg of an oil identified as intermediate Ic.1, are obtained. Method A: tr: 7.17 min; m/z: 355.

The following intermediates were prepared in a manner similar to intermediate Ic.1:

| Ex. | structure | name | method | tr (min) | m/z |
|---|---|---|---|---|---|
| Ic.2 | 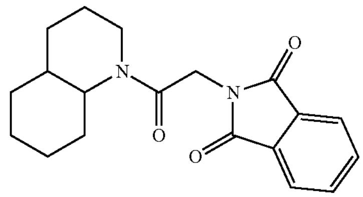 [SMILES: O=C1c2ccccc2C(=O)N1CC(=O)N1CCCC2CCCCC21] | 2-[2-(octahydroquinolin-1-yl)-2-oxoethyl]isoindole-1,3-dione | A | 6.93 | 327 |
| Ic.3 | 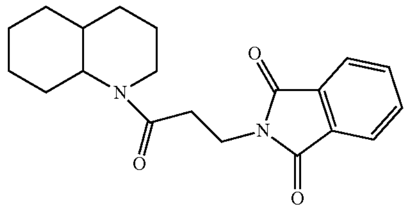 [SMILES: O=C1c2ccccc2C(=O)N1CCC(=O)N1CCCC2CCCCC21] | 2-[3-(octahydroquinolin-1-yl)-3-oxopropyl]isoindole-1,3-dione | A | 7.00 | 341 |
| Ic.4 | 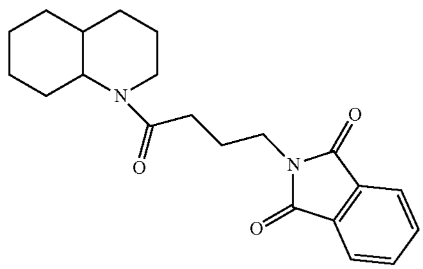 [SMILES: O=C1c2ccccc2C(=O)N1CCCC(=O)N1CCCC2CCCCC21] | 2-[4-(octahydroquinolin-1-yl)-4-oxobutyl]isoindole-1,3-dione | A | 7.17 | 355 |
| Ic.5 | 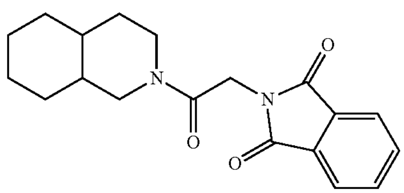 [SMILES: O=C(CN1C(=O)c2ccccc2C1=O)N1CCC2CCCCC2C1] | 2-[2-(octahydroisoquinolin-2-yl)-2-oxoethyl]isoindole-1,3-dione | A | 6.92<br>7.10 | 327<br>327 |
| Ic.6 | 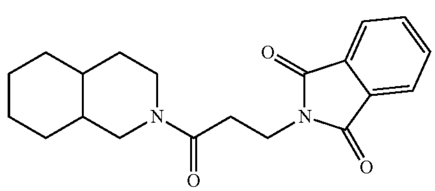 [SMILES: O=C(CCN1C(=O)c2ccccc2C1=O)N1CCC2CCCCC2C1] | 2-[3-(octahydroisoquinolin-2-yl)-3-oxopropyl]isoindole-1,3-dione | A | 6.96<br>7.12 | 341<br>341 |
| Ic.7 | 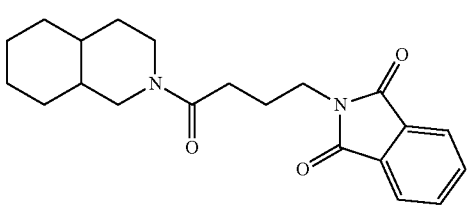 [SMILES: O=C(CCCN1C(=O)c2ccccc2C1=O)N1CCC2CCCCC2C1] | 2-[4-(octahydroisoquinolin-2-yl)-4-oxobutyl]isoindole-1,3-dione | A | 7.16<br>7.33 | 355<br>355 |
| Ic.8 | 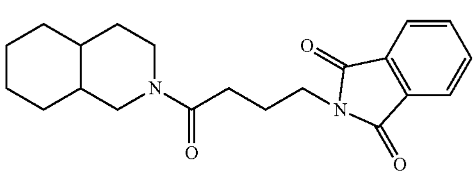 [SMILES: O=C(CCCN1C(=O)c2ccccc2C1=O)N1CCC2CCCCC2C1] | 2-[5-(octahydroisoquinolin-2-yl)-5-oxopentyl]isoindole-1,3-dione | A | 7.39<br>7.55 | 369<br>369 |

Intermediate Vc.1

4-amino-1-(octahydroquinolin-1-yl)butan-1-one

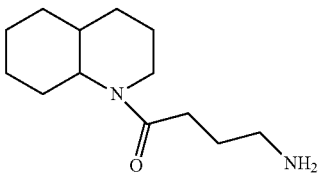 [SMILES: NCCCC(=O)N1CCCC2CCCCC21]

Option A: 0.1 mL of hydrazine (2.5 mmol) is added to a solution formed by 172 mg (0.48 mmol) of intermediate Ic.1 in 5 mL of EtOH and it is heated to reflux temperature for 2 h. The solution is then cooled and concentrated HCl is added until acidic pH is reached, stirring it for 2 h or more. The resulting suspension is filtered and the water is basified with 1N NaOH, extracting it with DCM. The pooled organic phases are washed with brine and are dried over anhydrous $Na_2SO_4$, it is filtered and the solvent is evaporated under reduced pressure. The resulting residue is purified by means of silica gel column chromatography, using a (10:1) mixture of DCM:MeOH as eluent, yielding 90 mg of an oil identified as intermediate Vc.1.

Option B: A suspension formed by 830 mg (3.32 mmol) of intermediate IVc.1 and 83 mg of 5% Pd/C in 35 mL of MeOH is stirred under hydrogen atmosphere until the disappearance of the starting product by monitoring by TLC. It is filtered through Celite and it is evaporated to dryness yielding 700 mg of an oil identified as intermediate Vc.1.

Method A: tr: 3.94 min; m/z: 225

The following intermediates were prepared in a manner similar to intermediate Vc.1:

| Int. | structure | name | method | tr (min) | m/z |
|---|---|---|---|---|---|
| Vc.2 | 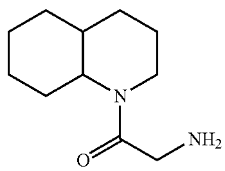 [SMILES: NCC(=O)N1CCCC2CCCCC21] | 2-amino-1-(octahydroquinolin-1-yl)ethanone | A | 3.41 | 197 |
| Vc.3 | 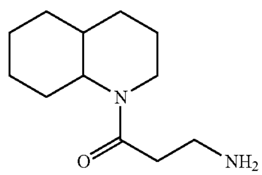 [SMILES: NCCC(=O)N1CCCC2CCCCC21] | 3-amino-1-(octahydroquinolin-1-yl)propan-1-one | A | 3.64 | 211 |
| Vc.4 | 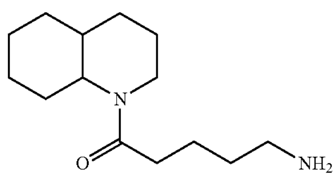 [SMILES: NCCCCC(=O)N1CCCC2CCCCC21] | 5-amino-1-(octahydroquinolin-1-yl)pentan-1-one | A | 4.01 | 239 |
| Vc.5 | 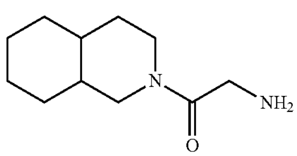 [SMILES: NCC(=O)N1CCC2CCCCC2C1] | 2-amino-1-(octahydroisoquinolin-2-yl)ethanone | A | 3.69 | 197 |
| Vc.6 | 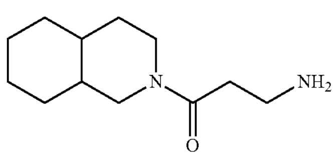 [SMILES: NCCC(=O)N1CCC2CCCCC2C1] | 3-amino-1-(octahydroisoquinolin-2-yl)propan-1-one | A | 4.00 | 211 |
| Vc.7 | 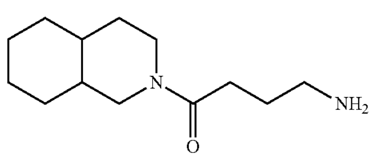 [SMILES: NCCCC(=O)N1CCC2CCCCC2C1] | 4-amino-1-(octahydroisoquinolin-2-yl)butan-1-one | A | 4.03 | 225 |

| Int. | structure | name | method | tr (min) | m/z |
|---|---|---|---|---|---|
| Vc.8 | 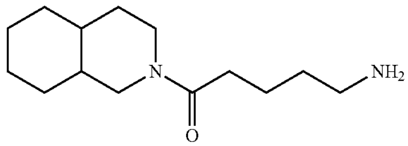 [SMILES: NCCCCC(=O)N1CCC2CCCCC2C1] | 5-amino-1-(octahydroisoquinolin-2-yl)pentan-1-one | A | 4.27 | 239 |
| Vc.9 | 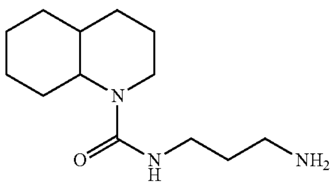 [SMILES: NCCCNC(=O)N1CCCC2CCCCC21] | Octahydroquinoline-1-carboxylic acid (3-aminopropyl)amide | B | 2.11 | 240 |
| Vc.10 | 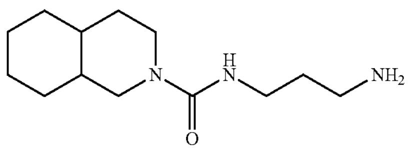 [SMILES: NCCCNC(=O)N1CCC2CCCCC2C1] | Octahydroisoquinoline-2-carboxylic acid (3-aminopropyl)amide | B | 2.22 | 240 |

Intermediate IVj.1

5-hydroxyl-1-(octahydroisoquinolin-2-yl)pentan-1-one

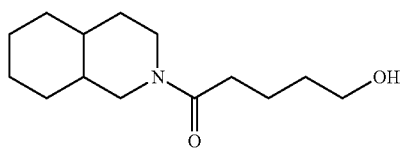 [SMILES: O=C(CCCCO)N1CCC2CCCCC2C1]

0.63 mL (4.93 mmol) of isobutyl chloroformate are added dropwise to a solution of 1.25 g (4.93 mmol) of intermediate IVa.8 and 0.6 mL of N-methylmorpholine (5.4 mmol) in 50 mL of anhydrous THF and cooled to 0° C. The resulting solution is left to stir for 30 minutes at that temperature and 370 mg (9.86 mmol) of sodium borohydride are then added. Once added it is left to reach rt and it is stirred for 2 h. It is then partitioned between AcOEt and water. The aqueous phase is extracted twice with AcOEt, the organic phases are pooled, dried over anhydrous $Na_2SO_4$, filtered and evaporated to dryness, 1 g of a yellow oil, which was used without subsequent purification, being obtained.

Method B: tr: 2.94 min/3.06 min; m/z: 240/240.

Intermediate IVj.2

5-hydroxyl-1-(octahydroquinolin-1-yl)pentan-1-one

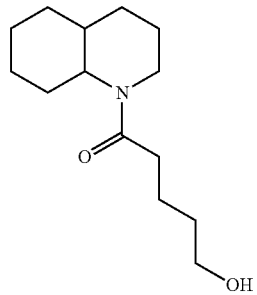 [SMILES: O=C(CCCCO)N1CCCC2CCCCC21]

It is prepared in a manner similar to that described for intermediate IVj.1. Method B: tr: 2.94 min; mfz: 240

Intermediate IVp.1

3-mercapto-1-(octahydroquinolin-1-yl)propan-1-one

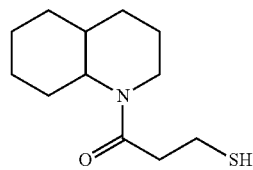 [SMILES: O=C(CCS)N1CCCC2CCCCC21]

8.5 mL of $Et_3N$, 6.5 g of EDC (mmol) and 5.7 g of HOBT (mmol) are added to a solution formed by 3 g (28.2 mmol) of 3-mercaptopropionic acid in 45 mL of DMF and cooled to 0° C. and it is left for 15 minutes under stirring at that temperature. 4.2 g (28.3 mmol) of decahydroquinoline are then added and it is stirred at rt for 18 h. Then, it is treated with water and AcOEt, the organic phase is separated and the aqueous phase is extracted once more with AcOEt. The organic phases are pooled and successively washed with saturated $NaHCO_3$ solution, 1N HCl and brine. It is then dried over anhydrous $Na_2SO_4$, it is filtered and the solvent is evaporated under reduced pressure. The resulting residue is purified by means of silica gel column chromatography, using a (50:1) mixture of DCM:MeOH as eluent, yielding 600 mg of the thiol intermediate Intermediate IVp.2

3-mercapto-1-(octahydroisoquinolin-2-yl)propan-1-one

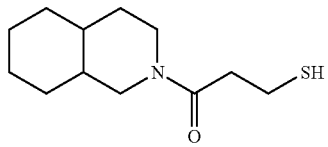 [SMILES: O=C(CCS)N1CCC2CCCCC2C1]

It is prepared in a manner similar to that described for intermediate IVp.1, Method B: tr: 3.59 min/3.72 min; m/z: 228/228

Intermediate IVp.3

4-mercapto-1-(octahydroquinolin-1-yl)butan-1-one

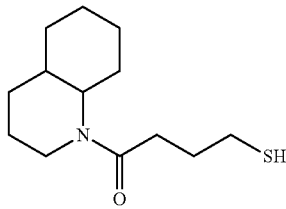 [SMILES: O=C(CCCS)N1CCCC2CCCCC21]

1.5 mL of decahydroquinoline (10 mmol) and 10 mg of camphorsulfonic acid are added to a solution formed by 0.9 mL (10 mmol) of γ-thiolactone in 80 mL of toluene. The resulting mixture is left to stir at 100° C. for 6 h. The solvent is then evaporated under reduced pressure and the resulting residue is purified by means of silica gel column chromatography, using a (50:1) mixture of DCM:MeOH as eluent, yielding 1.5 g of the thiol intermediate IVp.3. Method B: tr: 3.75 min; m/z: 242

Intermediate IVp.4

4-mercapto-1-(octahydroisoquinolin-2-yl)butan-1-one

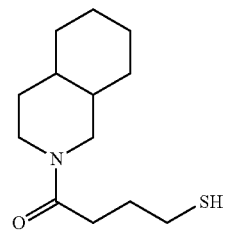 [SMILES: O=C(CCCS)N1CCC2CCCCC2C1]

It is prepared in a manner similar to that described for intermediate IVp.3. Method B: tr: 3.75 min/3.87 min; m/z: 242/242

Example Ia.1

N-bicyclo[2.2.1]hept-2-yl-3-(octahydroisoquinolin-2-yl)-3-oxopropionamide

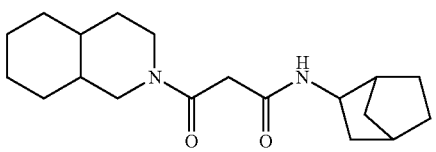 [SMILES: O=C(CC(=O)N1CCC2CCCCC2C1)NC1CC2CCC1C2]

43 μL (0.31 mmol) of $Et_3N$, 29 mg (0.21 mmol) of HOBT, 41 mg (0.21 mmol) of EDC and 18.6 μL (0.16 mmol) of 2-aminonorbornan are added to a solution of 32 mg (0.14 mmol) of the acid intermediate IVa.6 in 2 mL of AcOEt. The solution formed is kept under stirring for 18 h. It is then treated with water and more AcOEt is added, the organic phase is separated and the aqueous phase is extracted once more with more AcOEt. The organic phases are pooled and successively washed with saturated $NaHCO_3$ solution, 1N HCl and brine. It is then dried over anhydrous $Na_2SO_4$, it is filtered and the solvent is evaporated under reduced pressure. 27 mg of the compound identified as example Ia.1 are obtained. Method A: tr: 6.76 min/6.84 min; m/z: 319/319

The following examples were prepared in a manner similar to example Ia.1:

| Ex. | structure | name | method | tr (min) | m/z |
|---|---|---|---|---|---|
| Ia.2 | 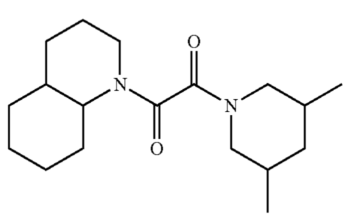 [SMILES: CC1CC(C)CN(C(=O)C(=O)N2CCCC3CCCCC32)C1] | 1-(3,5-dimethylpiperidin-1-yl)-2-(octahydroquinolin-1-yl)ethane-1,2-dione | A | 7.22<br>7.35 | 307<br>307 |

-continued

| Ex. | structure | name | method | tr (min) | m/z |
|---|---|---|---|---|---|
| Ia.3 | 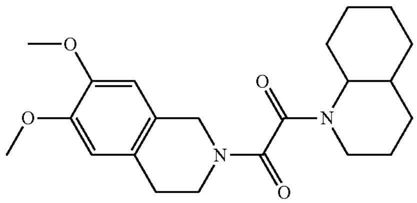 [SMILES: COc1cc2c(cc1OC)CN(C(=O)C(=O)N1CCCC3CCCCC31)CC2] | 1-(6,7-dimethoxy-3,4-dihydro-1-H-isoquinolin-2-yl)-2-(octahydroquinolin-1-yl)ethane-1,2-dione | A | 6.54 | 387 |
| Ia.4 | 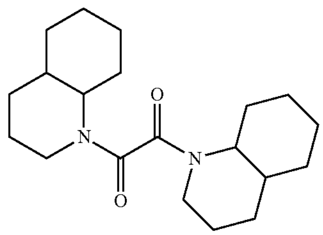 [SMILES: O=C(C(=O)N1CCCC2CCCCC21)N1CCCC2CCCCC21] | 1,2-bis-(octahydroquinolin-1-yl)ethane-1,2-dione | A | 7.66<br>7.76 | 333<br>333 |
| Ia.5 | 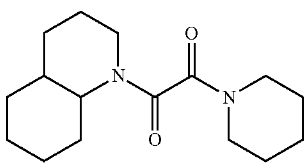 [SMILES: O=C(C(=O)N1CCCC2CCCCC21)N1CCCCC1] | 1-(octahydroquinolin-1-yl)-2-(piperidin-1-yl)ethane-1,2-dione | A | 6.19 | 279 |
| Ia.6 | 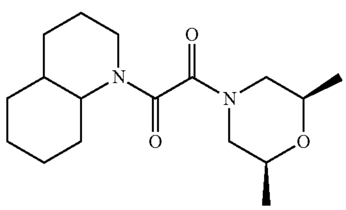 [SMILES: C[C@@H]1CN(C(=O)C(=O)N2CCCC3CCCCC32)C[C@H](C)O1] | 1-((2S,6R)-2,6-dimethylmorpholin-4-yl)-2-(octahydroquinolin-1-yl)ethane-1,2-dione | A | 6.19 | 309 |
| Ia.7 | 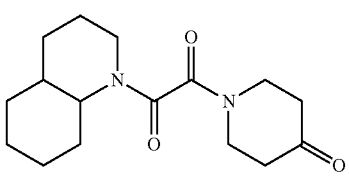 [SMILES: O=C1CCN(C(=O)C(=O)N2CCCC3CCCCC32)CC1] | 1-(octahydroquinolin-1-yl)-2-(4-oxopiperidin-1-yl)ethane-1,2-dione | A | 5.10 | 293 |
| Ia.8 | 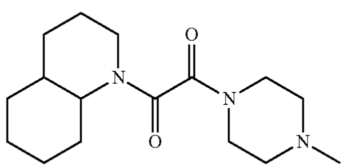 [SMILES: CN1CCN(C(=O)C(=O)N2CCCC3CCCCC32)CC1] | 1-(4-methylpiperazin-1-yl)-2-(octahydroquinolin-1-yl)ethane-1,2-dione | A | 3.82 | 294 |
| Ia.9 | 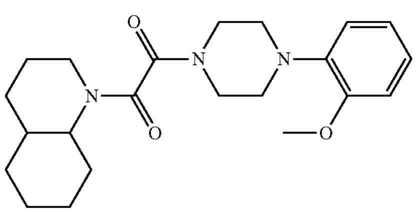 [SMILES: COc1ccccc1N1CCN(C(=O)C(=O)N2CCCC3CCCCC32)CC1] | 1-[4-(2-methoxyphenyl)piperazin-1-yl]-2-(octahydroquinolin-1-yl)ethane-1,2-dione | A | 7.00 | 386 |

-continued

| Ex. | structure | name | method | tr (min) | m/z |
|---|---|---|---|---|---|
| Ia.10 | 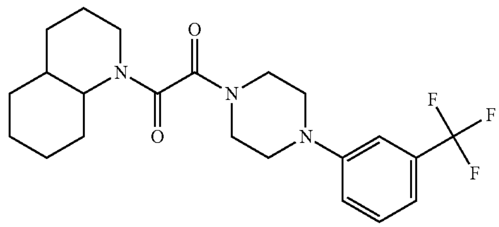 [SMILES: O=C(C(=O)N1CCCC2CCCCC21)N1CCN(c2cccc(C(F)(F)F)c2)CC1] | 1-(octahydroquinolin-1-yl)-2-[4-(3-trifluoromethylphenyl)piperazin-1-yl]-ethane-1,2-dione | A | 7.90 | 424 |
| Ia.11 | 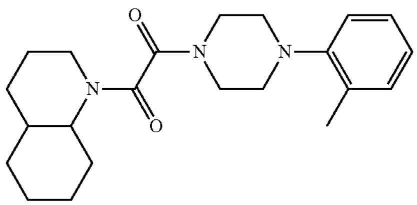 [SMILES: Cc1ccccc1N1CCN(C(=O)C(=O)N2CCCC3CCCCC32)CC1] | 1-(octahydroquinolin-1-yl)-2-(4-o-tolylpiperazin-1-yl)ethane-1,2-dione | A | 7.82 | 370 |
| Ia.12 | 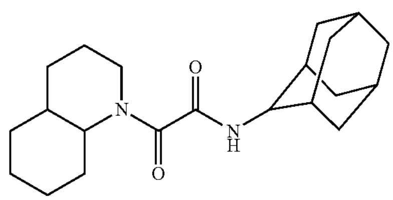 [SMILES: O=C(NC1C2CC3CC(C2)CC1C3)C(=O)N1CCCC2CCCCC21] | 2-(octahydroquinolin-1-yl)-2-oxo-N-tricyclo[3.3.1.1$^{3,7}$]decan-2-ylacetamide | A | 7.99<br>8.18 | 345<br>345 |
| Ia.13 | 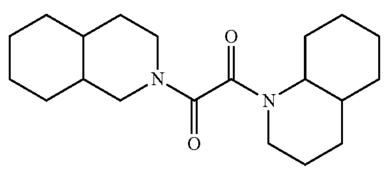 [SMILES: O=C(C(=O)N1CCCC2CCCCC21)N1CCC2CCCCC2C1] | 1-(octahydroisoquinolin-2-yl)-2-(octahydroquinolin-1-yl)ethane-1,2-dione | A | 7.69<br>7.84 | 333<br>333 |
| Ia.14 | 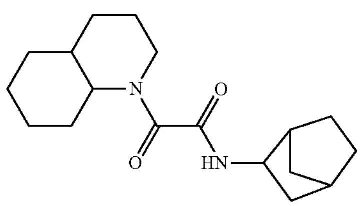 [SMILES: O=C(NC1CC2CCC1C2)C(=O)N1CCCC2CCCCC21] | N-(bicyclo[2.2.1]hept-2-yl)-2-(octahydroquinolin-1-yl)-2-oxoacetamide | A | 6.98<br>7.13 | 305<br>305 |
| Ia.15 | 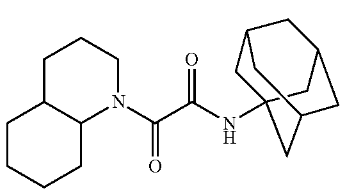 [SMILES: O=C(NC12CC3CC(CC(C3)C1)C2)C(=O)N1CCCC2CCCCC21] | 2-(octahydroquinolin-1-yl)-2-oxo-N-tricyclo[3.3.1.1$^{3,7}$]decan-1-ylacetamide | A | 8.15<br>8.33 | 345<br>345 |
| Ia.16 | 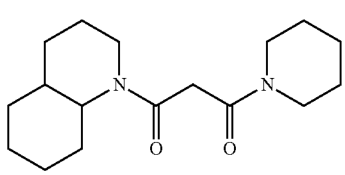 [SMILES: O=C(CC(=O)N1CCCC2CCCCC21)N1CCCCC1] | 1-(octahydroquinolin-1-yl)-3-(piperidin-1-yl)propane-1,3-dione | A | 6.09 | 293 |

| Ex. | structure | name | method | tr (min) | m/z |
| --- | --- | --- | --- | --- | --- |
| Ia.17 | 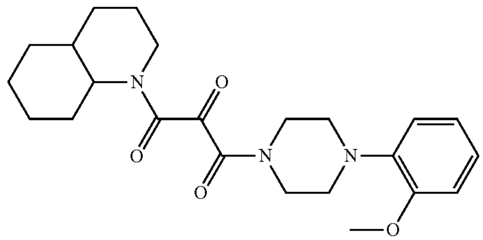 [SMILES: COc1ccccc1N1CCN(C(=O)C(=O)C(=O)N2CCCC3CCCCC32)CC1] | 1-[4-(2-methoxyphenyl)piperazin-1-yl]-3-(octahydroquinolin-1-yl)propane-1,3-dione | A | 6.46 | 400 |
| Ia.18 | 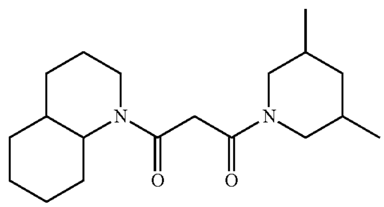 [SMILES: CC1CC(C)CN(C(=O)CC(=O)N2CCCC3CCCCC32)C1] | 1-(3,5-dimethylpiperidin-1-yl)-3-(octahydroquinolin-1-yl)propane-1,3-dione | A | 7.03<br>7.17 | 321<br>321 |
| Ia.19 | 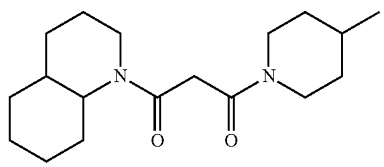 [SMILES: CC1CCN(C(=O)CC(=O)N2CCCC3CCCCC32)CC1] | 1-(4-methylpiperidin-1-yl)-3-(octahydroquinolin-1-yl)propane-1,3-dione | A | 6.62 | 307 |
| Ia.20 | 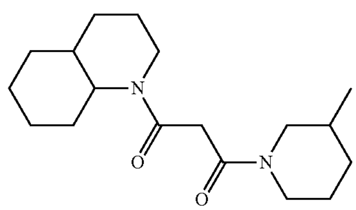 [SMILES: CC1CCCN(C(=O)CC(=O)N2CCCC3CCCCC32)C1] | 1-(3-methylpiperidin-1-yl)-3-(octahydroquinolin-1-yl)propane-1,3-dione | A | 6.62 | 307 |
| Ia.21 | 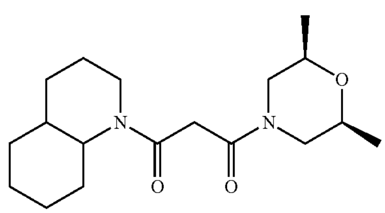 [SMILES: C[C@@H]1CN(C(=O)CC(=O)N2CCCC3CCCCC32)C[C@H](C)O1] | 1-((2S,6R)-2,6-dimethylmorpholin-4-yl)-3-(octahydroquinolin-1-yl)propane-1,3-dione | A | 5.90 | 323 |
| Ia.22 | 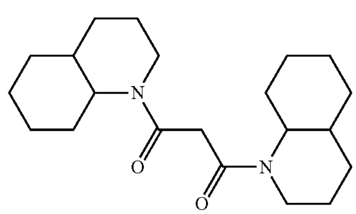 [SMILES: O=C(CC(=O)N1CCCC2CCCCC21)N1CCCC2CCCCC21] | 1,3-bis-(octahydroquinolin-1-yl)propane-1,3-dione | A | 7.53 | 347 |
| Ia.23 | 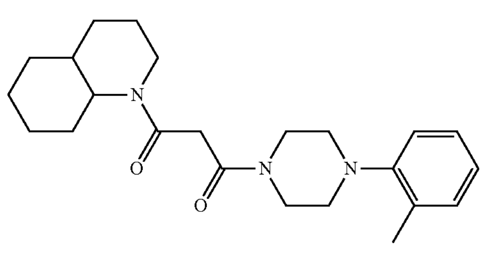 [SMILES: Cc1ccccc1N1CCN(C(=O)CC(=O)N2CCCC3CCCCC32)CC1] | 1-(octahydroquinolin-1-yl)-3-(4-o-tolylpiperazin-1-yl)propane-1,3-dione | A | 7.56 | 384 |

-continued

| Ex. | structure | name | method | tr (min) | m/z |
|---|---|---|---|---|---|
| Ia.24 | 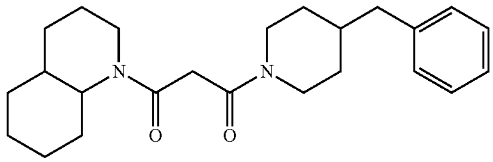 [SMILES: O=C(CC(=O)N1CCCC2CCCCC21)N1CCC(Cc2ccccc2)CC1] | 1-(4-benzylpiperidin-1-yl)-3-(octahydroquinolin-1-yl)propane-1,3-dione | A | 6.31 | 460 |
| Ia.25 | 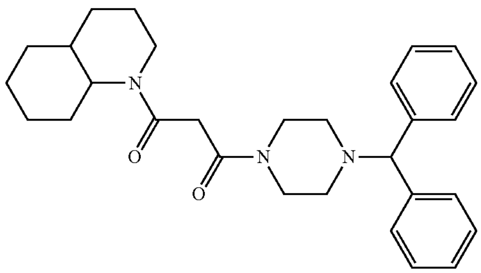 [SMILES: O=C(CC(=O)N1CCCC2CCCCC21)N1CCN(C(c2ccccc2)c2ccccc2)CC1] | 1-(4-benzhydrylpiperazin-1-yl)-3-(octahydroquinolin-1-yl)propane-1,3-dione | A | 7.72 | 383 |
| Ia.26 | 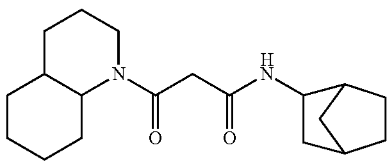 [SMILES: O=C(CC(=O)N1CCCC2CCCCC21)NC1CC2CCC1C2] | N-bicyclo[2.2.1]hept-2-yl-3-(octahydroquinolin-1-yl)-3-oxopropionamide | A | 6.76<br>6.84 | 319<br>319 |
| Ia.27 | 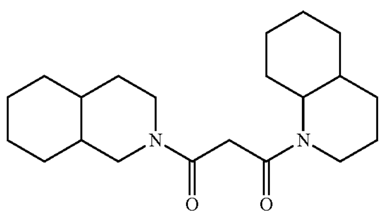 [SMILES: O=C(CC(=O)N1CCCC2CCCCC21)N1CCC2CCCCC2C1] | 1-(octahydroisoquinolin-2-yl)-3-(octahydroquinolin-1-yl)propane-1,3-dione | A | 7.54<br>7.68 | 347<br>347 |
| Ia.28 | 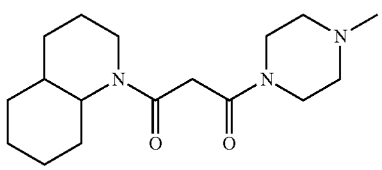 | 1-(4-methylpiperazin-1-yl)-3-(octahydroquinolin-1-yl)propane-1,3-dione | A | 3.90 | 308 |
| Ia.29 | 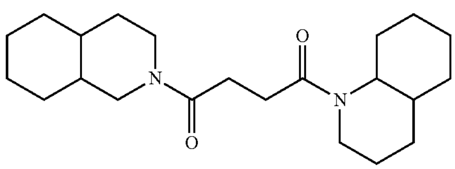 [SMILES: O=C(CCC(=O)N1CCCC2CCCCC21)N1CCC2CCCCC2C1] | 1-(octahydroisoquinolin-2-yl)-4-(octahydroquinolin-1-yl)butane-1,4-dione | A | 7.75<br>7.90 | 361<br>361 |
| Ia.30 | 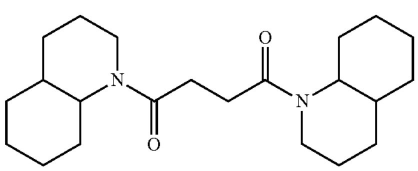 [SMILES: O=C(CCC(=O)N1CCCC2CCCCC21)N1CCCC2CCCCC21] | 1,4-bis-(octahydroquinolin-1-yl)butane-1,4-dione | A | 7.84 | 361 |
| Ia.31 | 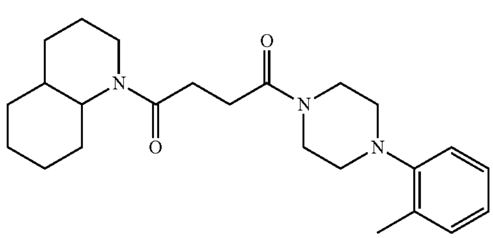 [SMILES: Cc1ccccc1N1CCN(C(=O)CCC(=O)N2CCCC3CCCCC32)CC1] | 1-(octahydroquinolin-1-yl)-4-(4-o-tolylpiperazin-1-yl)butane-1,4-dione | A | 7.78 | 398 |

-continued

| Ex. | structure | name | method | tr (min) | m/z |
|---|---|---|---|---|---|
| Ia.32 | 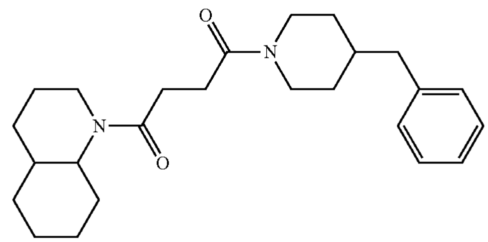 [SMILES: O=C(CCC(=O)N1CCCC2CCCCC21)N1CCC(Cc2ccccc2)CC1] | 1-(4-benzylpiperidin-1-yl)-4-(octahydroquinolin-1-yl)butane-1,4-dione | A | 7.99<br>8.11 | 397<br>397 |
| Ia.33 | 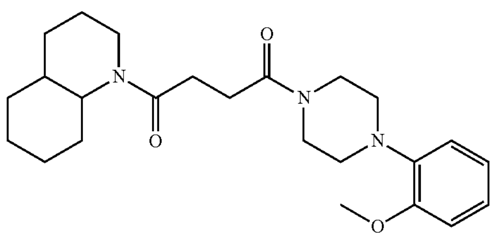 [SMILES: COc1ccccc1N1CCN(C(=O)CCC(=O)N2CCCC3CCCCC32)CC1] | 1-[4-(2-methoxyphenyl)piperazin-1-yl]-4-(octahydroquinolin-1-yl)butane-1,4-dione | A | 6.53 | 414 |
| Ia.34 | 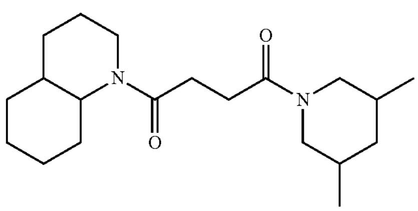 [SMILES: CC1CC(C)CN(C(=O)CCC(=O)N2CCCC3CCCCC32)C1] | 1-(3,5-dimethylpiperidin-1-yl)-4-(octahydroquinolin-1-yl)butane-1,4-dione | A | 7.32<br>7.48 | 335<br>335 |
| Ia.35 | 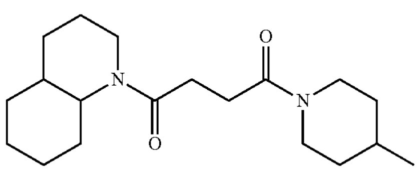 [SMILES: CC1CCN(C(=O)CCC(=O)N2CCCC3CCCCC32)CC1] | 1-(4-methylpiperidin-1-yl)-4-(octahydroquinolin-1-yl)butane-1,4-dione | A | 6.93 | 321 |
| Ia.36 | 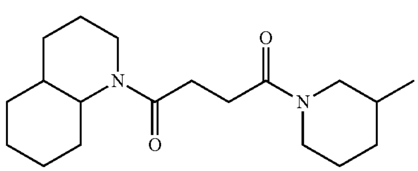 [SMILES: CC1CCCN(C(=O)CCC(=O)N2CCCC3CCCCC32)C1] | 1-(3-methylpiperidin-1-yl)-4-(octahydroquinolin-1-yl)butane-1,4-dione | A | 6.92 | 321 |
| Ia.37 | 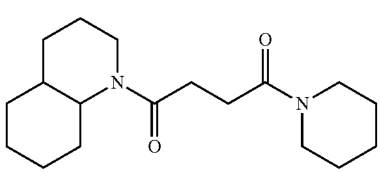 [SMILES: O=C(CCC(=O)N1CCCC2CCCCC21)N1CCCCC1] | 1-(octahydroquinolin-1-yl)-4-piperidin-1-ylbutane-1,4-dione | A | 6.36 | 307 |
| Ia.38 | 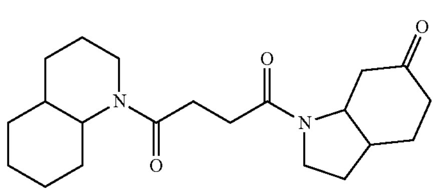 [SMILES: O=C1CCC2CCN(C(=O)CCC(=O)N3CCCC4CCCCC43)C2C1] | 1-(octahydroquinolin-1-yl)-4-(6-oxooctahydroindol-1-yl)butane-1,4-dione | A | 4.25 | 361 |
| Ia.39 | 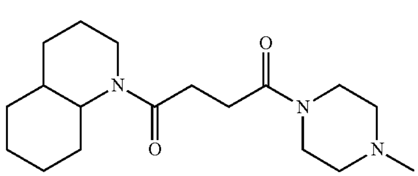 [SMILES: CN1CCN(C(=O)CCC(=O)N2CCCC3CCCCC32)CC1] | 1-(4-methylpiperazin-1-yl)-4-(octahydroquinolin-1-yl)butane-1,4-dione | A | 4.19 | 322 |

-continued

| Ex. | structure | name | method | tr (min) | m/z |
|---|---|---|---|---|---|
| Ia.40 | 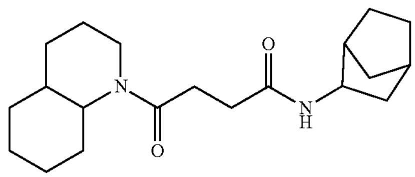 [SMILES: O=C(CCC(=O)N1CCCC2CCCCC21)NC1CC2CCC1C2] | N-bicyclo[2.2.1]hept-2-yl-4-(octahydroquinolin-1-yl)-4-oxobutyramide | A | 6.84 | 333 |
| Ia.41 | 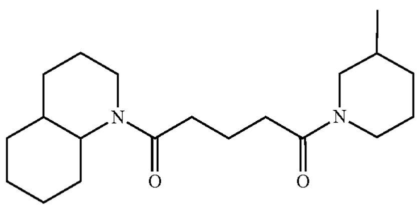 [SMILES: CC1CCCN(C(=O)CCCC(=O)N2CCCC3CCCCC32)C1] | 1-(3-methylpiperidin-1-yl)-5-(octahydroquinolin-1-yl)pentane-1,5-dione | A | 7.01 | 335 |
| Ia.42 | 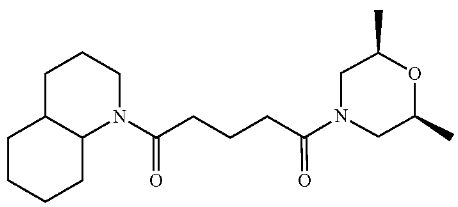 [SMILES: C[C@@H]1CN(C(=O)CCCC(=O)N2CCCC3CCCCC32)C[C@H](C)O1] | 1-((2S,6R)-2,6-dimethylmorpholin-4-yl)-5-(octahydroquinolin-1-yl)pentane-1,5-dione | A | 6.28 | 351 |
| Ia.43 | 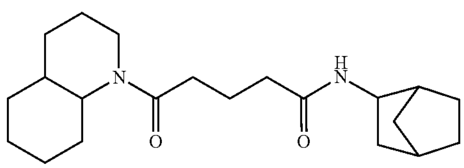 [SMILES: O=C(CCCC(=O)N1CCCC2CCCCC21)NC1CC2CCC1C2] | 5-(octahydroquinolin-1-yl)-5-oxopentanoic acid bicyclo[2.2.1]hept-2-ylamide | A | 6.88 | 347 |
| Ia.44 | 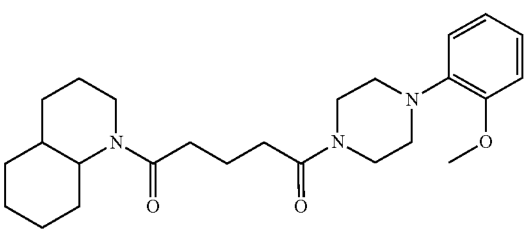 [SMILES: COc1ccccc1N1CCN(C(=O)CCCC(=O)N2CCCC3CCCCC32)CC1] | 1-[4-(2-methoxyphenyl)piperazin-1-yl]-5-(octahydroquinolin-1-yl)pentane-1,5-dione | A | 6.75 | 428 |
| Ia.45 | 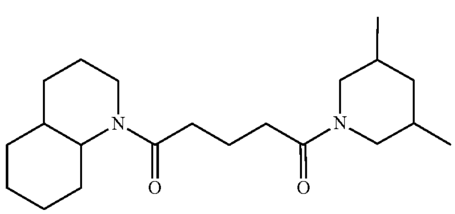 [SMILES: CC1CC(C)CN(C(=O)CCCC(=O)N2CCCC3CCCCC32)C1] | 1-(3,5-dimethylpiperidin-1-yl)-5-(octahydroquinolin-1-yl)pentane-1,5-dione | A | 7.41<br>7.57 | 349<br>349 |
| Ia.46 | 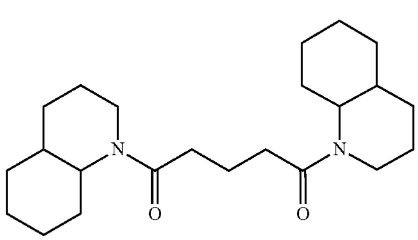 [SMILES: O=C(CCCC(=O)N1CCCC2CCCCC21)N1CCCC2CCCCC21] | 1,5-bis-(octahydroquinolin-1-yl)pentane-1,5-dione | A | 7.92 | 375 |

-continued

| Ex. | structure | name | method | tr (min) | m/z |
|---|---|---|---|---|---|
| Ia.47 | 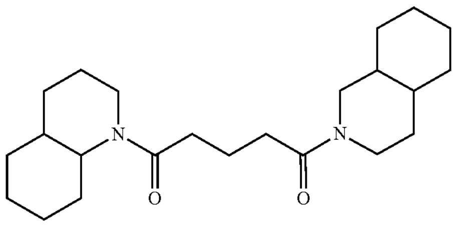 [SMILES: O=C(CCCC(=O)N1CCCC2CCCCC21)N1CCC2CCCCC2C1] | 1-(octahydroisoquinolin-2-yl)-5-(octahydroquinolin-1-yl)pentane-1,5-dione | A | 7.91<br>8.08 | 375<br>375 |
| Ia.48 | 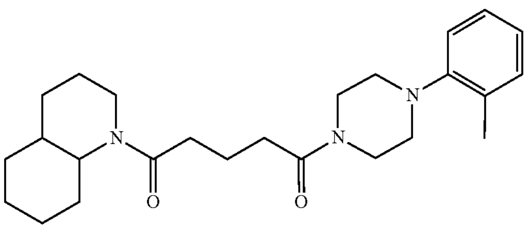 [SMILES: Cc1ccccc1N1CCN(C(=O)CCCC(=O)N2CCCC3CCCCC32)CC1] | 1-(octahydroquinolin-1-yl)-5-(4-o-tolylpiperazin-1-yl)pentane-1,5-dione | A | 7.89 | 412 |
| Ia.49 | 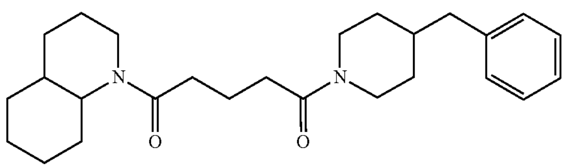 [SMILES: O=C(CCCC(=O)N1CCCC2CCCCC21)N1CCC(Cc2ccccc2)CC1] | 1-(4-benzylpiperidin-1-yl)-5-(octahydroquinolin-1-yl)pentane-1,5-dione | A | 8.05 | 411 |
| Ia.50 | 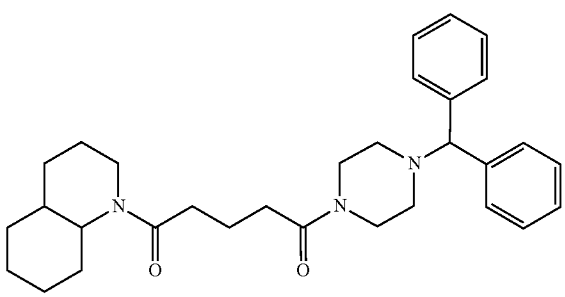 [SMILES: O=C(CCCC(=O)N1CCCC2CCCCC21)N1CCN(C(c2ccccc2)c2ccccc2)CC1] | 1-(4-benzhydrylpiperazin-1-yl)-5-(octahydroquinolin-1-yl)pentane-1,5-dione | A | 6.54 | 488 |
| Ia.51 | 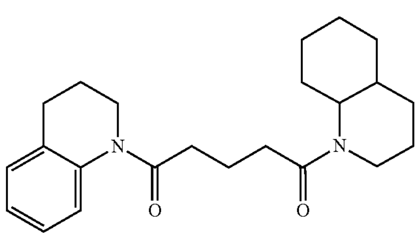 [SMILES: O=C(CCCC(=O)N1CCCC2CCCCC21)N1CCCc2ccccc21] | 1-(3,4-dihydro-2-H-quinolin-1-yl)-5-(octahydroquinolin-1-yl)pentane-1,5-dione | A | 7.49 | 369 |
| Ia.52 | 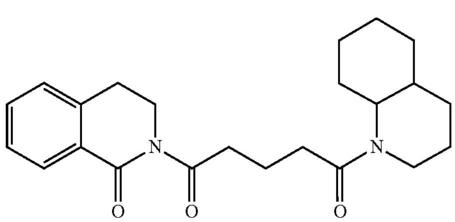 [SMILES: O=C(CCCC(=O)N1CCCC2CCCCC21)N1CCc2ccccc2C1=O] | 1-(octahydroquinolin-1-yl)-5-(1-oxo-3,4-dihydro-1-H-isoquinolin-2-yl)pentane-1,5-dione | A | 7.75 | 383 |

| Ex. | structure | name | method | tr (min) | m/z |
|---|---|---|---|---|---|
| Ia.53 | 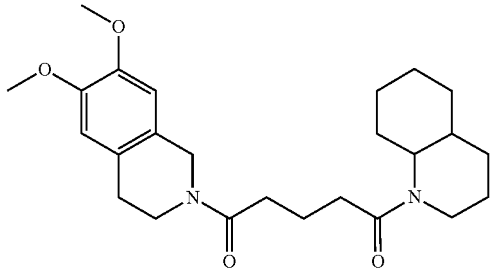 [SMILES: COc1cc2c(cc1OC)CN(C(=O)CCCC(=O)N1CCCC3CCCCC31)CC2] | 1-(6,7-dimethoxy-3,4-dihydro-1-H-isoquinolin-2-yl)-5-(octahydroquinolin-1-yl)pentane-1,5-dione | A | 6.58 | 429 |
| Ia.54 | 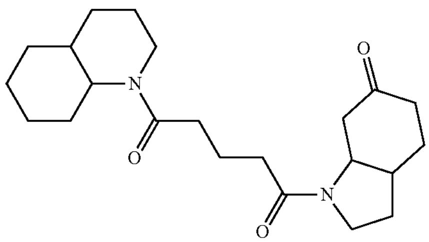 [SMILES: O=C1CCC2CCN(C(=O)CCCC(=O)N3CCCC4CCCCC43)C2C1] | 1-(octahydroquinolin-1-yl)-5-(6-oxooctahydroindol-1-yl)pentane-1,5-dione | A | 4.30 | 375 |
| Ia.55 | 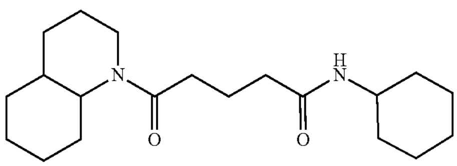 [SMILES: O=C(CCCC(=O)N1CCCC2CCCCC21)NC1CCCCC1] | 5-(octahydroquinolin-1-yl)-5-oxopentanoic acid cyclohexylamide | B | 3.68 | 335 |
| Ia.56 | 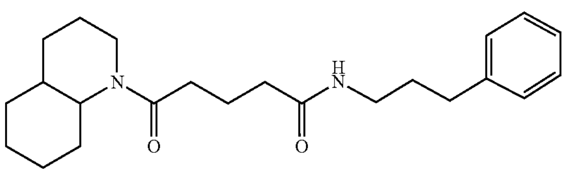 [SMILES: O=C(CCCC(=O)N1CCCC2CCCCC21)NCCCc1ccccc1] | 5-(octahydroquinolin-1-yl)-5-oxopentanoic acid (3-phenylpropyl)amide | B | 3.84 | 371 |
| Ia.57 | 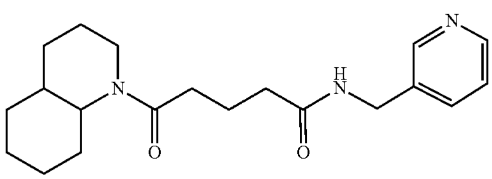 [SMILES: O=C(CCCC(=O)N1CCCC2CCCCC21)NCc1cccnc1] | 5-(octahydroquinolin-1-yl)-5-oxopentanoic acid (pyridin-3-ylmethyl)amide | B | 2.29 | 344 |
| Ia.58 | 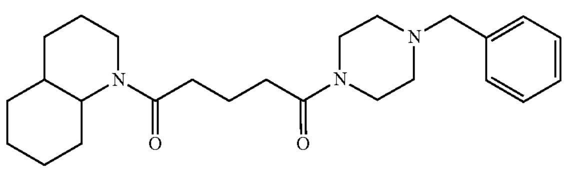 [SMILES: O=C(CCCC(=O)N1CCCC2CCCCC21)N1CCN(Cc2ccccc2)CC1] | 1-(4-benzylpiperazin-1-yl)-5-(octahydroquinolin-1-yl)pentane-1,5-dione | B | 2.63 | 412 |
| Ia.59 | 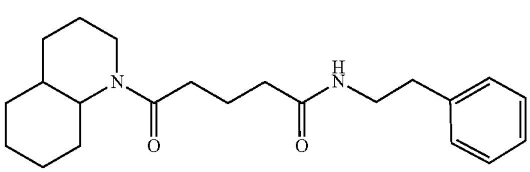 [SMILES: O=C(CCCC(=O)N1CCCC2CCCCC21)NCCc1ccccc1] | 5-(octahydroquinolin-1-yl)-5-oxopentanoic acid phenethylamide | B | 3.66 | 357 |
| Ia.60 | 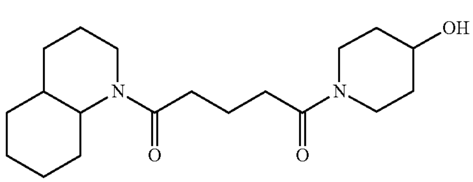 [SMILES: O=C(CCCC(=O)N1CCCC2CCCCC21)N1CCC(O)CC1] | 1-(4-hydroxypiperidin-1-yl)-5-(octahydroquinolin-1-yl)pentane-1,5-dione | B | 2.75 | 337 |

| Ex. | structure | name | method | tr (min) | m/z |
|---|---|---|---|---|---|
| Ia.61 | 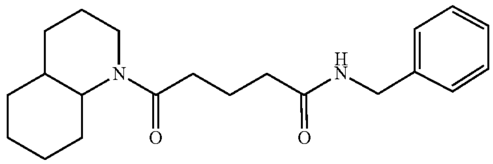 [SMILES: O=C(CCCC(=O)N1CCCC2CCCCC21)NCc1ccccc1] | 5-(octahydroquinolin-1-yl)-5-oxopentanoic acid benzylamide | B | 3.54 | 343 |
| Ia.62 | 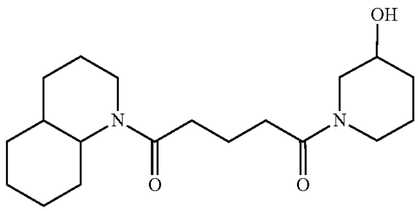 [SMILES: O=C(CCCC(=O)N1CCCC2CCCCC21)N1CCCC(O)C1] | 1-(3-hydroxypiperidin-1-yl)-5-(octahydroquinolin-1-yl)pentane-1,5-dione | B | 2.87 | 337 |
| Ia.63 | 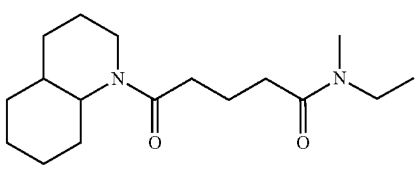 [SMILES: CCN(C)C(=O)CCCC(=O)N1CCCC2CCCCC21] | 5-(octahydroquinolin-1-yl)-5-oxopentanoic acid ethylmethylamide | B | 3.24 | 295 |
| Ia.64 | 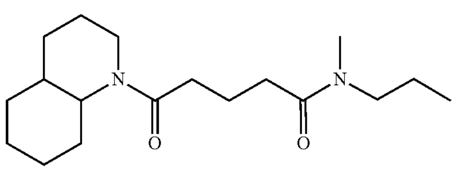 [SMILES: CCCN(C)C(=O)CCCC(=O)N1CCCC2CCCCC21] | 5-(octahydroquinolin-1-yl)-5-oxopentanoic acid methylpropylamide | B | 3.51 | 309 |
| Ia.65 | 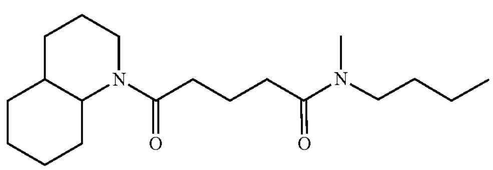 [SMILES: CCCCN(C)C(=O)CCCC(=O)N1CCCC2CCCCC21] | 5-(octahydroquinolin-1-yl)-5-oxopentanoic acid butylmethylamide | B | 3.79 | 323 |
| Ia.66 | 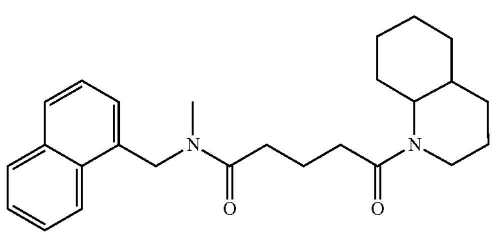 [SMILES: CN(Cc1cccc2ccccc12)C(=O)CCCC(=O)N1CCCC2CCCCC21] | 5-(octahydroquinolin-1-yl)-5-oxopentanoic acid methylnaphthalen-1-ylmethylamide | B | 4.24 | 407 |
| Ia.67 | 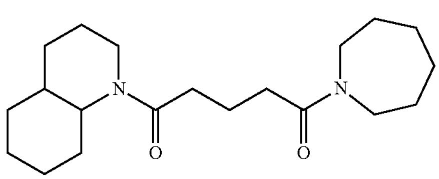 [SMILES: O=C(CCCC(=O)N1CCCC2CCCCC21)N1CCCCCC1] | 5-(octahydroquinolin-1-yl)-1-perhydroazepin-1-ylpentane-1,5-dione | B | 3.72 | 335 |
| Ia.68 | 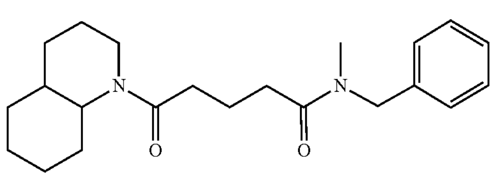 [SMILES: CN(Cc1ccccc1)C(=O)CCCC(=O)N1CCCC2CCCCC21] | 5-(octahydroquinolin-1-yl)-5-oxopentanoic acid benzylmethylamide | B | 3.84 | 357 |

-continued

| Ex. | structure | name | method | tr (min) | m/z |
|---|---|---|---|---|---|
| Ia.69 | 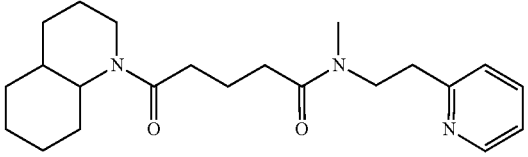 [SMILES: CN(CCc1ccccn1)C(=O)CCCC(=O)N1CCCC2CCCCC21] | 5-(octahydroquinolin-1-yl)-5-oxopentanoic acid methyl-(2-pyridin-2-ylethyl)amide | B | 2.47 | 372 |
| Ia.70 | 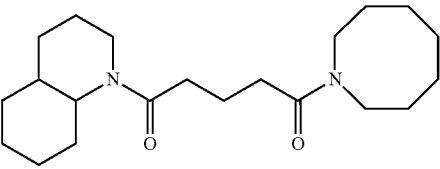 [SMILES: O=C(CCCC(=O)N1CCCC2CCCCC21)N1CCCCCCC1] | 5-(octahydroquinolin-1-yl)-1-perhydroazocin-1-ylpentane-1,5-dione | B | 3.84 | 349 |
| Ia.71 | 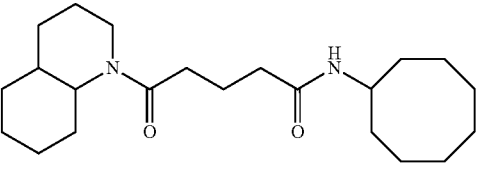 [SMILES: O=C(CCCC(=O)N1CCCC2CCCCC21)NC1CCCCCCC1] | 5-(octahydroquinolin-1-yl)-5-oxopentanoic acid cyclooctylamide | B | 4.10 | 363 |
| Ia.72 | 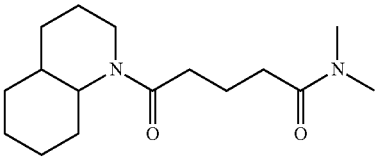 [SMILES: CN(C)C(=O)CCCC(=O)N1CCCC2CCCCC21] | 5-(octahydroquinolin-1-yl)-5-oxopentanoic acid dimethylamide | B | 3.01 | 281 |
| Ia.73 | 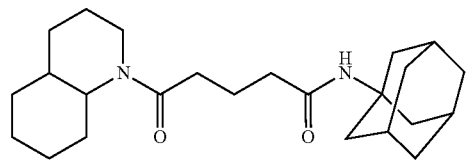 [SMILES: O=C(CCCC(=O)N1CCCC2CCCCC21)NC12CC3CC(CC(C3)C1)C2] | 5-(octahydroquinolin-1-yl)-5-oxopentanoic acid tricyclo[3.3.1.1$^{3,7}$]decan-1-ylamide | B | 4.35 | 387 |
| Ia.74 | 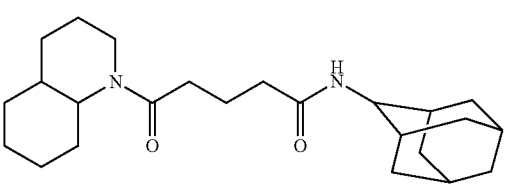 [SMILES: O=C(CCCC(=O)N1CCCC2CCCCC21)NC1C2CC3CC(C2)CC1C3] | 5-(octahydroquinolin-1-yl)-5-oxopentanoic acid tricyclo[3.3.1.1$^{3,7}$]decan-2-ylamide | B | 4.28 | 387 |
| Ia.75 | 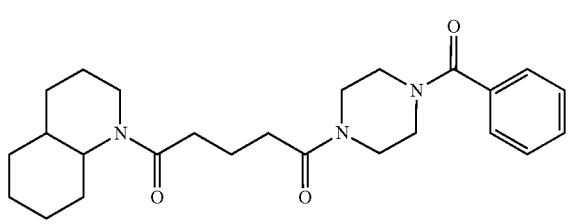 [SMILES: O=C(CCCC(=O)N1CCCC2CCCCC21)N1CCN(C(=O)c2ccccc2)CC1] | 1-(4-benzoylpiperazin-1-yl)-5-(octahydroquinolin-1-yl)pentane-1,5-dione | B | 3.34 | 426 |
| Ia.76 | 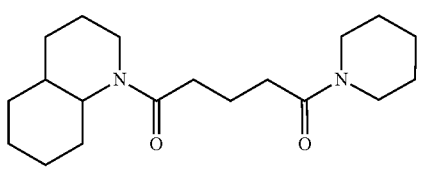 [SMILES: O=C(CCCC(=O)N1CCCC2CCCCC21)N1CCCCC1] | 1-(octahydroquinolin-1-yl)-5-piperidin-1-ylpentane-1,5-dione | A | 6.52 | 321 |

| Ex. | structure | name | method | tr (min) | m/z |
|---|---|---|---|---|---|
| Ia.77 | 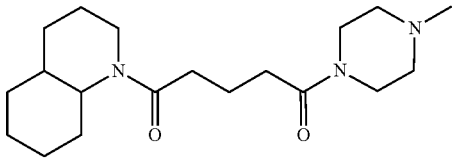 [SMILES: CN1CCN(C(=O)CCCC(=O)N2CCCC3CCCCC32)CC1] | 1-(4-methylpiperazin-1-yl)-5-(octahydroquinolin-1-yl)pentane-1,5-dione | A | 4.20 | 336 |
| Ia.78 | 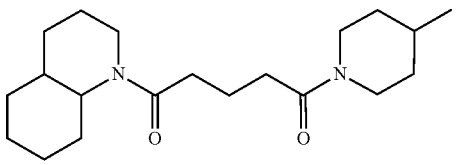 [SMILES: CC1CCN(C(=O)CCCC(=O)N2CCCC3CCCCC32)CC1] | 1-(4-methylpiperidin-1-yl)-5-(octahydroquinolin-1-yl)pentane-1,5-dione | A | 7.02 | 335 |
| Ia.79 | 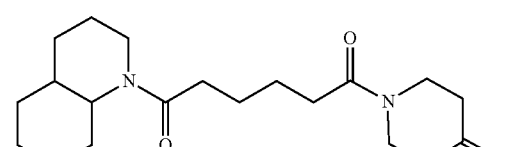 | 1-(octahydroquinolin-1-yl)-6-(4-oxopiperidin-1-yl)hexane-1,6-dione | B | 3.04 | 349 |
| Ia.80 | 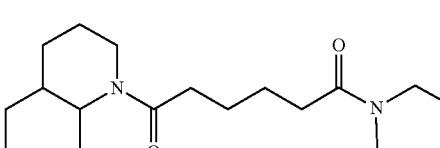 | 1-(octahydroquinolin-1-yl)-6-piperidin-1-ylhexane-1,6-dione | B | 3.65 | 335 |
| Ia.81 | 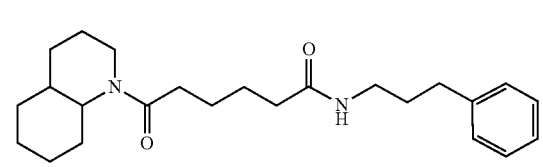 [SMILES: O=C(CCCCC(=O)N1CCCC2CCCCC21)NCCCc1ccccc1] | 6-(octahydroquinolin-1-yl)-6-oxohexanoic acid (3-phenylpropyl)amide | B | 3.94 | 385 |
| Ia.82 | 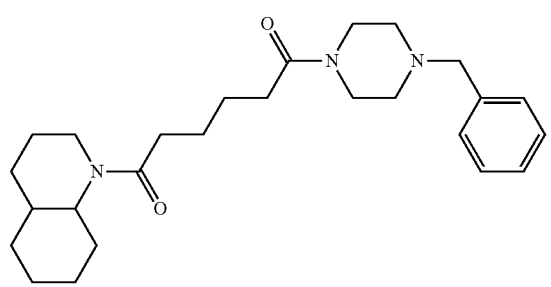 [SMILES: O=C(CCCCC(=O)N1CCCC2CCCCC21)N1CCN(Cc2ccccc2)CC1] | 1-(4-benzylpiperazin-1-yl)-6-(octahydroquinolin-1-yl)hexane-1,6-dione | B | 2.74 | 426 |
| Ia.83 | 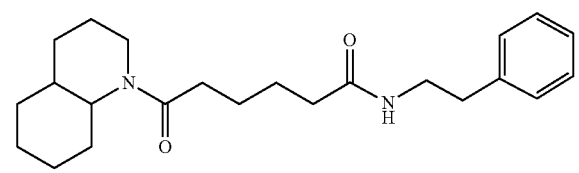 [SMILES: O=C(CCCCC(=O)N1CCCC2CCCCC21)NCCc1ccccc1] | 6-(octahydroquinolin-1-yl)-6-oxohexanoic acid phenethylamide | B | 3.76 | 371 |
| Ia.84 | 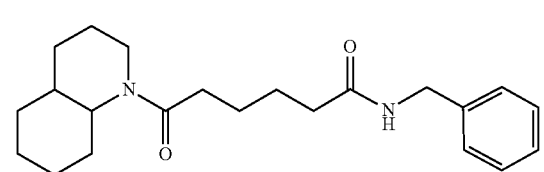 | 6-(octahydroquinolin-1-yl)-6-oxohexanoic acid benzylamide | B | 3.64 | 357 |

-continued

| Ex. | structure | name | method | tr (min) | m/z |
|---|---|---|---|---|---|
| Ia.85 | 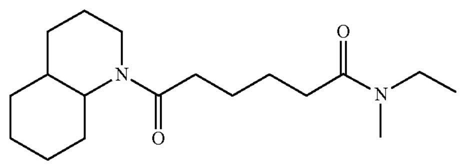 [SMILES: CCN(C)C(=O)CCCCC(=O)N1CCCC2CCCCC21] | 6-(octahydroquinolin-1-yl)-6-oxohexanoic acid ethylmethylamide | B | 3.36 | 309 |
| Ia.86 | 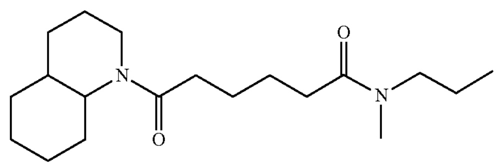 [SMILES: CCCN(C)C(=O)CCCCC(=O)N1CCCC2CCCCC21] | 6-(octahydroquinolin-1-yl)-6-oxohexanoic acid methylpropylamide | B | 3.62 | 323 |
| Ia.87 | 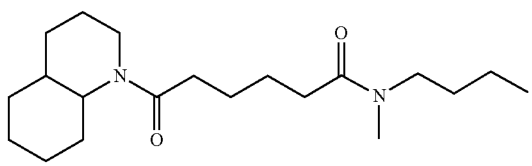 [SMILES: CCCCN(C)C(=O)CCCCC(=O)N1CCCC2CCCCC21] | 6-(octahydroquinolin-1-yl)-6-oxohexanoic acid butylmethylamide | B | 3.89 | 337 |
| Ia.88 | 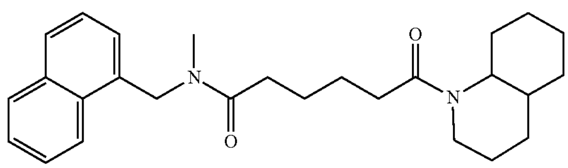 [SMILES: CN(Cc1cccc2ccccc12)C(=O)CCCCC(=O)N1CCCC2CCCCC21] | 6-(octahydroquinolin-1-yl)-6-oxohexanoic acid methylnaphthalen-1-ylmethylamide | B | 4.24<br>4.31 | 421<br>421 |
| Ia.89 | 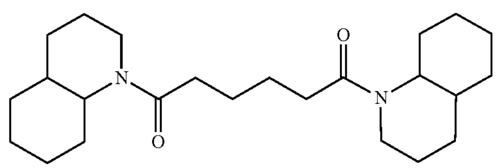 [SMILES: O=C(CCCCC(=O)N1CCCC2CCCCC21)N1CCCC2CCCCC21] | 1,6-bis-(octahydroquinolin-1-yl)hexane-1,6-dione | B | 4.39 | 389 |
| Ia.90 | 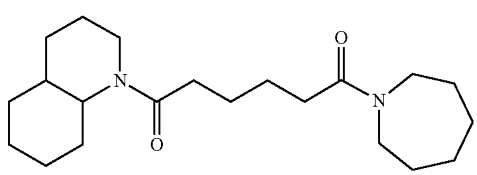 [SMILES: O=C(CCCCC(=O)N1CCCC2CCCCC21)N1CCCCCC1] | 6-(octahydroquinolin-1-yl)-1-perhydroazepin-1-ylhexane-1,6-dione | B | 3.83 | 349 |
| Ia.91 | 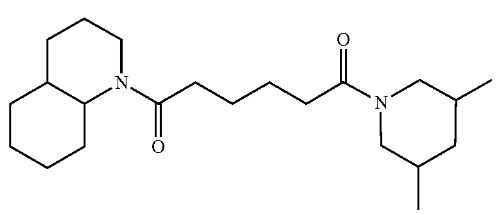 [SMILES: CC1CC(C)CN(C(=O)CCCCC(=O)N2CCCC3CCCCC32)C1] | 1-(3,5-dimethylpiperidin-1-yl)-6-(octahydroquinolin-1-yl)hexane-1,6-dione | B | 4.11<br>4.20 | 363<br>363 |
| Ia.92 | 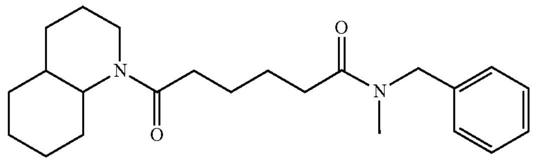 [SMILES: CN(Cc1ccccc1)C(=O)CCCCC(=O)N1CCCC2CCCCC21] | 6-(octahydroquinolin-1-yl)-6-oxohexanoic acid benzylmethylamide | B | 3.93 | 371 |

-continued

| Ex. | structure | name | method | tr (min) | m/z |
|---|---|---|---|---|---|
| Ia.93 | 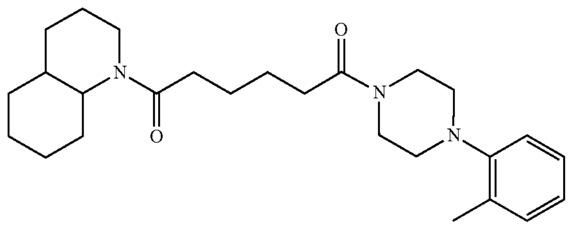 [SMILES: Cc1ccccc1N1CCN(C(=O)CCCCC(=O)N2CCCC3CCCCC32)CC1] | 1-(octahydroquinolin-1-yl)-6-(4-o-tolylpiperazin-1-yl)hexane-1,6-dione | B | 4.37 | 426 |
| Ia.94 | 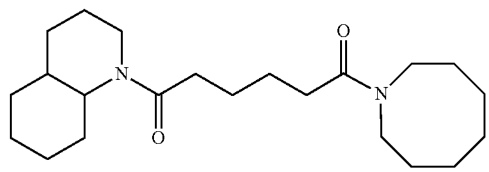 [SMILES: O=C(CCCCC(=O)N1CCCC2CCCCC21)N1CCCCCCC1] | 6-(octahydroquinolin-1-yl)-1-perhydroazocin-1-ylhexane-1,6-dione | B | 4.04 | 363 |
| Ia.95 | 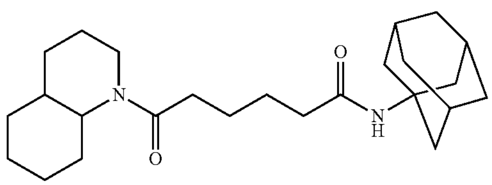 [SMILES: O=C(CCCCC(=O)N1CCCC2CCCCC21)NC12CC3CC(CC(C3)C1)C2] | 6-(octahydroquinolin-1-yl)-6-oxohexanoic acid tricyclo[3.3.1.1$^{3,7}$]decan-1-ylamide | B | 4.42 | 401 |
| Ia.96 | 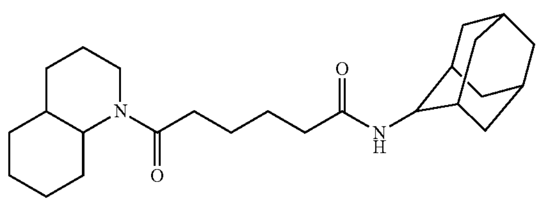 [SMILES: O=C(CCCCC(=O)N1CCCC2CCCCC21)NC1C2CC3CC(C2)CC1C3] | 6-(octahydroquinolin-1-yl)-6-oxohexanoic acid tricyclo[3.3.1.1$^{3,7}$]decan-2-ylamide | B | 4.34 | 401 |
| Ia.97 | 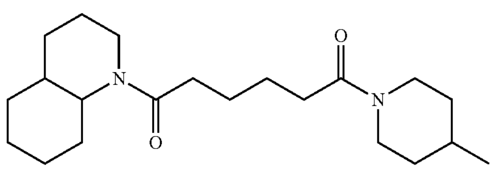 [SMILES: CC1CCN(C(=O)CCCCC(=O)N2CCCC3CCCCC32)CC1] | 1-(4-methylpiperidin-1-yl)-6-(octahydroquinolin-1-yl)hexane-1,6-dione | B | 3.92 | 349 |
| Ia.98 | 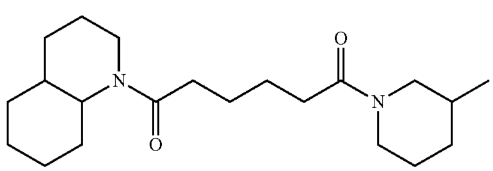 [SMILES: CC1CCCN(C(=O)CCCCC(=O)N2CCCC3CCCCC32)C1] | 1-(3-methylpiperidin-1-yl)-6-(octahydroquinolin-1-yl)hexane-1,6-dione | B | 3.92 | 349 |
| Ia.99 | 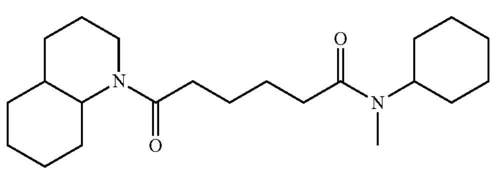 [SMILES: CN(C(=O)CCCCC(=O)N1CCCC2CCCCC21)C1CCCCC1] | 6-(octahydroquinolin-1-yl)-6-oxohexanoic acid cyclohexylmethylamide | B | 4.13 | 363 |
| Ia.100 | 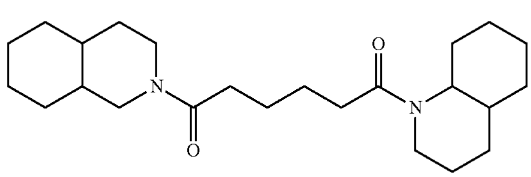 [SMILES: O=C(CCCCC(=O)N1CCCC2CCCCC21)N1CCC2CCCCC2C1] | 1-(octahydroisoquinolin-2-yl)-6-(octahydroquinolin-1-yl)hexane-1,6-dione | B | 4.38<br>4.47 | 389<br>389 |

-continued

| Ex. | structure | name | method | tr (min) | m/z |
|---|---|---|---|---|---|
| Ib.1 | 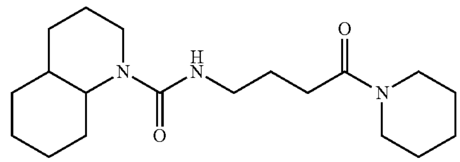 [SMILES: O=C(CCCNC(=O)N1CCCC2CCCCC21)N1CCCCC1] | Octahydroquinoline-1-carboxylic acid (4-oxo-4-piperidin-1-ylbutyl)amide | B | 3.42 | 336 |
| Ib.2 | 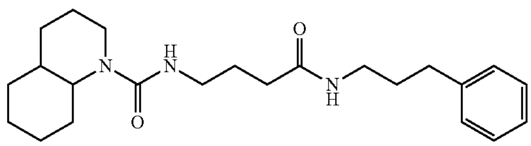 [SMILES: O=C(CCCNC(=O)N1CCCC2CCCCC21)NCCCc1ccccc1] | Octahydroquinoline-1-carboxylic acid [3-(3-phenylpropylcarbamoyl)propyl]amide | B | 3.81 | 386 |
| Ib.3 | 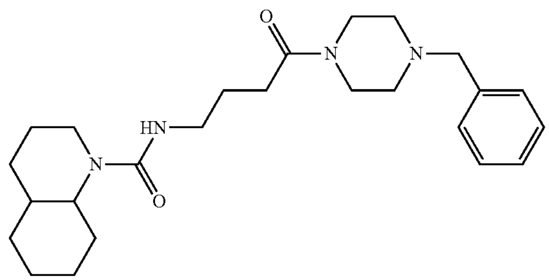 | Octahydroquinoline-1-carboxylic acid [4-(4-benzylpiperazin-1-yl)-4-oxobutyl]amide | B | 2.61 | 427 |
| Ib.4 | 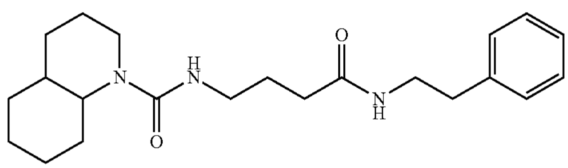 [SMILES: O=C(CCCNC(=O)N1CCCC2CCCCC21)NCCc1ccccc1] | Octahydroquinoline-1-carboxylic acid (3-phenethylcarbamoylpropyl)amide | B | 3.61 | 372 |
| Ib.5 | 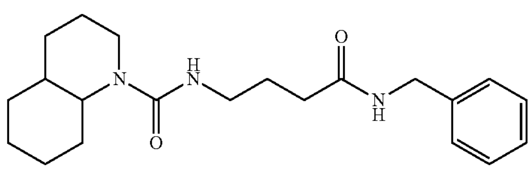 [SMILES: O=C(CCCNC(=O)N1CCCC2CCCCC21)NCc1ccccc1] | Octahydroquinoline-1-carboxylic acid (3-benzylcarbamoylpropyl)amide | B | 3.50 | 358 |
| Ib.6 | 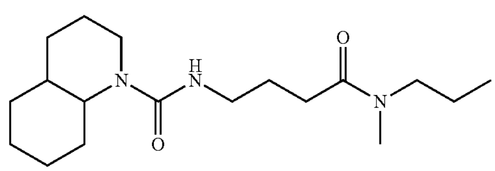 [SMILES: CCCN(C)C(=O)CCCNC(=O)N1CCCC2CCCCC21] | Octahydroquinoline-1-carboxylic acid [3-(methylpropylcarbamoyl)propyl]amide | B | 3.39 | 324 |
| Ib.7 | 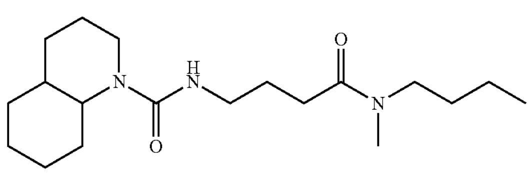 [SMILES: CCCCN(C)C(=O)CCCNC(=O)N1CCCC2CCCCC21] | Octahydroquinoline-1-carboxylic acid [3-(butylmethylcarbamoyl)propyl]amide | B | 3.65 | 338 |
| Ib.8 | 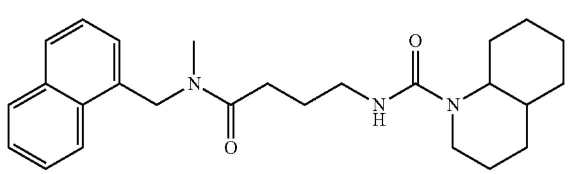 [SMILES: CN(Cc1cccc2ccccc12)C(=O)CCCNC(=O)N1CCCC2CCCCC21] | Octahydroquinoline-1-carboxylic acid [3-(methylnaphthalen-1-ylmethylcarbamoyl)propyl]amide | B | 4.08 | 422 |

| Ex. | structure | name | method | tr (min) | m/z |
|---|---|---|---|---|---|
| Ib.9 | 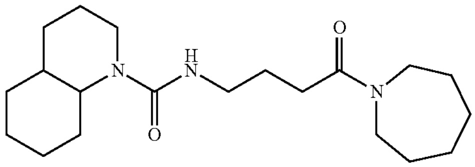 [SMILES: O=C(CCCNC(=O)N1CCCC2CCCCC21)N1CCCCCC1] | Octahydroquinoline-1-carboxylic acid (4-oxo-4-perhydroazepin-1-ylbutyl)amide | B | 3.59 | 350 |
| Ib.10 | 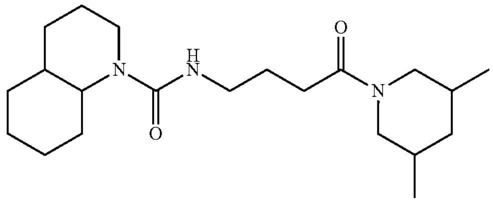 [SMILES: CC1CC(C)CN(C(=O)CCCNC(=O)N2CCCC3CCCCC32)C1] | Octahydroquinoline-1-carboxylic acid [4-(3,5-dimethylpiperidin-1-yl)-4-oxobutyl]amide | B | 3.87<br>3.96 | 364<br>364 |
| Ib.11 | 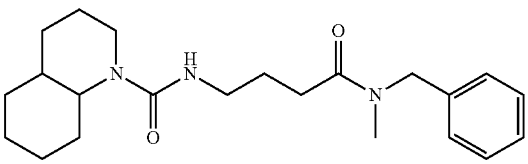 [SMILES: CN(Cc1ccccc1)C(=O)CCCNC(=O)N1CCCC2CCCCC21] | Octahydroquinoline-1-carboxylic acid [3-(benzylmethylcarbamoyl)propyl]amide | B | 3.71 | 372 |
| Ib.12 | 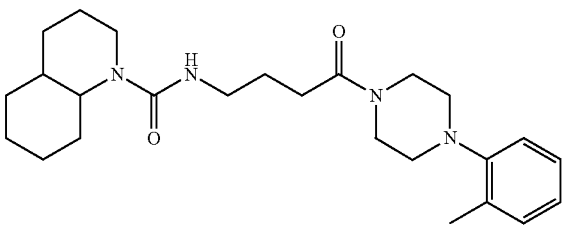 [SMILES: Cc1ccccc1N1CCN(C(=O)CCCNC(=O)N2CCCC3CCCCC32)CC1] | Octahydroquinoline-1-carboxylic acid [4-oxo-4-(4-o-tolylpiperazin-1-yl)butyl]amide | B | 4.14 | 427 |
| Ib.13 | 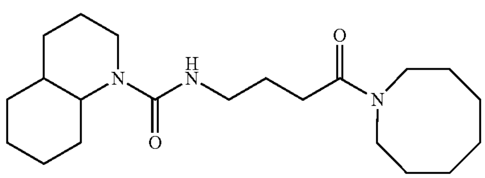 [SMILES: O=C(CCCNC(=O)N1CCCC2CCCCC21)N1CCCCCCC1] | Octahydroquinoline-1-carboxylic acid (4-oxo-4-perhydroazocin-1-ylbutyl)amide | B | 3.80 | 364 |
| Ib.14 | 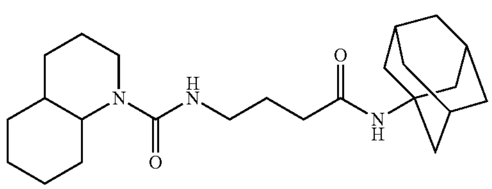 [SMILES: O=C(CCCNC(=O)N1CCCC2CCCCC21)NC12CC3CC(CC(C3)C1)C2] | Octahydroquinoline-1-carboxylic acid [3-(tricyclo[3.3.1.1$^{3,7}$]decan-1-ylcarbamoyl)propyl]amide | B | 4.31 | 402 |
| Ib.15 | 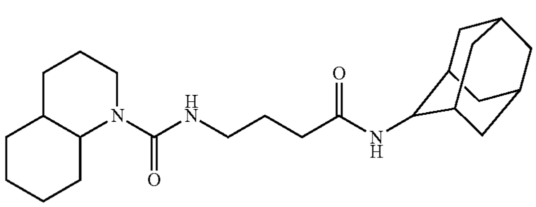 [SMILES: O=C(CCCNC(=O)N1CCCC2CCCCC21)NC1C2CC3CC(C2)CC1C3] | Octahydroquinoline-1-carboxylic acid [3-(tricyclo[3.3.1.1$^{3,7}$]decan-2-ylcarbamoyl)propyl]amide | B | 4.23 | 402 |
| Ib.16 | 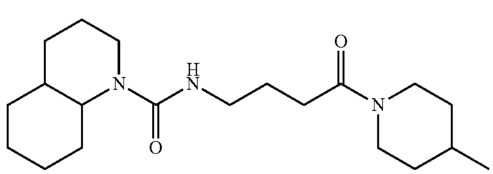 [SMILES: CC1CCN(C(=O)CCCNC(=O)N2CCCC3CCCCC32)CC1] | Octahydroquinoline-1-carboxylic acid [4-(4-methylpiperidin-1-yl)-4-oxobutyl]amide | B | 3.69 | 350 |

-continued

| Ex. | structure | name | method | tr (min) | m/z |
|---|---|---|---|---|---|
| Ib.17 | 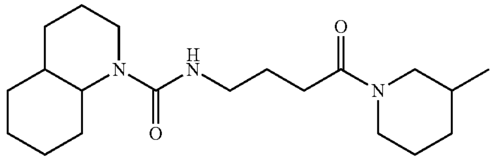 [SMILES: CC1CCCN(C(=O)CCCNC(=O)N2CCCC3CCCCC32)C1] | Octahydroquinoline-1-carboxylic acid [4-(3-methylpiperidin-1-yl)-4-oxobutyl]amide | B | 3.68 | 350 |
| Ib.18 | 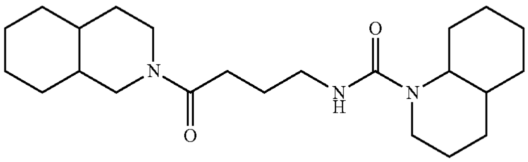 [SMILES: O=C(CCCNC(=O)N1CCCC2CCCCC21)N1CCC2CCCCC2C1] | Octahydroquinoline-1-carboxylic acid [4-(octahydroisoquinolin-2-yl)-4-oxobutyl]amide | B | 4.14<br>4.24 | 390<br>390 |
| Ib.19 | 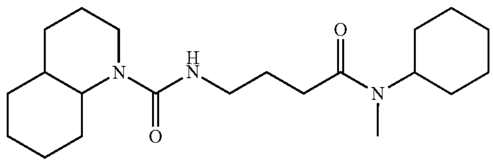 [SMILES: CN(C(=O)CCCNC(=O)N1CCCC2CCCCC21)C1CCCCC1] | Octahydroquinoline-1-carboxylic acid [3-(cyclohexylmethylcarbamoyl)propyl]amide | B | 3.89 | 364 |
| Ib.20 | 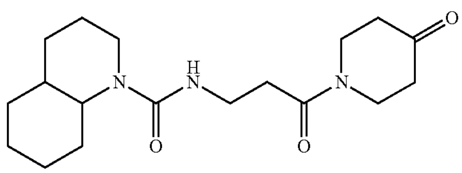 [SMILES: O=C1CCN(C(=O)CCNC(=O)N2CCCC3CCCCC32)CC1] | Octahydroquinoline-1-carboxylic acid [3-oxo-3-(4-oxopiperidin-1-yl)propyl]amide | B | 2.78 | 336 |
| Ib.21 | 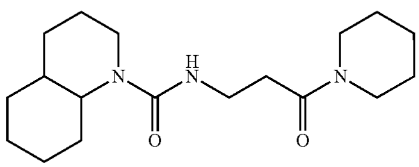 [SMILES: O=C(CCNC(=O)N1CCCC2CCCCC21)N1CCCCC1] | Octahydroquinoline-1-carboxylic acid (3-oxo-3-piperidin-1-yl propyl)amide | B | 3.35 | 322 |
| Ib.22 | 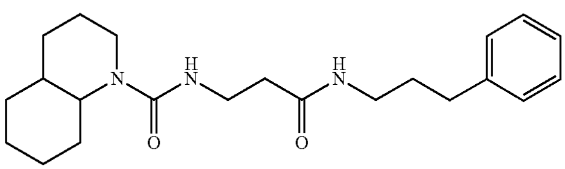 [SMILES: O=C(CCNC(=O)N1CCCC2CCCCC21)NCCCc1ccccc1] | Octahydroquinoline-1-carboxylic acid [2-(3-phenylpropylcarbamoyl)ethyl]amide | B | 3.72 | 372 |
| Ib.23 | 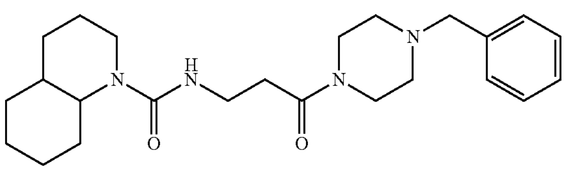 [SMILES: O=C(CCNC(=O)N1CCCC2CCCCC21)N1CCN(Cc2ccccc2)CC1] | Octahydroquinoline-1-carboxylic acid [3-(4-benzylpiperazin-1-yl)-3-oxopropyl]amide | B | 2.56 | 413 |
| Ib.24 | 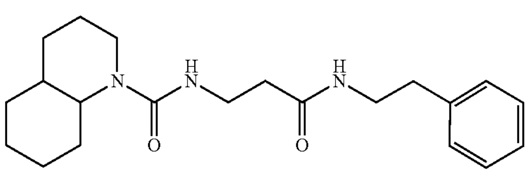 [SMILES: O=C(CCNC(=O)N1CCCC2CCCCC21)NCCc1ccccc1] | Octahydroquinoline-1-carboxylic acid (2-phenethylcarbamoylethyl)amide | B | 3.56 | 358 |
| Ib.25 | 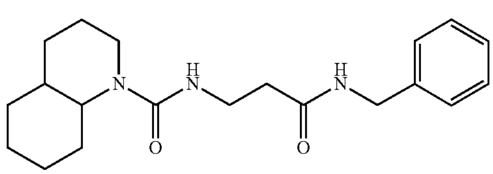 | Octahydroquinoline-1-carboxylic acid (2-benzylcarbamoylethyl)amide | B | 3.42 | 344 |

| Ex. | structure | name | method | tr (min) | m/z |
|---|---|---|---|---|---|
| Ib.26 | 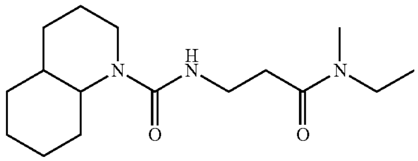 [SMILES: CCN(C)C(=O)CCNC(=O)N1CCCC2CCCCC21] | Octahydroquinoline-1-carboxylic acid [2-(ethylmethylcarbamoyl)ethyl]amide | B | 3.07 | 296 |
| Ib.27 | 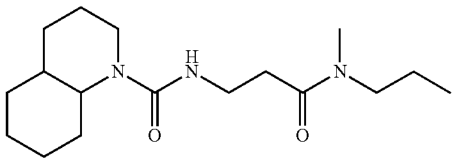 [SMILES: CCCN(C)C(=O)CCNC(=O)N1CCCC2CCCCC21] | Octahydroquinoline-1-carboxylic acid [2-(methylpropylcarbamoyl)ethyl]amide | B | 3.33 | 310 |
| Ib.28 | 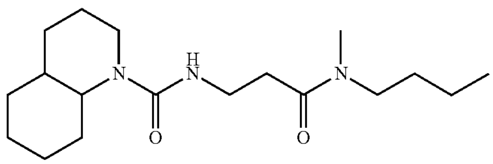 [SMILES: CCCCN(C)C(=O)CCNC(=O)N1CCCC2CCCCC21] | Octahydroquinoline-1-carboxylic acid [2-(butylmethylcarbamoyl)ethyl]amide | B | 3.60 | 324 |
| Ib.29 | 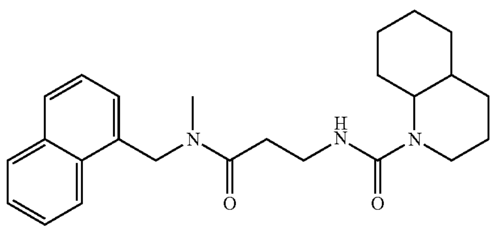 [SMILES: CN(Cc1cccc2ccccc12)C(=O)CCNC(=O)N1CCCC2CCCCC21] | Octahydroquinoline-1-carboxylic acid [2-(methylnaphthalen-1-ylmethylcarbamoyl)ethyl]amide | B | 4.08 | 408 |
| Ib.30 | 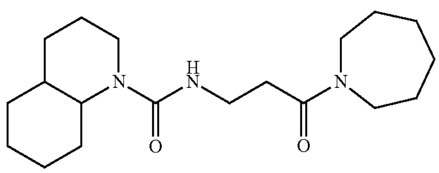 [SMILES: O=C(CCNC(=O)N1CCCC2CCCCC21)N1CCCCCC1] | Octahydroquinoline-1-carboxylic acid (3-oxo-3-perhydroazepin-1-ylpropyl)amide | B | 3.52 | 336 |
| Ib.31 | 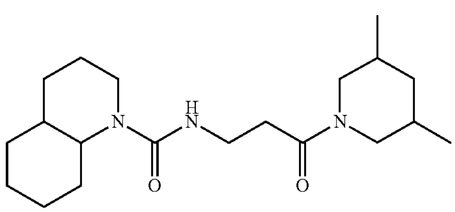 [SMILES: CC1CC(C)CN(C(=O)CCNC(=O)N2CCCC3CCCCC32)C1] | Octahydroquinoline-1-carboxylic acid [3-(3,5-dimethylpiperidin-1-yl)-3-oxopropyl]amide | B | 3.82<br>3.90 | 350<br>350 |
| Ib.32 | 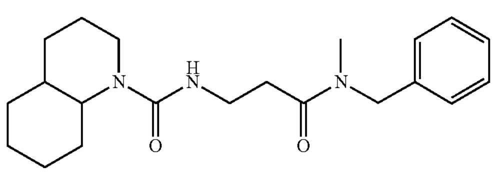 [SMILES: CN(Cc1ccccc1)C(=O)CCNC(=O)N1CCCC2CCCCC21] | Octahydroquinoline-1-carboxylic acid [2-(benzylmethylcarbamoyl)ethyl]amide | B | 3.67 | 358 |
| Ib.33 | 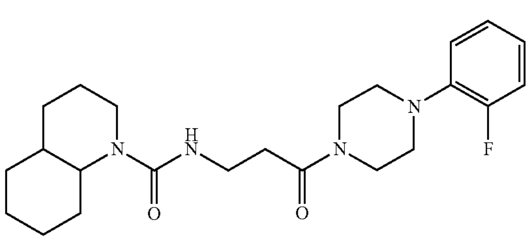 [SMILES: O=C(CCNC(=O)N1CCCC2CCCCC21)N1CCN(c2ccccc2F)CC1] | Octahydroquinoline-1-carboxylic acid {3-[4-(2-fluorophenyl)piperazin-1-yl]-3-oxopropyl}amide | B | 3.81 | 417 |

-continued

| Ex. | structure | name | method | tr (min) | m/z |
|---|---|---|---|---|---|
| Ib.34 | 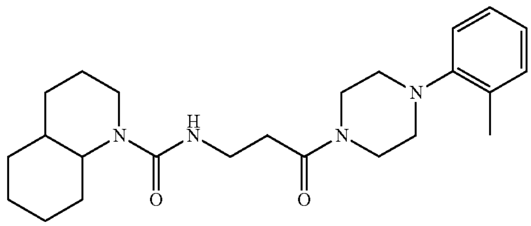 [SMILES: Cc1ccccc1N1CCN(C(=O)CCNC(=O)N2CCCC3CCCCC32)CC1] | Octahydroquinoline-1-carboxylic acid [3-oxo-3-(4-o-tolylpiperazin-1-yl)propyl]amide | B | 4.09 | 413 |
| Ib.35 | 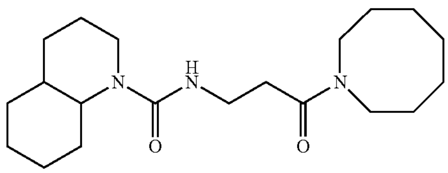 [SMILES: O=C(CCNC(=O)N1CCCC2CCCCC21)N1CCCCCCC1] | Octahydroquinoline-1-carboxylic acid (3-oxo-3-perhydroazocin-1-ylpropyl)amide | B | 3.74 | 350 |
| Ib.36 | 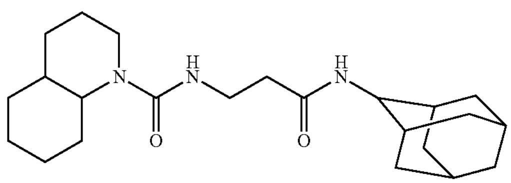 [SMILES: O=C(CCNC(=O)N1CCCC2CCCCC21)NC1C2CC3CC(C2)CC1C3] | Octahydroquinoline-1-carboxylic acid [2-(tricyclo[3.3.1.1$^{3,7}$]decan-2-ylcarbamoyl)ethyl]amide | B | 4.11 | 388 |
| Ib.37 | 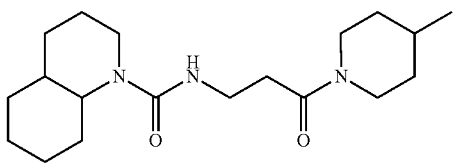 [SMILES: CC1CCN(C(=O)CCNC(=O)N2CCCC3CCCCC32)CC1] | Octahydroquinoline-1-carboxylic acid [3-(4-methylpiperidin-1-yl)-3-oxopropyl]amide | B | 3.62 | 336 |
| Ib.38 | 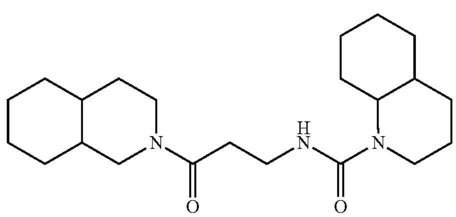 [SMILES: O=C(CCNC(=O)N1CCCC2CCCCC21)N1CCC2CCCCC2C1] | Octahydroquinoline-1-carboxylic acid [3-(octahydroisoquinolin-2-yl)-3-oxopropyl]amide | B | 4.08<br>4.17 | 376<br>376 |
| Ib.39 | 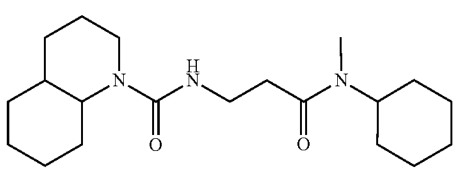 [SMILES: CN(C(=O)CCNC(=O)N1CCCC2CCCCC21)C1CCCCC1] | Octahydroquinoline-1-carboxylic acid [2-(cyclohexylmethylcarbamoyl)ethyl]amide | B | 3.83 | 350 |
| Ib.40 | 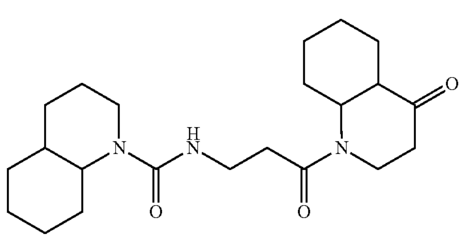 [SMILES: O=C1CCN(C(=O)CCNC(=O)N2CCCC3CCCCC32)C2CCCCC12] | Octahydroquinoline-1-carboxylic acid [3-oxo-3-(4-oxooctahydroquinolin-1-yl)propyl]amide | B | 3.44 | 390 |
| Ib.41 | 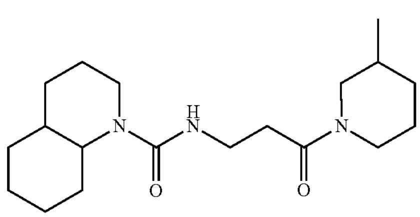 [SMILES: CC1CCCN(C(=O)CCNC(=O)N2CCCC3CCCCC32)C1] | Octahydroquinoline-1-carboxylic acid [3-(3-methylpiperidin-1-yl)-3-oxopropyl]amide | B | 3.61 | 336 |

-continued

| Ex. | structure | name | method | tr (min) | m/z |
|---|---|---|---|---|---|
| Ib.42 | 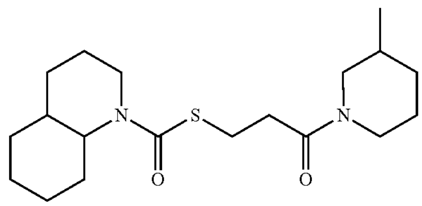 | Octahydroquinoline-1-carbothioic acid S-[3-(3-methylpiperidin-1-yl)-3-oxopropyl] ester | B | 4.55 | 353 |
| Ib.43 | 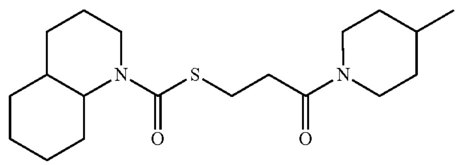 [SMILES: CC1CCN(C(=O)CCSC(=O)N2CCCC3CCCCC32)CC1] | Octahydroquinoline-1-carbothioic acid S-[3-(4-methylpiperidin-1-yl)-3-oxopropyl] ester | B | 3.57 | 353 |
| Ib.44 | 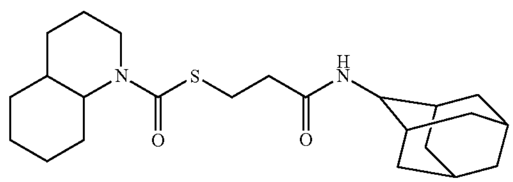 [SMILES: O=C(CCSC(=O)N1CCCC2CCCCC21)NC1C2CC3CC(C2)CC1C3] | Octahydroquinoline-1-carbothioic acid S-[2-(tricyclo[3.3.1.1$^{3,7}$]decan-2-ylcarbamoyl)ethyl] ester | B | 4.79 | 405 |
| Ib.45 | 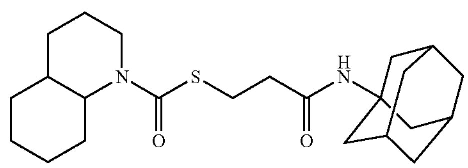 | Octahydroquinoline-1-carbothioic acid S-[2-(tricyclo[3.3.1.1$^{3,7}$]decan-1-ylcarbamoyl)ethyl] ester | B | 4.88 | 405 |
| Ib.46 | 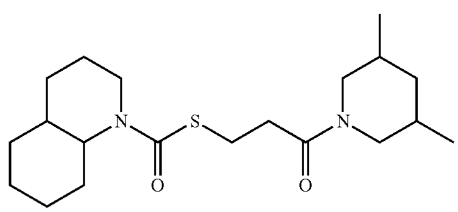 [SMILES: CC1CC(C)CN(C(=O)CCSC(=O)N2CCCC3CCCCC32)C1] | Octahydroquinoline-1-carbothioic acid S-[3-(3,5-dimethylpiperidin-1-yl)-3-oxopropyl] ester | B | 4.75 | 367 |
| Ib.47 | 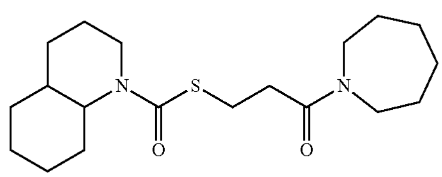 | Octahydroquinoline-1-carbothioic acid S-(3-oxo-3-perhydroazepin-1-ylpropyl) ester | B | 4.56 | 353 |
| Ib.48 | 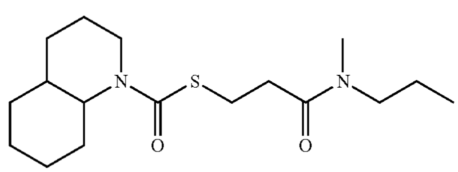 [SMILES: CCCN(C)C(=O)CCSC(=O)N1CCCC2CCCCC21] | Octahydroquinoline-1-carbothioic acid S-[2-(methylpropylcarbamoyl)ethyl] ester | B | 4.14 | 327 |
| Ib.49 | 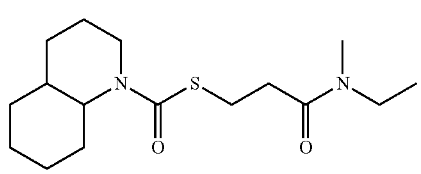 [SMILES: CCN(C)C(=O)CCSC(=O)N1CCCC2CCCCC21] | Octahydroquinoline-1-carbothioic acid S-[2-(ethylmethylcarbamoyl)ethyl] ester | B | 3.88 | 313 |

-continued

| Ex. | structure | name | method | tr (min) | m/z |
|---|---|---|---|---|---|
| Ib.50 | 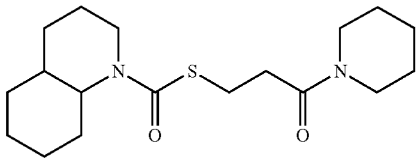 [SMILES: O=C(CCSC(=O)N1CCCC2CCCCC21)N1CCCCC1] | Octahydroquinoline-1-carbothioic acid S-(3-oxo-3-piperidin-1-ylpropyl) ester | B | 4.20 | 339 |
| Ib.51 | 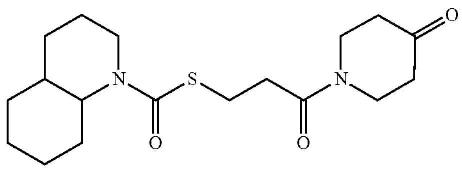 [SMILES: O=C1CCN(C(=O)CCSC(=O)N2CCCC3CCCCC32)CC1] | Octahydroquinoline-1-carbothioic acid S-[3-oxo-3-(4-oxopiperidin-1-yl)propyl] ester | B | 3.49 | 353 |
| Ib.52 | 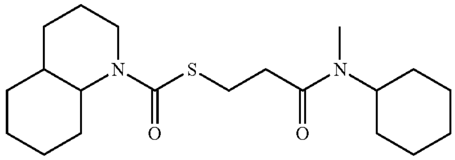 [SMILES: CN(C(=O)CCSC(=O)N1CCCC2CCCCC21)C1CCCCC1] | Octahydroquinoline-1-carbothioic acid S-[2-(cyclohexylmethyl-carbamoyl)ethyl] ester | B | 4.67 | 364 |
| Ib.53 | 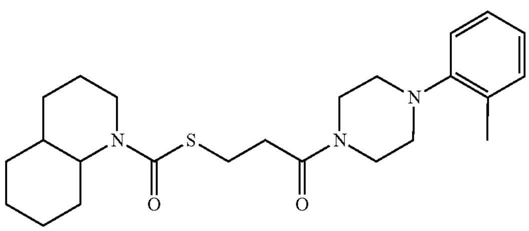 [SMILES: Cc1ccccc1N1CCN(C(=O)CCSC(=O)N2CCCC3CCCCC32)CC1] | Octahydroquinoline-1-carbothioic acid S-[3-oxo-3-(4-o-tolylpiperazin-1-yl)propyl] ester | B | 4.86 | 430 |
| Ib.54 | 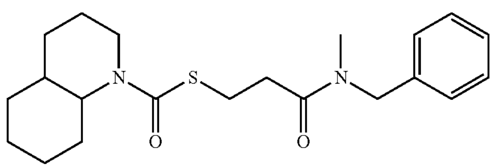 [SMILES: CN(Cc1ccccc1)C(=O)CCSC(=O)N1CCCC2CCCCC21] | Octahydroquinoline-1-carbothioic acid S-[2-(benzylmethylcarbamoyl)ethyl] ester | B | 4.42 | 375 |
| Ib.55 | 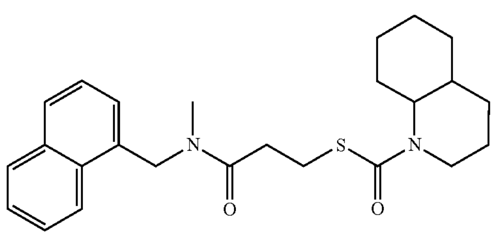 [SMILES: CN(Cc1cccc2ccccc12)C(=O)CCSC(=O)N1CCCC2CCCCC21] | Octahydroquinoline-1-carbothioic acid S-[2-(methylnaphthalen-1-ylmethylcarbamoyl)ethyl]ester | B | 4.78 | 425 |
| Ib.56 | 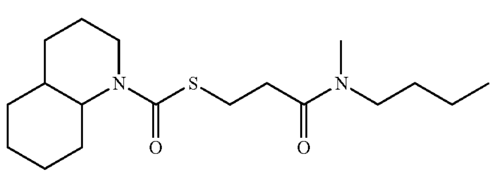 [SMILES: CCCCN(C)C(=O)CCSC(=O)N1CCCC2CCCCC21] | Octahydroquinoline-1-carbothioic acid S-[2-(butylmethylcarbamoyl)ethyl]ester | B | 4.41 | 341 |
| Ib.57 | 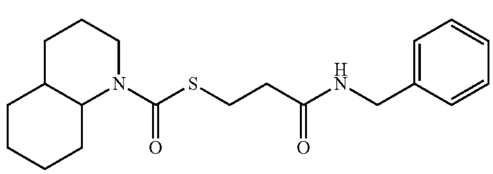 [SMILES: O=C(CCSC(=O)N1CCCC2CCCCC21)NCc1ccccc1] | Octahydroquinoline-1-carbothioic acid S-(2-benzylcarbamoylethyl) ester | B | 4.06 | 361 |

| Ex. | structure | name | method | tr (min) | m/z |
|---|---|---|---|---|---|
| Ib.58 | 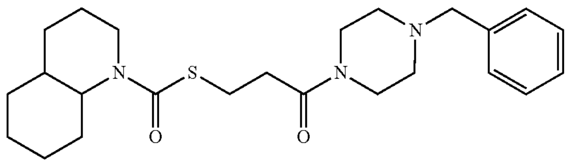 [SMILES: O=C(CCSC(=O)N1CCCC2CCCCC21)N1CCN(Cc2ccccc2)CC1] | Octahydroquinoline-1-carbothioic acid S-[3-(4-benzylpiperazin-1-yl)-3-ozopropyl] ester | B | 2.98 | 430 |
| Ib.59 | 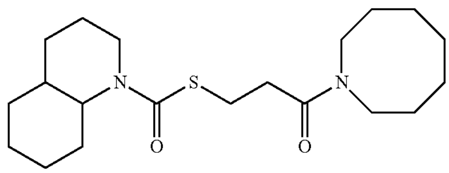 | Octahydroquinoline-1-carbothioic acid S-(3-oxo-3-perhydroazocin-1-ylpropyl) ester | B | 4.58 | 367 |
| Ib.60 | 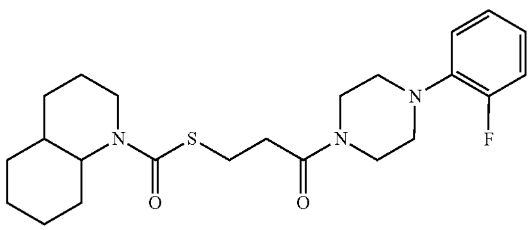 | Octahydroquinoline-1-carbothioic acid S-{3-[4-(2-fluorophenyl)piperazin-1-yl]-3-oxopropyl} ester | B | 4.59 | 434 |
| Ib.61 | 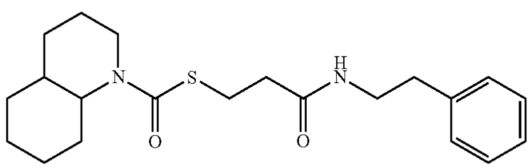 [SMILES: O=C(CCSC(=O)N1CCCC2CCCCC21)NCCc1ccccc1] | Octahydroquinoline-1-carbothioic acid S-(2-phenethylcarbamoylethyl) ester | B | 4.20 | 375 |
| Ib.62 | 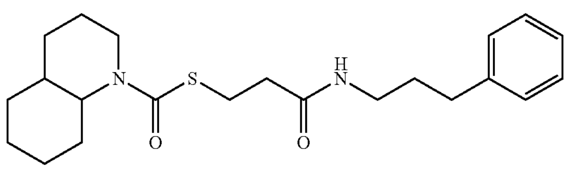 [SMILES: O=C(CCSC(=O)N1CCCC2CCCCC21)NCCCc1ccccc1] | Octahydroquinoline-1-carbothioic acid S-[2-(3-phenylpropylcarbamoyl)ethyl] ester | B | 4.34 | 389 |
| Im.1 | 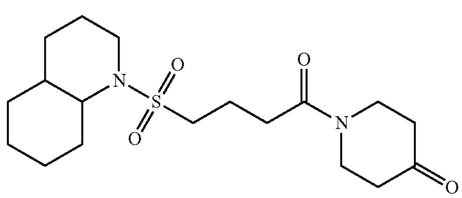 [SMILES: O=C1CCN(C(=O)CCCS(=O)(=O)N2CCCC3CCCCC32)CC1] | 1-[4-(octahydroquinoline-1-sulfonyl)butyryl]piperidin-4-one | B | 3.16 | 371 |
| Im.2 | 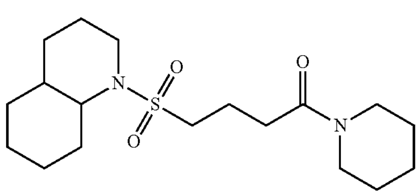 [SMILES: O=C(CCCS(=O)(=O)N1CCCC2CCCCC21)N1CCCCC1] | 4-(octahydroquinoline-1-sulfonyl)-1-piperidin-1-ylbutan-1-one | B | 3.79 | 357 |
| Im.3 | 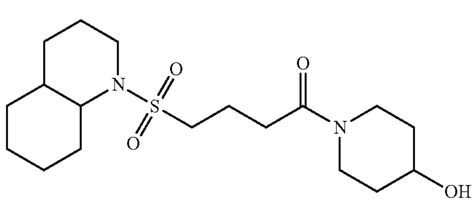 [SMILES: O=C(CCCS(=O)(=O)N1CCCC2CCCCC21)N1CCC(O)CC1] | 1-(4-hydroxypiperidin-1-yl)-4-(octahydroquinoline-1-sulfonyl)butan-1-one | B | 2.96 | 373 |

-continued

| Ex. | structure | name | method | tr (min) | m/z |
|---|---|---|---|---|---|
| Im.4 | 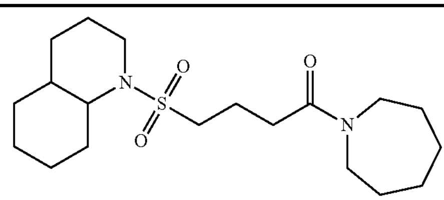 | 4-(octahydroquinoline-1-sulfonyl)-1-perhydroazepin-1-ylbutan-1-one | B | 3.96 | 371 |
| Im.5 | 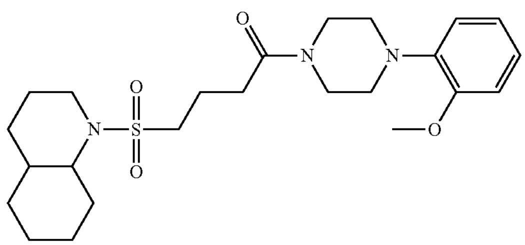 [SMILES: COc1ccccc1N1CCN(C(=O)CCCS(=O)(=O)N2CCCC3CCCCC32)CC1] | 1-[4-(2-methoxyphenyl)piperazin-1-yl]-4-(octahydroquinoline-1-sulfonyl)butan-1-one | B | 3.92 | 464 |
| Im.6 | 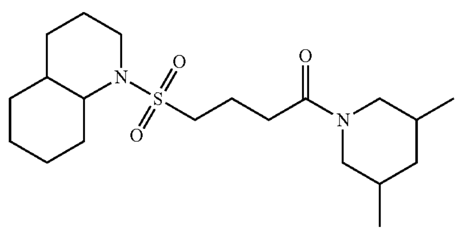 [SMILES: CC1CC(C)CN(C(=O)CCCS(=O)(=O)N2CCCC3CCCCC32)C1] | 1-(3.5-dimethylpiperidin-1-yl)-4-(octahydroquinoline-1-sulfonyl)butan-1-one | B | 4.34 | 385 |
| Im.7 | 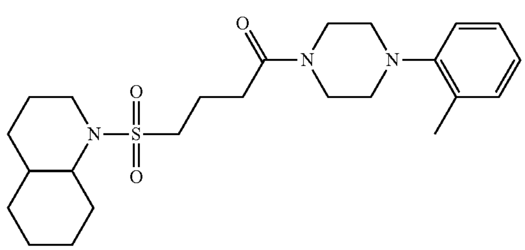 [SMILES: Cc1ccccc1N1CCN(C(=O)CCCS(=O)(=O)N2CCCC3CCCCC32)CC1] | 4-(octahydroquinoline-1-sulfonyl)-1-(4-o-tolylpiperazin-1-yl)butan-1-one | B | 4.49 | 448 |
| Im.8 | 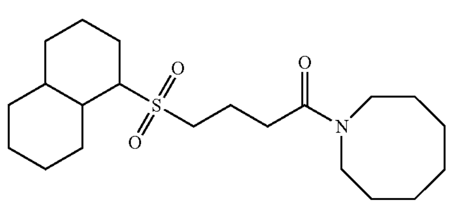 [SMILES: O=C(CCCS(=O)(=O)C1CCCC2CCCCC21)N1CCCCCCC1] | 4-(octahydroquinoline-1-sulfonyl)-1-perhydroazocin-1-ylbutan-1-one | B | 4.17 | 385 |
| Im.9 | 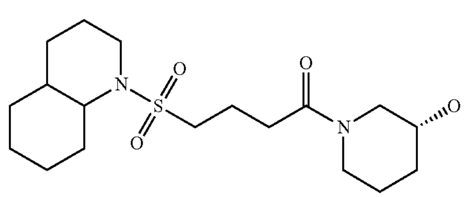 [SMILES: O=C(CCCS(=O)(=O)N1CCCC2CCCCC21)N1CCC[C@@H](O)C1] | 1-((R)-3-hydroxypiperidin-1-yl)-4-(octahydroquinoline-1-sulfonyl)butan-1-one | B | 3.07 | 373 |

| Ex. | structure | name | method | tr (min) | m/z |
|---|---|---|---|---|---|
| Im.10 | 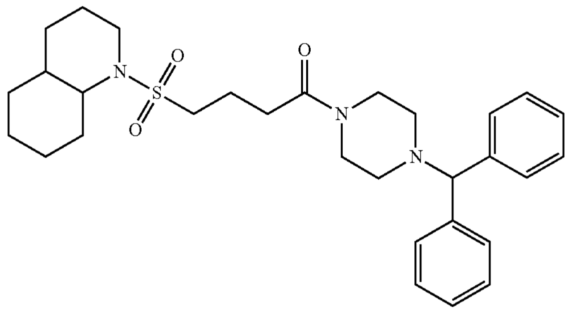 [SMILES: O=C(CCCS(=O)(=O)N1CCCC2CCCCC21)N1CCN(C(c2ccccc2)c2ccccc2)CC1] | 1-(4-benzhydrylpiperazin-1-yl)-4-(octahydroquinoline-1-sulfonyl)butan-1-one | B | 3.82 | 524 |
| Im.11 | 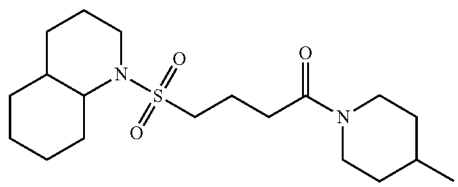 [SMILES: CC1CCN(C(=O)CCCS(=O)(=O)N2CCCC3CCCCC32)CC1] | 1-(4-methylpiperidin-1-yl)-4-(octahydroquinoline-1-sulfonyl)butan-1-one | B | 4.06 | 371 |
| Im.12 | 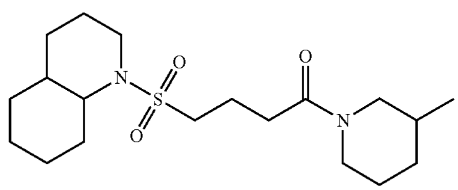 [SMILES: CC1CCCN(C(=O)CCCS(=O)(=O)N2CCCC3CCCCC32)C1] | 1-(3-methylpiperidin-1-yl)-4-(octahydroquinoline-1-sulfonyl)butan-1-one | B | 4.05 | 371 |
| Im.13 | 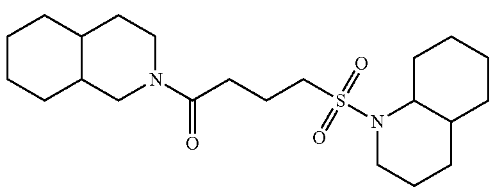 [SMILES: O=C(CCCS(=O)(=O)N1CCCC2CCCCC21)N1CCC2CCCCC2C1] | 1-(octahydroisoquinolin-2-yl)-4-(octahydroquinoline-1-sulfonyl)butan-1-one | B | 4.50<br>4.59 | 411<br>411 |
| Im.14 | 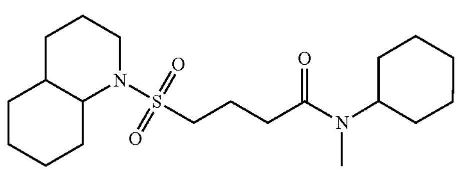 [SMILES: CN(C(=O)CCCS(=O)(=O)N1CCCC2CCCCC21)C1CCCCC1] | N-cyclohexyl-N-methyl-4-(octahydroquinoline-1-sulfonyl)butyramide | B | 4.26 | 385 |
| Im.15 | 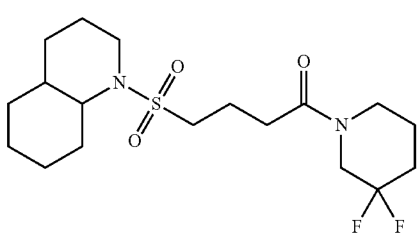 [SMILES: O=C(CCCS(=O)(=O)N1CCCC2CCCCC21)N1CCCC(F)(F)C1] | 1-(3,3-difluoropiperidin-1-yl)-4-(octahydroquinoline-1-sulfonyl)butan-1-one | B | 3.80 | 393 |
| Im.16 | 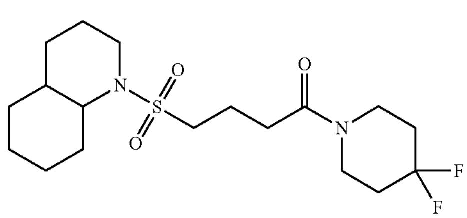 [SMILES: O=C(CCCS(=O)(=O)N1CCCC2CCCCC21)N1CCC(F)(F)CC1] | 1-(4,4-difluoropiperidin-1-yl)-4-(octahydroquinoline-1-sulfonyl)butan-1-one | B | 3.81 | 393 |

| Ex. | structure | name | method | tr (min) | m/z |
|---|---|---|---|---|---|
| Ia.101 | 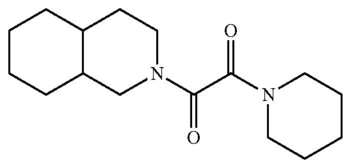 [SMILES: O=C(C(=O)N1CCC2CCCCC2C1)N1CCCCC1] | 1-(octahydroisoquinolin-2-yl)-2-piperidin-1-ylethane-1,2-dione | A | 6.28<br>6.45 | 279<br>279 |
| Ia.102 | 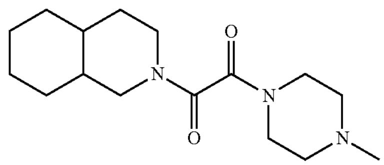 [SMILES: CN1CCN(C(=O)C(=O)N2CCC3CCCCC3C2)CC1] | 1-(4-methylpiperazin-1-yl)-2-(octahydroisoquinolin-2-yl)ethane-1,2-dione | A | 4.04 | 294 |
| Ia.103 | 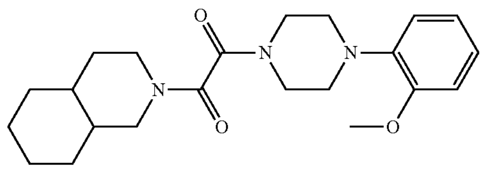 [SMILES: COc1ccccc1N1CCN(C(=O)C(=O)N2CCC3CCCCC3C2)CC1] | 1-[4-(2-methoxyphenyl)piperazin-1-yl]-2-(octahydroisoquinolin-2-yl)ethane-1,2-dione | A | 7.03<br>7.17 | 386<br>386 |
| Ia.104 | 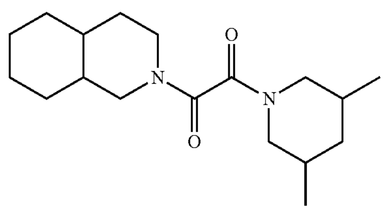 [SMILES: CC1CC(C)CN(C(=O)C(=O)N2CCC3CCCCC3C2)C1] | 1-(3,5-dimethylpiperidin-1-yl)-2-(octahydroisoquinolin-2-yl)ethane-1,2-dione | A | 7.41<br>7.53 | 307<br>307 |
| Ia.105 | 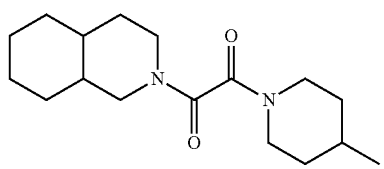 [SMILES: CC1CCN(C(=O)C(=O)N2CCC3CCCCC3C2)CC1] | 1-(4-methylpiperidin-1-yl)-2-(octahydroisoquinolin-2-yl)ethane-1,2-dione | A | 6.86<br>7.01 | 293<br>293 |
| Ia.106 | 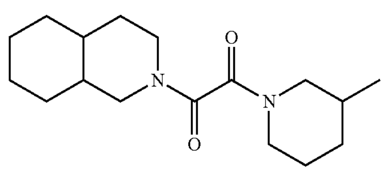 [SMILES: CC1CCCN(C(=O)C(=O)N2CCC3CCCCC3C2)C1] | 1-(3-methylpiperidin-1-yl)-2-(octahydroisoquinolin-2-yl)ethane-1,2-dione | A | 6.83<br>6.99 | 293<br>293 |
| Ia.107 | 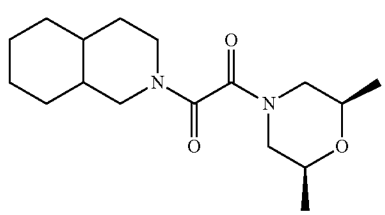 [SMILES: C[C@@H]1CN(C(=O)C(=O)N2CCC3CCCCC3C2)C[C@H](C)O1] | 1-((2S,6R)-2,6-dimethylmorpholin-4-yl)-2-(octahydroisoquinolin-2-yl)ethane-1,2-dione | A | 6.20<br>6.38 | 309<br>309 |
| Ia.108 | 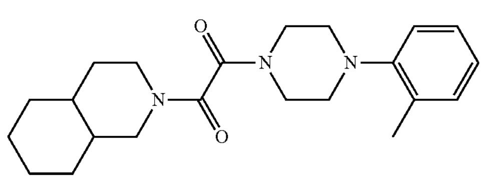 [SMILES: Cc1ccccc1N1CCN(C(=O)C(=O)N2CCC3CCCCC3C2)CC1] | 1-(octahydroisoquinolin-2-yl)-2-(4-o-tolylpiperazin-1-yl)ethane-1,2-dione | A | 7.98 | 370 |

-continued

| Ex. | structure | name | method | tr (min) | m/z |
|---|---|---|---|---|---|
| Ia.109 | 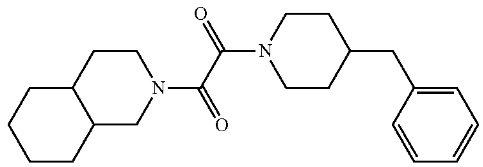 [SMILES: O=C(C(=O)N1CCC2CCCCC2C1)N1CCC(Cc2ccccc2)CC1] | 1-(4-benzylpiperidin-1-yl)-2-(octahydroisoquinolin-2-yl)ethane-1,2-dione | A | 8.04 | 369 |
| Ia.110 | 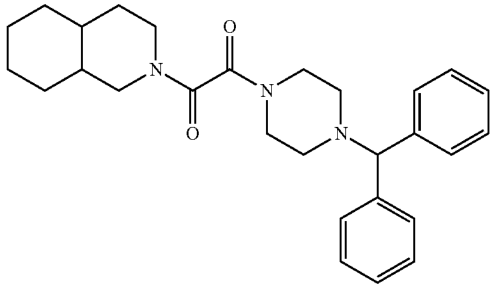 [SMILES: O=C(C(=O)N1CCC2CCCCC2C1)N1CCN(C(c2ccccc2)c2ccccc2)CC1] | 1-(4-benzhydrylpiperazin-1-yl)-2-(octahydroisoquinolin-2-yl)ethane-1,2-dione | A | 7.63<br>7.80 | 446<br>446 |
| Ia.111 | 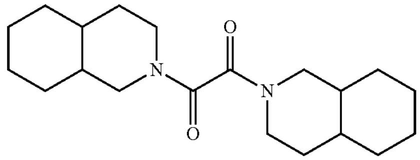 [SMILES: O=C(C(=O)N1CCC2CCCCC2C1)N1CCC2CCCCC2C1] | 1,2-bis-(octahydroisoquinolin-2-yl)ethane-1,2-dione | A | 8.06 | 333 |
| Ia.112 | 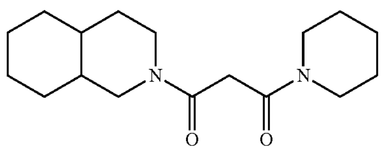 [SMILES: O=C(CC(=O)N1CCC2CCCCC2C1)N1CCCCC1] | 1-(octahydroisoquinolin-2-yl)-3-piperidin-1-ylpropane-1,3-dione | A | 6.11<br>6.28 | 293<br>293 |
| Ia.113 | 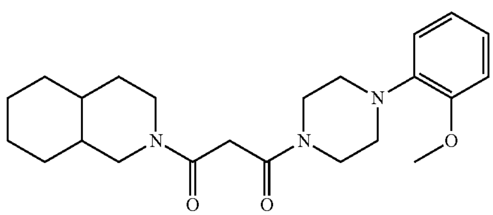 [SMILES: COc1ccccc1N1CCN(C(=O)CC(=O)N2CCC3CCCCC3C2)CC1] | 1-[4-(2-methoxyphenyl)piperazin-1-yl]-3-(octahydroisoquinolin-2-yl)propane-1,3-dione | A | 6.47<br>6.64 | 400<br>400 |
| Ia.114 | 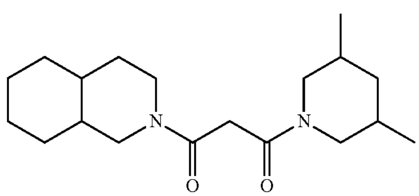 [SMILES: CC1CC(C)CN(C(=O)CC(=O)N2CCC3CCCCC3C2)C1] | 1-(3,5-dimethylpiperidin-1-yl)-3-(octahydroisoquinolin-2-yl)propane-1,3-dione | A | 7.20<br>7.33 | 321<br>321 |
| Ia.115 | 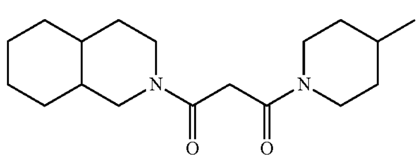 [SMILES: CC1CCN(C(=O)CC(=O)N2CCC3CCCCC3C2)CC1] | 1-(4-methylpiperidin-1-yl)-3-(octahydroisoquinolin-2-yl)propane-1,3-dione | A | 6.66<br>6.81 | 307<br>307 |
| Ia.116 | 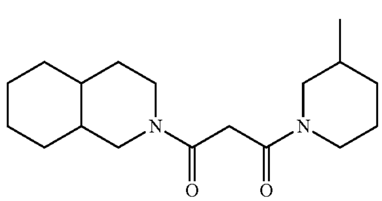 [SMILES: CC1CCCN(C(=O)CC(=O)N2CCC3CCCCC3C2)C1] | 1-(3-methylpiperidin-1-yl)-3-(octahydroisoquinolin-2-yl)propane-1,3-dione | A | 6.63<br>6.79 | 307<br>307 |

-continued

| Ex. | structure | name | method | tr (min) | m/z |
|---|---|---|---|---|---|
| Ia.117 | 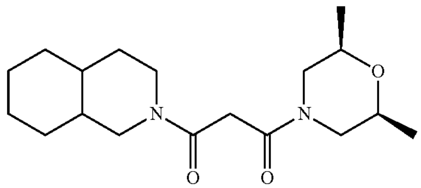 [SMILES: C[C@@H]1CN(C(=O)CC(=O)N2CCC3CCCCC3C2)C[C@H](C)O1] | 1-((2S,6R)-2,6-dimethylmorpholin-4-yl)-3-(octahydroisoquinolin-2-yl)propane-1,3-dione | A | 5.91<br>6.09 | 323<br>323 |
| Ia.118 | 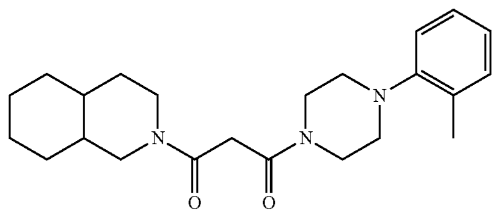 [SMILES: Cc1ccccc1N1CCN(C(=O)CC(=O)N2CCC3CCCCC3C2)CC1] | 1-(octahydroisoquinolin-2-yl)-3-(4-o-tolylpiperazin-1-yl)propane-1,3-dione | A | 7.57<br>7.70 | 384<br>384 |
| Ia.119 | 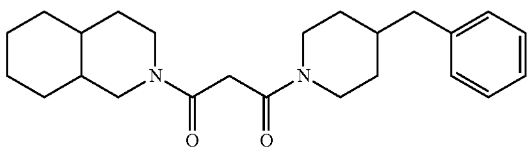 [SMILES: O=C(CC(=O)N1CCC2CCCCC2C1)N1CCC(Cc2ccccc2)CC1] | 1-(4-benzylpiperidin-1-yl)-3-(octahydroisoquinolin-2-yl)propane-1,3-dione | A | 7.73<br>7.85 | 383<br>383 |
| Ia.120 | 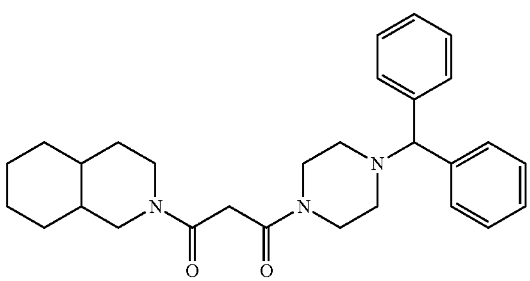 [SMILES: O=C(CC(=O)N1CCC2CCCCC2C1)N1CCN(C(c2ccccc2)c2ccccc2)CC1] | 1-(4-benzhydrylpiperazin-1-yl)-3-(octahydroisoquinolin-2-yl)propane-1,3-dione | A | 6.34<br>6.48 | 460<br>460 |
| Ia.121 | 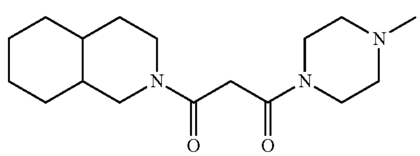 [SMILES: CN1CCN(C(=O)CC(=O)N2CCC3CCCCC3C2)CC1] | 1-(4-methylpiperazin-1-yl)-3-(octahydroisoquinolin-2-yl)propane-1,3-dione | A | 4.06 | 308 |
| Ia.122 | 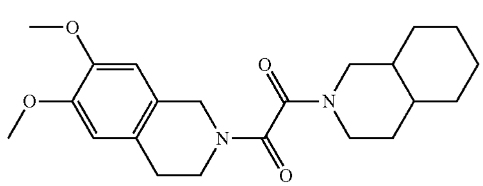 [SMILES: COc1cc2c(cc1OC)CN(C(=O)C(=O)N1CCC3CCCCC3C1)CC2] | 1-(6,7-dimethoxy-3,4-dihydro-1-H-isoquinolin-2-yl)-2-(octahydroisoquinolin-2-yl)ethane-1,2-dione | A | 6.65 | 387 |
| Ia.123 | 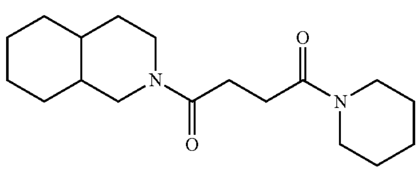 [SMILES: O=C(CCC(=O)N1CCC2CCCCC2C1)N1CCCCC1] | 1-(octahydroisoquinolin-2-yl)-4-piperidin-1-ylbutane-1,4-dione | A | 6.37<br>6.56 | 307<br>307 |
| Ia.124 | 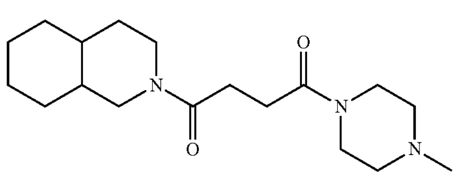 [SMILES: CN1CCN(C(=O)CCC(=O)N2CCC3CCCCC3C2)CC1] | 1-(4-methylpiperazin-1-yl)-4-(octahydroisoquinolin-2-yl)butane-1,4-dione | A | 4.32 | 322 |

-continued

| Ex. | structure | name | method | tr (min) | m/z |
|---|---|---|---|---|---|
| Ia.125 | 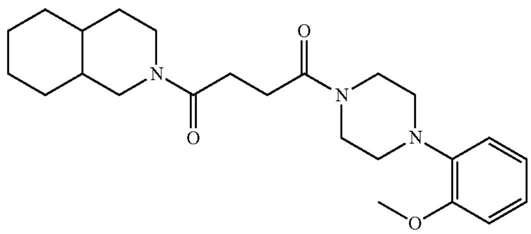 [SMILES: COc1ccccc1N1CCN(C(=O)CCC(=O)N2CCC3CCCCC3C2)CC1] | 1-[4-(2-methoxyphenyl)piperazin-1-yl]-4-(octahydroisoquinolin-2-yl)butane-1,4-dione | A | 6.52<br>6.71 | 414<br>414 |
| Ia.126 | 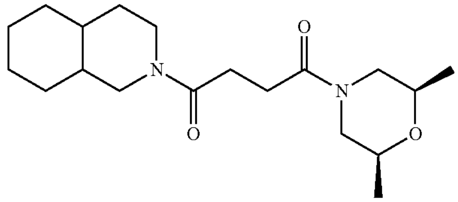 [SMILES: C[C@@H]1CN(C(=O)CCC(=O)N2CCC3CCCCC3C2)C[C@H](C)O1] | 1-((2S,6R)-2,6-dimethylmorpholin-4-yl)-4-(octahydroisoquinolin-2-yl)butane-1,4-dione | A | 6.15<br>6.34 | 337<br>337 |
| Ia.127 | 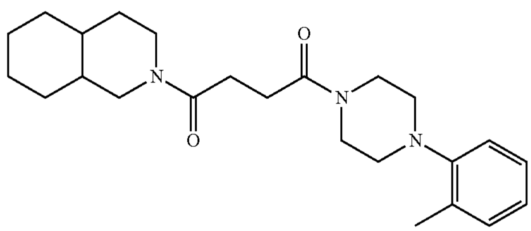 [SMILES: Cc1ccccc1N1CCN(C(=O)CCC(=O)N2CCC3CCCCC3C2)CC1] | 1-(octahydroisoquinolin-2-yl)-4-(4-o-tolylpiperazin-1-yl)butane-1,4-dione | A | 7.66<br>7.81 | 398<br>398 |
| Ia.128 | 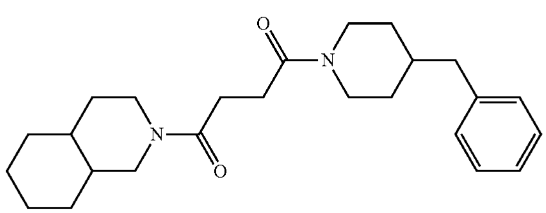 [SMILES: O=C(CCC(=O)N1CCC2CCCCC2C1)N1CCC(Cc2ccccc2)CC1] | 1-(4-benzylpiperidin-1-yl)-4-(octahydroisoquinolin-2-yl)butane-1,4-dione | A | 7.90<br>8.03 | 397<br>397 |
| Ia.129 | 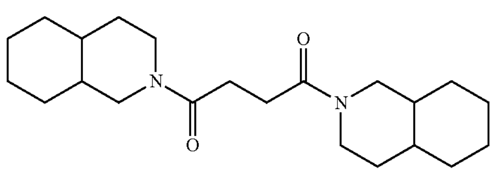 [SMILES: O=C(CCC(=O)N1CCC2CCCCC2C1)N1CCC2CCCCC2C1] | 1,4-bis-(octahydroisoquinolin-2-yl)butane-1,4-dione | A | 7.94<br>8.09 | 361<br>361 |
| Ia.130 | 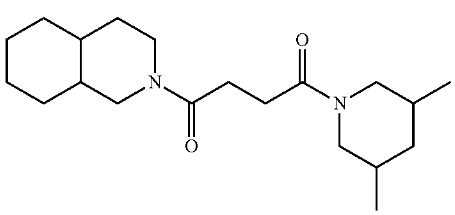 [SMILES: CC1CC(C)CN(C(=O)CCC(=O)N2CCC3CCCCC3C2)C1] | 1-(3,5-dimethylpiperidin-1-yl)-4-(octahydroisoquinolin-2-yl)butane-1,4-dione | A | 7.44<br>7.59 | 335<br>335 |
| Ia.131 | 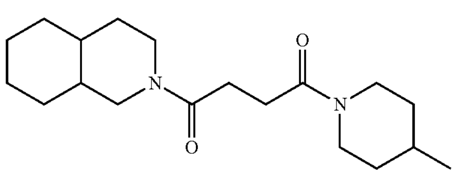 [SMILES: CC1CCN(C(=O)CCC(=O)N2CCC3CCCCC3C2)CC1] | 1-(4-methylpiperidin-1-yl)-4-(octahydroisoquinolin-2-yl)butane-1,4-dione | A | 6.91<br>7.08 | 321<br>321 |

-continued

| Ex. | structure | name | method | tr (min) | m/z |
|---|---|---|---|---|---|
| Ia.132 | 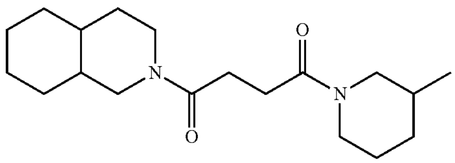 [SMILES: CC1CCCN(C(=O)CCC(=O)N2CCC3CCCCC3C2)C1] | 1-(3-methylpiperidin-1-yl)-4-(octahydroisoquinolin-2-yl)butane-1,4-dione | A | 6.89<br>7.06 | 321<br>321 |
| Ia.133 | 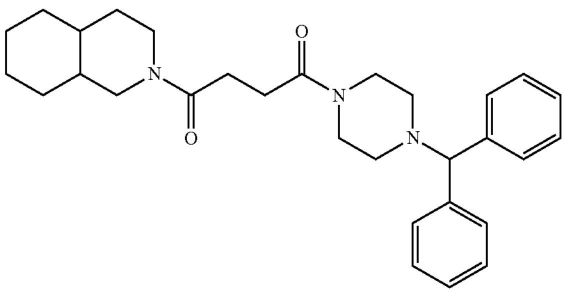 [SMILES: O=C(CCC(=O)N1CCC2CCCCC2C1)N1CCN(C(c2ccccc2)c2ccccc2)CC1] | 1-(4-benzhydrylpiperazin-1-yl)-4-(octahydroisoquinolin-2-yl)butane-1,4-dione | A | 6.24<br>6.34 | 474<br>474 |
| Ia.134 | 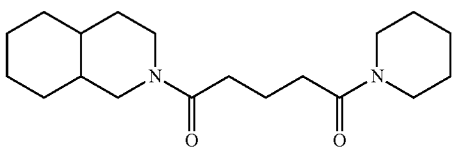 [SMILES: O=C(CCCC(=O)N1CCC2CCCCC2C1)N1CCCCC1] | 1-(octahydroisoquinolin-2-yl)-5-piperidin-1-ylpentane-1,5-dione | A | 6.51<br>6.70 | 321<br>321 |
| Ia.135 | 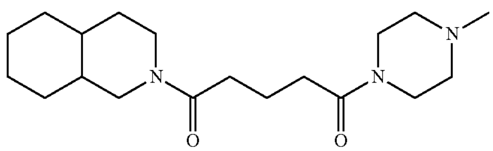 [SMILES: CN1CCN(C(=O)CCCC(=O)N2CCC3CCCCC3C2)CC1] | 1-(4-methylpiperazin-1-yl)-5-(octahydroisoquinolin-2-yl)pentane-1,5-dione | A | 4.27 | 336 |
| Ia.136 | 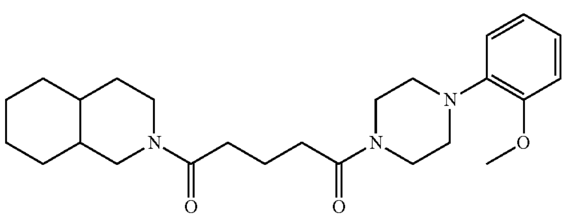 [SMILES: COc1ccccc1N1CCN(C(=O)CCCC(=O)N2CCC3CCCCC3C2)CC1] | 1-[4-(2-methoxyphenyl)piperazin-1-yl]-5-(octahydroisoquinolin-2-yl)pentane-1,5-dione | A | 6.74<br>6.93 | 428<br>428 |
| Ia.137 | 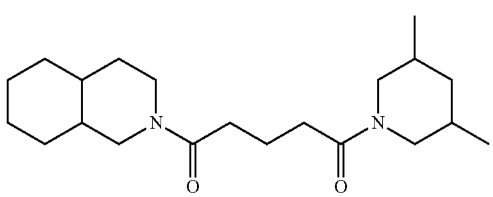 [SMILES: CC1CC(C)CN(C(=O)CCCC(=O)N2CCC3CCCCC3C2)C1] | 1-(3,5-dimethylpiperidin-1-yl)-5-(octahydroisoquinolin-2-yl)pentane-1,5-dione | A | 7.52<br>7.68 | 349<br>349 |
| Ia.138 | 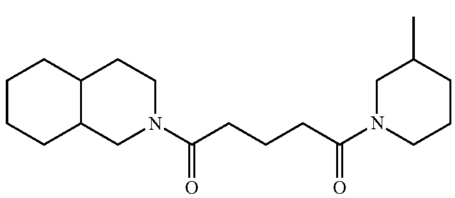 [SMILES: CC1CCCN(C(=O)CCCC(=O)N2CCC3CCCCC3C2)C1] | 1-(3-methylpiperidin-1-yl)-5-(octahydroisoquinolin-2-yl)pentane-1,5-dione | A | 7.01<br>7.19 | 335<br>335 |
| Ia.139 | 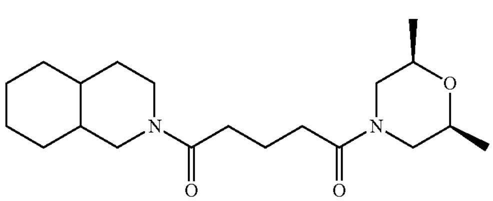 [SMILES: C[C@@H]1CN(C(=O)CCCC(=O)N2CCC3CCCCC3C2)C[C@H](C)O1] | 1-((2S,6R)-2,6-dimethylmorpholin-4-yl)-5-(octahydroisoquinolin-2-yl)pentane-1,5-dione | A | 6.26<br>6.45 | 351<br>351 |

-continued

| Ex. | structure | name | method | tr (min) | m/z |
|---|---|---|---|---|---|
| Ia.140 | 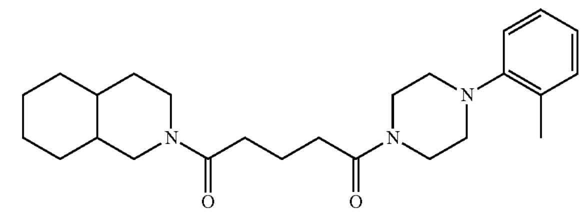 [SMILES: Cc1ccccc1N1CCN(C(=O)CCCC(=O)N2CCC3CCCCC3C2)CC1] | 1-(octahydroisoquinolin-2-yl)-5-(4-o-tolylpiperazin-1-yl)pentane-1,5-dione | A | 7.85<br>8.01 | 412<br>412 |
| Ia.141 | 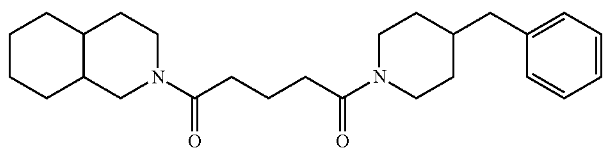 [SMILES: O=C(CCCC(=O)N1CCC2CCCCC2C1)N1CCC(Cc2ccccc2)CC1] | 1-(4-benzylpiperidin-1-yl)-5-(octahydroisoquinolin-2-yl)pentane-1,5-dione | A | 8.01<br>8.16 | 411<br>411 |
| Ia.142 | 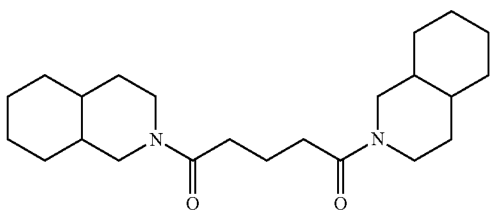 [SMILES: O=C(CCCC(=O)N1CCC2CCCCC2C1)N1CCC2CCCCC2C1] | 1,5-bis-(octahydroisoquinolin-2-yl)pentane-1,5-dione | A | 8.04<br>8.21 | 375<br>375 |
| Ia.143 | 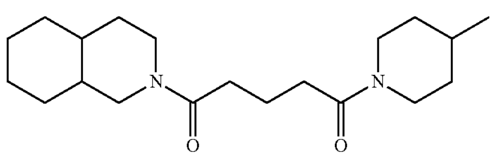 [SMILES: CC1CCN(C(=O)CCCC(=O)N2CCC3CCCCC3C2)CC1] | 1-(4-methylpiperidin-1-yl)-5-(octahydroisoquinolin-2-yl)pentane-1,5-dione | A | 7.03<br>7.22 | 335<br>335 |
| Ia.144 | 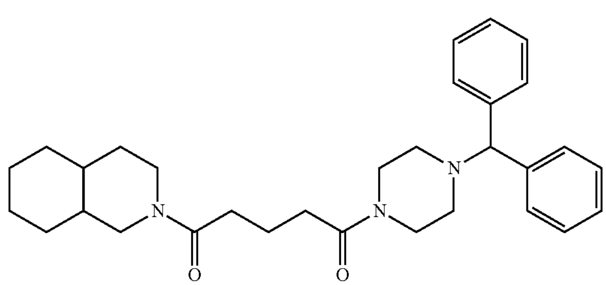 [SMILES: O=C(CCCC(=O)N1CCC2CCCCC2C1)N1CCN(C(c2ccccc2)c2ccccc2)CC1] | 1-(4-benzhydrylpiperazin-1-yl)-5-(octahydroisoquinolin-2-yl)pentane-1,5-dione | A | 6.53<br>6.67 | 488<br>448 |
| Ia.145 | 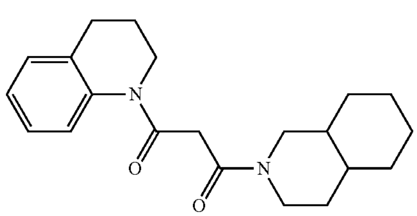 [SMILES: O=C(CC(=O)N1CCCc2ccccc21)N1CCC2CCCCC2C1] | 1-(3,4-dihydro-2-H-quinolin-1-yl)-5-(octahydroisoquinolin-2-yl)pentane-1,5-dione | A | 7.49<br>7.66 | 369<br>370 |
| Ia.146 | 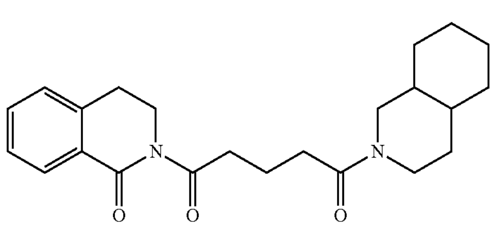 [SMILES: O=C(CCCC(=O)N1CCc2ccccc2C1=O)N1CCC2CCCCC2C1] | 1-(octahydroisoquinolin-2-yl)-5-(1-oxo-3,4-dihydro-1-H-isoquinolin-2-yl)pentane-1,5-dione | A | 7.73<br>7.90 | 383<br>383 |

-continued

| Ex. | structure | name | method | tr (min) | m/z |
|---|---|---|---|---|---|
| Ia.147 | 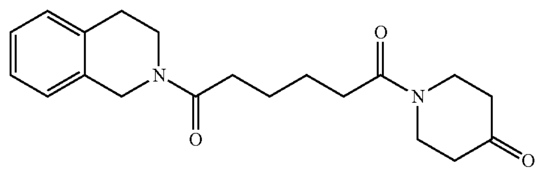 [SMILES: O=C1CCN(C(=O)CCCCC(=O)N2CCc3ccccc3C2)CC1] | 1-(octahydroisoquinolin-2-yl)-6-(4-oxopiperidin-1-yl)hexane-1,6-dione | B | 3.04<br>3.14 | 349<br>349 |
| Ia.148 | 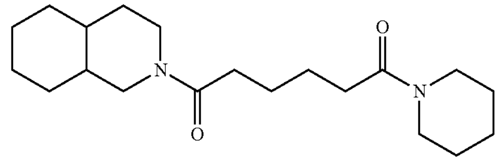 [SMILES: O=C(CCCCC(=O)N1CCC2CCCCC2C1)N1CCCCC1] | 1-(octahydroisoquinolin-2-yl)-6-piperidin-1-ylhexane-1,6-dione | B | 3.64<br>3.75 | 335<br>335 |
| Ia.149 | 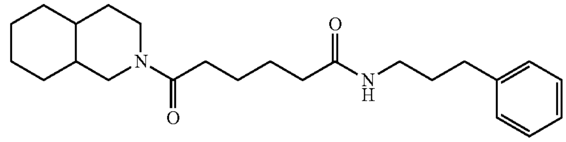 [SMILES: O=C(CCCCC(=O)N1CCC2CCCCC2C1)NCCCc1ccccc1] | 6-(octahydroisoquinolin-2-yl)-6-oxohexanoic acid (3-phenylpropyl)amide | B | 3.93<br>4.02 | 385<br>385 |
| Ia.150 | 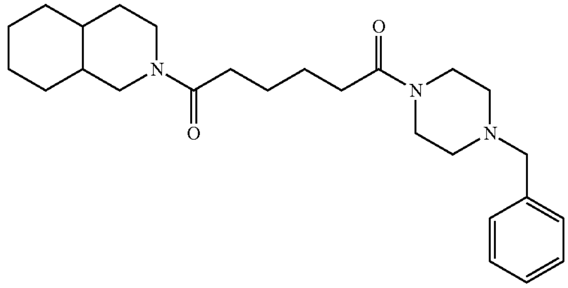 [SMILES: O=C(CCCCC(=O)N1CCC2CCCCC2C1)N1CCN(Cc2ccccc2)CC1] | 1-(4-benzylpiperazin-1-yl)-6-(octahydroisoquinolin-2-yl)hexane-1,6-dione | B | 2.77<br>2.83 | 426<br>426 |
| Ia.151 | 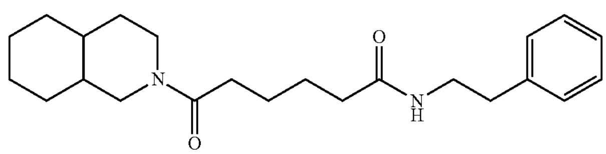 [SMILES: O=C(CCCCC(=O)N1CCC2CCCCC2C1)NCCc1ccccc1] | 6-(octahydroisoquinolin-2-yl)-6-oxohexanoic acid phenethylamide | B | 3.75<br>3.84 | 371<br>371 |
| Ia.152 | 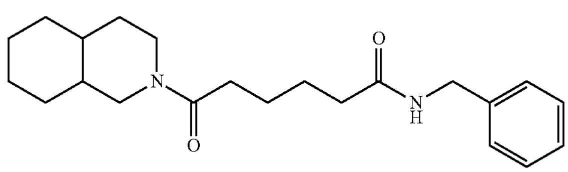 [SMILES: O=C(CCCCC(=O)N1CCC2CCCCC2C1)NCc1ccccc1] | 6-(octahydroisoquinolin-2-yl)-6-oxohexanoic acid benzylamide | B | 3.63<br>3.73 | 357<br>357 |
| Ia.153 | 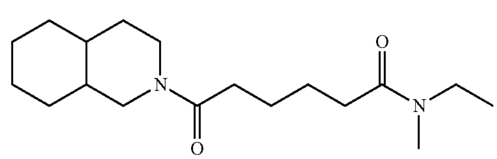 [SMILES: CCN(C)C(=O)CCCCC(=O)N1CCC2CCCCC2C1] | 6-(octahydroisoquinolin-2-yl)-6-oxohexanoic acid ethylmethylamide | B | 3.36<br>3.46 | 309<br>309 |
| Ia.154 | 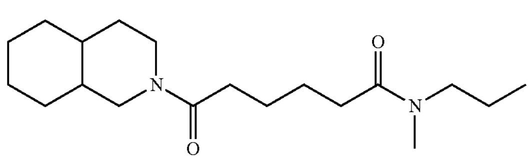 [SMILES: CCCN(C)C(=O)CCCCC(=O)N1CCC2CCCCC2C1] | 6-(octahydroisoquinolin-2-yl)-6-oxohexanoic acid methylpropylamide | B | 3.61<br>3.72 | 323<br>323 |
| Ia.155 | 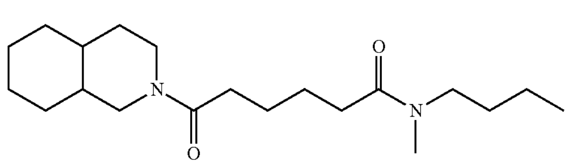 [SMILES: CCCCN(C)C(=O)CCCCC(=O)N1CCC2CCCCC2C1] | 6-(octahydroisoquinolin-2-yl)-6-oxohexanoic acid butylmethylamide | B | 3.88<br>3.98 | 337<br>337 |

-continued

| Ex. | structure | name | method | tr (min) | m/z |
|---|---|---|---|---|---|
| Ia.156 | 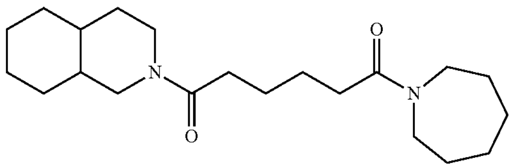 [SMILES: O=C(CCCCC(=O)N1CCC2CCCCC2C1)N1CCCCCC1] | 6-(octahydroisoquinolin-2-yl)-1-perhydroazepin-1-ylhexane-1,6-dione | B | 3.82<br>3.92 | 349<br>349 |
| Ia.157 | 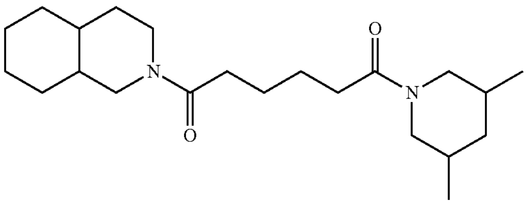 [SMILES: CC1CC(C)CN(C(=O)CCCCC(=O)N2CCC3CCCCC3C2)C1] | 1-(3,5-dimethylpiperidin-1-yl)-6-(octahydroisoquinolin-2-yl)hexane-1,6-dione | B | 4.20<br>4.29 | 363<br>363 |
| Ia.158 | 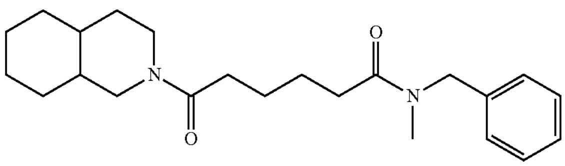 [SMILES: CN(Cc1ccccc1)C(=O)CCCCC(=O)N1CCC2CCCCC2C1] | 6-(octahydroisoquinolin-2-yl)-6-oxohexanoic acid benzylmethylamide | B | 3.92<br>4.02 | 371<br>371 |
| Ia.159 | 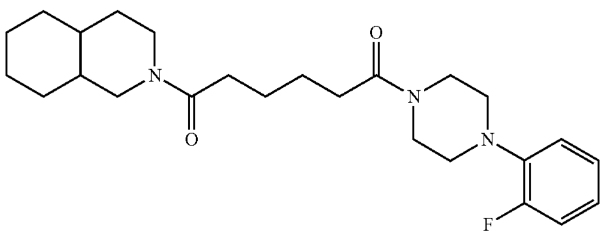 [SMILES: O=C(CCCCC(=O)N1CCC2CCCCC2C1)N1CCN(c2ccccc2F)CC1] | 1-[4-(2-fluorophenyl)piperazin-1-yl]-6-(octahydroisoquinolin-2-yl)hexane-1,6-dione | B | 4.08<br>4.17 | 430<br>430 |
| Ia.160 | 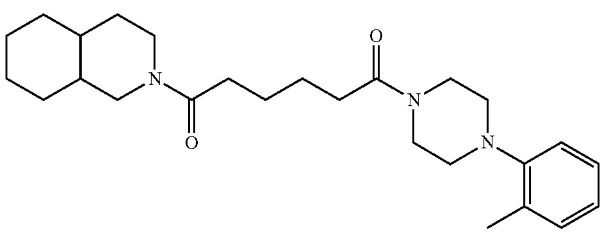 [SMILES: Cc1ccccc1N1CCN(C(=O)CCCCC(=O)N2CCC3CCCCC3C2)CC1] | 1-(octahydroisoquinolin-2-yl)-6-(4-o-tolylpiperazin-1-yl)hexane-1,6-dione | B | 4.35<br>4.44 | 426<br>426 |
| Ia.161 | 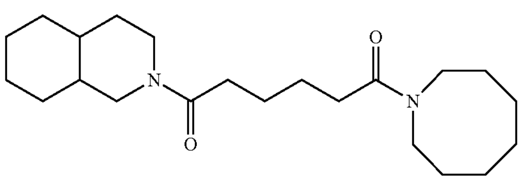 [SMILES: O=C(CCCCC(=O)N1CCC2CCCCC2C1)N1CCCCCCC1] | 6-(octahydroisoquinolin-2-yl)-1-perhydroazocin-1-ylhexane-1,6-dione | B | 4.03<br>4.13 | 363<br>363 |
| Ia.162 | 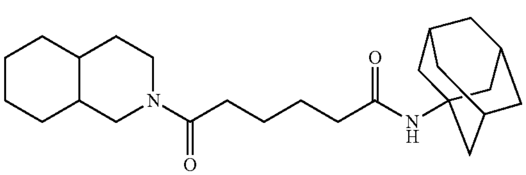 [SMILES: O=C(CCCCC(=O)N1CCC2CCCCC2C1)NC12CC3CC(CC(C3)C1)C2] | 6-(octahydroisoquinolin-2-yl)-6-oxohexanoic acid tricyclo[3.3.1.1$^{3,7}$]decan-1-ylamide | B | 4.41<br>4.50 | 401<br>401 |
| Ia.163 | 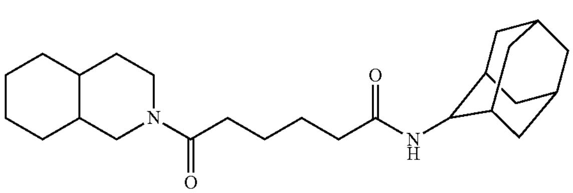 [SMILES: O=C(CCCCC(=O)N1CCC2CCCCC2C1)NC1C2CC3CC(C2)CC1C3] | 6-(octahydroisoquinolin-2-yl)-6-oxohexanoic acid tricyclo[3.3.1.1$^{3,7}$]decan-2-ylamide | B | 4.32<br>4.41 | 401<br>401 |

| Ex. | structure | name | method | tr (min) | m/z |
|---|---|---|---|---|---|
| Ia.164 | 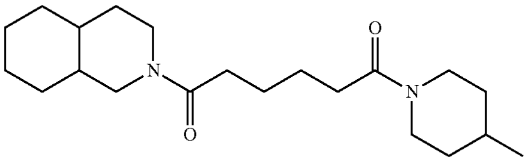 [SMILES: CC1CCN(C(=O)CCCCC(=O)N2CCC3CCCCC3C2)CC1] | 1-(4-methylpiperidin-1-yl)-6-(octahydroisoquinolin-2-yl)hexane-1,6-dione | B | 3.92<br>4.02 | 349<br>349 |
| Ia.165 | 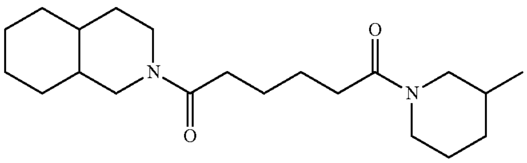 [SMILES: CC1CCCN(C(=O)CCCCC(=O)N2CCC3CCCCC3C2)C1] | 1-(3-methylpiperidin-1-yl)-6-(octahydroisoquinolin-2-yl)hexane-1,6-dione | B | 3.91<br>4.02 | 349<br>349 |
| Ia.166 | 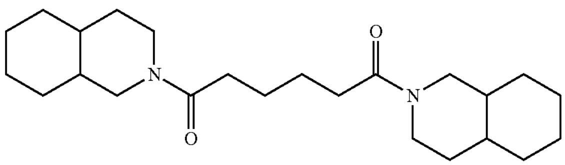 [SMILES: O=C(CCCCC(=O)N1CCC2CCCCC2C1)N1CCC2CCCCC2C1] | 1,6-bis-(octahydroisoquinolin-2-yl)hexane-1,6-dione | B | 4.47<br>4.56 | 389<br>389 |
| Ia.167 | 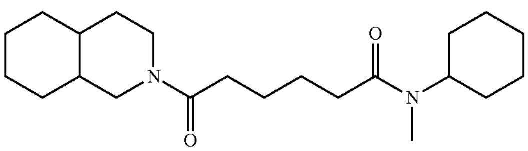 [SMILES: CN(C(=O)CCCCC(=O)N1CCC2CCCCC2C1)C1CCCCC1] | 6-(octahydroisoquinolin-2-yl)-6-oxohexanoic acid cyclohexylmethylamide | B | 4.12<br>4.21 | 363<br>363 |
| Ib.63 | 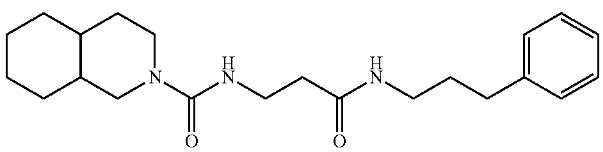 [SMILES: O=C(CCNC(=O)N1CCC2CCCCC2C1)NCCCc1ccccc1] | Octahydroisoquinoline-2-carboxylic acid [2-(3-phenylpropylcarbamoyl)ethyl]amide | B | 3.72<br>3.80 | 372<br>372 |
| Ib.64 | 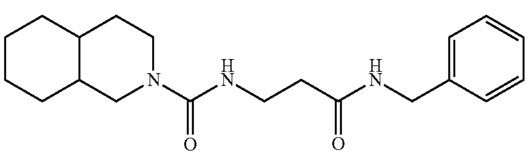 [SMILES: O=C(CCNC(=O)N1CCC2CCCCC2C1)NCc1ccccc1] | Octahydroisoquinoline-2-carboxylic acid (2-benzylcarbamoylethyl)amide | B | 3.42<br>3.50 | 344<br>344 |
| Ib.65 | 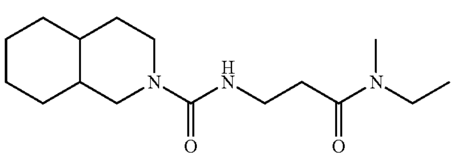 [SMILES: CCN(C)C(=O)CCNC(=O)N1CCC2CCCCC2C1] | Octahydroisoquinoline-2-carboxylic acid [2-(ethylmethylcarbamoyl)ethyl]amide | B | 3.06<br>3.17 | 296<br>296 |
| Ib.66 | 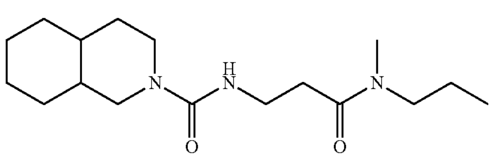 [SMILES: CCCN(C)C(=O)CCNC(=O)N1CCC2CCCCC2C1] | Octahydroisoquinoline-2-carboxylic acid [2-(methylpropylcarbamoyl)ethyl]amide | B | 3.32<br>3.42 | 310<br>310 |
| Ib.67 | 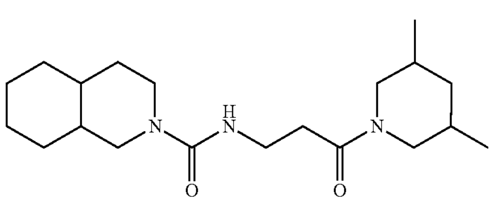 [SMILES: CC1CC(C)CN(C(=O)CCNC(=O)N2CCC3CCCCC3C2)C1] | Octahydroisoquinoline-2-carboxylic acid [3-(3,5-dimethylpiperidin-1-yl)-3-oxopropyl]amide | B | 3.91<br>3.98 | 350<br>350 |

| Ex. | structure | name | method | tr (min) | m/z |
|---|---|---|---|---|---|
| Ib.68 | 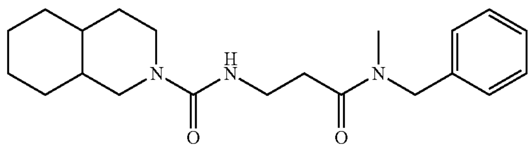 [SMILES: CN(Cc1ccccc1)C(=O)CCNC(=O)N1CCC2CCCCC2C1] | Octahydroisoquinoline-2-carboxylic acid [2-(benzylmethylcarbamoyl)ethyl]amide | B | 3.66<br>3.75 | 358<br>358 |
| Ib.69 | 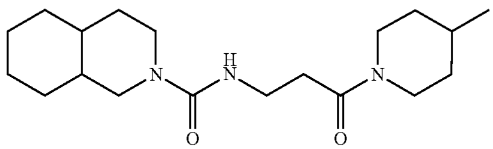 [SMILES: CC1CCN(C(=O)CCNC(=O)N2CCC3CCCCC3C2)CC1] | Octahydroisoquinoline-2-carboxylic acid [3-(4-methylpiperidin-1-yl)-3-oxopropyl]amide | B | 3.62<br>3.71 | 336<br>336 |
| Ib.70 | 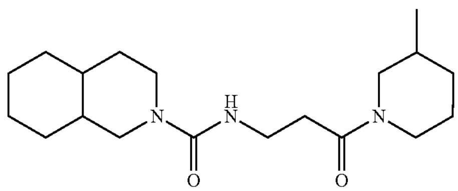 [SMILES: CC1CCCN(C(=O)CCNC(=O)N2CCC3CCCCC3C2)C1] | Octahydroisoquinoline-2-carboxylic acid [3-(3-methylpiperidin-1-yl)-3-oxopropyl]amide | B | 3.61<br>3.70 | 336<br>336 |
| Ib.71 | 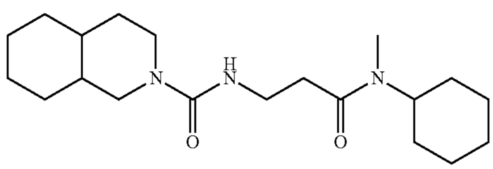 [SMILES: CN(C(=O)CCNC(=O)N1CCC2CCCCC2C1)C1CCCCC1] | Octahydroisoquinoline-2-carboxylic acid [2-(cyclohexylmethylcarbamoyl)ethyl]amide | B | 3.83<br>3.91 | 350<br>350 |
| Ib.72 | 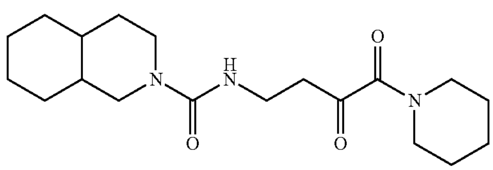 [SMILES: O=C(CCNC(=O)N1CCC2CCCCC2C1)C(=O)N1CCCCC1] | Octahydroisoquinoline-2-carboxylic acid (4-oxo-4-piperidin-1-ylbutyl)amide | B | 3.41<br>3.51 | 336<br>336 |
| Ib.73 | 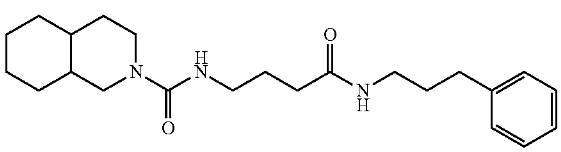 [SMILES: O=C(CCCNC(=O)N1CCC2CCCCC2C1)NCCCc1ccccc1] | Octahydroisoquinoline-2-carboxylic acid [3-(3-phenylpropylcarbamoyl)propyl]amide | B | 3.88 | 386 |
| Ib.74 | 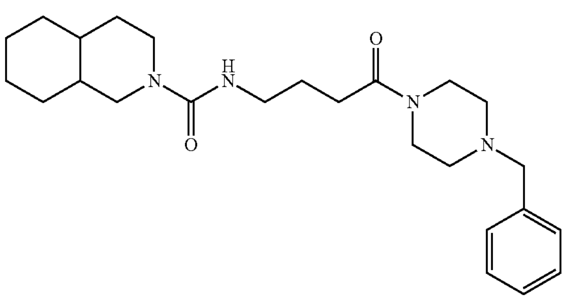 [SMILES: O=C(CCCNC(=O)N1CCC2CCCCC2C1)N1CCN(Cc2ccccc2)CC1] | Octahydroisoquinoline-2-carboxylic acid [4-(4-benzylpiperazin-1-yl)-4-oxobutyl]amide | B | 2.67 | 427 |
| Ib.75 | 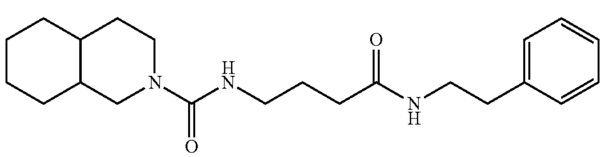 [SMILES: O=C(CCCNC(=O)N1CCC2CCCCC2C1)NCCc1ccccc1] | Octahydroisoquinoline-2-carboxylic acid (3-phenethylcarbamoylpropyl)amide | B | 3.70 | 372 |

-continued

| Ex. | structure | name | method | tr (min) | m/z |
|---|---|---|---|---|---|
| Ib.76 | 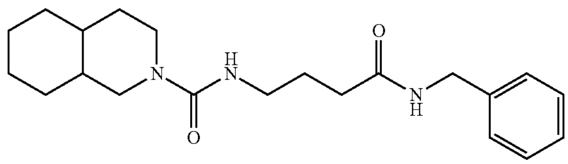 [SMILES: O=C(CCCNC(=O)N1CCC2CCCCC2C1)NCc1ccccc1] | Octahydroisoquinoline-2-carboxylic acid (3-benzylcarbamoylpropyl)amide | B | 3.58 | 358 |
| Ib.77 | 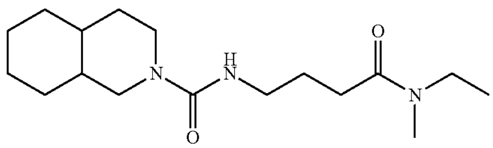 [SMILES: CCN(C)C(=O)CCCNC(=O)N1CCC2CCCCC2C1] | Octahydroisoquinoline-2-carboxylic acid [3-(ethylmethylcarbamoyl)propyl]amide | B | 3.24 | 310 |
| Ib.78 | 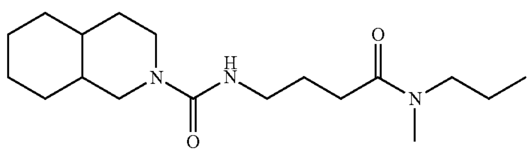 [SMILES: CCCN(C)C(=O)CCCNC(=O)N1CCC2CCCCC2C1] | Octahydroisoquinoline-2-carboxylic acid [3-(methylpropylcarbamoyl)propyl]amide | B | 3.37<br>3.47 | 324<br>324 |
| Ib.79 | 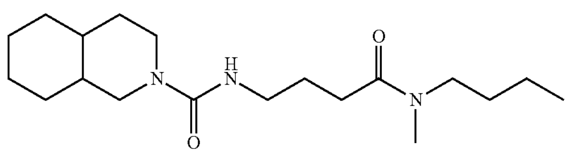 [SMILES: CCCCN(C)C(=O)CCCNC(=O)N1CCC2CCCCC2C1] | Octahydroisoquinoline-2-carboxylic acid [3-(butylmethylcarbamoyl)propyl]amide | B | 3.74 | 338 |
| Ib.80 | 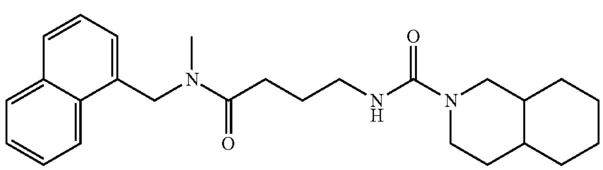 [SMILES: CN(Cc1cccc2ccccc12)C(=O)CCCNC(=O)N1CCC2CCCCC2C1] | Octahydroisoquinoline-2-carboxylic acid [3-(methylnaphthalen-1-ylmethylcarbamoyl)propyl]amide | B | 4.15 | 422 |
| Ib.81 | 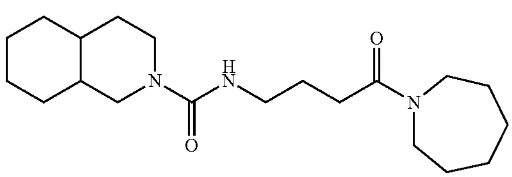 [SMILES: O=C(CCCNC(=O)N1CCC2CCCCC2C1)N1CCCCCC1] | Octahydroisoquinoline-2-carboxylic acid (4-oxo-4-perhydroazepin-1-ylbutyl)amide | B | 3.57<br>3.67 | 350<br>350 |
| Ib.82 | 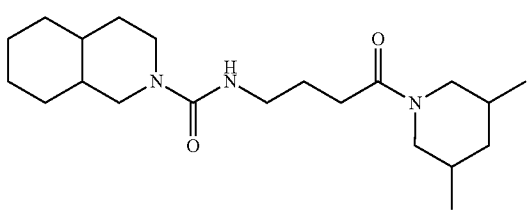 [SMILES: CC1CC(C)CN(C(=O)CCCNC(=O)N2CCC3CCCCC3C2)C1] | Octahydroisoquinoline-2-carboxylic acid [4-(3,5-dimethylpiperidin-1-yl)-4-oxobutyl]amide | B | 3.95<br>4.04 | 364<br>364 |
| Ib.83 | 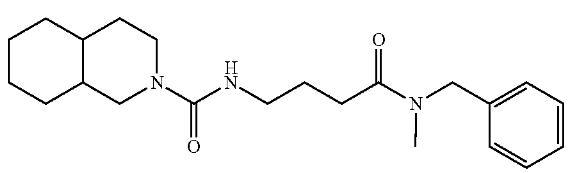 [SMILES: CN(Cc1ccccc1)C(=O)CCCNC(=O)N1CCC2CCCCC2C1] | Octahydroisoquinoline-2-carboxylic acid [3-(benzylmethylcarbamoyl)propyl]amide | B | 3.69<br>3.78 | 372<br>372 |

| Ex. | structure | name | method | tr (min) | m/z |
|---|---|---|---|---|---|
| Ib.84 | 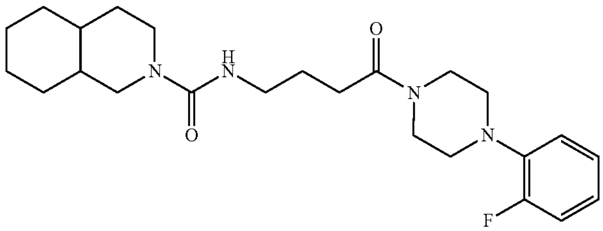 [SMILES: O=C(CCCNC(=O)N1CCC2CCCCC2C1)N1CCN(c2ccccc2F)CC1] | Octahydroisoquinoline-2-carboxylic acid {4-[4-(2-fluorophenyl)piperazin-1-yl]-4-oxobutyl}amide | B | 3.85<br>3.94 | 431<br>431 |
| Ib.85 | 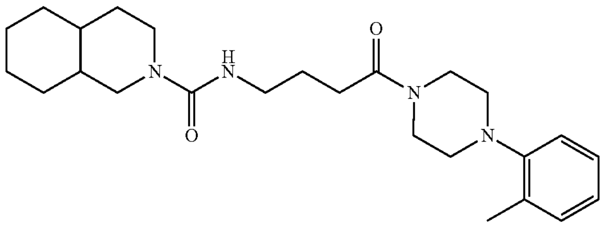 [SMILES: Cc1ccccc1N1CCN(C(=O)CCCNC(=O)N2CCC3CCCCC3C2)CC1] | Octahydroisoquinoline-2-carboxylic acid [4-oxo-4-(4-o-tolylpiperazin-1-yl)butyl]amide | B | 4.12<br>4.20 | 427<br>427 |
| Ib.86 | 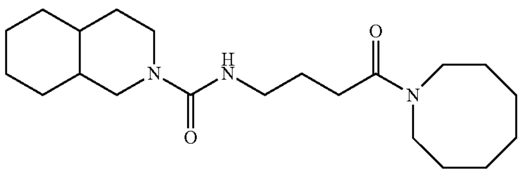 [SMILES: O=C(CCCNC(=O)N1CCC2CCCCC2C1)N1CCCCCCC1] | Octahydroisoquinoline-2-carboxylic acid (4-oxo-4-perhydroazocin-1-ylbutyl)amide | B | 3.78<br>3.87 | 364<br>364 |
| Ib.87 | 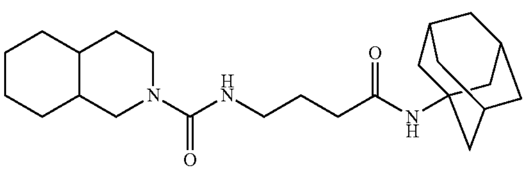 [SMILES: O=C(CCCNC(=O)N1CCC2CCCCC2C1)NC12CC3CC(CC(C3)C1)C2] | Octahydroisoquinoline-2-carboxylic acid [3-(tricyclo[3.3.1.1$^{3,7}$]decan-1-ylcarbamoyl)propyl]amide | B | 4.38 | 402 |
| Ib.88 | 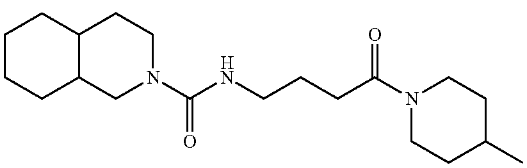 [SMILES: CC1CCN(C(=O)CCCNC(=O)N2CCC3CCCCC3C2)CC1] | Octahydroisoquinoline-2-carboxylic acid [4-(4-methylpiperidin-1-yl)-4-oxobutyl]amide | B | 3.67<br>3.77 | 350<br>350 |
| Ib.89 | 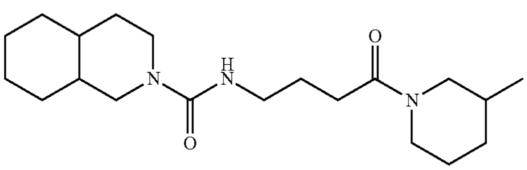 [SMILES: CC1CCCN(C(=O)CCCNC(=O)N2CCC3CCCCC3C2)C1] | Octahydroisoquinoline-2-carboxylic acid [4-(3-methylpiperidin-1-yl)-4-oxobutyl]amide | B | 3.66<br>3.76 | 350<br>350 |
| Ib.90 | 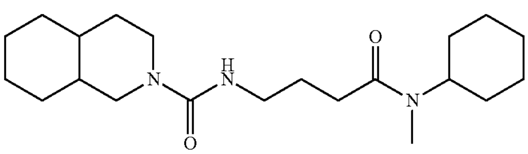 [SMILES: CN(C(=O)CCCNC(=O)N1CCC2CCCCC2C1)C1CCCCC1] | Octahydroisoquinoline-2-carboxylic acid [3-(cyclohexylmethylcarbamoyl)propyl]amide | B | 3.87<br>3.96 | 364<br>364 |
| Ib.91 | 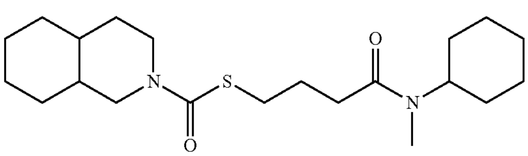 [SMILES: CN(C(=O)CCCSC(=O)N1CCC2CCCCC2C1)C1CCCCC1] | Octahydroisoquinoline-2-carbothioic acid S-[3-(cyclohexylmethylcarbamoyl)propyl] ester | B | 4.49 | 381 |

| Ex. | structure | name | method | tr (min) | m/z |
|---|---|---|---|---|---|
| Ib.92 | 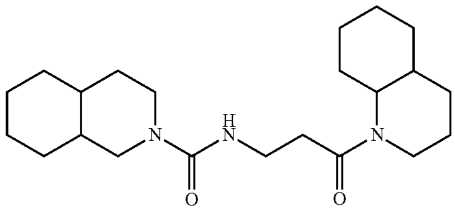 [SMILES: O=C(NCCC(=O)N1CCCC2CCCCC21)N1CCC2CCCCC2C1] | Octahydroisoquinoline-2-carboxylic acid [3-(octahydroquinolin-1-yl)-3-oxopropyl]amide | B | 4.10<br>4.17 | 376<br>376 |
| Ib.93 | 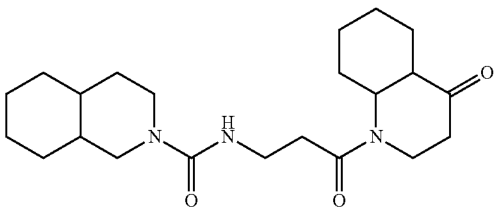 [SMILES: O=C1CCN(C(=O)CCNC(=O)N2CCC3CCCCC3C2)C2CCCCC12] | Octahydroisoquinoline-2-carboxylic acid [3-oxo-3-(4-oxooctahydroquinolin-1-yl)propyl]amide | B | 3.46<br>3.53 | 390<br>390 |
| Ib.94 | 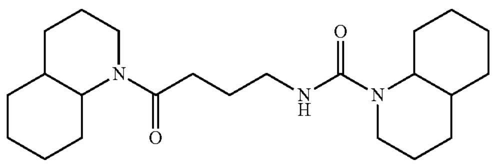 [SMILES: O=C(CCCNC(=O)N1CCCC2CCCCC21)N1CCCC2CCCCC21] | Octahydroquinoline-1-carboxylic acid [4-(octahydroquinolin-1-yl)-4-oxobutyl]amide | B | 4.15 | 390 |
| Ib.95 | 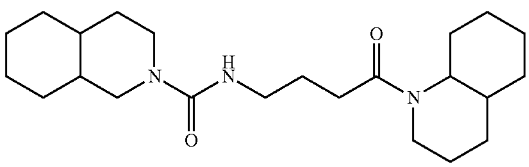 [SMILES: O=C(NCCCC(=O)N1CCCC2CCCCC21)N1CCC2CCCCC2C1] | Octahydroisoquinoline-2-carboxylic acid [4-(octahydroquinolin-1-yl)-4-oxobutyl]amide | B | 4.22 | 390 |
| Ib.96 | 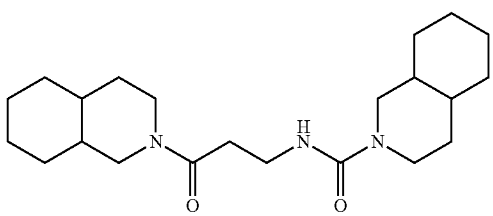 [SMILES: O=C(CCNC(=O)N1CCC2CCCCC2C1)N1CCC2CCCCC2C1] | Octahydroisoquinoline-2-carboxylic acid [3-(octahydroisoquinolin-2-yl)-3-oxopropyl]amide | B | 4.17<br>4.25 | 376<br>376 |
| Ib.97 | 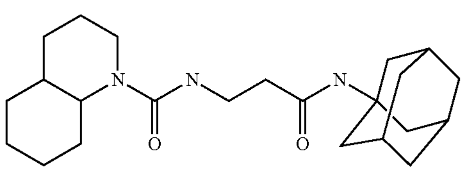 [SMILES: O=C(CCNC(=O)N1CCCC2CCCCC21)NC12CC3CC(CC(C3)C1)C2] | Octahydroquinoline-1-carboxylic acid N-[3-[(3s,5s,7s)-adamantan-1-ylamino-3-oxopropyl]amide | B | 4.18 | 388 |
| Im.17 | 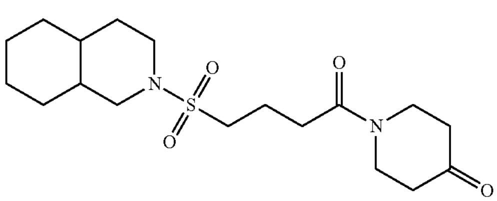 [SMILES: O=C1CCN(C(=O)CCCS(=O)(=O)N2CCC3CCCCC3C2)CC1] | 1-[4-(octahydroisoquinoline-2-sulfonyl)butyryl]piperidin-4-one | B | 3.25<br>3.31 | 371<br>371 |
| Im.18 | 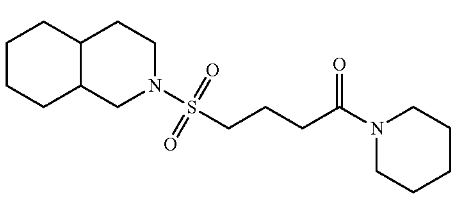 [SMILES: O=C(CCCS(=O)(=O)N1CCC2CCCCC2C1)N1CCCCC1] | 4-(octahydroisoquinoline-2-sulfonyl)-1-piperidin-1-ylbutan-1-one | B | 3.93 | 357 |

-continued

| Ex. | structure | name | method | tr (min) | m/z |
|---|---|---|---|---|---|
| Im.19 | 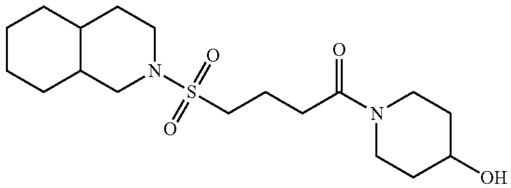 [SMILES: O=C(CCCS(=O)(=O)N1CCC2CCCCC2C1)N1CCC(O)CC1] | 1-(4-hydroxypiperidin-1-yl)-4-(octahydroisoquinoline-2-sulfonyl)butan-1-one | B | 3.04<br>3.11 | 373<br>373 |
| Im.20 | 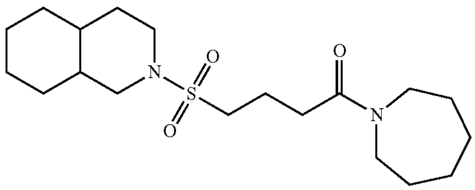 [SMILES: O=C(CCCS(=O)(=O)N1CCC2CCCCC2C1)N1CCCCCC1] | 4-(octahydroisoquinoline-2-sulfonyl)-1-perhydroazepin-1-ylbutan-1-one | B | 4.02<br>4.09 | 371<br>371 |
| Im.21 | 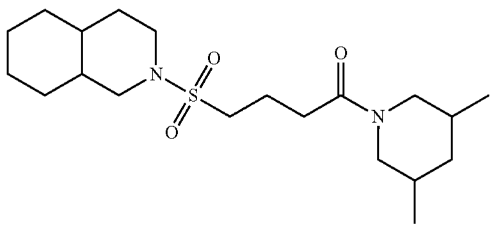 [SMILES: CC1CC(C)CN(C(=O)CCCS(=O)(=O)N2CCC3CCCCC3C2)C1] | 1-(3,5-dimethylpiperidin-1-yl)-4-(octahydroisoquinoline-2-sulfonyl)butan-1-one | B | 4.37<br>4.45 | 385<br>385 |
| Im.22 | 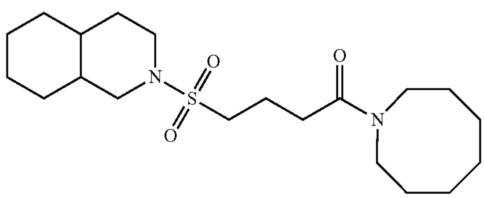 [SMILES: O=C(CCCS(=O)(=O)N1CCC2CCCCC2C1)N1CCCCCCC1] | 4-(octahydroisoquinoline-2-sulfonyl)-1-perhydroazocin-1-ylbutan-1-one | B | 4.23<br>4.30 | 385<br>385 |
| Im.23 | 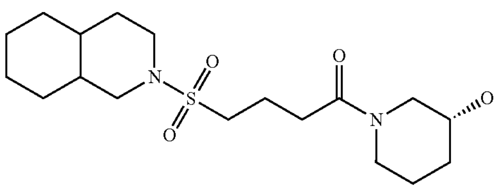 [SMILES: O=C(CCCS(=O)(=O)N1CCC2CCCCC2C1)N1CCC[C@@H](O)C1] | 1-((R)-3-hydroxypiperidin-1-yl)-4-(octahydroisoquinolin-2-sulfonyl)butan-1-one | B | 3.15<br>3.22 | 373<br>373 |
| Im.24 | 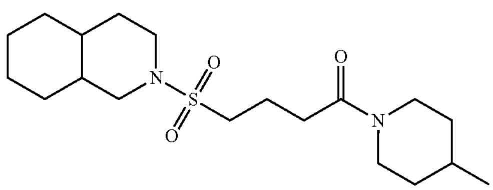 [SMILES: CC1CCN(C(=O)CCCS(=O)(=O)N2CCC3CCCCC3C2)CC1] | 1-(4-methylpiperidin-1-yl)-4-(octahydroisoquinoline-2-sulfonyl)butan-1-one | B | 4.12<br>4.19 | 371<br>371 |
| Im.25 | 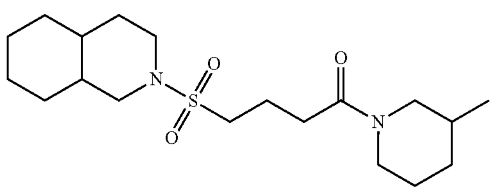 [SMILES: CC1CCCN(C(=O)CCCS(=O)(=O)N2CCC3CCCCC3C2)C1] | 1-(3-methylpiperidin-1-yl)-4-(octahydroisoquinoline-2-sulfonyl)butan-1-one | B | 4.11<br>4.18 | 371<br>371 |
| Im.26 | 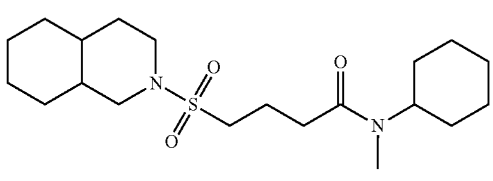 [SMILES: CN(C(=O)CCCS(=O)(=O)N1CCC2CCCCC2C1)C1CCCCC1] | N-cyclohexyl-N-methyl-4-(octahydroisoquinoline-2-sulfonyl)butyramide | B | 4.31<br>4.37 | 385<br>385 |

-continued

| Ex. | structure | name | method | tr (min) | m/z |
|---|---|---|---|---|---|
| Im.27 | 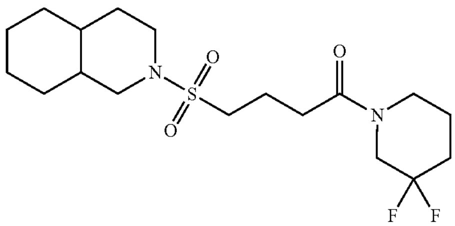 [SMILES: O=C(CCCS(=O)(=O)N1CCC2CCCCC2C1)N1CCCC(F)(F)C1] | 1-(3,3-difluoropiperidin-1-yl)-4-(octahydroisoquinoline-2-sulfonyl)butan-1-one | B | 3.87<br>3.93 | 393<br>393 |
| Im.28 | 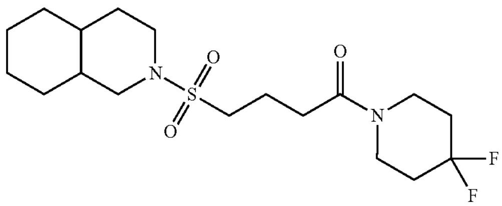 [SMILES: O=C(CCCS(=O)(=O)N1CCC2CCCCC2C1)N1CCC(F)(F)CC1] | 1-(4,4-difluoropiperidin-1-yl)-4-(octahydroisoquinoline-2-sulfonyl)butan-1-one | B | 3.87<br>3.94 | 393<br>393 |
| Im.29 | 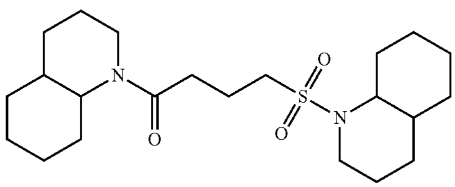 [SMILES: O=C(CCCS(=O)(=O)N1CCCC2CCCCC21)N1CCCC2CCCCC21] | 4-(octahydroquinoline-1-sulfonyl)-1-(octahydroquinolin-1-yl)butan-1-one | B | 4.51 | 411 |
| Im.30 | 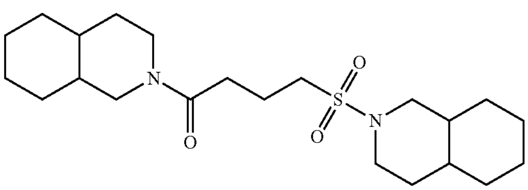 [SMILES: O=C(CCCS(=O)(=O)N1CCC2CCCCC2C1)N1CCC2CCCCC2C1] | 4-(octahydroisoquinoline-2-sulfonyl)-1-(octahydroisoquinolin-2-yl)butan-1-one | B | 4.63<br>4.70 | 411<br>411 |
| Ia.168 | 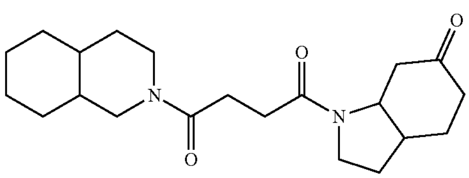 [SMILES: O=C1CCC2CCN(C(=O)CCC(=O)N3CCC4CCCCC4C3)C2C1] | 1-(octahydroisoquinolin-2-yl)-4-(6-oxooctahydroindol-1-yl)butane-1,4-dione | B | 4.33<br>4.41 | 361<br>361 |
| Ia.169 | 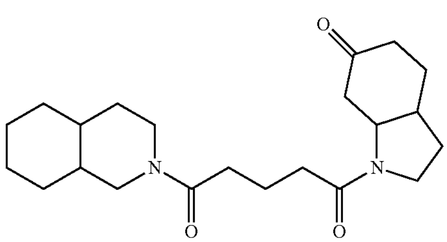 [SMILES: O=C1CCC2CCN(C(=O)CCCC(=O)N3CCC4CCCCC4C3)C2C1] | 1-(octahydroisoquinolin-2-yl)-5-(6-oxooctahydroindol-1-yl)pentane-1,5-dione | B | 4.38<br>4.48 | 375<br>375 |
| Ia.170 | 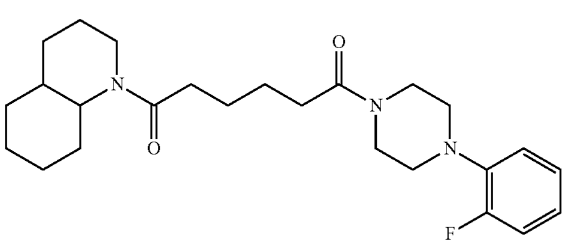 [SMILES: O=C(CCCCC(=O)N1CCCC2CCCCC21)N1CCN(c2ccccc2F)CC1] | 1-[4-(2-fluorophenyl)piperazin-1-yl]-6-(octahydroquinolin-1-yl)hexane-1,6-dione | B | 4.09 | 430 |

| Ex. | structure | name | method | tr (min) | m/z |
|---|---|---|---|---|---|
| Ia.171 | 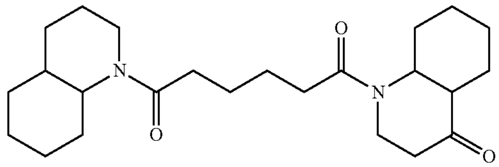 [SMILES: O=C1CCN(C(=O)CCCCC(=O)N2CCCC3CCCCC32)C2CCCCC12] | 1-(octahydroquinolin-1-yl)-6-(4-oxooctahydroquinolin-1-yl)hexane-1,6-dione | B | 3.72 | 403 |
| Ia.172 | 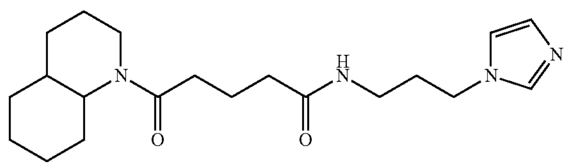 [SMILES: O=C(CCCC(=O)N1CCCC2CCCCC21)NCCCn1ccnc1] | 5-(octahydroquinolin-1-yl)-5-oxopentanoic acid N-[3-(1H-imidazol-1-yl)propyl]amide | B | 2.29 | 361 |
| Ia.173 | 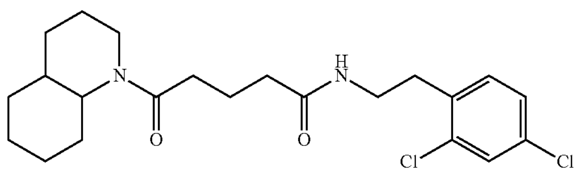 [SMILES: O=C(CCCC(=O)N1CCCC2CCCCC21)NCCc1ccc(Cl)cc1Cl] | 5-(octahydroquinolin-1-yl)-5-oxopentanoic acid N-(2,4-dichlorophenethyl)amide | B | 4.20 | 425, 427 |
| Ia.174 | 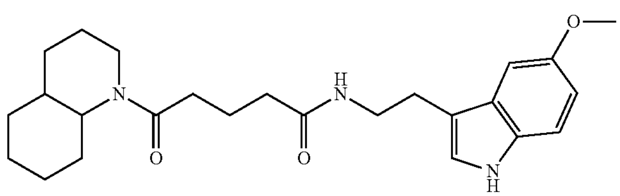 [SMILES: COc1ccc2[nH]cc(CCNC(=O)CCCC(=O)N3CCCC4CCCCC43)c2c1] | 5-(octahydroquinolin-1-yl)-5-oxopentanoic acid N-[2-(5-methoxy-1H-indol-3-yl)ethyl]amide | B | 3.47 | 426 |
| Ia.175 | 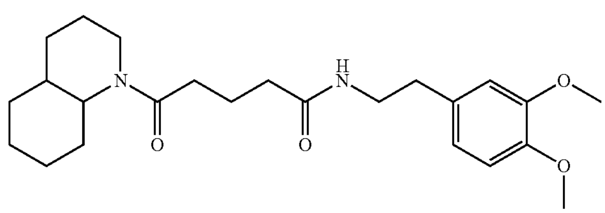 [SMILES: COc1ccc(CCNC(=O)CCCC(=O)N2CCCC3CCCCC32)cc1OC] | 5-(octahydroquinolin-1-yl)-5-oxopentanoic acid N-(3,4-dimethoxyphenethyl]amide | B | 3.41 | 417 |
| Ia.176 | 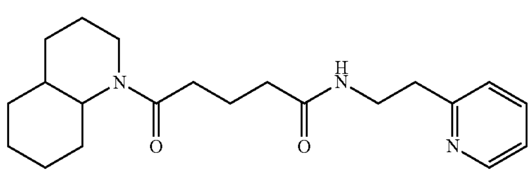 [SMILES: O=C(CCCC(=O)N1CCCC2CCCCC21)NCCc1ccccn1] | 5-(octahydroquinolin-1-yl)-5-oxopentanoic acid N-[2-(pyridin-2-yl)ethyl]amide | B | 2.34 | 358 |
| Ia.177 | 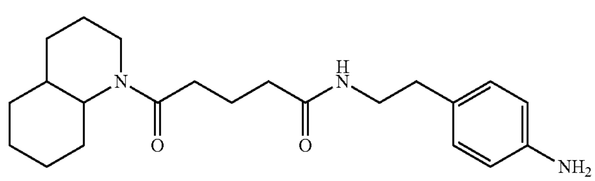 [SMILES: Nc1ccc(CCNC(=O)CCCC(=O)N2CCCC3CCCCC32)cc1] | 5-(octahydroquinolin-1-yl)-5-oxopentanoic acid N-(4-aminophenethyl)amide | B | 2.44 | 372 |
| Ia.178 | 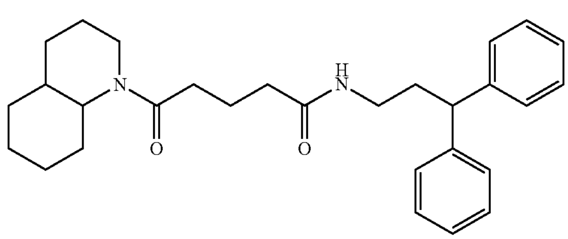 [SMILES: O=C(CCCC(=O)N1CCCC2CCCCC21)NCCC(c1ccccc1)c1ccccc1] | 5-(octahydroquinolin-1-yl)-5-oxopentanoic acid N-(3,3-diphenylpropyl)amide | B | 4.28 | 447 |

-continued

| Ex. | structure | name | method | tr (min) | m/z |
|---|---|---|---|---|---|
| Ia.179 | 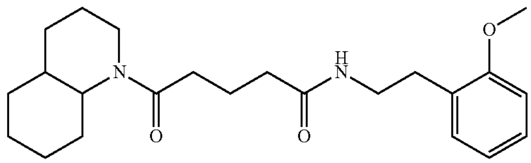 [SMILES: COc1ccccc1CCNC(=O)CCCC(=O)N1CCCC2CCCCC21] | 5-(octahydroquinolin-1-yl)-5-oxopentanoic acid N-(2-methoxyphenyl)amide | B | 3.74 | 387 |
| Ia.180 | 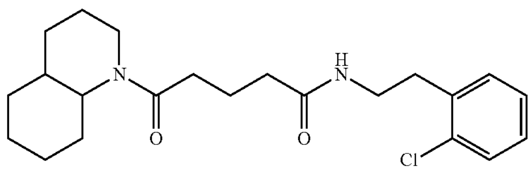 [SMILES: O=C(CCCC(=O)N1CCCC2CCCCC21)NCCc1ccccc1Cl] | 5-(octahydroquinolin-1-yl)-5-oxopentanoic acid N-(2-chlorophenethyl)amide | B | 3.88 | 391 |
| Ia.181 | 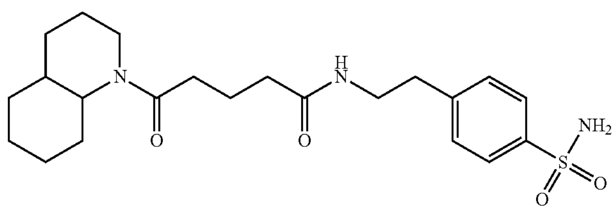 [SMILES: NS(=O)(=O)c1ccc(CCNC(=O)CCCC(=O)N2CCCC3CCCCC32)cc1] | 5-(octahydroquinolin-1-yl)-5-oxopentanoic acid N-(4-sulfamoylphenethyl)amide | B | 2.97 | 436 |
| Ia.182 | 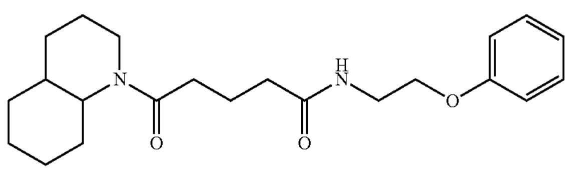 [SMILES: O=C(CCCC(=O)N1CCCC2CCCCC21)NCCOc1ccccc1] | 5-(octahydroquinolin-1-yl)-5-oxopentanoic acid N-(2-phenoxyethyl)amide | B | 3.67 | 373 |
| Ia.183 | 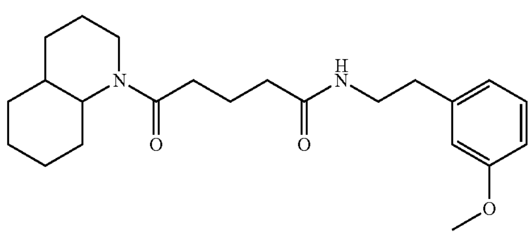 [SMILES: COc1cccc(CCNC(=O)CCCC(=O)N2CCCC3CCCCC32)c1] | 5-(octahydroquinolin-1-yl)-5-oxopentanoic acid N-(3-methoxyphenethyl)amide | B | 3.65 | 387 |
| Ia.184 | 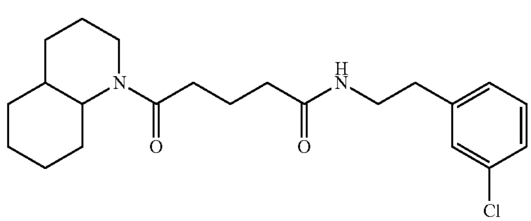 [SMILES: O=C(CCCC(=O)N1CCCC2CCCCC21)NCCc1cccc(Cl)c1] | 5-(octahydroquinolin-1-yl)-5-oxopentanoic acid N-(3-chlorophenethyl)amide | B | 3.92 | 391 |
| Ia.185 | 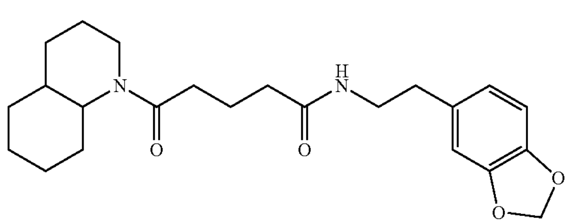 [SMILES: O=C(CCCC(=O)N1CCCC2CCCCC21)NCCc1ccc2c(c1)OCO2] | 5-(octahydroquinolin-1)-yl)-5-oxopentanoic acid N-[2-(benzo[d][1,3]dioxol-5-yl)ethyl]amide | B | 3.56 | 401 |

| Ex. | structure | name | method | tr (min) | m/z |
|---|---|---|---|---|---|
| Ia.186 | 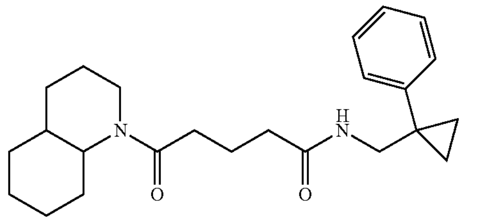 [SMILES: O=C(CCCC(=O)N1CCCC2CCCCC21)NCC1(c2ccccc2)CC1] | 5-(octahydroquinolin-1-yl)-5-oxopentanoic acid N-[(1-phenylcyclopropyl)methyl]amide | B | 3.92 | 383 |
| Ia.187 | 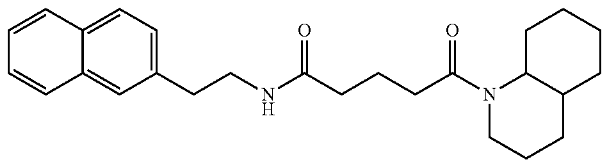 [SMILES: O=C(CCCC(=O)N1CCCC2CCCCC21)NCCc1ccc2ccccc2c1] | 5-(octahydroquinolin-1-yl)-5-oxopentanoic acid N-[2-(naphthalen-2-yl)ethyl]amide | B | 4.05 | 407 |
| Ia.188 | 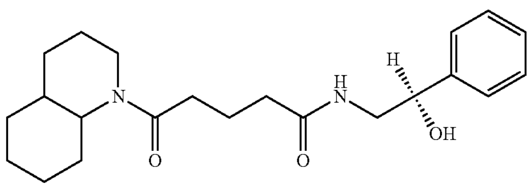 [SMILES: O=C(CCCC(=O)N1CCCC2CCCCC21)NC[C@H](O)c1ccccc1] | 5-(octahydroquinolin-1-yl)-5-oxopentanoic acid N-[(R)-2-phenyl-2-hydroxyethyl]amide | B | 3.19 | 373 |
| Ia.189 | 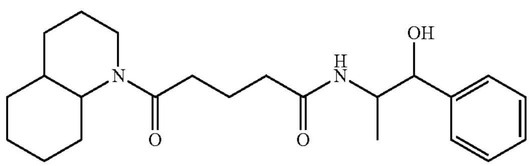 [SMILES: CC(NC(=O)CCCC(=O)N1CCCC2CCCCC21)C(O)c1ccccc1] | 5-(octahydroquinolin-1-yl)-5-oxopentanoic acid N-[(1R,2S)-1-phenyl-1-hydroxypropan-2-yl]amide | B | 3.37 | 387 |
| Ia.190 | 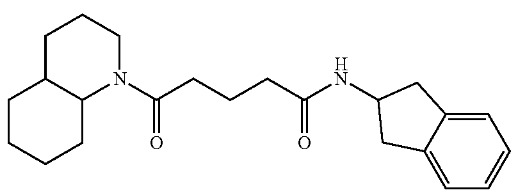 [SMILES: O=C(CCCC(=O)N1CCCC2CCCCC21)NC1Cc2ccccc2C1] | 5-(octahydroquinolin-1-yl)-5-oxopentanoic acid N-(2,3-dihydro-1H-inden-2-yl)amide | B | 3.77 | 369 |
| Ia.191 | 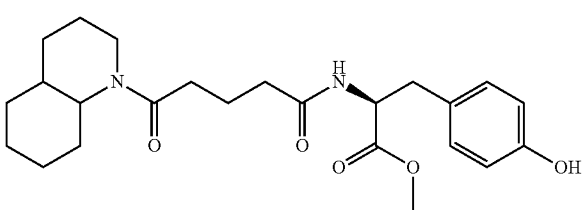 [SMILES: COC(=O)[C@H](Cc1ccc(O)cc1)NC(=O)CCCC(=O)N1CCCC2CCCCC21] | (2S)-3-(4-hydroxyphenyl)-2-[5-(octahydroquinolin-1-yl)-5-oxopentanamide]propanoic acid methyl ester | B | 3.21 | 431 |
| Ia.192 | 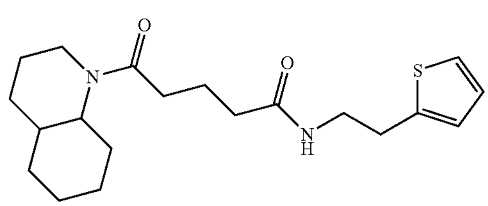 [SMILES: O=C(CCCC(=O)N1CCCC2CCCCC21)NCCc1cccs1] | 5-(octahydroquinolin-1-yl)-5-oxopentanoic acid N-[2-(thiophen-2-yl)ethyl]amide | B | 3.58 | 363 |
| Ia.193 | 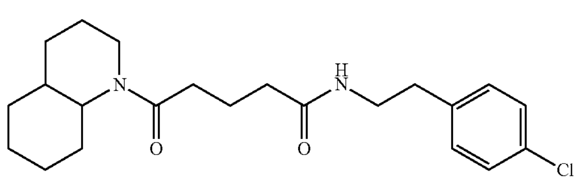 [SMILES: O=C(CCCC(=O)N1CCCC2CCCCC21)NCCc1ccc(Cl)cc1] | 5-(octahydroquinolin-1-yl)-5-oxopentanoic acid N-(4-chlorophenethyl)amide | B | 3.93 | 391 |

-continued

| Ex. | structure | name | method | tr (min) | m/z |
|---|---|---|---|---|---|
| Ia.194 | 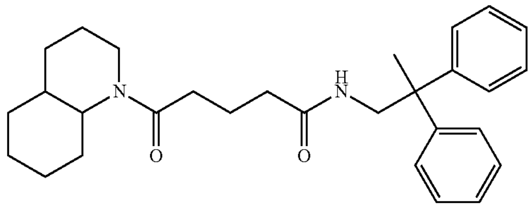 [SMILES: CC(CNC(=O)CCCC(=O)N1CCCC2CCCCC21)(c1ccccc1)c1ccccc1] | 5-(octahydroquinolin-1-yl)-5-oxopentanoic acid N-(2,2-diphenylpropyl)amide | B | 4.39 | 447 |
| Ia.195 | 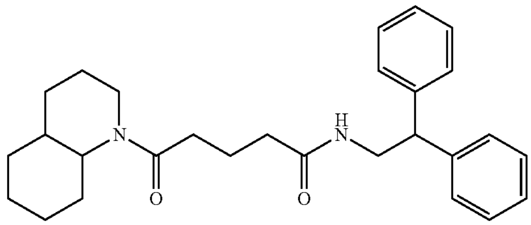 [SMILES: O=C(CCCC(=O)N1CCCC2CCCCC21)NCC(c1ccccc1)c1ccccc1] | 5-(octahydroquinolin-1-yl)-5-oxopentanoic acid N-(2,2-diphenylethyl)amide | B | 4.16 | 433 |
| Ia.196 | 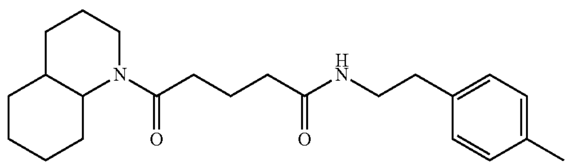 [SMILES: Cc1ccc(CCNC(=O)CCCC(=O)N2CCCC3CCCCC32)cc1] | 5-(octahydroquinolin-1-yl)-5-oxopentanoic acid N-(4-methylphenethyl)amide | B | 3.88 | 371 |
| Ia.197 | 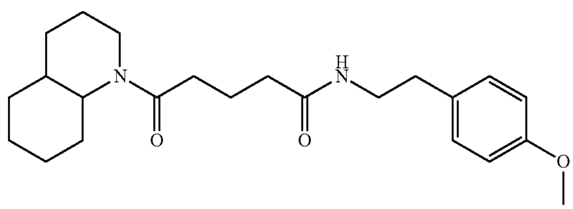 [SMILES: COc1ccc(CCNC(=O)CCCC(=O)N2CCCC3CCCCC32)cc1] | 5-(octahydroquinolin-1-yl)-5-oxopentanoic acid N-(4-methoxyphenethyl)amide | B | 3.61 | 387 |
| Ia.198 | 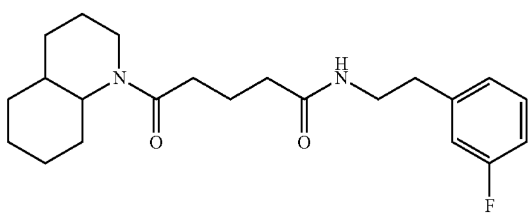 [SMILES: O=C(CCCC(=O)N1CCCC2CCCCC21)NCCc1cccc(F)c1] | 5-(octahydroquinolin-1-yl)-5-oxopentanoic acid N-(3-fluorophenethyl)amide | B | 3.72 | 375 |
| Ia.199 | 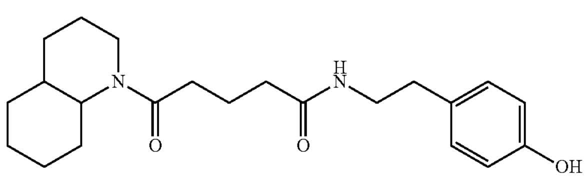 [SMILES: O=C(CCCC(=O)N1CCCC2CCCCC21)NCCc1ccc(O)cc1] | 5-(octahydroquinolin-1-yl)-5-oxopentanoic acid N-(4-hydroxyphenethyl)amide | B | 3.10 | 373 |
| Ia.200 | 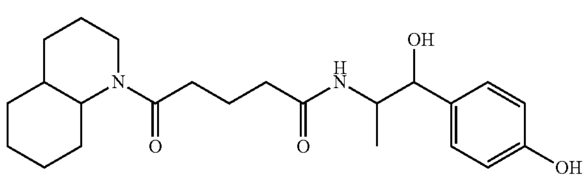 [SMILES: CC(NC(=O)CCCC(=O)N1CCCC2CCCCC21)C(O)c1ccc(O)cc1] | 5-(octahydroquinolin-1-yl)-5-oxopentanoic acid N-(1-hydroxyl-1-(4-hydroxyphenyl)propan-2-yl)amide | B | 2.88 | 403 |
| Ia.201 | 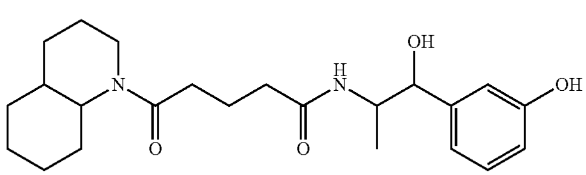 [SMILES: CC(NC(=O)CCCC(=O)N1CCCC2CCCCC21)C(O)c1cccc(O)c1] | 5-(octahydroquinolin-1-yl)-5-oxopentanoic acid N-(1-hydroxyl-1-(3-hydroxyphenyl)propan-2-yl)amide | B | 3.00 | 403 |

| Ex. | structure | name | method | tr (min) | m/z |
|---|---|---|---|---|---|
| Ia.202 | 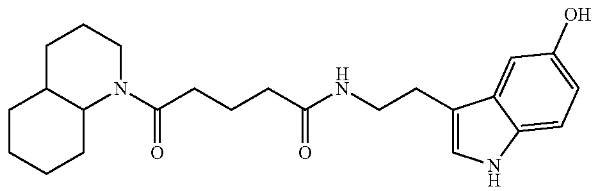 [SMILES: O=C(CCCC(=O)N1CCCC2CCCCC21)NCCc1c[nH]c2ccc(O)cc12] | 5-(octahydroquinolin-1-yl)-5-oxopentanoic acid N-[2-(5-hydroxyl-1H-indol-3-yl)ethyl]amide | B | 3.04 | 412 |
| Ia.203 | 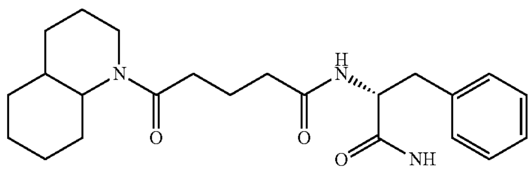 [SMILES: NC(=O)[C@@H](Cc1ccccc1)NC(=O)CCCC(=O)N1CCCC2CCCCC21] | 5-(octahydroquinolin-1-yl)-5-oxopentanoic acid N-[(R)-1-amino-3-phenyl-1-oxopropan-2-yl]amide | B | 3.19 | 400 |
| Ia.204 | 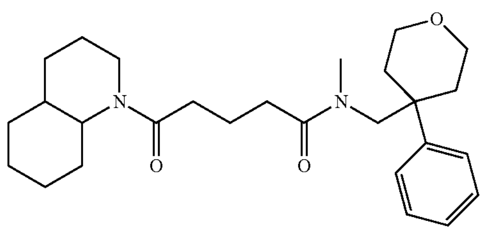 [SMILES: CN(CC1(c2ccccc2)CCOCC1)C(=O)CCCC(=O)N1CCCC2CCCCC21] | N-methyl-5-(octahydroquinolin-1-yl)-5-oxopentanoic acid N-((4-phenyltetrahydro-2H-pyran-4-yl)methyl)amide | B | 3.89 | 441 |
| Ia.205 | 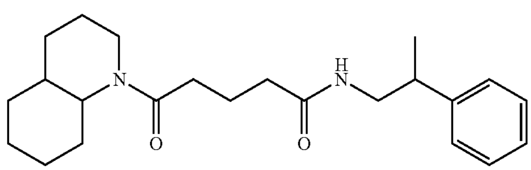 [SMILES: CC(CNC(=O)CCCC(=O)N1CCCC2CCCCC21)c1ccccc1] | 5-(octahydroquinolin-1-yl)-5-oxopentanoic acid N-(2-phenylpropyl)amide | B | 4.02 | 385 |
| Ia.206 | 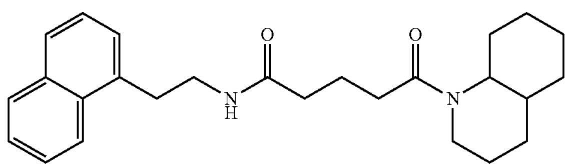 [SMILES: O=C(CCCC(=O)N1CCCC2CCCCC21)NCCc1cccc2ccccc12] | 5-(octahydroquinolin-1-yl)-5-oxopentanoic acid N-[2-(naphthalen-1-yl)ethyl]amide | B | 4.06 | 407 |
| Ia.207 | 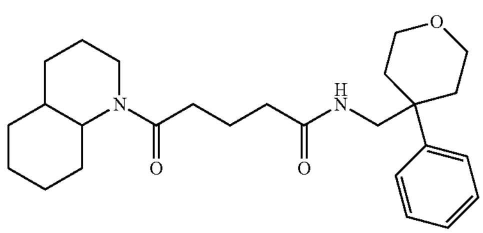 [SMILES: O=C(CCCC(=O)N1CCCC2CCCCC21)NCC1(c2ccccc2)CCOCC1] | 5-(octahydroquinolin-1-yl)-5-oxopentanoic acid N-[(4-phenyltetrahydro-2H-pyran-4-yl)methyl]amide | B | 3.06 | 427 |
| Ia.208 | 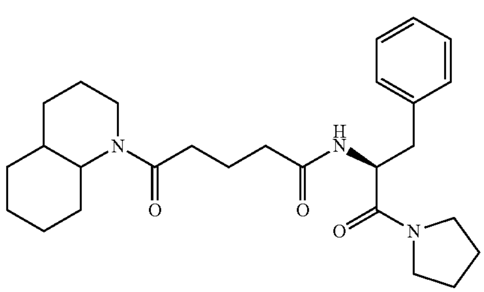 [SMILES: O=C(CCCC(=O)N1CCCC2CCCCC21)N[C@@H](Cc1ccccc1)C(=O)N1CCCC1] | 5-(octahydroquinolin-1-yl)-5-oxopropanoic acid N-[(S)-3-phenyl-1-oxo-1-(pyrrolidin-1-yl)propan-2-yl]amide | B | 3.65 | 454 |

| Ex. | structure | name | method | tr (min) | m/z |
|---|---|---|---|---|---|
| Ia.209 | 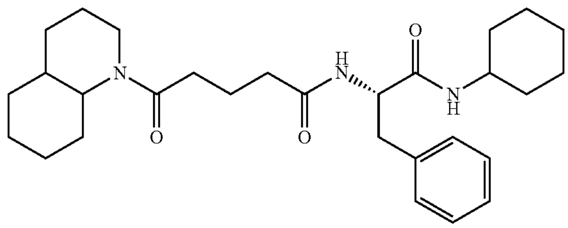 [SMILES: O=C(CCCC(=O)N1CCCC2CCCCC21)N[C@@H](Cc1ccccc1)C(=O)NC1CCCCC1] | 5-(octahydroquinolin-1-yl)-5-oxopentanoic acid N-[(S)-1-(cyclohexylamino)-3-phenylpropane-1-oxo-2-yl]amide | B | 4.06 | 482 |
| Ia.210 | 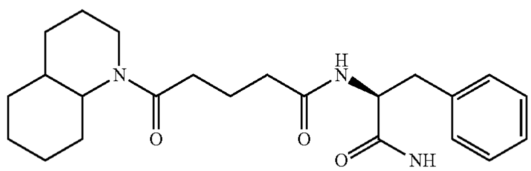 [SMILES: NC(=O)[C@H](Cc1ccccc1)NC(=O)CCCC(=O)N1CCCC2CCCCC21] | 5-(octahydroquinolin-1-yl)-5-oxopentanoic acid N-[(S)-1-amino-3-phenyl-1-oxopropan-2-yl]amide | B | 3.19 | 400 |
| Ia.211 | 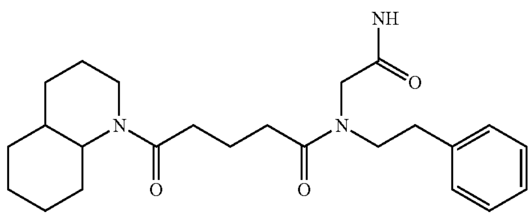 [SMILES: NC(=O)CN(CCc1ccccc1)C(=O)CCCC(=O)N1CCCC2CCCCC21] | N-(2-amino-2-oxoethyl)-5-(octahydroquinolin-1-yl)-5-oxopentanoic acid N-phenethylamide | B | 3.41 | 414 |
| Ia.212 | 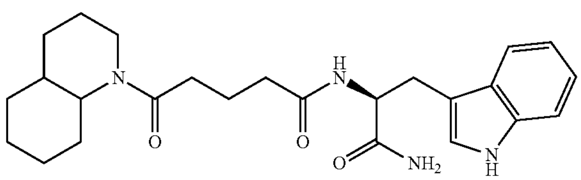 [SMILES: NC(=O)[C@H](Cc1c[nH]c2ccccc12)NC(=O)CCCC(=O)N1CCCC2CCCCC21] | 5-(octahydroquinolin-1-yl)-5-oxopentanoic acid N-[(S)-1-amino-3-(1H-indol-3-yl)-1-oxopropan-2-yl]amide | B | 3.15 | 439 |
| Ia.213 | 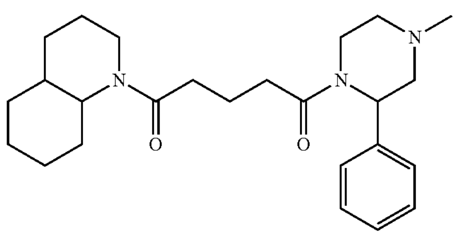 [SMILES: CN1CCN(C(=O)CCCC(=O)N2CCCC3CCCCC32)C(c2ccccc2)C1] | 1-(2-phenyl-4-methylpiperazin-1-yl)-5-(octahydroquinolin-1-yl)pentane-1,5-dione | B | 2.58 | 412 |
| Ia.214 | 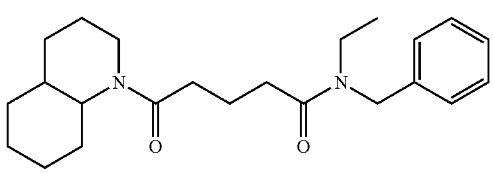 [SMILES: CCN(Cc1ccccc1)C(=O)CCCC(=O)N1CCCC2CCCCC21] | 5-(octahydroquinolin-1-yl)-5-oxopentanoic acid N-benzyl-N-ethylamide | B | 4.06 | 371 |
| Ia.215 | 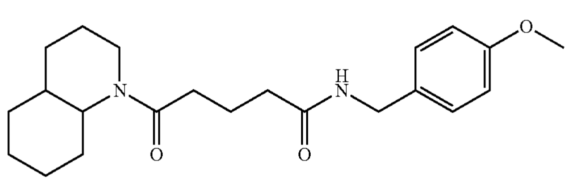 [SMILES: COc1ccc(CNC(=O)CCCC(=O)N2CCCC3CCCCC32)cc1] | 5-(octahydroquinolin-1-yl)-5-oxopentanoic acid N-(4-methoxybenzyl)amide | B | 3.50 | 373 |

-continued

| Ex. | structure | name | method | tr (min) | m/z |
|---|---|---|---|---|---|
| Ia.216 | 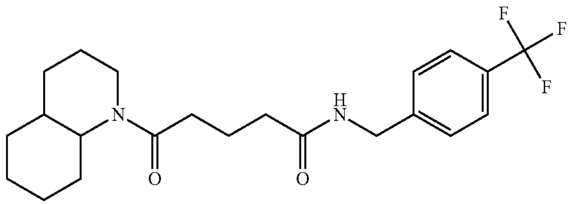 [SMILES: O=C(CCCC(=O)N1CCCC2CCCCC21)NCc1ccc(C(F)(F)F)cc1] | 5-(octahydroquinolin-1-yl)-5-oxopentanoic acid N-(4-(trifluoromethyl)benzyl)amide | B | 3.97 | 411 |
| Ia.217 | 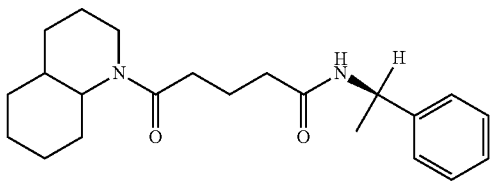 [SMILES: C[C@@H](NC(=O)CCCC(=O)N1CCCC2CCCCC21)c1ccccc1] | 5-(octahydroquinolin-1-yl)-5-oxopentanoic acid N-[(R)-1-phenylethyl]amide | B | 3.70 | 357 |
| Ia.218 | 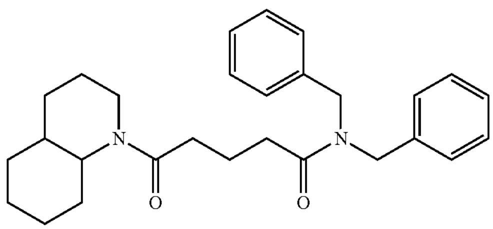 [SMILES: O=C(CCCC(=O)N1CCCC2CCCCC21)N(Cc1ccccc1)Cc1ccccc1] | 5-(octahydroquinolin-1-yl)-5-oxopentanoic acid N,N-dibenzylamide | B | 4.53 | 433 |
| Ia.219 | 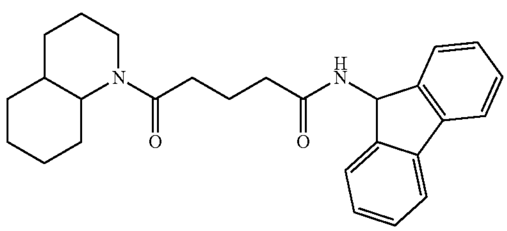 [SMILES: O=C(CCCC(=O)N1CCCC2CCCCC21)NC1c2ccccc2-c2ccccc21] | 5-(octahydroquinolin-1-yl)-5-oxopentanoic acid N-(9H-fluoren-9-yl)amide | B | 4.18 | 417 |
| Ia.220 | 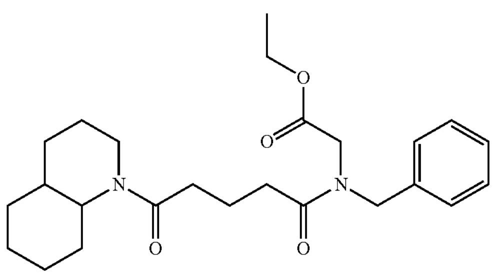 [SMILES: CCOC(=O)CN(Cc1ccccc1)C(=O)CCCC(=O)N1CCCC2CCCCC21] | 2-(N-benzyl-5-(octahydroquinolin-1-yl)-5-oxopentanamide)acetic acid ethyl ester | B | 4.12 | 429 |
| Ia.221 | 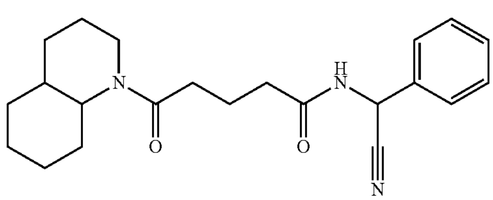 [SMILES: N#CC(NC(=O)CCCC(=O)N1CCCC2CCCCC21)c1ccccc1] | 5-(octahydroquinolin-1-yl)-5-oxopentanoic acid N-[cyano(phenyl)methyl]amide | B | 3.68 | 368 |
| Ia.222 | 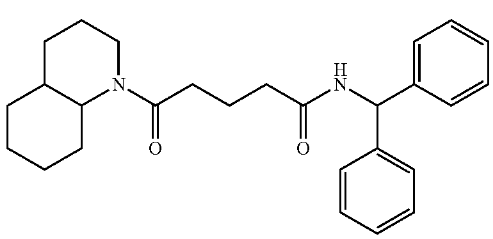 [SMILES: O=C(CCCC(=O)N1CCCC2CCCCC21)NC(c1ccccc1)c1ccccc1] | 5-(octahydroquinolin-1-yl)-5-oxopentanoic acid N-benzhydrylamide | B | 4.15 | 419 |

| Ex. | structure | name | method | tr (min) | m/z |
|---|---|---|---|---|---|
| Ia.223 | 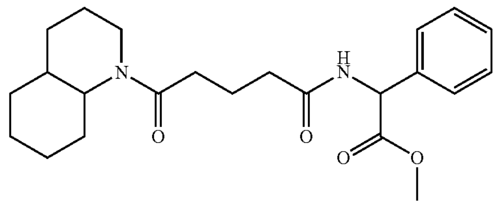 [SMILES: COC(=O)C(NC(=O)CCCC(=O)N1CCCC2CCCCC21)c1ccccc1] | (2R)-2-(5-(octahydroquinolin-1-yl)-5-oxopentanamido)-2-phenylacetic acid methyl ester | B | 3.67 | 401 |
| Ia.224 | 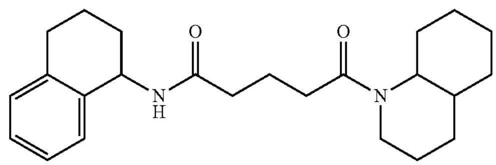 [SMILES: O=C(CCCC(=O)N1CCCC2CCCCC21)NC1CCCc2ccccc21] | 5-(octahydroquinolin-1-yl)-5-oxopentanoic acid N-(1,2,3,4-tetrahydronaphthalen-1-yl)amide | B | 3.96 | 383 |
| Ia.225 | 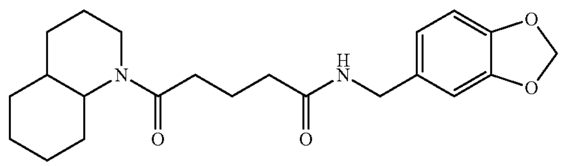 [SMILES: O=C(CCCC(=O)N1CCCC2CCCCC21)NCc1ccc2c(c1)OCO2] | 5-(octahydroquinolin-1-yl)-5-oxopentanoic acid N-(benzo[d][1,3]dioxol-5-yl methyl)amide | B | 3.46 | 387 |
| Ia.226 | 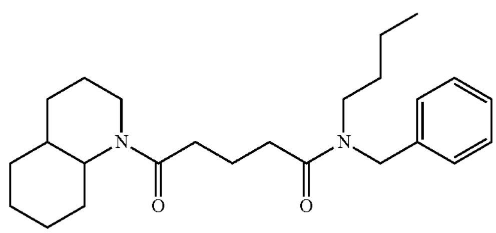 [SMILES: CCCCN(Cc1ccccc1)C(=O)CCCC(=O)N1CCCC2CCCCC21] | 5-(octahydroquinolin-1-yl)-5-oxopentanoic acid N-benzyl-N-butylamide | B | 4.51 | 399 |
| Ia.227 | 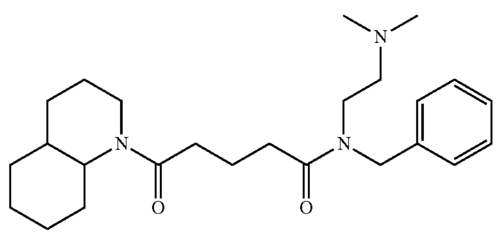 [SMILES: CN(C)CCN(Cc1ccccc1)C(=O)CCCC(=O)N1CCCC2CCCCC21] | 5-(octahydroquinolin-1-yl)-5-oxopentanoic acid N-benzyl-N-[2-(dimethylamino)ethyl]amide | B | 2.83 | 414 |
| Ia.228 | 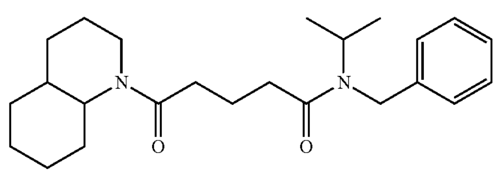 [SMILES: CC(C)N(Cc1ccccc1)C(=O)CCCC(=O)N1CCCC2CCCCC21] | 5-(octahydroquinolin-1-yl)-5-oxopentanoic acid N-benzyl-N-isopropylamide | B | 4.22 | 385 |
| Ia.229 | 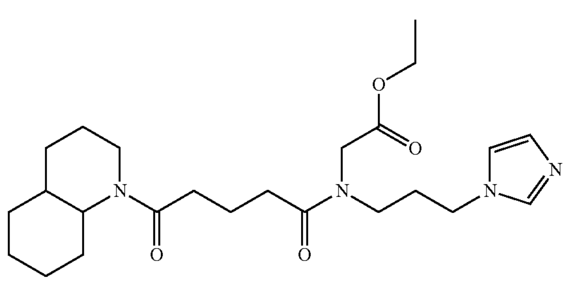 [SMILES: CCOC(=O)CN(CCCn1ccnc1)C(=O)CCCC(=O)N1CCCC2CCCCC21] | 2-[N-[3-(1H-imidazol-1-yl)propyl]-5-(octahydroquinolin-1-yl)-5-oxopentanamido]acetic acid ethyl ester | B | 2.67 | 447 |

-continued

| Ex. | structure | name | method | tr (min) | m/z |
|---|---|---|---|---|---|
| Ia.230 | 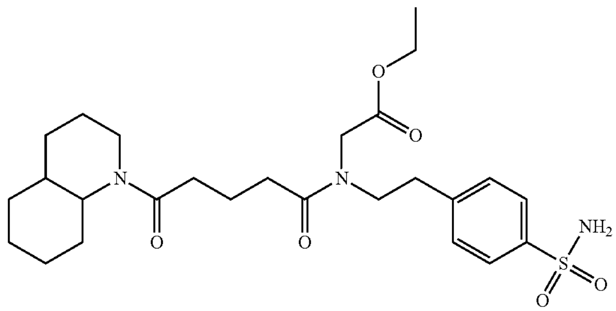 [SMILES: CCOC(=O)CN(CCc1ccc(S(N)(=O)=O)cc1)C(=O)CCCC(=O)N1CCCC2CCCCC21] | 2-[5-(octahydroquinolin-1-yl)-5-oxo-N-(4-sulfamoylphenethyl)pentan-amido]acetic acid ethyl ester | B | 3.43 | 522 |
| Ia.231 | 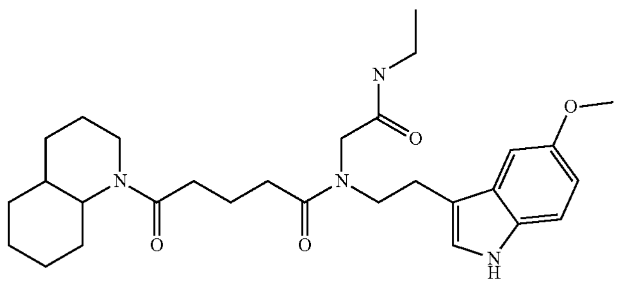 [SMILES: CCNC(=O)CN(CCc1c[nH]c2ccc(OC)cc12)C(=O)CCCC(=O)N1CCCC2CCCCC21] | 2-[N-[2-(5-methoxy-1H-indol-3-yl)ethyl]-5-(octahydroquinolin-1-yl)-5-oxopentanamido]acetic acid ethyl ester | B | 3.92 | 512 |
| Ia.232 | 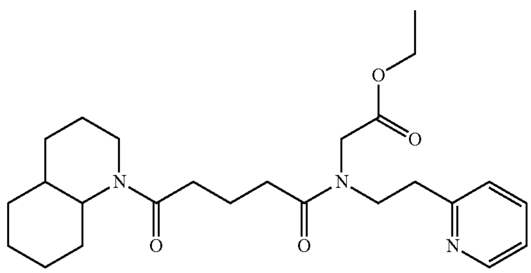 [SMILES: CCOC(=O)CN(CCc1ccccn1)C(=O)CCCC(=O)N1CCCC2CCCCC21] | 2-[5-(octahydroquinolin-1-yl)-5-oxo-N-[2-(pyridin-2-yl)ethyl]pentanamido]acetic acid ethyl ester | B | 2.79 | 444 |
| Ia.233 | 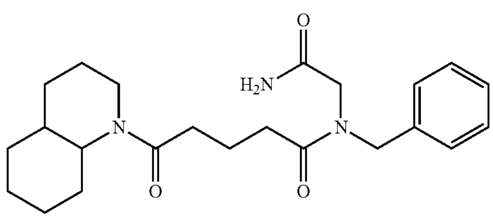 [SMILES: NC(=O)CN(Cc1ccccc1)C(=O)CCCC(=O)N1CCCC2CCCCC21] | 5-(octahydroquinolin-1-yl)-5-oxopentanoic acid N-(2-amino-2-oxoethyl)-N-benzylamide | B | 3.28 | 400 |
| Ia.234 | 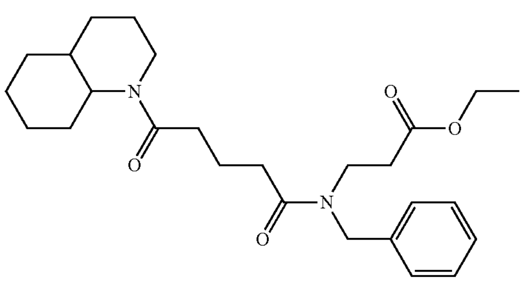 [SMILES: CCOC(=O)CCN(Cc1ccccc1)C(=O)CCCC(=O)N1CCCC2CCCCC21] | 3-[N-benzyl-5-(octahydroquinolin-1-yl)-5-oxopentanamido]propanoic acid ethyl ester | B | 4.15 | 443 |
| Ia.235 | 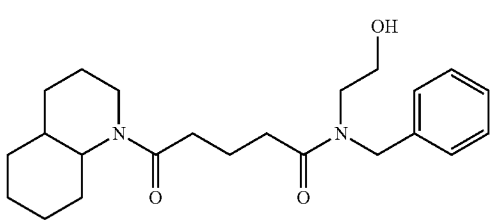 [SMILES: O=C(CCCC(=O)N1CCCC2CCCCC21)N(CCO)Cc1ccccc1] | 5-(octahydroquinolin-1-yl)-5-oxopentanoic acid N-benzyl-N-(2-hydroxyethyl)amide | B | 3.47 | 387 |

-continued

| Ex. | structure | name | method | tr (min) | m/z |
|---|---|---|---|---|---|
| Ia.236 | 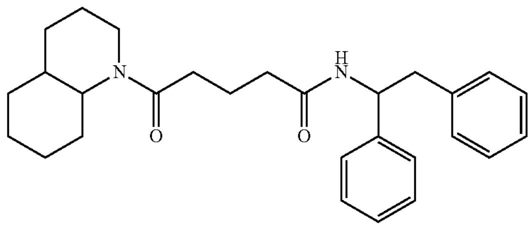 [SMILES: O=C(CCCC(=O)N1CCCC2CCCCC21)NC(Cc1ccccc1)c1ccccc1] | 5-(octahydroquinolin-1-yl)-5-oxopentanoic acid N-(1,2-diphenylethyl)amide | B | 4.21 | 433 |
| Ia.237 | 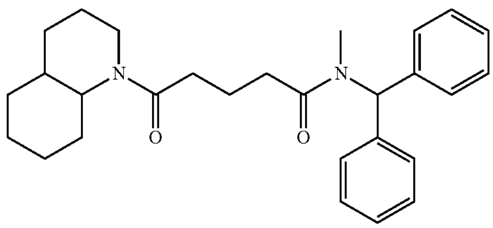 [SMILES: CN(C(=O)CCCC(=O)N1CCCC2CCCCC21)C(c1ccccc1)c1ccccc1] | 5-(octahydroquinolin-1-yl)-5-oxopentanoic acid N-benzhydryl-N-methylamide | B | 4.53 | 433 |
| Ia.238 | 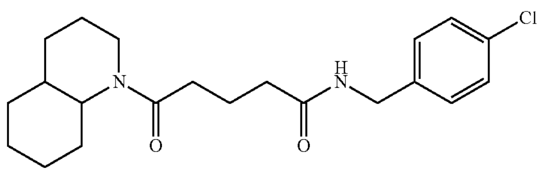 [SMILES: O=C(CCCC(=O)N1CCCC2CCCCC21)NCc1ccc(Cl)cc1] | 5-(octahydroquinolin-1-yl)-5-oxopentanoic acid N-(4-chlorobenzyl)amide | B | 3.82 | 377 |
| Ia.239 | 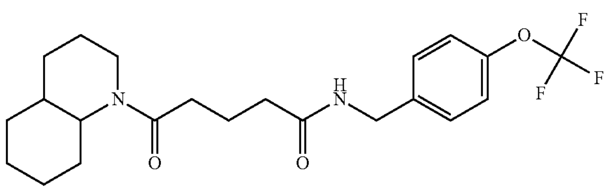 [SMILES: O=C(CCCC(=O)N1CCCC2CCCCC21)NCc1ccc(OC(F)(F)F)cc1] | 5-(octahydroquinolin-1-yl)-5-oxopentanoic acid N-[4-(trifluoromethoxy)benzyl]amide | B | 4.06 | 427 |
| Ia.240 | 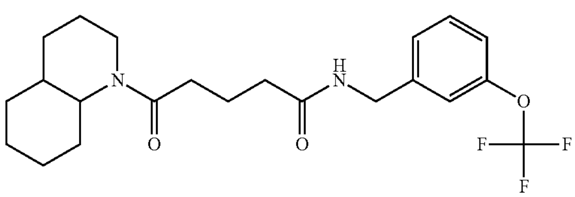 [SMILES: O=C(CCCC(=O)N1CCCC2CCCCC21)NCc1cccc(OC(F)(F)F)c1] | 5-(octahydroquinolin-1-yl)-5-oxopentanoic acid N-[3-(trifluoromethoxy)benzyl]amide | B | 4.06 | 427 |
| Ia.241 | 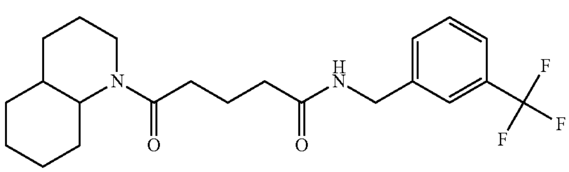 [SMILES: O=C(CCCC(=O)N1CCCC2CCCCC21)NCc1cccc(C(F)(F)F)c1] | 5-(octahydroquinolin-1-yl)-5-oxopentanoic acid N-[3-(trifluoromethyl)benzyl]amide | B | 3.97 | 411 |
| Ia.242 | 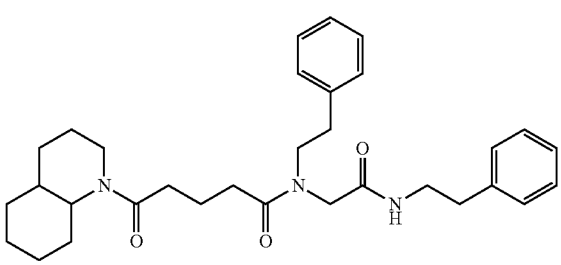 [SMILES: O=C(CN(CCc1ccccc1)C(=O)CCCC(=O)N1CCCC2CCCCC21)NCCc1ccccc1] | 5-(octahydroquinolin-1-yl)-5-oxopentanoic acid N-phenethyl-N-[2-(phenethylamino)-2-oxoethyl]amide | B | 4.25 | 518 |

-continued

| Ex. | structure | name | method | tr (min) | m/z |
|---|---|---|---|---|---|
| Ia.243 | 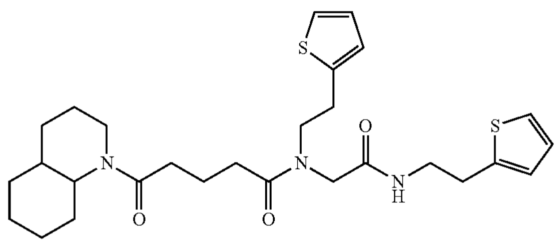 [SMILES: O=C(CN(CCc1cccs1)C(=O)CCCC(=O)N1CCCC2CCCCC21)NCCc1cccs1] | 5-(octahydroquinolin-1-yl) 5-oxopentanoic acid N-[2-oxo-2-{[2-(thiophen-2-yl)ethyl]amino}ethyl]-N-[2-(thiophen-2-yl)ethyl]amide | B | 4.11 | 530 |
| Ia.244 | 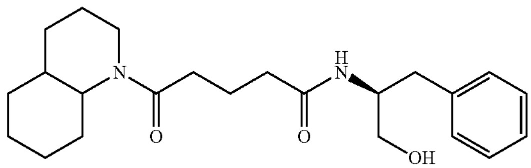 [SMILES: O=C(CCCC(=O)N1CCCC2CCCCC21)N[C@H](CO)Cc1ccccc1] | 5-(octahydroquinolin-1-yl)-5-oxopentanoic acid N-[(S)-3-phenyl-1-hydroxypropan-2-yl]amide | B | 3.31 | 387 |
| Ia.245 | 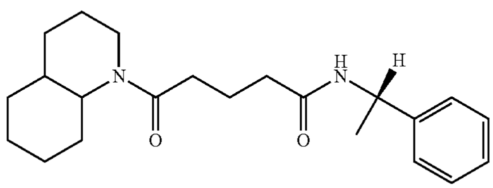 [SMILES: C[C@H](NC(=O)CCCC(=O)N1CCCC2CCCCC21)c1ccccc1] | 5-(octahydroquinolin-1-yl)-5-oxopentanoic acid N-[(S)-1-phenylethyl]amide | B | 3.70 | 357 |
| Ia.246 | 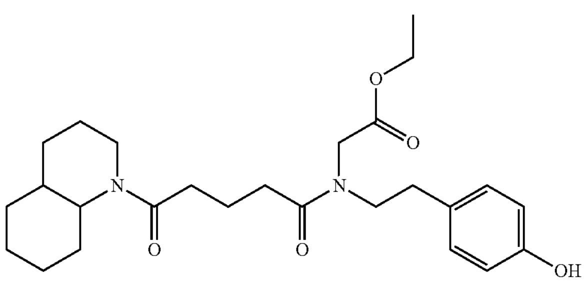 [SMILES: CCOC(=O)CN(CCc1ccc(O)cc1)C(=O)CCCC(=O)N1CCCC2CCCCC21] | 2-[N-(4-hydroxyphenethyl)-5-(octahydroquinolin-1-yl)-5-oxopentanamido]acetic acid ethyl ester | B | 3.59 | 459 |
| Ia.247 | 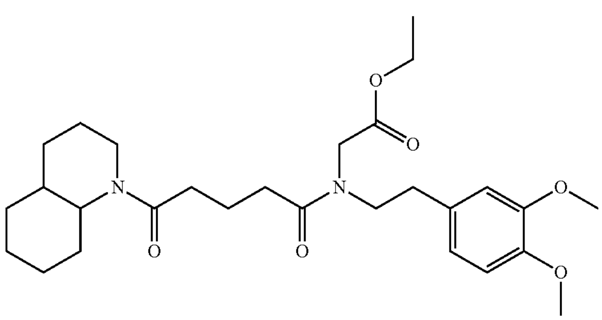 [SMILES: CCOC(=O)CN(CCc1ccc(OC)c(OC)c1)C(=O)CCCC(=O)N1CCCC2CCCCC21] | 2-(N-(3,4-dimethoxyphenethyl)-5-(octahydroquinolin-1-yl)-5-oxopentanamido]acetic acid ethyl ester | B | 3.91 | 503 |
| Ia.248 | 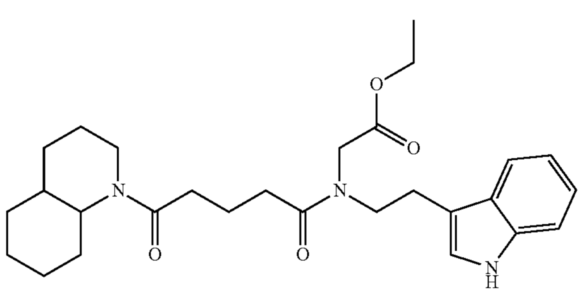 [SMILES: CCOC(=O)CN(CCc1c[nH]c2ccccc12)C(=O)CCCC(=O)N1CCCC2CCCCC21] | 2-[N-[2-(1H-indol-3-yl)ethyl]-5-(octahydroquinolin-1-yl)-5-oxopentanamido]acetic acid ethyl ester | B | 4.04 | 482 |

-continued

| Ex. | structure | name | method | tr (min) | m/z |
|---|---|---|---|---|---|
| Ia.249 | 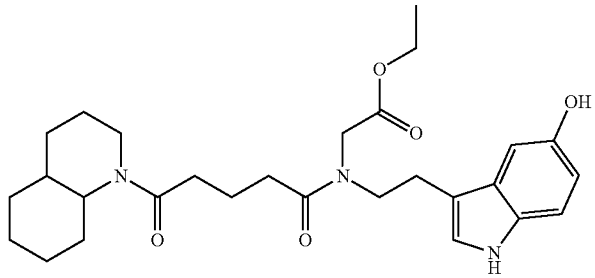 [SMILES: CCOC(=O)CN(CCc1c[nH]c2ccc(O)cc12)C(=O)CCCC(=O)N1CCCC2CCCCC21] | 2-[N-[2-(5-hydroxy-1H-indol-3-yl)ethyl]-5-(octahydroquinolin-1-yl)-5-oxopentanamido]acetic acid ethyl ester | B | 3.47 | 498 |
| Ia.250 | 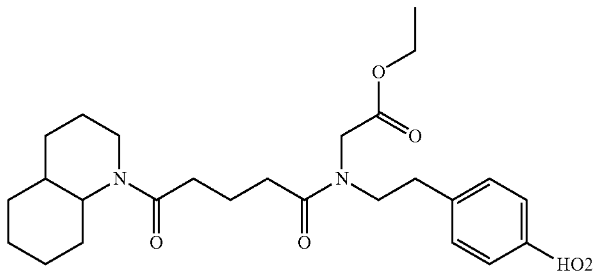 | 2-[N-(4-nitrophenethyl)-5-(octahydroquinolin-1-yl)-5-oxopentanamido]acetic acid ethyl ester | B | 4.10 | 488 |
| Ia.251 | 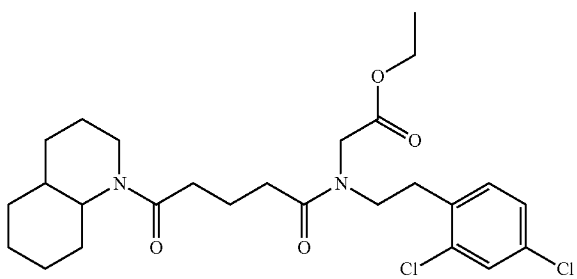 [SMILES: CCOC(=O)CN(CCc1ccc(Cl)cc1Cl)C(=O)CCCC(=O)N1CCCC2CCCCC21] | 2-(N-(2,4-dichlorophenethyl)-5-(octahydroquinolin-1-yl)-5-oxopentanamido]acetic acid ethyl ester | B | 4.73 | 511 |
| Ia.252 | 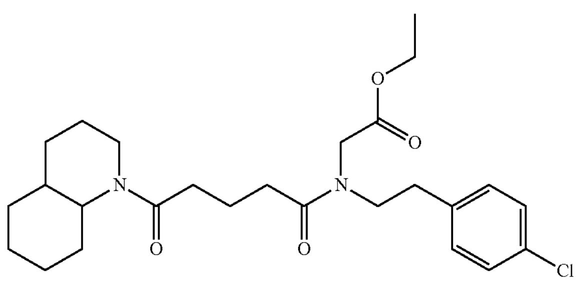 [SMILES: CCOC(=O)CN(CCc1ccc(Cl)cc1)C(=O)CCCC(=O)N1CCCC2CCCCC21] | 2-[N-(4-chlorophenethyl)-5-(octahydroquinolin-1-yl)-5-oxopentanamido]acetic acid ethyl ester | B | 4.45 | 477 |
| Ia.253 | 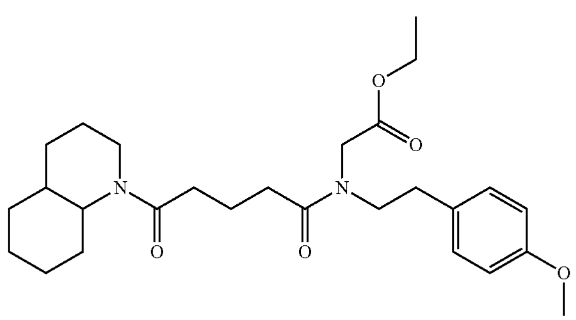 [SMILES: CCOC(=O)CN(CCc1ccc(OC)cc1)C(=O)CCCC(=O)N1CCCC2CCCCC21] | 2-[N-(4-methoxyphenethyl)-5-(octahydroquinolin-1-yl)-5-oxopentanamido]acetic acid ethyl ester | B | 4.14 | 473 |

| Ex. | structure | name | method | tr (min) | m/z |
|---|---|---|---|---|---|
| Ia.254 | 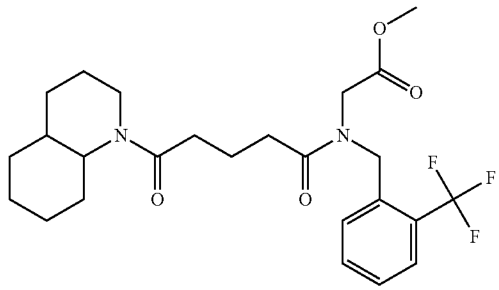 [SMILES: COC(=O)CN(Cc1ccccc1C(F)(F)F)C(=O)CCCC(=O)N1CCCC2CCCCC21] | 2-[5-(octahydroquinolin-1-yl)-5-oxo-N-[2-(trifluoromethyl)benzyl]pentanamido]acetic acid methyl ester | B | 4.27 | 483 |
| Ia.255 | 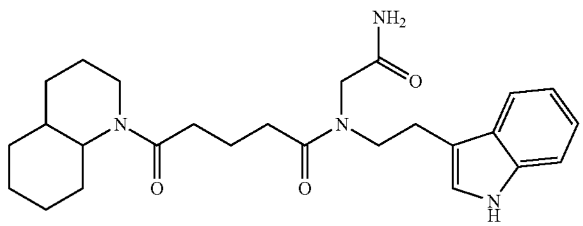 [SMILES: NC(=O)CN(CCc1c[nH]c2ccccc12)C(=O)CCCC(=O)N1CCCC2CCCCC21] | 5-(octahydroquinolin-1-yl)-5-oxopentanoic acid N-(2-amino-2-oxoethyl)-N-[2-(1H-indol-3-yl)ethyl]amide | B | 3.34 | 453 |
| Ia.256 | 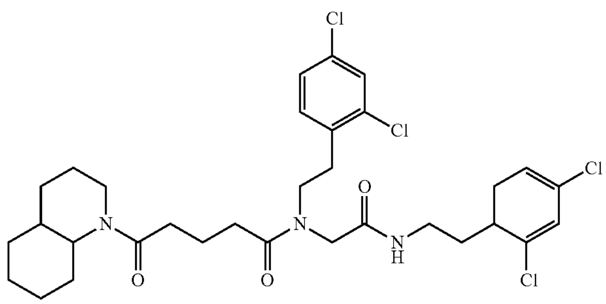 [SMILES: O=C(CN(CCc1ccc(Cl)cc1Cl)C(=O)CCCC(=O)N1CCCC2CCCCC21)NCCC1CC=C(Cl)C=C1Cl] | 5-(octahydroquinolin-1-yl)-5-oxopentanoic acid N-(2,4-dichlorophenethyl)-N-[2-[(2,4-dichlorophenethyl)amino]-2-oxoethyl]amide | B | 5.13 | 654, 656 |
| Ia.257 | 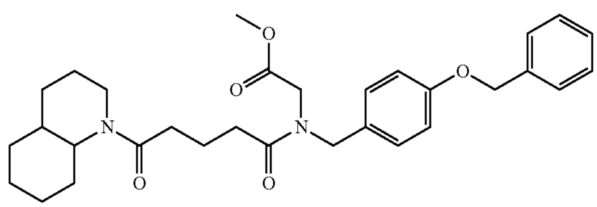 [SMILES: COC(=O)CN(Cc1ccc(OCc2ccccc2)cc1)C(=O)CCCC(=O)N1CCCC2CCCCC21] | 2-[N-[4-(benzyloxy)benzyl]-5-(octahydroquinolin-1-yl)-5-oxopentanamido]acetic acid methyl ester | B | 4.46 | 521 |
| Ia.258 | 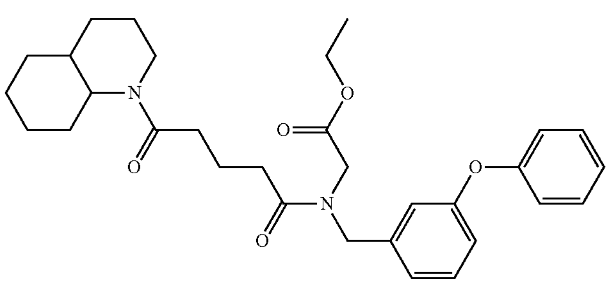 [SMILES: CCOC(=O)CN(Cc1cccc(Oc2ccccc2)c1)C(=O)CCCC(=O)N1CCCC2CCCCC21] | 2-[5-(octahydroquinolin-1-yl)-5-oxo-N-(3-phenoxybenzyl)pentan-amido]acetic acid ethyl ester | B | 4.65 | 521 |
| Ia.259 | 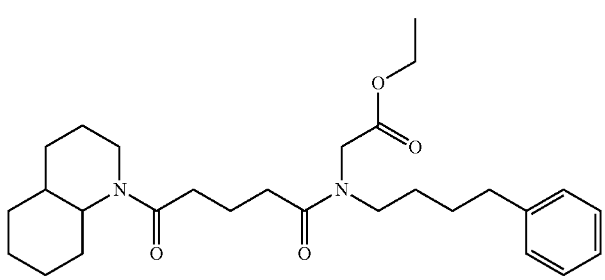 [SMILES: CCOC(=O)CN(CCCCc1ccccc1)C(=O)CCCC(=O)N1CCCC2CCCCC21] | 2-[5-(octahydroquinolin-1-yl)-5-oxo-N-(4-phenylbutyl)pentanamido]acetic acid ethyl ester | B | 4.54 | 471 |

-continued

| Ex. | structure | name | method | tr (min) | m/z |
|---|---|---|---|---|---|
| Ia.260 | 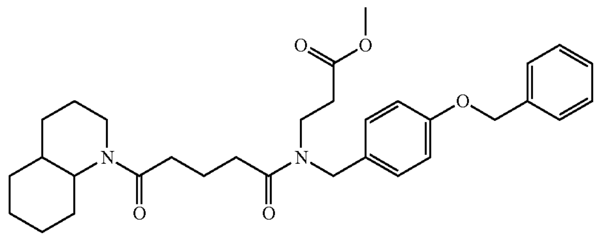 [SMILES: COC(=O)CCN(Cc1ccc(OCc2ccccc2)cc1)C(=O)CCCC(=O)N1CCCC2CCCCC21] | 3-[N-[4-(benzyloxy)benzyl]-5-(octahydroquinolin-1-yl)-5-oxopentanamido]propanoic acid methyl ester | B | 4.48 | 535 |
| Ia.261 | 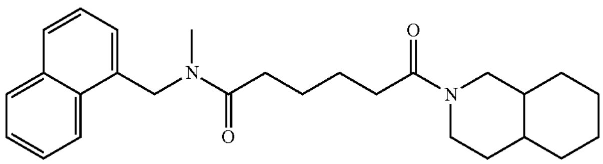 [SMILES: CN(Cc1cccc2ccccc12)C(=O)CCCCC(=O)N1CCC2CCCCC2C1] | 6-(octahydroisoquinolin-2-yl)-6-oxohexanoic acid N-methyl-N-(naphthalen-1-ylmethyl)amide | B | 4.31<br>4.40 | 421<br>421 |
| Ia.262 | 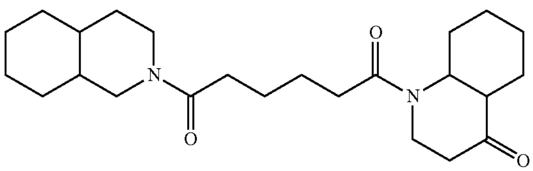 [SMILES: O=C1CCN(C(=O)CCCCC(=O)N2CCC3CCCCC3C2)C2CCCCC12] | 1-(octahydroisoquinolin-2-yl)-6-(4-oxooctahydroquinolin-1-yl)hexane-1,6-dione | B | 3.72<br>3.81 | 403<br>403 |
| Ia.263 | 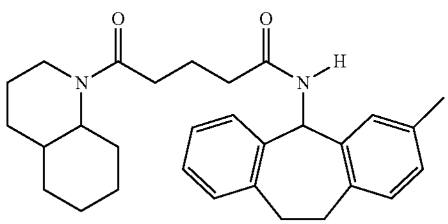 [SMILES: Cc1ccc2c(c1)C(NC(=O)CCCC(=O)N1CCCC3CCCCC31)c1ccccc1CC2] | 5-(octahydro-quinolin-1-yl)-5-oxo-pentanoic acid (3-methyl-10,11-dihydro-5H-dibenzo[a,d]cyclohepten-5-yl)amide | C | 5.01 | 459 |
| Ia.264 | 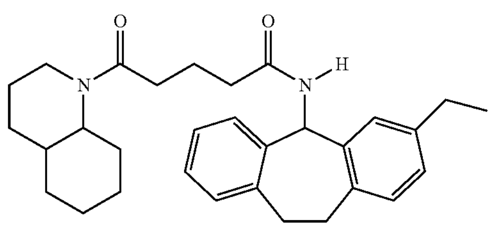 [SMILES: CCc1ccc2c(c1)C(NC(=O)CCCC(=O)N1CCCC3CCCCC31)c1ccccc1CC2] | 5-(octahydro-quinolin-1-yl)-5-oxo-pentanoic acid (3-ethyl-10,11-dihydro-5H-dibenzo[a,d]cyclohepten-5-yl)amide | C | 5.20 | 473 |
| Ia.265 | 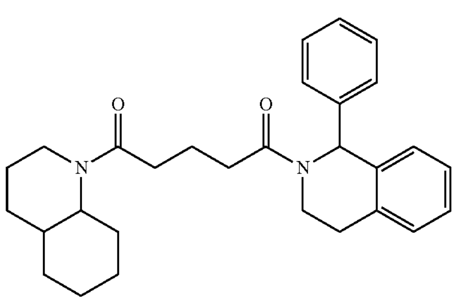 [SMILES: O=C(CCCC(=O)N1CCCC2CCCCC21)N1CCc2ccccc2C1c1ccccc1] | 5-[(R)-1-phenyl-3,4-dihydro-1H-isoquinolin-2-yl]-1-(octahydro-quinolin-1-yl)-pentane-1,5-dione | C | 5.02 | 445 |
| Ia.266 | 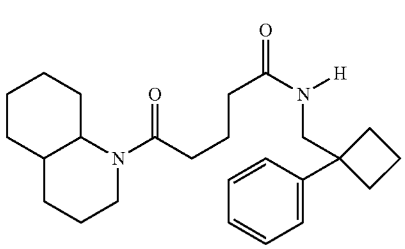 [SMILES: O=C(CCCC(=O)N1CCCC2CCCCC21)NCC1(c2ccccc2)CCC1] | 5-(octahydro-quinolin-1-yl)-5-oxo-pentanoic acid (1-phenyl-cyclobutylmethyl)amide | C | 4.64 | 397 |

| Ex. | structure | name | method | tr (min) | m/z |
|---|---|---|---|---|---|
| Ia.267 | 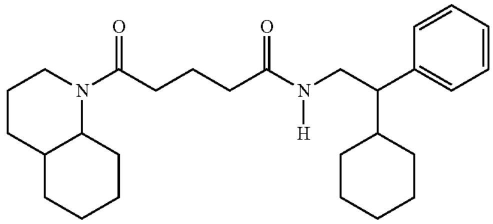 [SMILES: O=C(CCCC(=O)N1CCCC2CCCCC21)NCC(c1ccccc1)C1CCCCC1] | 5-(octahydro-quinolin-1-yl)-5-oxo-pentanoic acid (2-cyclohexyl-2-phenyl-ethyl)amide | C | 5.19 | 439 |

Ex. Ie.1

1-[5-(octahydroquinolin-1-yl)-5-oxopentyl]-3-tricyclo[3.3.1.1$^{3,7}$]decan-1-ylurea

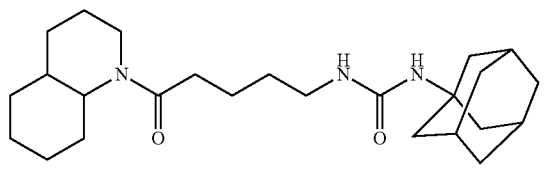 [SMILES: O=C(NCCCCC(=O)N1CCCC2CCCCC21)NC12CC3CC(CC(C3)C1)C2]

35 mg (0.15 mmol) of intermediate Vc.4 are dissolved in 2 mL of anhydrous THF and 23 μL (0.25 mmol) of Et$_3$N. Once dissolved 17.3 mg (0.1 mmol) of 1-adamantyl isocyanate are slowly added and it is refluxed for 2 days. AcOEt is then added and the resulting solution is sequentially washed with water, 1N HCl and brine. The organic phase is dried over anhydrous Na$_2$SO$_4$, it is filtered and the solvent is evaporated under reduced pressure yielding 47.5 mg of a yellowish oil identified as example Ie.1. Method B: tr: 4.27 min; m/z: 416.

The following examples were prepared in a manner similar to example Ie.1.

| Ex. | structure | name | method | tr (min) | m/z |
|---|---|---|---|---|---|
| Ie.2 | 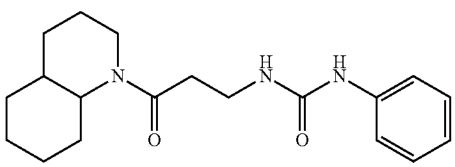 [SMILES: O=C(NCCC(=O)N1CCCC2CCCCC21)Nc1ccccc1] | 1-[3-(octahydroquinolin-1-yl)-3-oxopropyl]-3-phenylurea | B | 3.49 | 330 |
| Ie.3 | 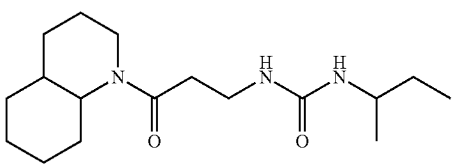 [SMILES: CCC(C)NC(=O)NCCC(=O)N1CCCC2CCCCC21] | 1-s-butyl-3-[3-(octahydroquinolin-1-yl)-3-oxopropyl]urea | B | 3.28<br>3.56 | 310<br>310 |
| Ie.4 | 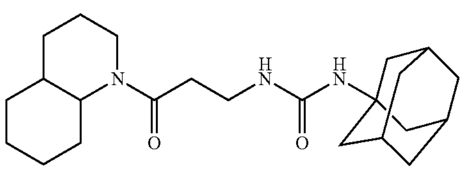 [SMILES: O=C(NCCC(=O)N1CCCC2CCCCC21)NC12CC3CC(CC(C3)C1)C2] | 1-[3-(octahydroquinolin-1-yl)-3-oxopropyl]-3-tricyclo[3.3.1.1$^{3.7}$]decan-1-ylurea | B | 4.18 | 388 |
| Ie.5 | 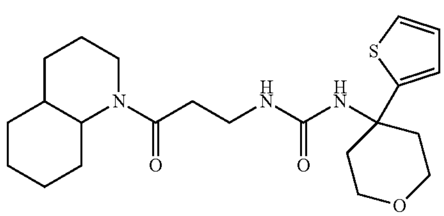 [SMILES: O=C(NCCC(=O)N1CCCC2CCCCC21)NC1(c2cccs2)CCOCC1] | 1-[3-(octahydroquinolin-1-yl)-3-oxopropyl]-3-(4-thiophen-2-yltetrahydropyran-4-yl)urea | B | 3.40 | 420 |
| Ie.6 | 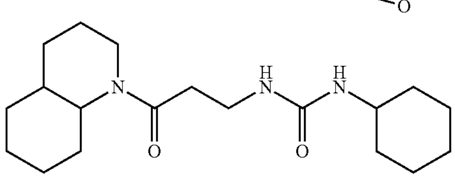 | 1-cyclohexyl-3-[3-(octahydroquinolin-1-yl)-3-oxopropyl]urea | A | 6.55 | 336 |

-continued

| Ex. | structure | name | method | tr (min) | m/z |
|---|---|---|---|---|---|
| Ie.7 | 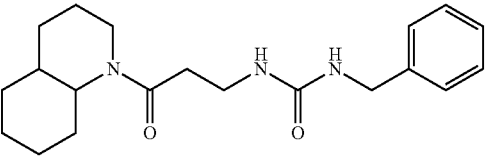 | 1-benzyl-3-[3-(octahydroquinolin-1-yl)-3-oxopropyl]urea | A | 6.28 | 344 |
| Ie.8 | 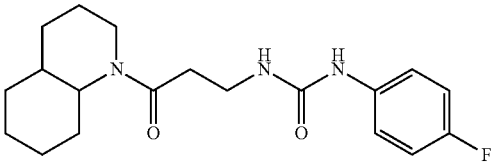 [SMILES: O=C(NCCC(=O)N1CCCC2CCCCC21)Nc1ccc(F)cc1] | 1-(4-fluorophenyl)-3-[3-(octahydroquinolin-1-yl)-3-oxopropyl]urea | A | 6.56 | 348 |
| Ie.9 | 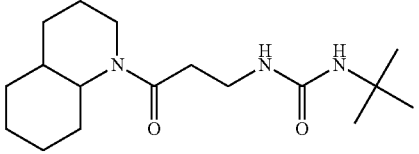 [SMILES: CC(C)(C)NC(=O)NCCC(=O)N1CCCC2CCCCC21] | 1-t-butyl-3-[3-(octahydroquinolin-1-yl)-3-oxopropyl]urea | A | 6.25 | 310 |
| Ie.10 | 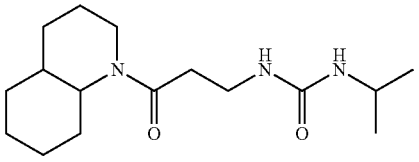 [SMILES: CC(C)NC(=O)NCCC(=O)N1CCCC2CCCCC21] | 1-isopropyl-3-[3-(octahydroquinolin-1-yl)-3-oxopropyl]urea | A | 5.65 | 296 |
| Ie.11 | 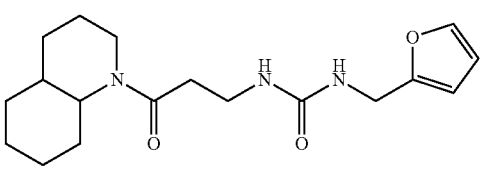 [SMILES: O=C(NCCC(=O)N1CCCC2CCCCC21)NCc1ccco1] | 1-furan-2-ylmethyl-3-[3-(octahydroquinolin-1-yl)-3-oxopropyl]urea | A | 5.85 | 334 |
| Ie.12 | 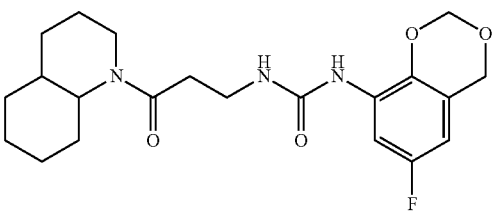 [SMILES: O=C(NCCC(=O)N1CCCC2CCCCC21)Nc1cc(F)cc2c1OCOC2] | 1-(6-fluoro-4-H-1,3-benzodioxin-8-yl)-3-[3-(octahydroquinolin-1-yl)-3-oxopropyl]urea | A | 6.75 | 406 |
| Ie.13 | 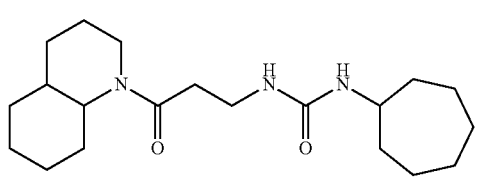 [SMILES: O=C(NCCC(=O)N1CCCC2CCCCC21)NC1CCCCCC1] | 1-cycloheptyl-3-[3-(octahydroquinolin-1-yl)-3-oxopropyl]urea | A | 6.93 | 350 |

| Ex. | structure | name | method | tr (min) | m/z |
|---|---|---|---|---|---|
| Ie.18 | 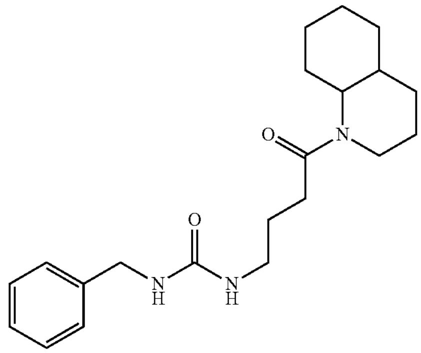 [SMILES: O=C(NCCCC(=O)N1CCCC2CCCCC21)NCc1ccccc1] | 1-benzyl-3-[4-(octahydroquinolin-1-yl)-4-oxobutyl]urea | B | 3.44 | 358 |
| Ie.19 | 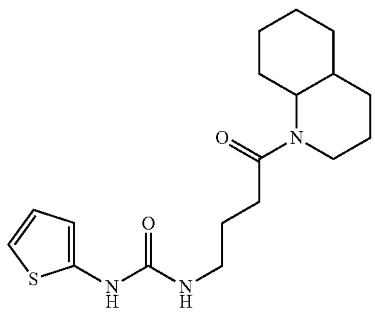 [SMILES: O=C(NCCCC(=O)N1CCCC2CCCCC21)Nc1cccs1] | 1-[4-(octahydroquinolin-1-yl)-4-oxobutyl]-3-thiophen-2-ylurea | B | 3.41 | 350 |
| Ie.20 | 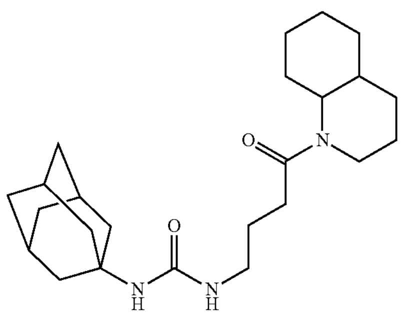 [SMILES: O=C(NCCCC(=O)N1CCCC2CCCCC21)NC12CC3CC(CC(C3)C1)C2] | 1-[4-(octahydroquinolin-1-yl)-4-ozobutyl]-3-tricyclo[3.3.1.1$^{3.7}$]decan-1-ylurea | B | 4.18 | 402 |
| Ie.21 | 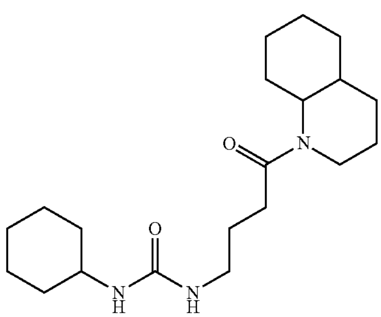 | 1-cyclohexyl-3-[4-(octahydroquinolin-1-yl)-4-oxobutyl]urea | B | 3.59 | 350 |
| Ie.22 | 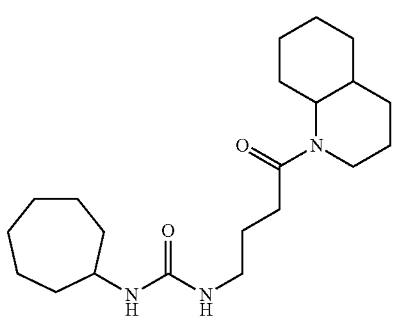 [SMILES: O=C(NCCCC(=O)N1CCCC2CCCCC21)NC1CCCCCC1] | 1-cycloheptyl-3-[4-(octahydroquinolin-1-yl)-4-oxobutyl]urea | B | 3.80 | 364 |

| Ex. | structure | name | method | tr (min) | m/z |
|---|---|---|---|---|---|
| Ie.23 | 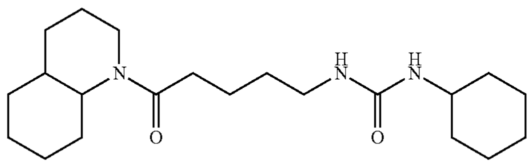 [SMILES: O=C(NCCCCC(=O)N1CCCC2CCCCC21)NC1CCCCC1] | 1-cyclohexyl-3-[5-(octahydroquinolin-1-yl)-5-oxopentyl]urea | B | 3.69 | 364 |
| Ie.24 | 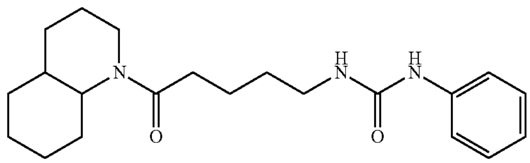 | 1-[5-(octahydroquinolin-1-yl)-5-oxopentyl]-3-phenylurea | B | 3.61 | 358 |
| Ie.25 | 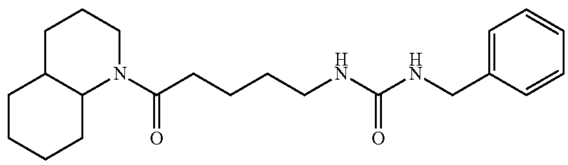 [SMILES: O=C(NCCCCC(=O)N1CCCC2CCCCC21)NCc1ccccc1] | 1-benzyl-3-[5-(octahydroquinolin-1-yl)-5-oxopentyl]urea | B | 3.55 | 372 |
| Ie.26 | 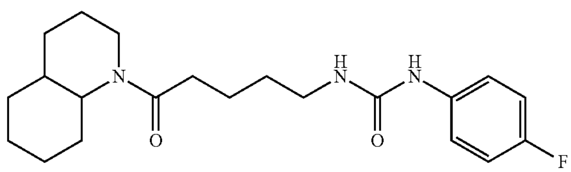 [SMILES: O=C(NCCCCC(=O)N1CCCC2CCCCC21)Nc1ccc(F)cc1] | 1-(4-fluorophenyl)-3-[5-(octahydroquinolin-1-yl)-5-oxopentyl]urea | B | 3.67 | 376 |
| Ie.27 | 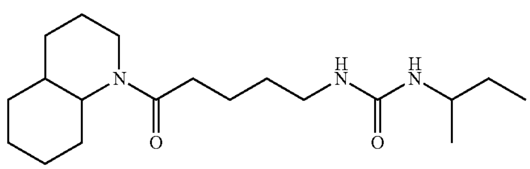 [SMILES: CCC(C)NC(=O)NCCCCC(=O)N1CCCC2CCCCC21] | 1-s-butyl-3-[5-(octahydroquinolin-1-yl)-5-oxopentyl]urea | B | 3.44 | 338 |
| Ie.28 | 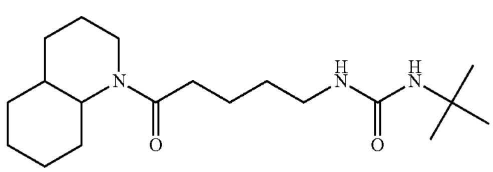 [SMILES: CC(C)(C)NC(=O)NCCCCC(=O)N1CCCC2CCCCC21] | 1-t-butyl-3-[5-(octahydroquinolin-1-yl)-5-oxopentyl]urea | B | 3.55 | 338 |
| Ie.29 | 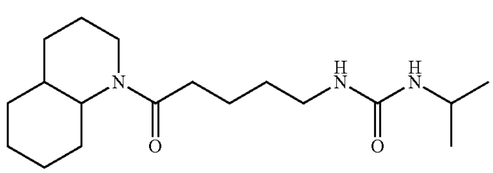 [SMILES: CC(C)NC(=O)NCCCCC(=O)N1CCCC2CCCCC21] | 1-isopropyl-3-[5-(octahydroquinolin-1-yl)-5-oxopentyl]urea | B | 3.24 | 324 |
| Ie.30 | 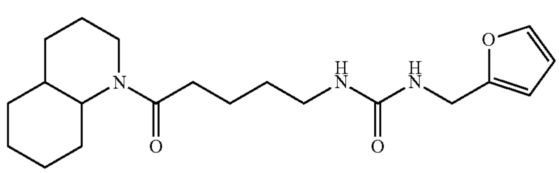 [SMILES: O=C(NCCCCC(=O)N1CCCC2CCCCC21)NCc1ccco1] | 1-furan-2-ylmethyl-3-[5-(octahydroquinolin-1-yl)-5-oxopentyl]urea | B | 3.33 | 362 |
| Ie.31 | 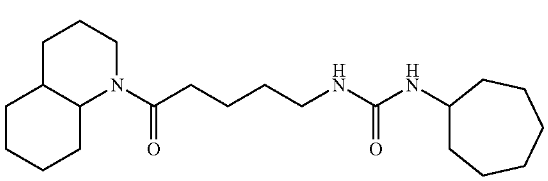 [SMILES: O=C(NCCCCC(=O)N1CCCC2CCCCC21)NC1CCCCCC1] | 1-cycloheptyl-3-[5-(octahydroquinolin-1-yl)-5-oxopentyl]urea | B | 3.88 | 378 |

-continued

| Ex. | structure | name | method | tr (min) | m/z |
|---|---|---|---|---|---|
| Ig.1 | 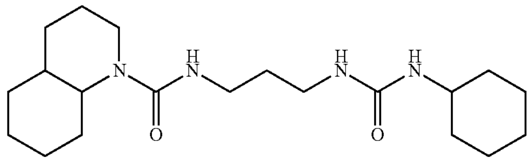 [SMILES: O=C(NCCCNC(=O)N1CCCC2CCCCC21)NC1CCCCC1] | Octahydroquinoline-1-carboxylic acid [3-(3-cyclohexylureido)propyl]amide | B | 3.60 | 365 |
| Ig.2 | 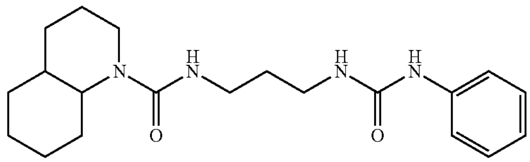 [SMILES: O=C(NCCCNC(=O)N1CCCC2CCCCC21)Nc1ccccc1] | Octahydroquinoline-1-carboxylic acid [3-(3-phenylureido)propyl]amide | B | 3.52 | 359 |
| Ig.3 | 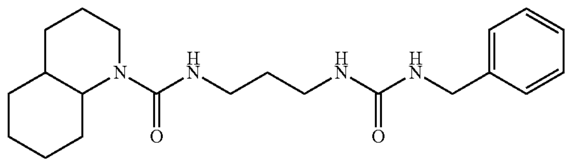 [SMILES: O=C(NCCCNC(=O)N1CCCC2CCCCC21)NCc1ccccc1] | Octahydroquinoline-1-carboxylic acid [3-(3-benzylureido)propyl]amide | B | 3.45 | 373 |
| Ig.4 | 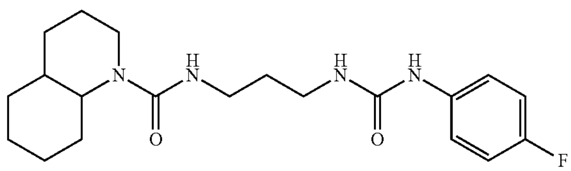 [SMILES: O=C(NCCCNC(=O)N1CCCC2CCCCC21)Nc1ccc(F)cc1] | Octahydroquinoline-1-carboxylic acid {3-[3-(4-fluorophenyl)ureido]propyl}amide | B | 3.58 | 377 |
| Ig.5 | 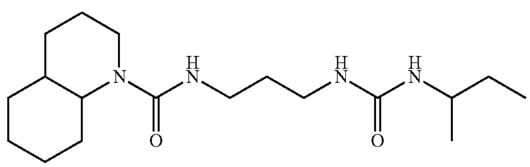 [SMILES: CCC(C)NC(=O)NCCCNC(=O)N1CCCC2CCCCC21] | Octahydroquinoline-1-carboxylic acid [3-(3-s-butylureido)propyl]amide | B | 3.33 | 339 |
| Ig.6 | 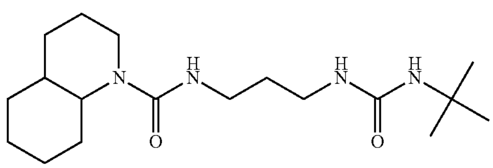 [SMILES: CC(C)(C)NC(=O)NCCCNC(=O)N1CCCC2CCCCC21] | Octahydroquinoline-1-carboxylic acid [3-(3-t-butylureido)propyl]amide | B | 3.48 | 339 |
| Ig.7 | 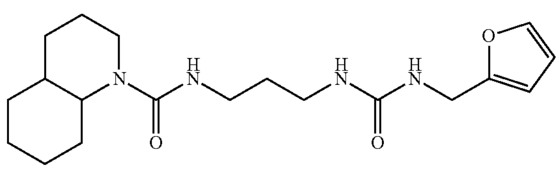 [SMILES: O=C(NCCCNC(=O)N1CCCC2CCCCC21)NCc1ccco1] | Octahydroquinoline-1-carboxylic acid [3-(3-furan-2-ylmethylureido)propyl]amide | B | 3.22 | 363 |
| Ig.8 | 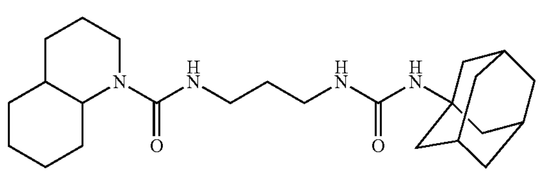 [SMILES: O=C(NCCCNC(=O)N1CCCC2CCCCC21)NC12CC3CC(CC(C3)C1)C2] | Octahydroquinoline-1-carboxylic acid [3-(3-tricyclo[3.3.1.1$^{3,7}$]decan-1-ylureido)propyl]amide | B | 4.26 | 417 |
| Ig.9 | 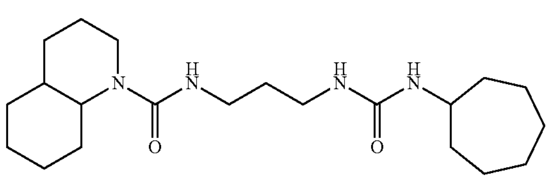 [SMILES: O=C(NCCCNC(=O)N1CCCC2CCCCC21)NC1CCCCCC1] | Octahydroquinoline-1-carboxylic acid [3-(3-cycloheptylureido)propyl]amide | B | 3.80 | 379 |

| Ex. | structure | name | method | tr (min) | m/z |
|---|---|---|---|---|---|
| Ig.10 | 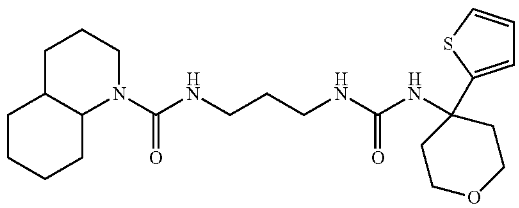 [SMILES: O=C(NCCCNC(=O)N1CCCC2CCCCC21)NC1(c2cccs2)CCOCC1] | Octahydroquinoline-1-carboxylic acid {3-[3-(4-thiophen-2-yltetrahydropyran-4-yl)ureido]propyl}amide | B | 3.47 | 449 |
| Ie.32 | 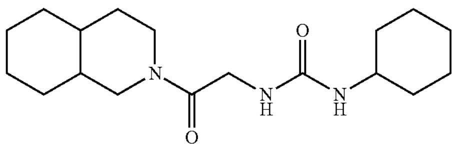 [SMILES: O=C(NCC(=O)N1CCC2CCCCC2C1)NC1CCCCC1] | 1-cyclohexyl-3-[2-(octahydroisoquinolin-2-yl)-2-oxoethyl]urea | B | 3.52<br>3.62 | 322<br>322 |
| Ie.33 | 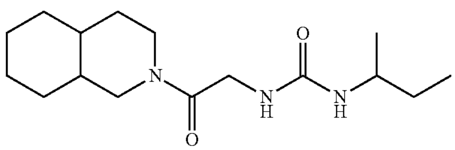 [SMILES: CCC(C)NC(=O)NCC(=O)N1CCC2CCCCC2C1] | 1-s-butyl-3-[2-(octahydroisoquinolin-2-yl)-2-oxoethyl]urea | B | 3.35 | 296 |
| Ie.34 | 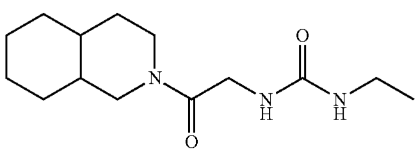 [SMILES: CCNC(=O)NCC(=O)N1CCC2CCCCC2C1] | 1-ethyl-3-[2-(octahydroisoquinolin-2-yl)-2-oxoethyl]urea | B | 2.78<br>2.90 | 268<br>268 |
| Ie.35 | 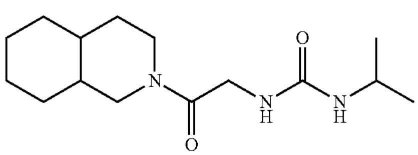 [SMILES: CC(C)NC(=O)NCC(=O)N1CCC2CCCCC2C1] | 1-isopropyl-3-[2-(octahydroisoquinolin-2-yl)-2-oxoethyl]urea | B | 3.01<br>3.12 | 282<br>282 |
| Ie.36 | 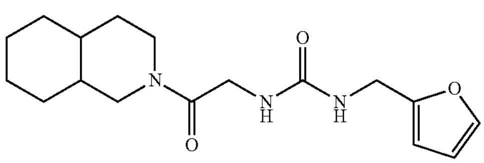 [SMILES: O=C(NCC(=O)N1CCC2CCCCC2C1)NCc1ccco1] | 1-furan-2-ylmethyl-3-[2-(octahydroisoquinolin-2-yl)-2-oxoethyl]urea | B | 3.15<br>3.26 | 320<br>320 |
| Ie.37 | 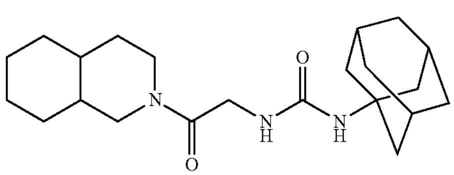 [SMILES: O=C(NCC(=O)N1CCC2CCCCC2C1)NC12CC3CC(CC(C3)C1)C2] | 1-[2-(octahydroisoquinolin-2-yl)-2-oxoethyl]-3-tricyclo[3.3.1.1$^{3.7}$]decan-1-ylurea | B | 4.25 | 374 |
| Ie.38 | 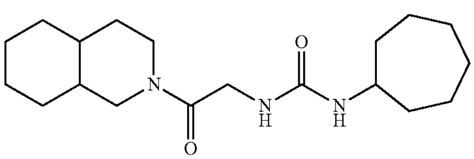 [SMILES: O=C(NCC(=O)N1CCC2CCCCC2C1)NC1CCCCCC1] | 1-cycloheptyl-3-[2-(octahydroisoquinolin-2-yl)-2-oxoethyl]urea | B | 3.83 | 336 |
| Ie.39 | 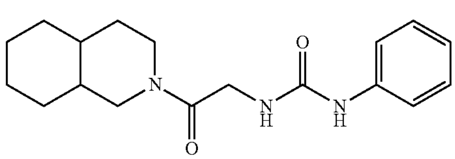 [SMILES: O=C(NCC(=O)N1CCC2CCCCC2C1)Nc1ccccc1] | 1-[2-(octahydroisoquinolin-2-yl)-2-oxoethyl]-3-phenylurea | B | 3.60 | 316 |

| Ex. | structure | name | method | tr (min) | m/z |
|---|---|---|---|---|---|
| Ie.40 | 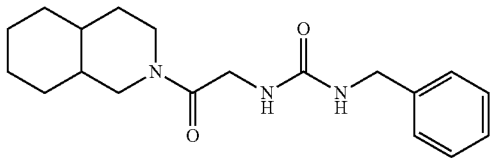 [SMILES: O=C(NCC(=O)N1CCC2CCCCC2C1)NCc1ccccc1] | 1-benzyl-3-[2-(octahydroisoquinolin-2-yl)-2-oxoethyl]urea | B | 3.41<br>3.50 | 330<br>330 |
| Ie.41 | 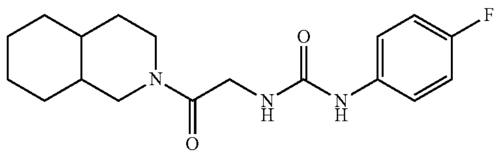 [SMILES: O=C(NCC(=O)N1CCC2CCCCC2C1)Nc1ccc(F)cc1] | 1-(4-fluorophenyl)-3-[2-(octahydroisoquinolin-2-yl)-2-oxoethyl]urea | B | 3.57<br>3.67 | 334<br>334 |
| Ig.11 | 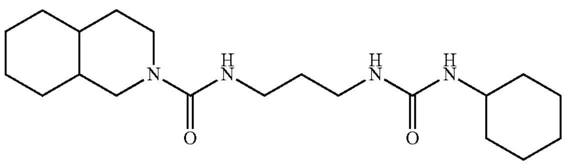 [SMILES: O=C(NCCCNC(=O)N1CCC2CCCCC2C1)NC1CCCCC1] | octahydroisoquinoline-2-carboxylic acid [3-(3-cyclohexylureido)propyl]amide | B | 3.59<br>3.68 | 365<br>365 |
| Ig.12 | 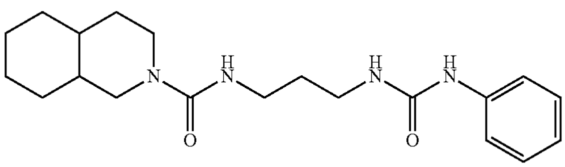 [SMILES: O=C(NCCCNC(=O)N1CCC2CCCCC2C1)Nc1ccccc1] | Octahydroisoquinoline-2-carboxylic acid [3-(3-phenylureido)propyl]amide | B | 3.51<br>3.60 | 359<br>359 |
| Ig.13 | 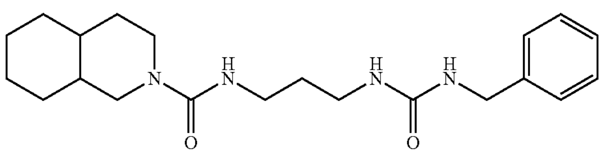 | Octahydroisoquinoline-2-carboxylic acid [3-(3-benzylureido)propyl]amide | B | 3.45<br>3.54 | 373<br>373 |
| Ig.14 | 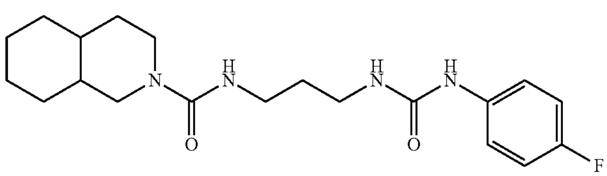 [SMILES: O=C(NCCCNC(=O)N1CCC2CCCCC2C1)Nc1ccc(F)cc1] | Octahydroisoquinoline-2-caxboxylic acid {3-[3-(4-fluorophenyl)ureido]propyl}amide | B | 3.57<br>3.66 | 377<br>377 |
| Ig.15 | 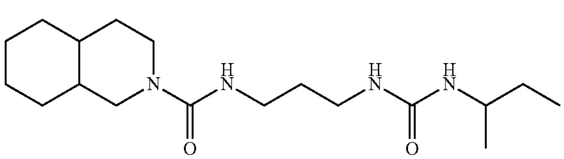 [SMILES: CCC(C)NC(=O)NCCCNC(=O)N1CCC2CCCCC2C1] | Octahydroisoquinoline-2-carboxylic acid [3-(3-s-butylureido)propyl]amide | B | 3.33<br>3.42 | 339<br>339 |
| Ig.16 | 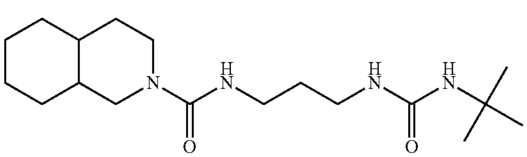 | Octahydroisoquinoline-2-carboxylic acid [3-(3-t-butylureido)propyl]amide | B | 3.46<br>3.56 | 339<br>339 |
| Ig.17 | 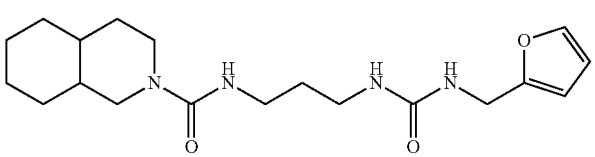 [SMILES: O=C(NCCCNC(=O)N1CCC2CCCCC2C1)NCc1ccco1] | Octahydroisoquinoline-2-carboxylic acid [3-(3-furan-2-ylmethylureido)propyl]amide | B | 3.22<br>3.32 | 363<br>363 |

-continued

| Ex. | structure | name | method | tr (min) | m/z |
|---|---|---|---|---|---|
| Ig.18 | 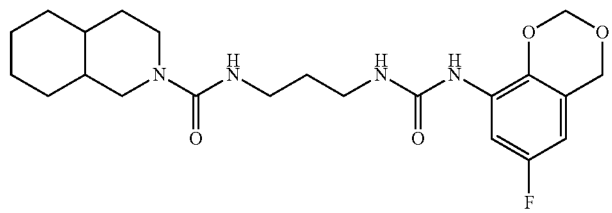 [SMILES: O=C(NCCCNC(=O)N1CCC2CCCCC2C1)Nc1cc(F)cc2c1OCOC2] | Octahydroisoquinoline-2-carboxylic acid {3-[3-(6-fluoro-4H-1,3-benzodioxin-8-yl)ureido]propyl}amide | B | 3.67<br>3.75 | 435<br>435 |
| Ig.19 | 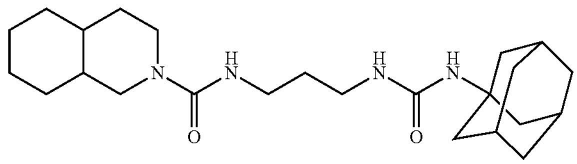 [SMILES: O=C(NCCCNC(=O)N1CCC2CCCCC2C1)NC12CC3CC(CC(C3)C1)C2] | Octahydroisoquinoline-2-carboxylic acid [3-(3-tricyclo[3.3.1.1$^{3.7}$]decan-1-ylureido)propyl]amide | B | 4.23<br>4.31 | 417<br>417 |
| Ig.20 | 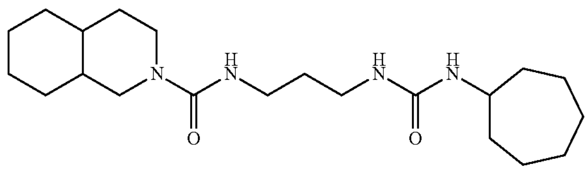 [SMILES: O=C(NCCCNC(=O)N1CCC2CCCCC2C1)NC1CCCCCC1] | Octahydroisoquinoline-2-carboxylic acid [3-(3-cycloheptylureido)propyl]amide | B | 3.79<br>3.88 | 379<br>379 |
| Ie.43 | 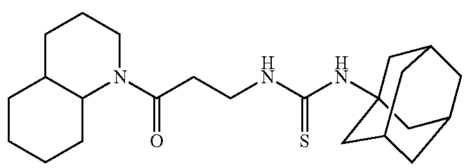 [SMILES: O=C(CCNC(=S)NC12CC3CC(CC(C3)C1)C2)N1CCCC2CCCCC21] | 1-[3-(octahydroquinolin-1-yl)-3-oxopropyl]-3-tricyclo[3.3.1.1$^{3.7}$]decan-1-ylthiourea | B | 4.68 | 404 |
| Ie.44 | 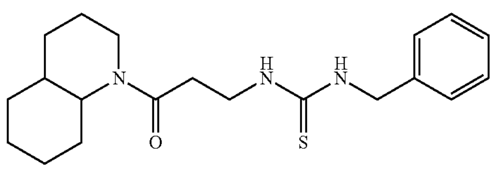 [SMILES: O=C(CCNC(=S)NCc1ccccc1)N1CCCC2CCCCC21] | 1-benzyl-3-[3-(octahydroquinolin-1-yl)-3-oxopropyl]thiourea | B | 3.88 | 360 |
| Ie.45 | 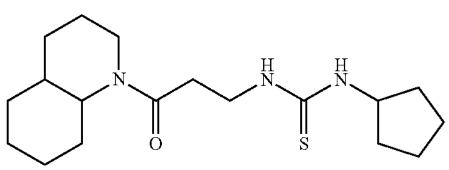 [SMILES: O=C(CCNC(=S)NC1CCCC1)N1CCCC2CCCCC21] | 1-cyclopentyl-3-[3-(octahydroquinolin-1-yl)-3-oxopropyl]thiourea | B | 3.84 | 338 |
| Ie.46 | 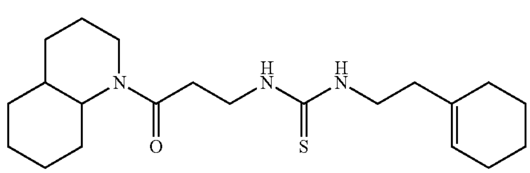 [SMILES: O=C(CCNC(=S)NCCC1=CCCCC1)N1CCCC2CCCCC21] | 1-(2-cyclohex-1-enylethyl)-3-[3-(octahydroquinolin-1-yl)-3-oxopropyl]thiourea | B | 4.40 | 378 |
| Ie.47 | 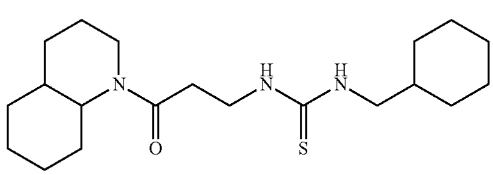 [SMILES: O=C(CCNC(=S)NCC1CCCCC1)N1CCCC2CCCCC21] | 1-cyclohexylmethyl-3-[3-(octahydroquinolin-1-yl)-3-oxopropyl]thiourea | A | 7.92 | 366 |
| Ie.48 | 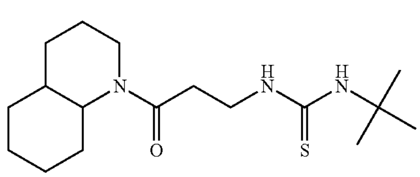 | 1-t-butyl-3-[3-(octahydroquinolin-1-yl)-3-oxopropyl]thiourea | A | 7.11 | 326 |

| Ex. | structure | name | method | tr (min) | m/z |
|---|---|---|---|---|---|
| Ie.49 | 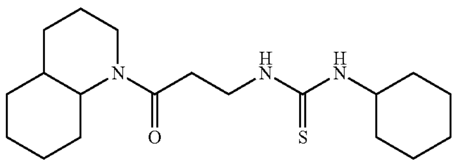 [SMILES: O=C(CCNC(=S)NC1CCCCC1)N1CCCC2CCCCC21] | 1-cyclohexyl-3-[3-(octahydroquinolin-1-yl)-3-oxopropyl]thiourea | A | 7.47 | 352 |
| Ie.50 | 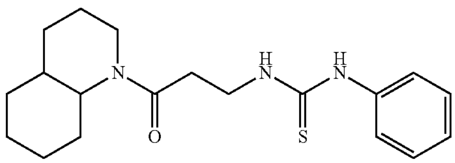 [SMILES: O=C(CCNC(=S)Nc1ccccc1)N1CCCC2CCCCC21] | 1-[3-(octahydroquinolin-1-yl)-3-oxopropyl]-3-phenylthiourea | A | 6.94 | 346 |
| Ie.51 | 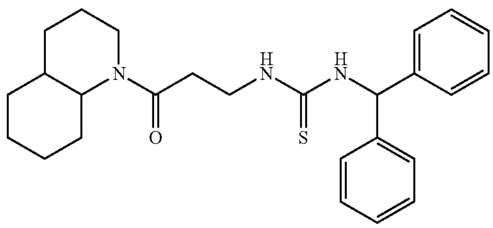 [SMILES: O=C(CCNC(=S)NC(c1ccccc1)c1ccccc1)N1CCCC2CCCCC21] | 1-benzhydryl-3-{3-(octahydroquinolin-1-yl)-3-oxopropyl]thiourea | A | 8.22 | 436 |
| Ie.52 | 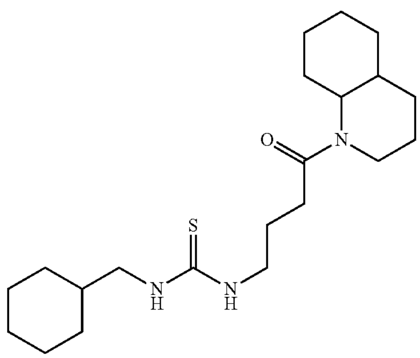 [SMILES: O=C(CCCNC(=S)NCC1CCCCC1)N1CCCC2CCCCC21] | 1-cyclohexylmethyl-3-[4-(octahydroquinolin-1-yl)-4-oxobutyl]thiourea | B | 4.33 | 380 |
| Ie.53 | 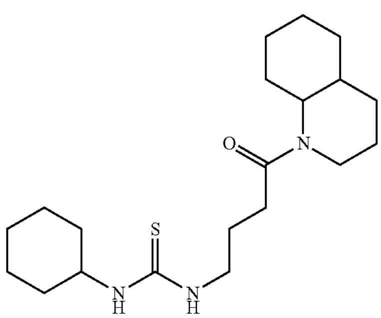 [SMILES: O=C(CCCNC(=S)NC1CCCCC1)N1CCCC2CCCCC21] | 1-cyclohexyl-3-[4-(octahydroquinolin-1-yl)-4-oxobutyl]thiourea | B | 4.10 | 366 |
| Ig.21 | 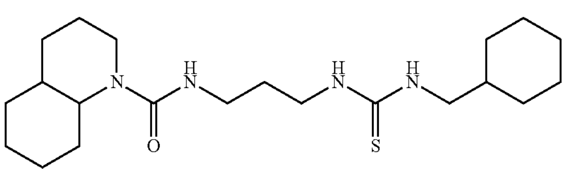 [SMILES: O=C(NCCCNC(=S)NCC1CCCCC1)N1CCCC2CCCCC21] | Octahydroquinoline-1-carboxylic acid [3-(3-cyclohexylmethyl-thioureido)propyl]amide | B | 4.23 | 395 |
| Ig.22 | 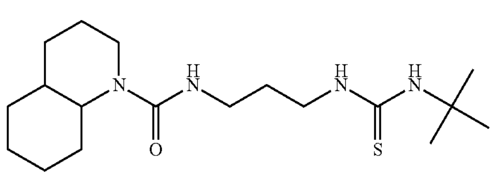 | Octahydroquinoline-1-carboxylic acid [3-(3-t-butylthioureido)propyl]amide | B | 3.79 | 355 |

| Ex. | structure | name | method | tr (min) | m/z |
|---|---|---|---|---|---|
| Ig.23 | 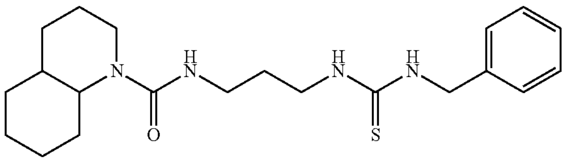 [SMILES: O=C(NCCCNC(=S)NCc1ccccc1)N1CCCC2CCCCC21] | Octahydroquinoline-1-carboxylic acid [3-(3-benzylthioureido)propyl]amide | B | 3.82 | 389 |
| Ig.24 | 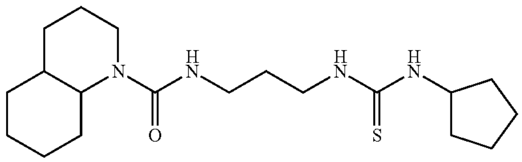 [SMILES: O=C(NCCCNC(=S)NC1CCCC1)N1CCCC2CCCCC21] | Octahydroquinoline-1-carboxylic acid [3-(3-cyclopentylthioureido)propyl]amide | B | 3.79 | 367 |
| Ig.25 | 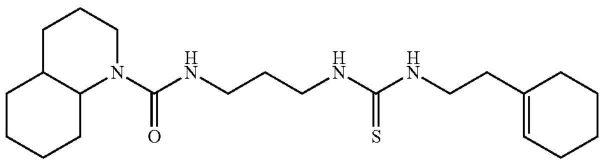 [SMILES: O=C(NCCCNC(=S)NCCC1=CCCCC1)N1CCCC2CCCCC21] | Octahydroquinoline-1-carboxylic acid {3-[3-(2-cyclohex-1-enylethyl)thioureido]propyl}amide | B | 4.32 | 407 |
| Ig.26 | 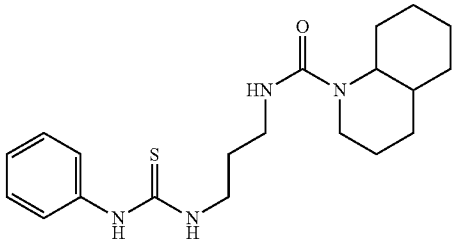 [SMILES: O=C(NCCCNC(=S)Nc1ccccc1)N1CCCC2CCCCC21] | Octahydroquinoline-1-carboxylic acid [3-(3-phenylthioureido)propyl]amide | B | 3.66 | 375 |
| Ig.27 | 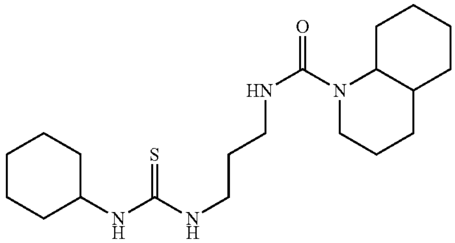 [SMILES: O=C(NCCCNC(=S)NC1CCCCC1)N1CCCC2CCCCC21] | Octahydroquinoline-1-carboxylic acid [3-(3-cyclohexylthioureido)propyl]amide | B | 4.00 | 381 |
| Ig.28 | 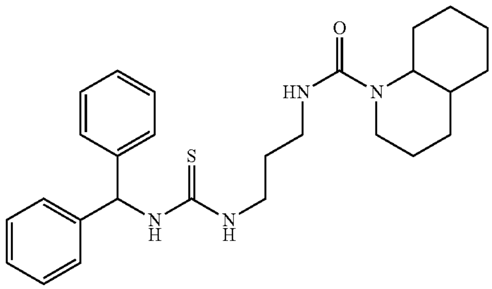 [SMILES: O=C(NCCCNC(=S)NC(c1ccccc1)c1ccccc1)N1CCCC2CCCCC21] | Octahydroquinoline-1-carboxylic acid [3-(3-benzhydrylthioureido)propyl]amide | B | 4.41 | 465 |
| Ie.54 | 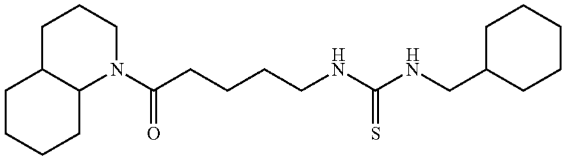 [SMILES: O=C(CCCCNC(=S)NCC1CCCCC1)N1CCCC2CCCCC21] | 1-cyclohexylmethyl-3-[5-(octahydroquinolin-1-yl)-5-oxopentyl]thiourea | B | 4.32 | 394 |

-continued

| Ex. | structure | name | method | tr (min) | m/z |
|---|---|---|---|---|---|
| Ie.55 | 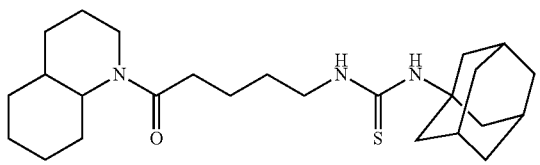 [SMILES: O=C(CCCCNC(=S)NC12CC3CC(CC(C3)C1)C2)N1CCCC2CCCCC21] | 1-[5-(octahydroquinolin-1-yl)-5-oxopentyl]-3-tricyclo[3.3.1.1³·⁷]decan-1-ylthiourea | B | 4.67 | 432 |
| Ie.56 | 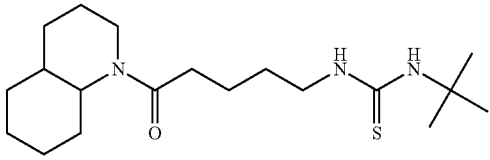 | 1-t-butyl-3-[5-(octahydroquinolin-1-yl)-5-oxopentyl]thiourea | B | 3.90 | 354 |
| Ie.57 | 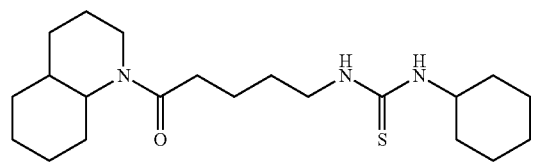 [SMILES: O=C(CCCCNC(=S)NC1CCCCC1)N1CCCC2CCCCC21] | 1-cyclohexyl-3-[5-(octahydroquinolin-1-yl)-5-oxopentyl]thiourea | B | 4.10 | 380 |
| Ie.58 | 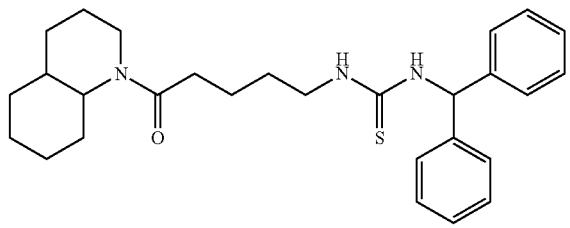 [SMILES: O=C(CCCCNC(=S)NC(c1ccccc1)c1ccccc1)N1CCCC2CCCCC21] | 1-benzhydryl-3-[5-(octahydroquinolin-1-yl)-5-oxopentyl]thiourea | B | 4.49 | 464 |
| Ie.59 | 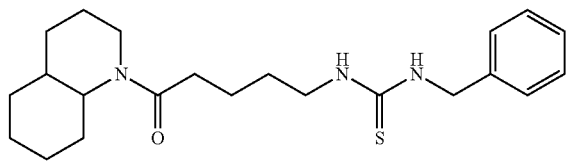 [SMILES: O=C(CCCCNC(=S)NCc1ccccc1)N1CCCC2CCCCC21] | 1-benzyl-3-[5-(octahydroquinolin-1-yl)-5-oxopentyl]thiourea | B | 3.93 | 388 |
| Ie.60 | 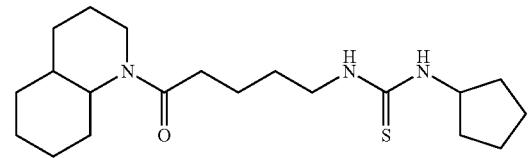 [SMILES: O=C(CCCCNC(=S)NC1CCCC1)N1CCCC2CCCCC21] | 1-cyclopentyl-3-[5-(octahydroquinolin-1-yl)-5-oxopentyl]thiourea | B | 3.89 | 366 |
| Ie.61 | 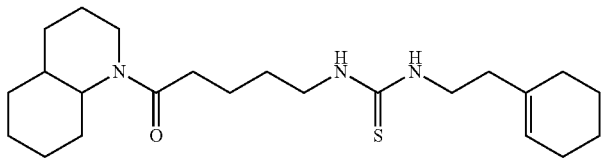 [SMILES: O=C(CCCCNC(=S)NCCC1=CCCCC1)N1CCCC2CCCCC21] | 1-(2-cyclohex-1-enylethyl)-3-[5-(octahydroquinolin-1-yl)-5-oxopentyl]thiourea | B | 4.42 | 406 |
| Ie.62 | 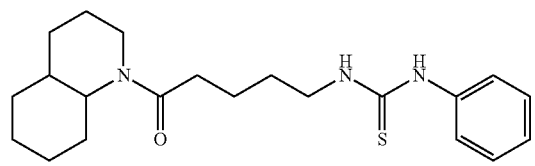 [SMILES: O=C(CCCCNC(=S)Nc1ccccc1)N1CCCC2CCCCC21] | 1-[5-(octahydroquinolin-1-yl)-5-oxopentyl]-3-phenylthiourea | B | 3.81 | 374 |
| Ie.63 | 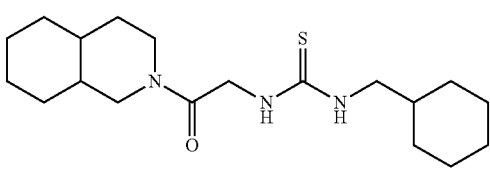 [SMILES: O=C(CNC(=S)NCC1CCCCC1)N1CCC2CCCCC2C1] | 1-cyclohexylmethyl-3-[2-(octahydroisoquinolin-2-yl)-2-oxoethyl]thiourea | B | 4.35<br>4.44 | 352<br>352 |

-continued

| Ex. | structure | name | method | tr (min) | m/z |
|---|---|---|---|---|---|
| Ie.64 | 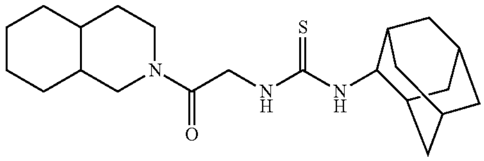 [SMILES: O=C(CNC(=S)NC1C2CC3CC(C2)CC1C3)N1CCC2CCCCC2C1] | 1-[2-(octahydroisoquinolin-2-yl)-2-oxoethyl]-3-tricyclo[3.3.1.1³,⁷]decan-1-yl thiourea | B | 4.77<br>4.81 | 390<br>390 |
| Ie.65 | 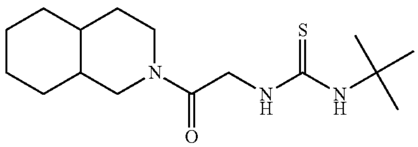 [SMILES: CC(C)(C)NC(=S)NCC(=O)N1CCC2CCCCC2C1] | 1-t-butyl-3-[2-(octahydroisoquinolin-2-yl)-2-oxoethyl]thiourea | B | 3.90<br>4.01 | 312<br>312 |
| Ie.66 | 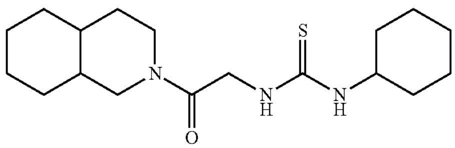 | 1-cyclohexyl-3-[2-(octahydroisoquinolin-2-yl)-2-oxoethyl]thiourea | B | 4.10<br>4.19 | 338<br>338 |
| Ie.67 | 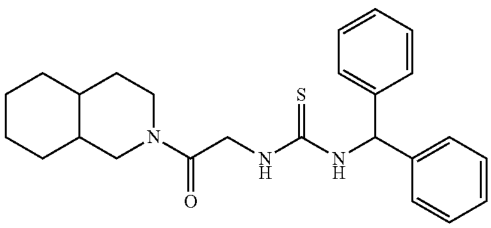 [SMILES: O=C(CNC(=S)NC(c1ccccc1)c1ccccc1)N1CCC2CCCCC2C1] | 1-benzhydryl-3-[2-(octahydroisoquinolin-2-yl)-2-oxoethyl]thiourea | B | 4.52<br>4.59 | nd<br>nd |
| Ie.68 | 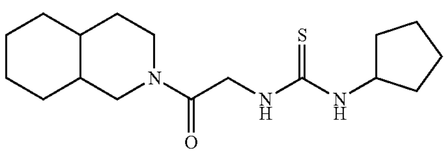 [SMILES: O=C(CNC(=S)NC1CCCC1)N1CCC2CCCCC2C1] | 1-cyclopentyl-3-[2-(octahydroisoquinolin-2-yl)-2-oxoethyl]thiourea | B | 3.89<br>3.99 | 324<br>324 |
| Ie.69 | 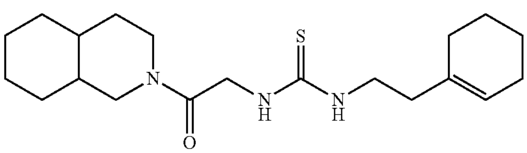 [SMILES: O=C(CNC(=S)NCCC1=CCCCC1)N1CCC2CCCCC2C1] | 1-(2-cyclohex-1-enylethyl)-3-[2-(octahydroisoquinolin-2-yl)-2-oxoethyl]thiourea | B | 4.45<br>4.53 | 364<br>364 |
| Ig.29 | 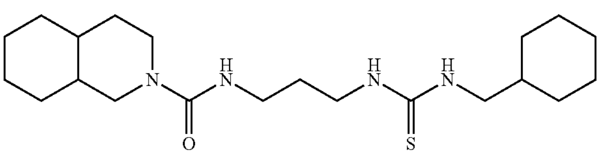 [SMILES: O=C(NCCCNC(=S)NCC1CCCCC1)N1CCC2CCCCC2C1] | Octahydroisoquinoline-2-carboxylic acid [3-(3-cyclohexylmethyl-thioureido)propyl]amide | B | 4.22<br>4.30 | 395<br>395 |
| Ig.30 | 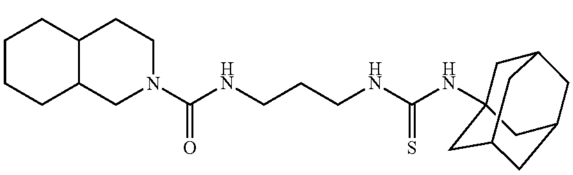 | Octahydroisoquinoline-2-carboxylic acid [3-(3-tricyclo[3.3.1.1³,⁷]decan-1-ylthioureido)propyl]amide | B | 4.65<br>4.71 | 433<br>433 |
| Ig.31 | 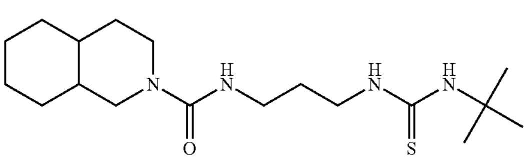 [SMILES: CC(C)(C)NC(=S)NCCCNC(=O)N1CCC2CCCCC2C1] | Octahydroisoquinoline-2-carboxylic acid [3-(3-t-butylthioureido)propyl]amide | B | 3.78<br>3.87 | 355<br>355 |

-continued

| Ex. | structure | name | method | tr (min) | m/z |
|---|---|---|---|---|---|
| Ig.32 | 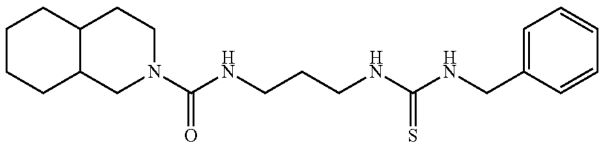 [SMILES: O=C(NCCCNC(=S)NCc1ccccc1)N1CCC2CCCCC2C1] | Octahydroisoquinoline-2-carboxylic acid [3-(3-benzylthioureido)propyl]amide | B | 3.81<br>3.89 | 389<br>389 |
| Ig.33 | 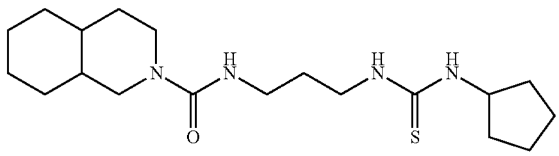 [SMILES: O=C(NCCCNC(=S)NC1CCCC1)N1CCC2CCCCC2C1] | Octahydroisoquinoline-2-carboxylic acid [3-(3-cyclopentylthioureido)propyl]amide | B | 3.78<br>3.87 | 367<br>367 |
| Ig.34 | 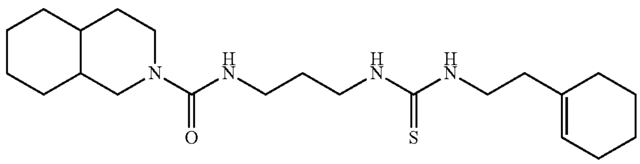 [SMILES: O=C(NCCCNC(=S)NCCC1=CCCCC1)N1CCC2CCCCC2C1] | Octahydroisoquinoline-2-carboxylic acid {3-[3-(2-cyclohex-1-enylethyl)thioureido]propyl}amide | B | 4.31<br>4.39 | 407<br>407 |
| Ig.35 | 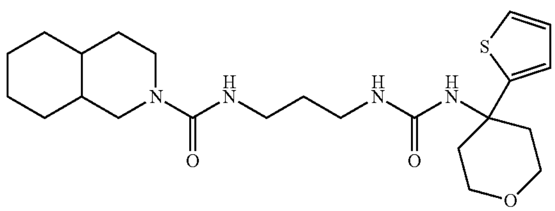 [SMILES: O=C(NCCCNC(=O)N1CCC2CCCCC2C1)NC1(c2cccs2)CCOCC1] | Octahydroisoquinoline-2-carboxylic acid{3-[3-(4-thiophen-2-yltetrahydropyran-4-yl)ureido]propyl}amide | B | 3.45<br>3.54 | 449<br>449 |
| Ie.70 | 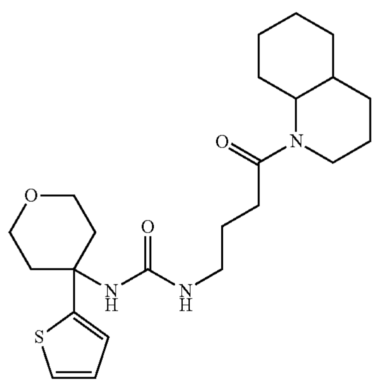 [SMILES: O=C(NCCCC(=O)N1CCCC2CCCCC21)NC1(c2cccs2)CCOCC1] | 1-[4-(octahydroquinolin-1-yl)-4-oxobutyl]-3-[4-(thiophen-2-yl)tetrahydropyran-4-yl]urea | B | 3.43 | 434 |
| Ie.71 | 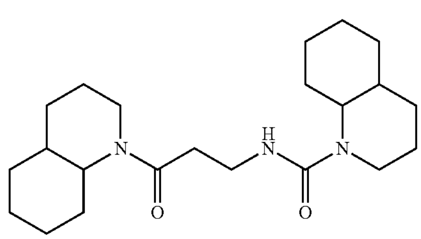 [SMILES: O=C(CCNC(=O)N1CCCC2CCCCC21)N1CCCC2CCCCC21] | Octahydroquinoline-1-carboxylic acid N-[3-(octahydroquinolin-1-yl)-3-oxopropyl]amide | B | 4.09 | 376 |
| Ie.72 | 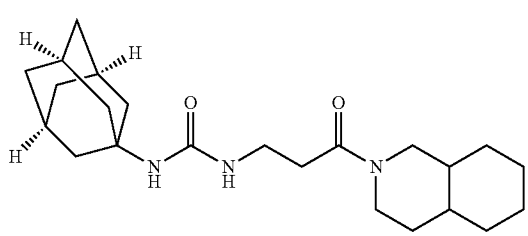 [SMILES: O=C(NCCC(=O)N1CCC2CCCCC2C1)NC12C[C@H]3C[C@H](C1)C[C@@H](C2)C3] | 1-[(3s,5s,7s)-adamantan-1-yl]-3-[3-(octahydroisoquinolin-2-yl)-3-oxopropyl]urea | B | 4.17<br>4.26 | 388<br>388 |

| Ex. | structure | name | method | tr (min) | m/z |
|---|---|---|---|---|---|
| Ie.73 | 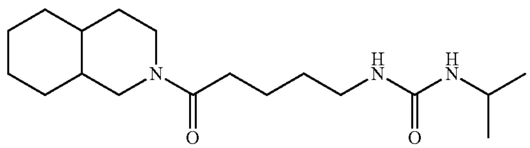 [SMILES: CC(C)NC(=O)NCCCCC(=O)N1CCC2CCCCC2C1] | 1-isopropyl-3-[5-(octahydroisoquinolin-2-yl)-5-oxopentyl]urea | B | 4.60<br>4.68 | 324<br>324 |
| Ie.74 | 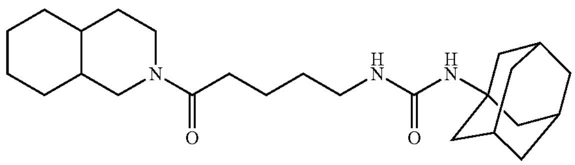 | 1-[(3s,5s,7s)-adamantan-1-yl]-3-[5-(octahydroisoquinolin-2-yl)-5-oxopentyl]urea | B | 4.27<br>4.35 | 416<br>416 |
| Ie.75 | 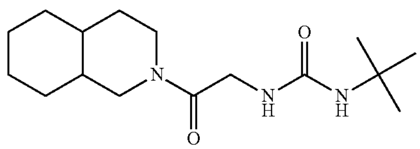 | 1-t-butyl-3-[2-(octahydroisoquinolin-2-yl)-2-oxoethyl]urea | B | 3.47 | 296 |
| Ie.76 | 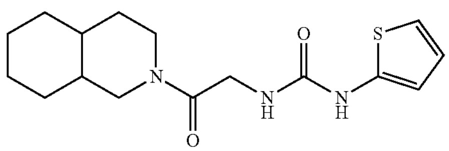 [SMILES: O=C(NCC(=O)N1CCC2CCCCC2C1)Nc1cccs1] | 1-[2-(octahydroisoquinolin-2-yl)-2-oxoethyl]-3-(thiophen-2-yl)urea | B | 3.50 | 322 |
| Ie.77 | 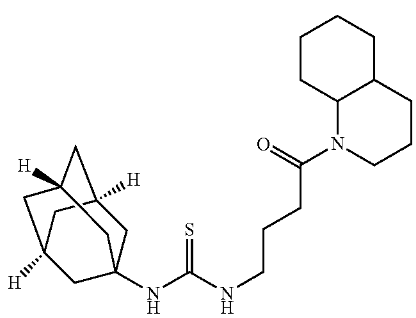 [SMILES: O=C(CCCNC(=S)NC12C[C@H]3C[C@@H](C1)C[C@@H](C2)C3)N1CCCC2CCCCC21] | 1-[(3s,5s,7s)-adamantan-1-yl]-3-[4-(octahydroquinolin-1-yl)-4-oxobutyl]thiourea | B | 4.68 | 418 |
| Ie.78 | 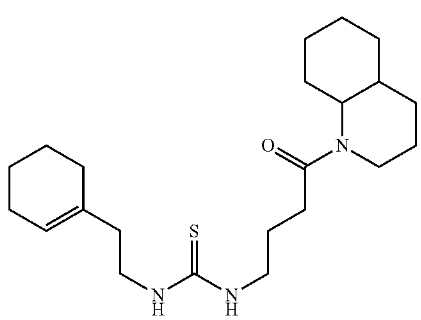 [SMILES: O=C(CCCNC(=S)NCCC1=CCCCC1)N1CCCC2CCCCC21] | 1-[2-(cyclohex-1-en-1-yl)ethyl]-3-[4-(octahydroquinolin-1-yl)-4-oxobutyl]thiourea | B | 4.44 | 392 |
| Ie.79 | 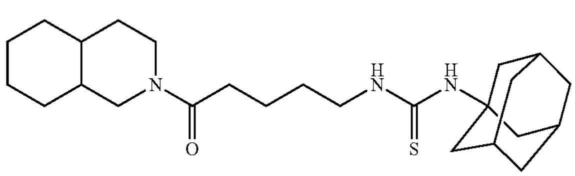 [SMILES: O=C(CCCCNC(=S)NC12CC3CC(CC(C3)C1)C2)N1CCC2CCCCC2C1] | 1-[(3s.,5s,7s)-adamantan-1-yl]-3-[5-(octahydroisoquinolin-2-yl)-5-oxopentyl]thiourea | B | 4.67<br>4.74 | 432<br>432 |
| Ie.80 | 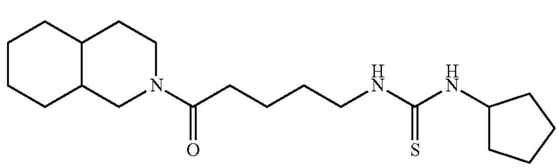 [SMILES: O=C(CCCCNC(=S)NC1CCCC1)N1CCC2CCCCC2C1] | 1-cyclopentyl-3-[5-(octahydroisoquinolin-2-yl)-5-oxopentyl]thiourea | B | 3.88<br>3.98 | 366<br>366 |

-continued

| Ex. | structure | name | method | tr (min) | m/z |
|---|---|---|---|---|---|
| Ie.81 | 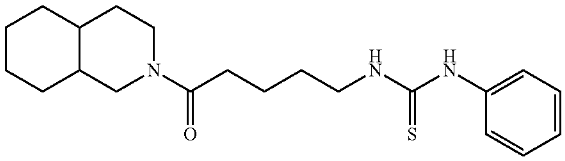 [SMILES: O=C(CCCCNC(=S)Nc1ccccc1)N1CCC2CCCCC2C1] | 3-phenyl-1-[5-(octahydroisoquinolin-2-yl)-5-oxopentyl]-thiourea | B | 3.81<br>3.87 | 374<br>374 |
| Ie.82 | 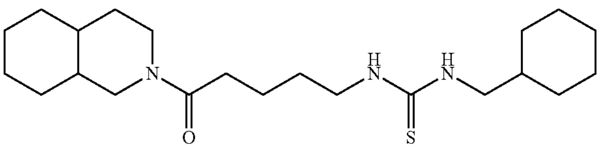 [SMILES: O=C(CCCCNC(=S)NCC1CCCCC1)N1CCC2CCCCC2C1] | 1-(cyclohexylmethyl)-3-[5-(octahydroisoquinolin-2-yl)-5-oxopentyl]thiourea | B | 4.32<br>4.40 | 394<br>394 |
| Ie.83 | 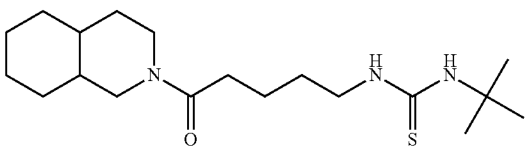 [SMILES: CC(C)(C)NC(=S)NCCCCC(=O)N1CCC2CCCCC2C1] | 1-t-butyl-3-[5-(octahydroisoquinolin-2-yl)-5-oxopenty]thiourea | B | 3.89<br>3.99 | 354<br>354 |
| Ie.84 | 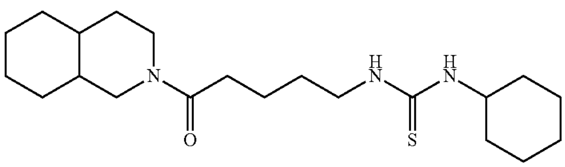 [SMILES: O=C(CCCCNC(=S)NC1CCCCC1)N1CCC2CCCCC2C1] | 1-cyclohexyl-3-[5-(octahydroisoquinolin-2-yl)-5-oxopentyl]thiourea | B | 4.09<br>4.18 | 380<br>380 |
| Ie.85 | 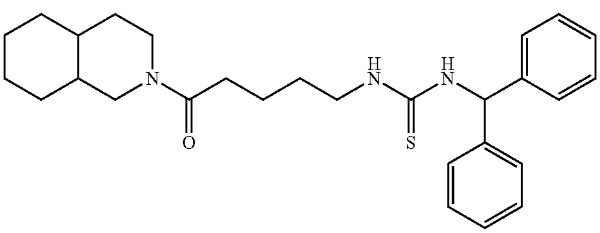 [SMILES: O=C(CCCCNC(=S)NC(c1ccccc1)c1ccccc1)N1CCC2CCCCC2C1] | 1-benzhydryl-3-[5-(octahydroisoquinolin-2-yl)-5-oxopentyl]thiourea | B | 4.49<br>4.56 | 464<br>464 |
| Ie.86 | 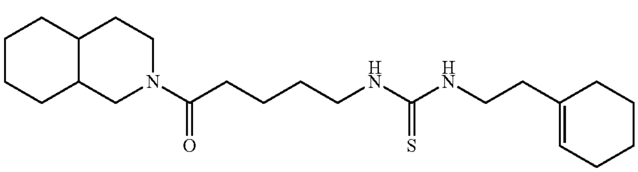 [SMILES: O=C(CCCCNC(=S)NCCC1=CCCCC1)N1CCC2CCCCC2C1] | 1-[2-(cyclohex-1-en-1-yl)ethyl]-3-[5-(octahydroisoquinolin-2-yl)-5-oxopentyl]thiourea | B | 4.41<br>4.49 | 406<br>406 |
| Ig.36 | 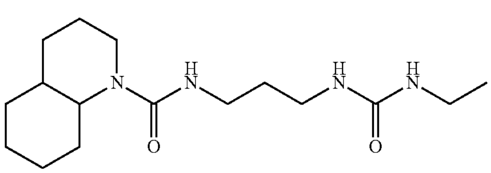 [SMILES: CCNC(=O)NCCCNC(=O)N1CCCC2CCCCC21] | Octahydroquinoline-1-carboxylic acid N-[3-(3-ethylureido)propyl]amide | B | 2.91 | 311 |
| Ie.37 | 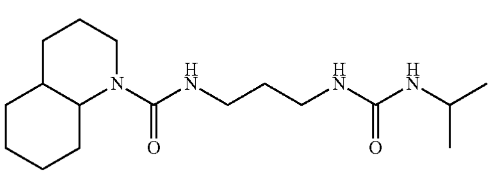 [SMILES: CC(C)NC(=O)NCCCNC(=O)N1CCCC2CCCCC21] | Octahydroquinoline-1-carboxylic acid N-[3-(3-isopropylureido)propyl]amide | B | 3.13 | 325 |

| Ex. | structure | name | method | tr (min) | m/z |
|---|---|---|---|---|---|
| Ig.38 | 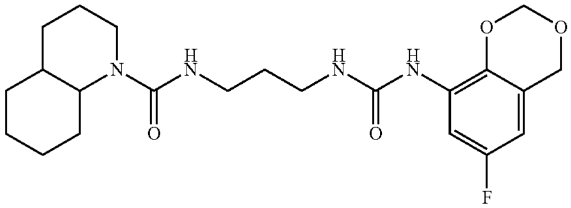 [SMILES: O=C(NCCCNC(=O)N1CCCC2CCCCC21)Nc1cc(F)cc2c1OCOC2] | Octahydroquinoline-1-carboxylic acid N-[3-[3-(6-fluoro-4H-benzo[d][1,3]dioxin-8-yl)ureido]propyl]amide | B | 3.69 | 435 |
| Ig.39 | 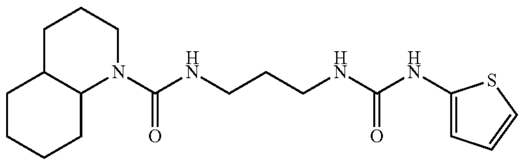 [SMILES: O=C(NCCCNC(=O)N1CCCC2CCCCC21)Nc1cccs1] | Octahydroquinoline-1-carboxylic acid N-[3-[3-thiophen-2-yl)ureido]propyl]amide | B | 3.34 | 365 |
| Ig.40 | 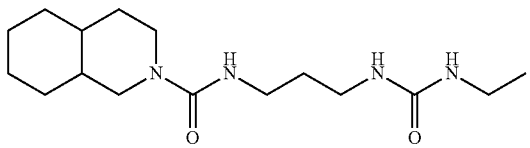 [SMILES: CCNC(=O)NCCCNC(=O)N1CCC2CCCCC2C1] | Octahydroisoquinoline-2-carboxylic acid N-[3-(3-ethylureido)propyl]amide | B | 3.02 | 311 |
| Ig.41 | 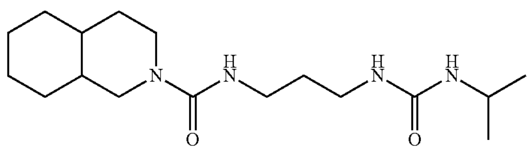 | Octahydroisoquinoline-2-carboxylic acid N-[3-(3-isopropylureido)propyl]amide | B | 3.23 | 325 |
| Ig.42 | 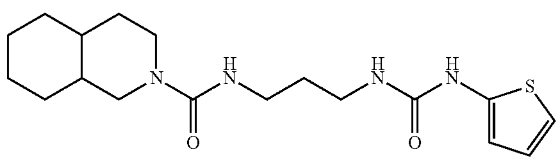 [SMILES: O=C(NCCCNC(=O)N1CCC2CCCCC2C1)Nc1cccs1] | Octahydroisoquinoline-2-carboxylic acid N-[3-[3-(thiophen-2-yl)ureido]propyl]amide | B | 3.51 | 365 |
| Ig.43 | 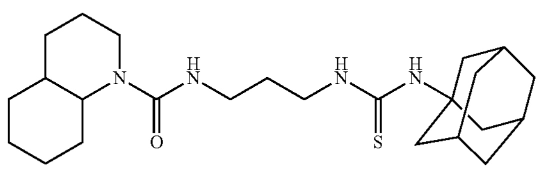 [SMILES: O=C(NCCCNC(=S)NC12CC3CC(CC(C3)C1)C2)N1CCCC2CCCCC21] | Octahydroquinoline-1-carboxylic acid N-[3-[3-[(3s,5s,7s)-adamantan-1-yl]thioureido]propyl]amide | B | 4.67 | 433 |

Example Id.1

N-[3-(octahydroquinolin-1-yl)-3-oxopropyl]-2-thiophen-2-ylacetamide

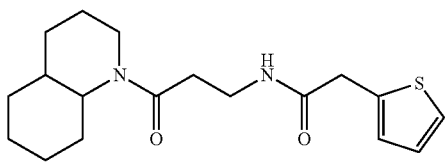 [SMILES: O=C(Cc1cccs1)NCCC(=O)N1CCCC2CCCCC21]

46 µL of Et₃N, 30.4 mg (0.22 mmol) of HOBT and 43.1 mg (0.22 mmol) of EDC are added to a solution of 21.3 mg (0.15 mmol) of 2-thienylacetic acid in 2 mL of AcOEt; 35 mg (0.17 mmol) of the intermediate amine Vc.3 are added to it. The suspension formed is kept under stirring for 18 h. It is then treated with water and more AcOEt is added, the organic phase is separated and the aqueous phase is extracted once more with more AcOEt. The organic phases are pooled and successively washed with saturated NaHCO₃ solution, 1N HCl and brine. It is then dried over anhydrous Na₂SO₄, it is filtered and the solvent is evaporated under reduced pressure. The residue is purified by means of silica gel column chromatography, using a (30:1) mixture of DCM-MeOH as eluent, yielding 5 mg of an oil identified as example Id.1. Method A: tr: 6.30 min; m/z: 335.

Example Id.2

N-[3-(octahydroquinolin-1-yl)-3-oxopropyl]propionamide

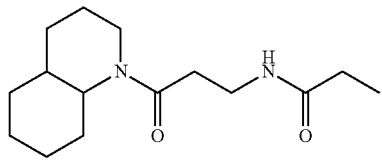 [SMILES: CCC(=O)NCCC(=O)N1CCCC2CCCCC21]

35 mg (0.17 mmol) of the intermediate amine Vc.3 and 46 µL of $Et_3N$ are added to a solution of 13 µL (0.15 mmol) of propionyl chloride in 2 mL of AcOEt. The solution formed is kept under stirring for 18 h. It is then treated with water and more AcOEt is added, the organic phase is separated and the aqueous phase is extracted once more with more AcOEt. The organic phases are pooled and successively washed with saturated $NaHCO_3$ solution, 1N HCl and brine. It is then dried over anhydrous $Na_2SO_4$, it is filtered and the solvent is evaporated under reduced pressure, 11 mg of example Id.2 being obtained. Method A: tr: 5.35 min; m/z: 267.

The following examples were prepared in a manner similar to examples 1d.1 or Id.2:

| Ex. | structure | name | method | tr (min) | m/z |
|---|---|---|---|---|---|
| Id.3 | 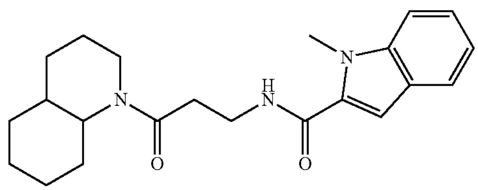 [SMILES: Cn1c(C(=O)NCCC(=O)N2CCCC3CCCCC32)cc2ccccc21] | 1-methyl-1H-indole-2-carboxylic acid [3-(octahydroquinolin-1-yl)-3-oxopropyl]amide | A | 7.41 | 368 |
| Id.4 | 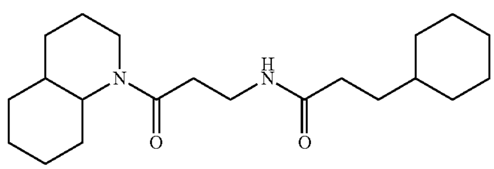 [SMILES: O=C(CCC1CCCCC1)NCCC(=O)N1CCCC2CCCCC21] | 3-cyclohexyl-N-[3-(octahydroquinolin-1-yl)-3-oxopropyl]propionamide | A | 7.70 | 349 |
| Id.5 | 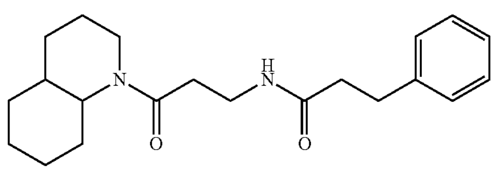 [SMILES: O=C(CCc1ccccc1)NCCC(=O)N1CCCC2CCCCC21] | N-[3-(octahydroquinolin-1-yl)-3-oxopropyl]-3-phenylpropionamide | A | 6.71 | 343 |
| Id.6 | 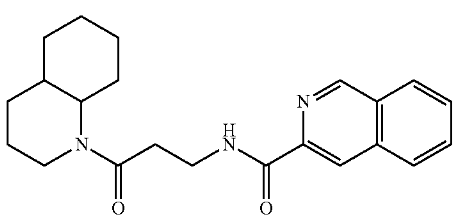 [SMILES: O=C(NCCC(=O)N1CCCC2CCCCC21)c1cc2ccccc2cn1] | Isoquinoline-3-carboxylic acid [3-(octahydroquinolin-1-yl)-3-oxopropyl]amide | A | 7.05 | 366 |
| Id.7 | 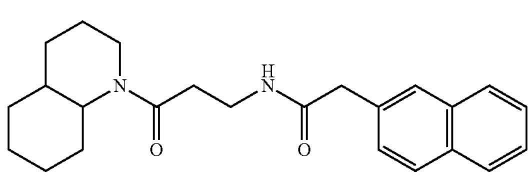 [SMILES: O=C(Cc1ccc2ccccc2c1)NCCC(=O)N1CCCC2CCCCC21] | 2-naphthalen-2-yl-N-[3-(octahydroquinolin-1-yl)-3-oxopropyl]acetamide | A | 7.16 | 379 |
| Id.8 | 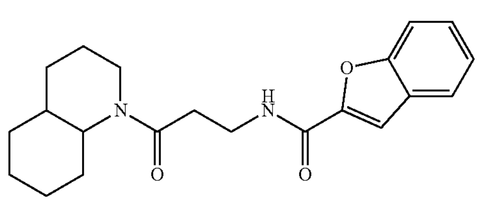 [SMILES: O=C(NCCC(=O)N1CCCC2CCCCC21)c1cc2ccccc2o1] | Benzofuran-2-carboxylic acid [3-(octahydroquinolin-1-yl)-3-oxopropyl]amide | A | 7.03 | 355 |

| Ex. | structure | name | method | tr (min) | m/z |
|---|---|---|---|---|---|
| Id.9 | 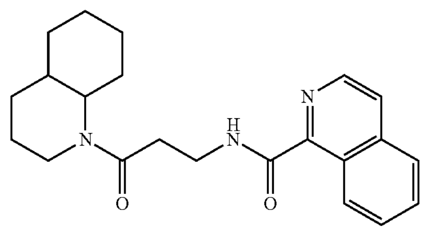 [SMILES: O=C(NCCC(=O)N1CCCC2CCCCC21)c1nccc2ccccc12] | Isoquinoline-1-carboxylic acid [3-(octahydroquinolin-1-yl)-3-oxopropyl]amide | A | 7.11 | 366 |
| Id.10 | 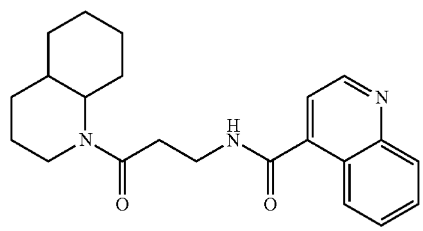 [SMILES: O=C(NCCC(=O)N1CCCC2CCCCC21)c1ccnc2ccccc12] | Quinoline-4-carboxylic acid [3-(octahydroquinolin-1-yl)-3-oxopropyl]amide | A | 5.65 | 366 |
| Id.11 | 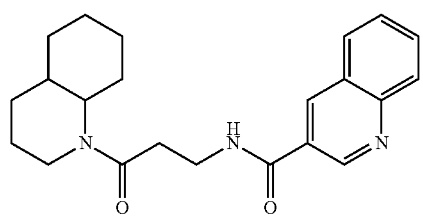 [SMILES: O=C(NCCC(=O)N1CCCC2CCCCC21)c1cnc2ccccc2c1] | Quinoline-3-carboxylic acid [3-(octahydroquinolin-1-yl)-3-oxopropyl]amide | A | 6.00 | 366 |
| Id.12 | 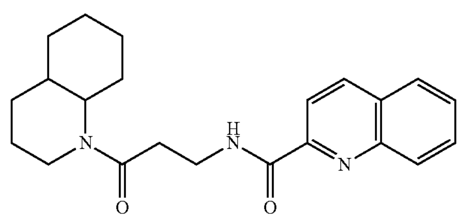 [SMILES: O=C(NCCC(=O)N1CCCC2CCCCC21)c1ccc2ccccc2n1] | Quinoline-2-carboxylic acid [3-(octahydroquinolin-1-yl)-3-oxopropyl]amide | A | 7.29 | 366 |
| Id.13 | 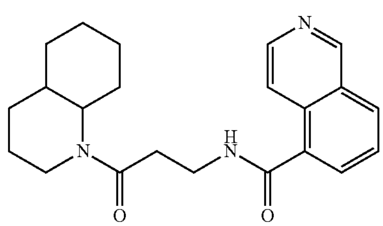 [SMILES: O=C(NCCC(=O)N1CCCC2CCCCC21)c1cccc2cnccc12] | Isoquinoline-5-carboxylic acid [3-(octahydroquinolin-1-yl)-3-oxopropyl]amide | A | 4.68 | 366 |
| Id.14 | 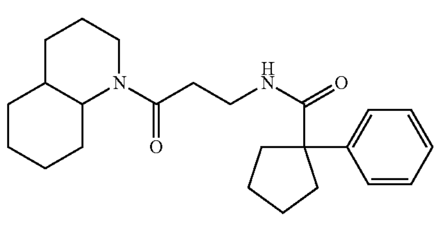 [SMILES: O=C(CCNC(=O)C1(c2ccccc2)CCCC1)N1CCCC2CCCCC21] | 1-phenylcyclopentanecarboxylic acid [3-(octahydroquinolin-1-yl)-3-oxopropyl]amide | A | 7.87 | 383 |
| Id.15 | 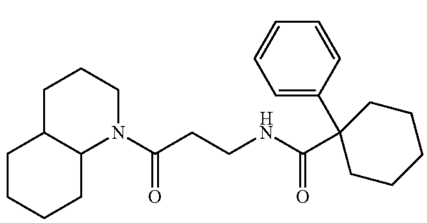 [SMILES: O=C(CCNC(=O)C1(c2ccccc2)CCCCC1)N1CCCC2CCCCC21] | 1-phenylcyclohexanecarboxylic acid [3-(octahydroquinolin-1-yl)-3-oxopropyl]amide | A | 8.21 | 397 |

| Ex. | structure | name | method | tr (min) | m/z |
|---|---|---|---|---|---|
| Id.16 | 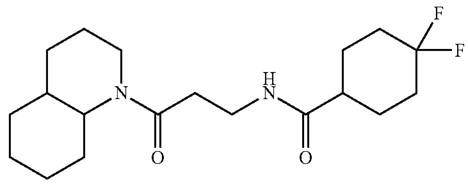 [SMILES: O=C(NCCC(=O)N1CCCC2CCCCC21)C1CCC(F)(F)CC1] | 4,4-difluorocyclohexanecarboxylic acid [3-(octahydroquinolin-1-yl)-3-oxopropyl]amide | A | 6.49 | 357 |
| Id.17 | 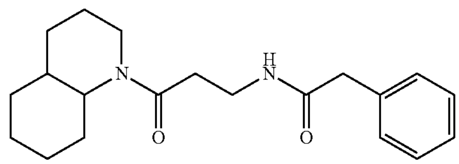 [SMILES: O=C(Cc1ccccc1)NCCC(=O)N1CCCC2CCCCC21] | N-[3-(octahydroquinolin-1-yl)-3-oxopropyl]-2-phenylacetamide | A | 6.42 | 329 |
| Id.18 | 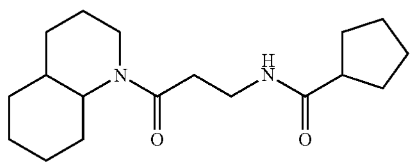 [SMILES: O=C(NCCC(=O)N1CCCC2CCCCC21)C1CCCC1] | Cyclopentanecarboxylic acid [3-(octahydroquinolin-1-yl)-3-oxopropyl]amide | A | 6.39 | 307 |
| Id.19 | 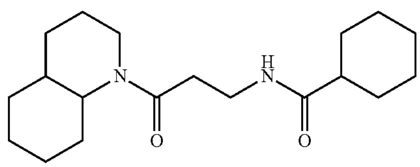 [SMILES: O=C(NCCC(=O)N1CCCC2CCCCC21)C1CCCCC1] | Cyclohexanecarboxylic acid [3-(octahydroquinolin-1-yl)-3-oxopropyl]amide | A | 6.76 | 321 |
| Id.20 | 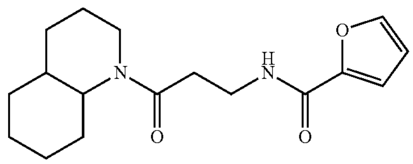 [SMILES: O=C(NCCC(=O)N1CCCC2CCCCC21)c1ccco1] | Furan-2-carboxylic acid [3-(octahydroquinolin-1-yl)-3-oxopropyl]amide | A | 5.89 | 305 |
| Id.21 | 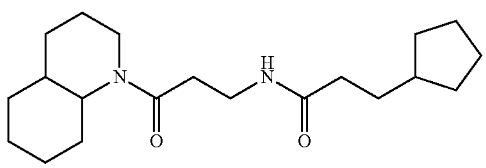 [SMILES: O=C(CCC1CCCC1)NCCC(=O)N1CCCC2CCCCC21] | 3-cyclopentyl-N-[3-(octahydroquinolin-1-yl)-3-oxopropyl]propionamide | A | 7.28 | 335 |
| Id.22 | 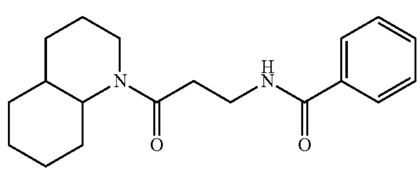 [SMILES: O=C(NCCC(=O)N1CCCC2CCCCC21)c1ccccc1] | N-[3-(octahydroquinolin-1-yl)-3-oxopropyl]benzamide | A | 6.39 | 315 |
| Id.23 | 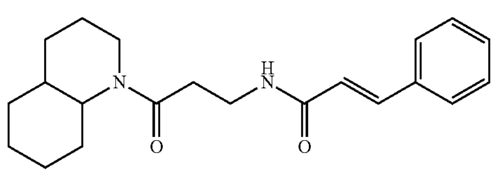 [SMILES: O=C(/C=C/c1ccccc1)NCCC(=O)N1CCCC2CCCCC21] | (E)-N-[3-(octahydroquinolin-1-yl)-3-oxopropyl]-3-phenylacrylamide | A | 6.77 | 341 |
| Id.24 | 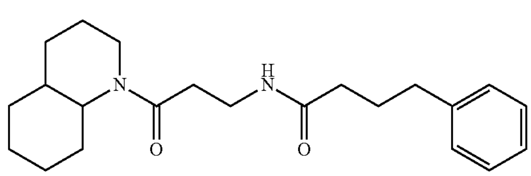 [SMILES: O=C(CCCc1ccccc1)NCCC(=O)N1CCCC2CCCCC21] | N-[3-(octahydroquinolin-1-yl)-3-oxopropyl]-4-phenylbutyramide | A | 7.05 | 357 |

| Ex. | structure | name | method | tr (min) | m/z |
|---|---|---|---|---|---|
| Id.25 | 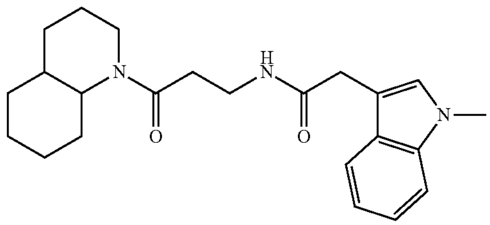 [SMILES: Cn1cc(CC(=O)NCCC(=O)N2CCCC3CCCCC32)c2ccccc21] | 2-(1-methyl-1H-indol-3-yl)-N-[3-(octahydroquinolin-1-yl)-3-oxopropyl]acetamide | A | 6.83 | 382 |
| Id.26 | 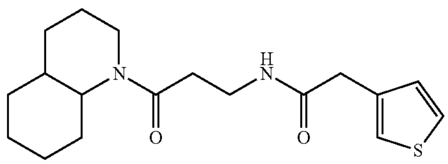 [SMILES: O=C(Cc1ccsc1)NCCC(=O)N1CCCC2CCCCC21] | N-[3-(octahydroquinolin-1-yl)-3-oxopropyl]-2-thiophen-3-ylacetamide | A | 6.27 | 335 |
| Id.27 | 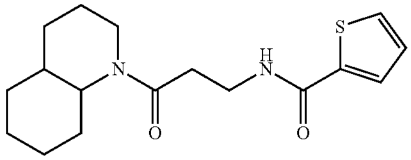 [SMILES: O=C(NCCC(=O)N1CCCC2CCCCC21)c1cccs1] | Thiophene-2-carboxylic acid [3-(octahydroquinolin-1-yl)-3-oxopropyl]amide | A | 6.26 | 321 |
| Id.28 | 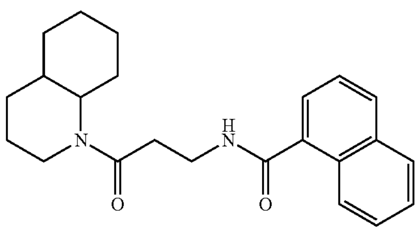 [SMILES: O=C(NCCC(=O)N1CCCC2CCCCC21)c1cccc2ccccc12] | Naphthalene-1-carboxylic acid [3-(octahydroquinolin-1-yl)-3-oxopropyl]amide | A | 7.09 | 365 |
| Id.29 | 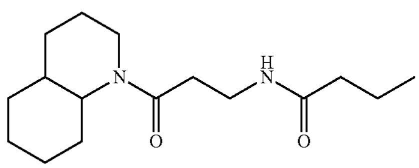 [SMILES: CCCC(=O)NCCC(=O)N1CCCC2CCCCC21] | N-[3-(octahydroquinolin-1-yl)-3-oxopropyl]butyramide | A | 5.79 | 281 |
| Id.30 | 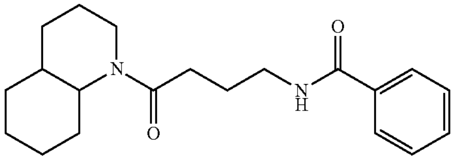 [SMILES: O=C(NCCCC(=O)N1CCCC2CCCCC21)c1ccccc1] | N-[4-(octahydroquinolin-1-yl)-4-oxobutyl]benzamide | A | 6.43 | 329 |
| Id.31 | 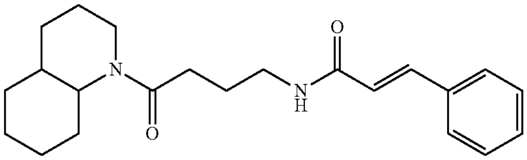 [SMILES: O=C(/C=C/c1ccccc1)NCCCC(=O)N1CCCC2CCCCC21] | (E)-N-[4-(octahydroquinolin-1-yl)-4-oxobutyl]-3-phenylacrylamide | A | 6.75 | 355 |
| Id.32 | 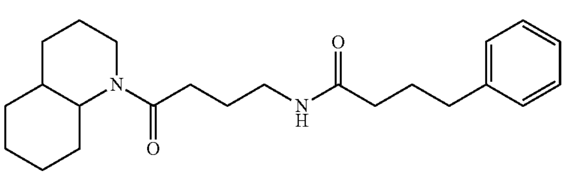 [SMILES: O=C(CCCc1ccccc1)NCCCC(=O)N1CCCC2CCCCC21] | N-[4-(octahydroquinolin-1-yl)-4-oxobutyl]-4-phenylbutyramide | A | 7.03 | 371 |

| Ex. | structure | name | method | tr (min) | m/z |
|---|---|---|---|---|---|
| Id.33 | 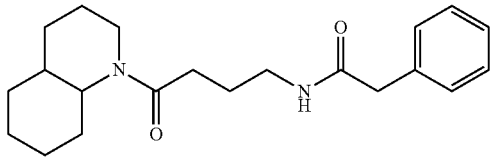 [SMILES: O=C(Cc1ccccc1)NCCCC(=O)N1CCCC2CCCCC21] | N-[4-(octahydroquinolin-1-yl)-4-oxobutyl]-2-phenylacetamide | A | 6.44 | 343 |
| Id.34 | 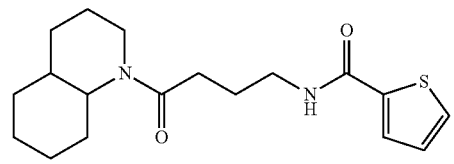 [SMILES: O=C(NCCCC(=O)N1CCCC2CCCCC21)c1cccs1] | Thiophene-2-carboxylic acid [4-(octahydroquinolin-1-yl)-4-oxobutyl]amide | A | 6.32 | 335 |
| Id.35 | 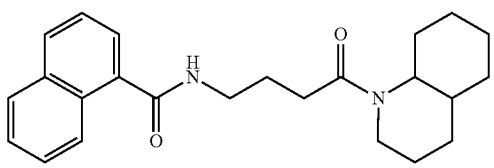 [SMILES: O=C(NCCCC(=O)N1CCCC2CCCCC21)c1cccc2ccccc12] | Naphthalene-1-carboxylic acid [4-(octahydroquinolin-1-yl)-4-oxobutyl]amide | A | 7.04 | 379 |
| Id.36 | 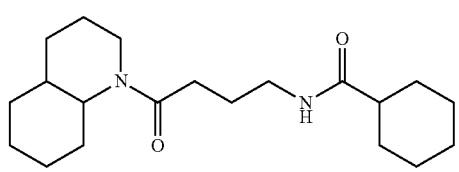 [SMILES: O=C(NCCCC(=O)N1CCCC2CCCCC21)C1CCCCC1] | Cyclohexanecarboxylic acid [4-(octahydroquinolin-1-yl)-4-oxobutyl]amide | A | 6.77 | 335 |
| Id.37 | 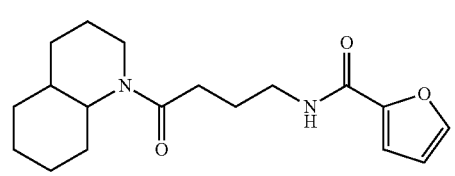 [SMILES: O=C(NCCCC(=O)N1CCCC2CCCCC21)c1ccco1] | Furan-2-carboxylic acid [4-(octahydroquinolin-1-yl)-4-oxobutyl]amide | A | 5.87 | 319 |
| Id.38 | 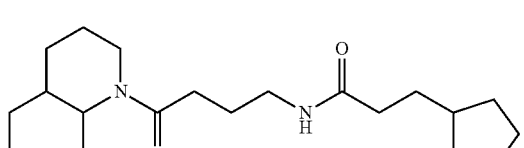 | 3-cyclopentyl-N-[4-(octahydroquinolin-1-yl)-4-oxobutyl]propionamide | A | 7.27 | 349 |
| Id.39 | 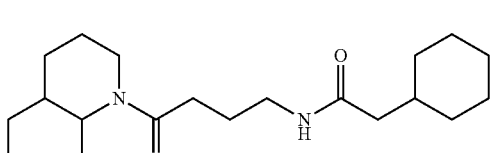 | 2-cyclohexyl-N-[4-(octahydroquinolin-1-yl)-4-oxobutyl]acetamide | A | 7.14 | 349 |
| Id.40 | 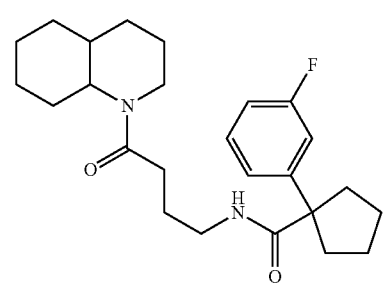 [SMILES: O=C(CCCNC(=O)C1(c2cccc(F)c2)CCCC1)N1CCCC2CCCCC21] | 1-(3-fluorophenyl)cyclopentanecarboxylic acid [4-(octahydroquinolin-1-yl)-4-oxobutyl]amide | A | 7.95 | 415 |

| Ex. | structure | name | method | tr (min) | m/z |
|---|---|---|---|---|---|
| Id.41 | 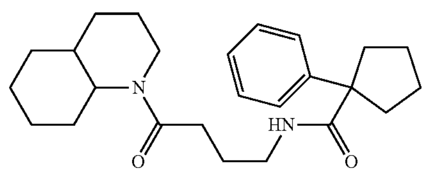 [SMILES: O=C(CCCNC(=O)C1(c2ccccc2)CCCC1)N1CCCC2CCCCC21] | 1-phenylcyclopentanecarboxylic acid [4-(octahydroquinolin-1-yl)-4-oxobutyl]amide | A | 7.83 | 397 |
| Id.42 | 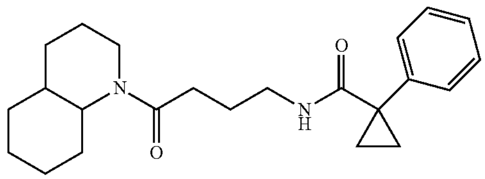 [SMILES: O=C(CCCNC(=O)C1(c2ccccc2)CC1)N1CCCC2CCCCC21] | 1-phenylcyclopropanecarboxylic acid [4-(octahydroquinolin-1-yl)-4-oxobutyl]amide | A | 7.23 | 369 |
| Id.43 | 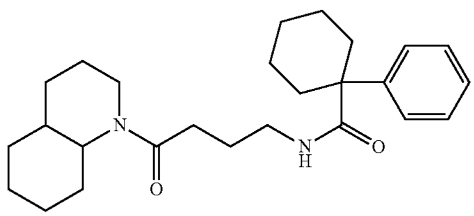 [SMILES: O=C(CCCNC(=O)C1(c2ccccc2)CCCCC1)N1CCCC2CCCCC21] | 1-phenylcyclohexanecarboxylic acid [4-(octahydroquinolin-1-yl)-4-oxobutyl]amide | A | 8.16 | 411 |
| Id.44 | 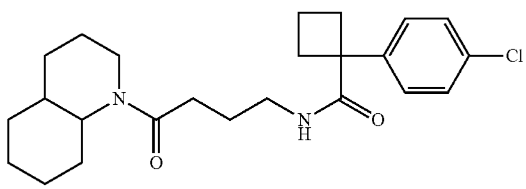 [SMILES: O=C(CCCNC(=O)C1(c2ccc(Cl)cc2)CCC1)N1CCCC2CCCCC21] | 1-(4-chlorophenyl)cyclobutanecarboxylic acid [4-(octahydroquinolin-1-yl)-4-oxobutyl]amide | A | 7.94 | 417 |
| Id.45 | 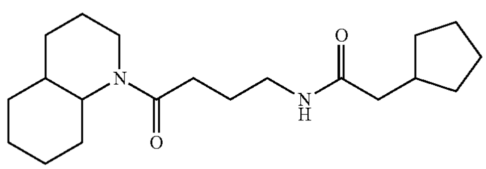 [SMILES: O=C(CC1CCCC1)NCCCC(=O)N1CCCC2CCCCC21] | 2-cyclopentyl-N-[4-(octahydroquinolin-1-yl)-4-oxobutyl]acetamide | A | 6.77 | 335 |
| Id.46 | 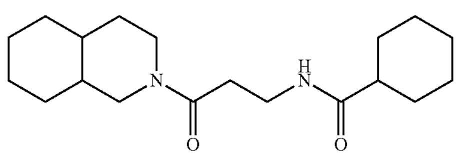 [SMILES: O=C(NCCC(=O)N1CCC2CCCCC2C1)C1CCCCC1] | Cyclohexanecarboxylic acid [3-(octahydroisoquinolin-2-yl)-3-oxopropyl]amide | A | 6.74<br>6.93 | 321<br>321 |
| Id.47 | 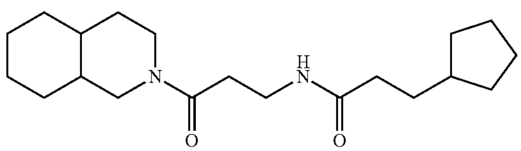 [SMILES: O=C(CCC1CCCC1)NCCC(=O)N1CCC2CCCCC2C1] | 3-cyclopentyl-N-[3-(octahydroisoquinolin-2-yl)-3-oxopropyl]propionamide | A | 7.27<br>7.44 | 335<br>335 |
| Id.48 | 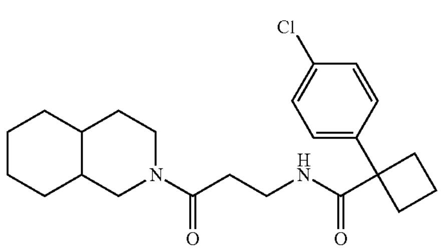 [SMILES: O=C(CCNC(=O)C1(c2ccc(Cl)cc2)CCC1)N1CCC2CCCCC2C1] | 1-(4-chlorophenyl)cyclobutanecarboxylic acid [3-(octahydroisoquinolin-2-yl)-3-oxopropyl]amide | A | 7.95<br>8.09 | 403, 405<br>403, 405 |

-continued

| Ex. | structure | name | method | tr (min) | m/z |
|---|---|---|---|---|---|
| Id.49 | 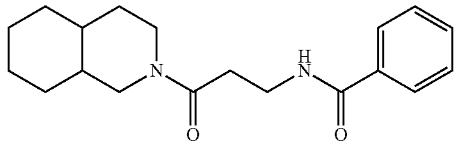 [SMILES: O=C(NCCC(=O)N1CCC2CCCCC2C1)c1ccccc1] | N-[3-(octahydroisoquinolin-2-yl)-3-oxopropyl]benzamide | A | 6.34<br>6.53 | 315<br>315 |
| Id.50 | 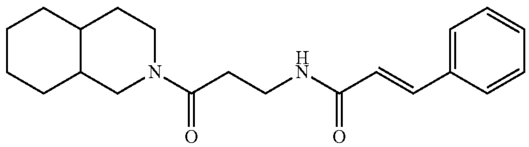 [SMILES: O=C(/C=C/c1ccccc1)NCCC(=O)N1CCC2CCCCC2C1] | (E)-N-[3-(octahydroisoquinolin-2-yl)-3-oxopropyl]-3-phenylacrylamide | A | 6.71<br>6.88 | 341<br>341 |
| Id.51 | 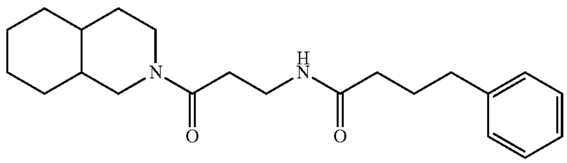 [SMILES: O=C(CCCc1ccccc1)NCCC(=O)N1CCC2CCCCC2C1] | N-[3-(octahydroisoquinolin-2-yl)-3-oxopropyl]-4-phenylbutyramide | A | 7.02<br>7.19 | 357<br>357 |
| Id.52 | 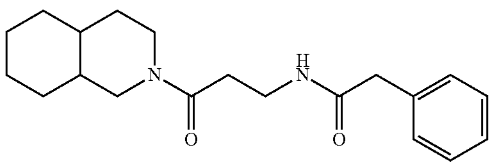 [SMILES: O=C(Cc1ccccc1)NCCC(=O)N1CCC2CCCCC2C1] | N-[3-(octahydroisoquinolin-2-yl)-3-oxopropyl]-2-phenylacetamide | A | 6.41<br>6.59 | 329<br>329 |
| Id.53 | 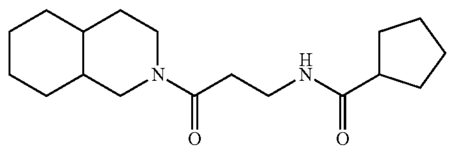 [SMILES: O=C(NCCC(=O)N1CCC2CCCCC2C1)C1CCCC1] | Cyclopentanecarboxylic acid [3-(octahydroisoquinolin-2-yl)-3-oxopropyl]amide | A | 6.38<br>6.57 | 307<br>307 |
| Id.54 | 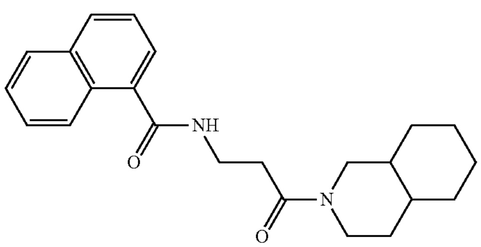 [SMILES: O=C(NCCC(=O)N1CCC2CCCCC2C1)c1cccc2ccccc12] | Naphthalene-1-carboxylic acid [3-(octahydroisoquinolin-2-yl)-3-oxopropyl]amide | A | 7.04<br>7.21 | 365<br>365 |
| Id.55 | 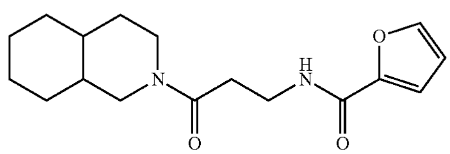 | Furan-2-carboxylic acid [3-(octahydroisoquinolin-2-yl)-3-oxopropyl]amide | A | 5.84<br>6.05 | 305<br>305 |
| Id.56 | 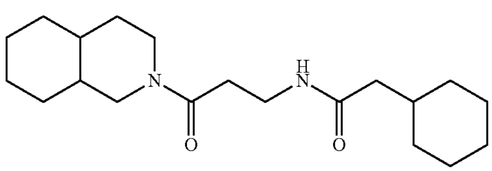 [SMILES: O=C(CC1CCCCC1)NCCC(=O)N1CCC2CCCCC2C1] | 2-cyclohexyl-N-[3-(octahydroisoquinolin-2-yl)-3-oxopropyl]acetamide | A | 7.14<br>7.30 | 335<br>335 |
| Id.57 | 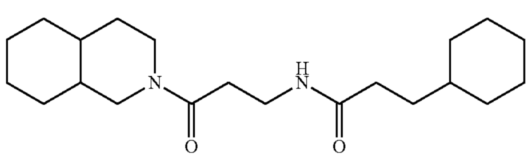 [SMILES: O=C(CCC1CCCCC1)NCCC(=O)N1CCC2CCCCC2C1] | 3-cyclohexyl-N-[3-(octahydroisoquinolin-2-yl)-3-oxopropyl]propionamide | A | 7.67<br>7.83 | 349<br>349 |

| Ex. | structure | name | method | tr (min) | m/z |
|---|---|---|---|---|---|
| Id.58 | 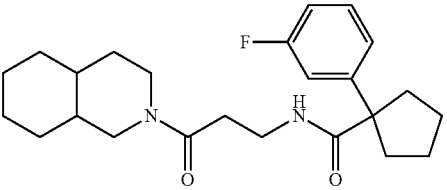 [SMILES: O=C(CCNC(=O)C1(c2cccc(F)c2)CCCC1)N1CCC2CCCCC2C1] | 1-(3-fluorophenyl)cyclopentanecarboxylic acid [3-(octahydroisoquinolin-2-yl)-3-oxopropyl]amide | A | 7.95<br>8.09 | 401<br>401 |
| Id.59 | 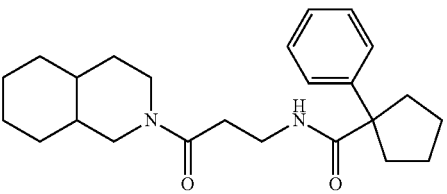 [SMILES: O=C(CCNC(=O)C1(c2ccccc2)CCCC1)N1CCC2CCCCC2C1] | 1-phenylcyclopentanecarboxylic acid [3-(octahydroisoquinolin-2-yl)-3-oxopropyl]amide | A | 7.84<br>7.99 | 383<br>383 |
| Id.60 | 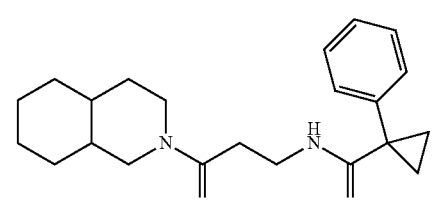 | 1-phenylcyclopropanecarboxylic acid [3-(octahydroisoquinolin-2-yl)-3-oxopropyl]amide | A | 7.25<br>7.41 | 355<br>355 |
| Id.61 | 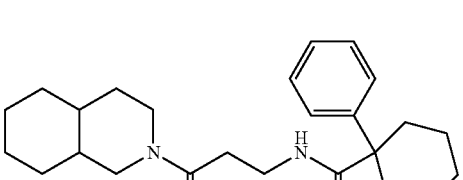 | 1-phenylcyclohexanecarboxylic acid [3-(octahydroisoquinolin-2-yl)-3-oxopropyl]amide | A | 8.17<br>8.31 | 397<br>397 |
| Id.62 | 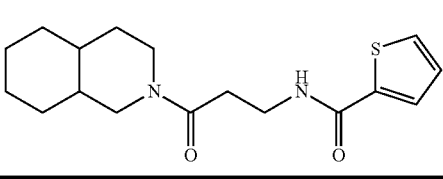 | Thiophene-2-carboxylic acid [3-(octahydroisoquinolin-2-yl)-3-oxopropyl]amide | A | 6.21<br>6.39 | 321<br>321 |

Example It.1

N-[3-(octahydroquinolin-1-yl)-3-oxopropyl]propionamide

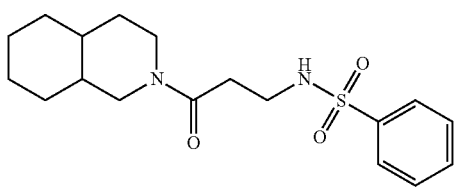 [SMILES: O=C(CCNS(=O)(=O)c1ccccc1)N1CCC2CCCCC2C1]

23.4 mg (0.11 mmol) of the intermediate amine Vc.6 and 29 μL of Et₃N are added to a solution of 18.1 mg (0.10 mmol) of benzenesulfonyl chloride in 2 mL of AcOEt. The solution formed is kept under stirring at rt for 18 h. It is then treated with water and more AcOEt is added, the organic phase is separated and the aqueous phase is extracted once more with more AcOEt. The organic phases are pooled and successively washed with saturated NaHCO₃ solution, 1N HCl and brine. It is then dried over anhydrous Na₂SO₄, it is filtered and the solvent is evaporated under reduced pressure. The residue is purified by means of silica gel column chromatography, using a (1:1) mixture of hexane-AcOEt as eluent, yielding 23 mg of a yellowish paste identified as example It.1. Method A: tr: 6.76 min/6.97 min; m/z: 351/351

The following examples were prepared in a manner similar to example 1t.1:

| Ex. | structure | name | method | tr (min) | m/z |
|---|---|---|---|---|---|
| It.2 | 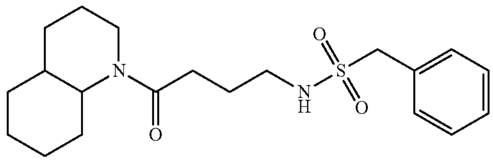 [SMILES: O=C(CCCNS(=O)(=O)Cc1ccccc1)N1CCCC2CCCCC21] | N-[4-(octahydroquinolin-1-yl)-4-oxobutyl]-C-phenylmethanesulfonamide | A | 6.84 | 379 |
| It.3 | 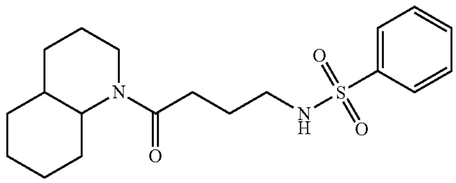 [SMILES: O=C(CCCNS(=O)(=O)c1ccccc1)N1CCCC2CCCCC21] | N-[4-(octahydroquinolin-1-yl)-4-oxobutyl]benzosulfonamide | A | 6.79 | 365 |
| It.4 | 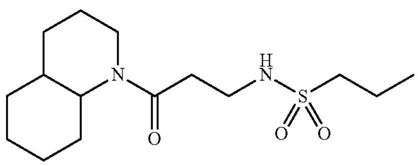 [SMILES: CCCS(=O)(=O)NCCC(=O)N1CCCC2CCCCC21] | Propane-1-sulfonic acid [3-(octahydroquinolin-1-yl)-3-oxopropyl]amide | A | 6.26 | 317 |
| It.5 | 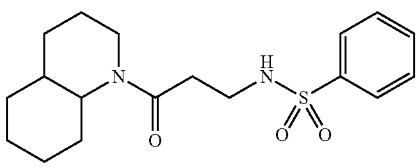 [SMILES: O=C(CCNS(=O)(=O)c1ccccc1)N1CCCC2CCCCC21] | N-[3-(octahydroquinolin-1-yl)-3-oxopropyl]benzesulfonamide | A | 6.82 | 351 |
| It.6 | 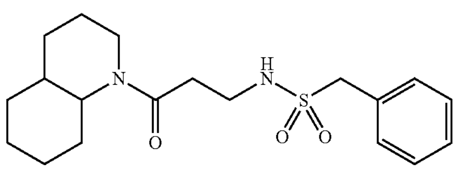 [SMILES: O=C(CCNS(=O)(=O)Cc1ccccc1)N1CCCC2CCCCC21] | N-[3-(octahydroquinolin-1-yl)-3-oxopropyl]-C-phenylmethanesulfonamide | A | 6.85 | 365 |
| It.7 | 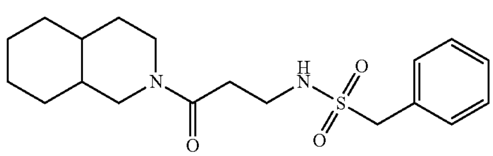 [SMILES: O=C(CCNS(=O)(=O)Cc1ccccc1)N1CCC2CCCCC2C1] | N-[3-(octahydroisoquinolin-2-yl)-3-oxopropyl]-C-phenylmethanesulfonamide | A | 6.84<br>7.01 | 365<br>365 |

Example Ip.1

Cycloheptylthiocarbamic acid S-[4-(octahydroisoquinolin-2-yl)-4-oxobutyl]ester

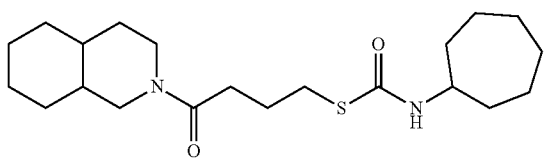 [SMILES: O=C(NC1CCCCCC1)SCCCC(=O)N1CCC2CCCCC2C1]

12.8 µL of cycloheptylisocyanate (0.1 mmol) are added to a solution of 35 mg (0.15 mmol) of intermediate IVp.4 and 23 µL of Et₃N in 2 mL of THF at 0° C. Once added it is left to stir at reflux for 24 h. AcOEt is then added to the reaction mixture and it is sequentially washed with water and brine. The organic phase is dried over anhydrous Na₂SO₄, it is filtered and the solvent is evaporated under reduced pressure. The residue is purified by means of silica gel column chromatography, using a (200:3) mixture of DCM-MeOH as eluent, yielding 23 mg of a colorless paste identified as example Ip.1. Method B: tr: 4.63 min; m/z: 381

The following compounds were prepared in a manner similar to example Ip.1:

| Ex. | structure | name | method | tr (min) | m/z |
|---|---|---|---|---|---|
| Ip.2 | 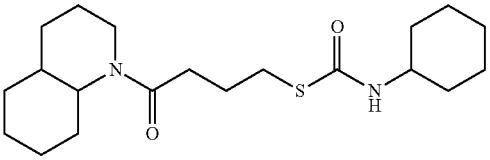 [SMILES: O=C(NC1CCCCC1)SCCCC(=O)N1CCCC2CCCCC21] | Cyclohexylthiocarbamic acid S-[4-(octahydroquinolin-1-yl)-4-oxobutyl] ester | B | 4.34 | 367 |
| Ip.3 | 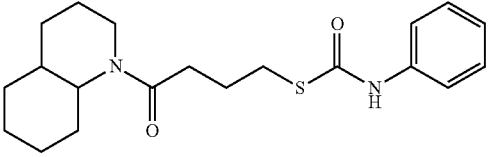 [SMILES: O=C(Nc1ccccc1)SCCCC(=O)N1CCCC2CCCCC21] | Phenylthiocarbamic acid S-[4-(octahydroquinolin-1-yl)-4-oxobutyl] ester | B | 4.14 | 361 |
| Ip.4 | 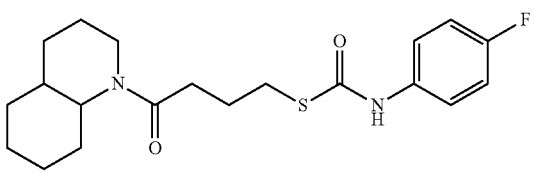 [SMILES: O=C(Nc1ccc(F)cc1)SCCCC(=O)N1CCCC2CCCCC21] | (4-fluorophenyl)thiocarbamic acid S-[4-(octahydroquinolin-1-yl)-4-oxobutyl] ester | B | 4.19 | 379 |
| Ip.5 | 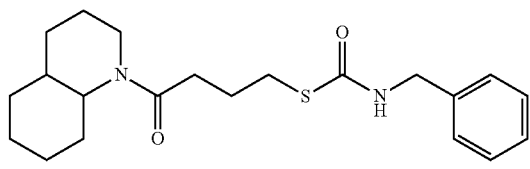 [SMILES: O=C(NCc1ccccc1)SCCCC(=O)N1CCCC2CCCCC21] | Benzylthiocarbamic acid S-[4-(octahydroquinolin-1-yl)-4-oxobutyl] ester | B | 4.08 | 375 |
| Ip.6 | 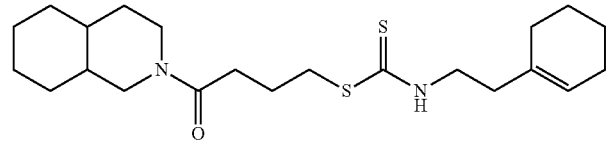 [SMILES: O=C(CCCSC(=S)NCCC1=CCCCC1)N1CCC2CCCCC2C1] | (2-cyclohex-1-enylethyl)dithiocarbamic acid 4-(octahydroisoquinolin-2-yl)-4-oxobutyl ester | B | 5.19 | 409 |
| Ip.7 | 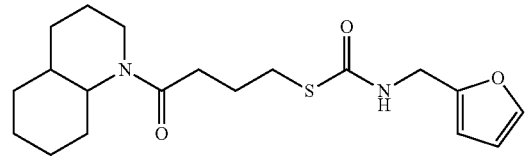 [SMILES: O=C(NCc1ccco1)SCCCC(=O)N1CCCC2CCCCC21] | (Furan-2-ylmethyl)carbamic acid S-[4-(octahydroquinolin-1-yl)-4-oxobutyl] ester | B | 3.82 | 365 |
| Ip.8 | 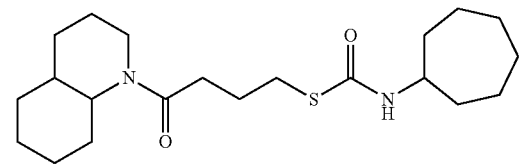 [SMILES: O=C(NC1CCCCCC1)SCCCC(=O)N1CCCC2CCCCC21] | Cycloheptylthiocarbamic acid S-[4-(octahydroquinolin-1-yl)-4-oxobutyl] ester | B | 4.54 | 381 |
| Ip.9 | 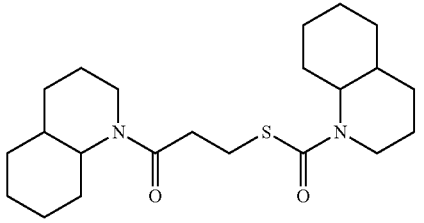 [SMILES: O=C(CCSC(=O)N1CCCC2CCCCC21)N1CCCC2CCCCC21] | Octahydroquinoline-1-thiocarbamic acid S-[3-(octahydroquinolin-1-yl)-3-oxopropyl] ester | B | 4.94 | 393 |
| Ip.10 | 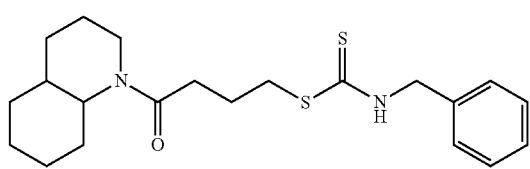 [SMILES: O=C(CCCSC(=S)NCc1ccccc1)N1CCCC2CCCCC21] | Benzyldithiocarbamic acid 4-(octahydroquinolin-1-yl)-4-oxobutyl ester | B | 4.54 | 391 |

-continued

| Ex. | structure | name | method | tr (min) | m/z |
|---|---|---|---|---|---|
| Ip.11 | 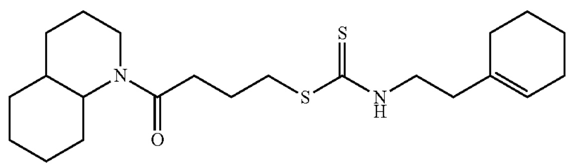 [SMILES: O=C(CCCSC(=S)NCCC1=CCCCC1)N1CCCC2CCCCC21] | [2-(cyclohex-1-en-1-yl)ethyl]dithiocarbamic acid 4-(octahydroquinolin-1-yl)-4-oxobutyl ester | B | 5.13 | 409 |
| Ip.12 | 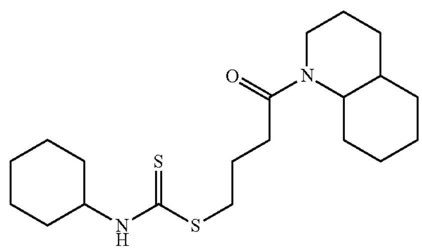 [SMILES: O=C(CCCSC(=S)NC1CCCCC1)N1CCCC2CCCCC21] | Cyclohexyldithiocarbamic acid 4-(octahydroquinolin-1-yl)-4-oxobutyl ester | B | 4.82 | 383 |
| Ip.13 | 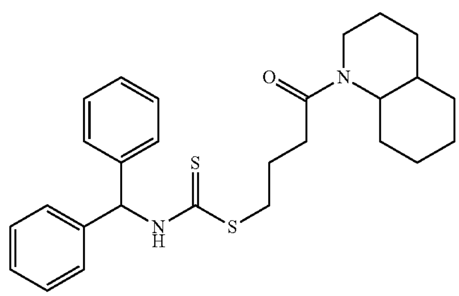 [SMILES: O=C(CCCSC(=S)NC(c1ccccc1)c1ccccc1)N1CCCC2CCCCC21] | Benzhydryldithiocarbamic acid 4-(octahydroquinolin-1-yl)-4-oxobutyl ester | B | 4.98 | 467 |
| Ip.14 | 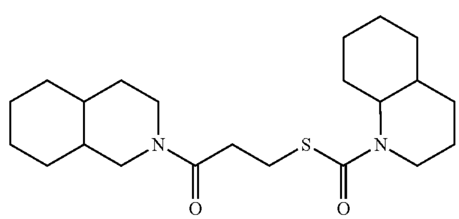 [SMILES: O=C(CCSC(=O)N1CCCC2CCCCC21)N1CCC2CCCCC2C1] | Octahydroquinoline-1-thiocarbamic acid S-[3-(octahydroisoquinolin-2-yl)-3-oxopropyl] ester | B | 4.93<br>5.02 | 393<br>393 |
| Ip.15 | 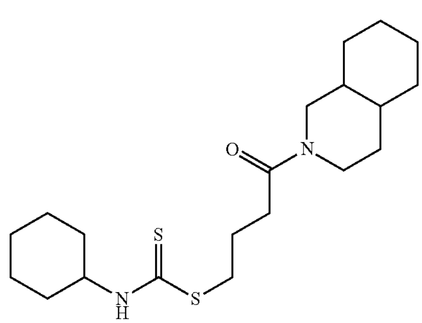 [SMILES: O=C(CCCSC(=S)NC1CCCCC1)N1CCC2CCCCC2C1] | Cyclohexyldithiocarbamic acid 4-(octahydroisoquinolin-2-yl)-4-oxobutyl ester | B | 4.83<br>4.89 | 383<br>383 |

Example Ik.1

1-[2-(octahydroquinolin-1-yl)-2-oxoethyl]-3,4-diphenylpyrrole-2,5-dione

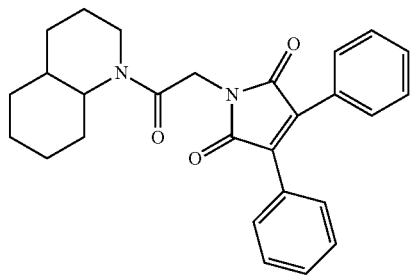 [SMILES: O=C1C(c2ccccc2)=C(c2ccccc2)C(=O)N1CC(=O)N1CCCC2CCCCC21]

22 mg of the intermediate amine Vc.2 (0.11 mmol) are added to a solution of 34 mg (0.13 mmol) of 3,4-diphenylfuran-2,5-dione in 2 mL of DMF. Once added it is left to stir at 100° C. for 48 h. AcOEt is then added to the reaction mixture and it is sequentially washed with water, 5% $NaHCO_3$ solution and brine. The organic phase is dried over anhydrous $Na_2SO_4$, it is filtered and the solvent is evaporated under reduced pressure. The residue is purified by means of silica gel column chromatography, using a (3:2) mixture of hexane-AcOEt as eluent, yielding 7.5 mg of a paste identified as example Ik.1. Method A: tr: 8.55 min; m/z; 429

The following compounds were prepared in a manner similar to example Ik.1:

| Ex. | structure | name | method | tr (min) | m/z |
|---|---|---|---|---|---|
| Ik.2 | 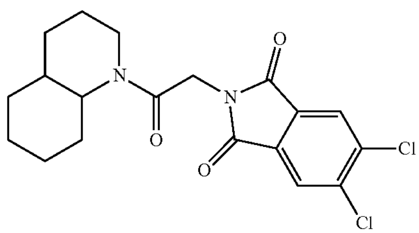 [SMILES: O=C1c2cc(Cl)c(Cl)cc2C(=O)N1CC(=O)N1CCCC2CCCCC21] | 5,6-dichloro-2-[2-(octahydroquinolin-1-yl)-2-oxoethyl]isoindole-1,3-dione | A | 8.12 | 395, 397, 399 |
| Ik.3 | RAC | (2R,6S)-4-[2-(octahydroquinolin-1-yl)-2-oxoethyl]-4-azatricyclo[5.2.2.0$^{(2,6)}$]undec-8-ene-3,5-dione | A | 6.85 | 357 |
| Ik.4 | 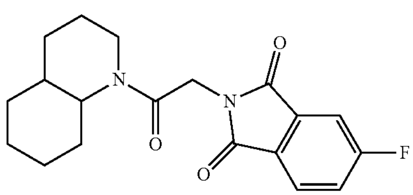 [SMILES: O=C1c2ccc(F)cc2C(=O)N1CC(=O)N1CCCC2CCCCC21] | 5-fluoro-2-[2-(octahydroquinolin-1-yl)-2-oxoethyl]isoindole-1,3-dione | A | 7.16 | 345 |
| Ik.5 | 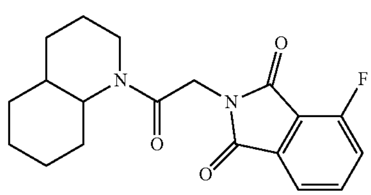 [SMILES: O=C1c2cccc(F)c2C(=O)N1CC(=O)N1CCCC2CCCCC21] | 4-fluoro-2-[2-(octahydroquinolin-1-yl)-2-oxoethyl]isoindole-1,3-dione | A | 7.03 | 345 |
| Ik.6 | RAC | (3aR,7aS)-2-[2-(octahydroquinolin-1-yl)-2-oxoethyl]hexahydroisoindole-1,3-dione | A | 6.76 | 333 |

-continued

| Ex. | structure | name | method | tr (min) | m/z |
|---|---|---|---|---|---|
| Ik.7 | RAC | (3aS,7aR)-2-[3-(octahydroquinolin-1-yl)-3-oxopropyl]hexahydroisoindole-1,3-dione | A | 6.89 | 347 |
| Ik.8 | RAC | (2R,6S)-4-[3-(octahydroquinolin-1-yl)-3-oxopropyl]-4-azatricyclo[5.2.2.0$^{(2,6)}$]undec-8-ene-3,5-dione | A | 7.07 | 371 |
| Ik.9 | RAC | (3aS,7aS)-2-[3-(octahydroquinolin-1-yl)-3-oxopropyl]hexahydroisoindole-1,3-dione | A | 6.89 | 347 |
| Ik.10 | 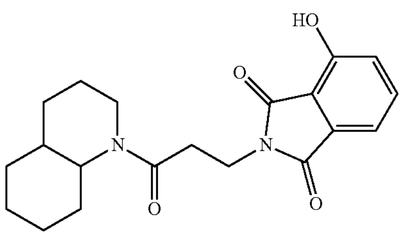 | 4-hydroxy-2-[3-(octahydroquinolin-1-yl)-3-oxopropyl]isoindole-1,3-dione | A | 6.28 | 357 |
| Ik.11 | 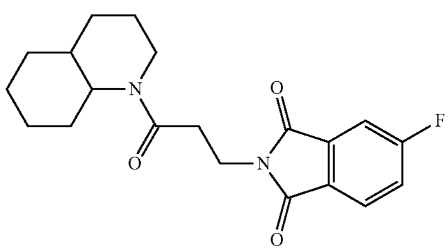 | 5-fluoro-2-[3-(octahydroquinolin-1-yl)-3-oxopropyl]isoindole-1,3-dione | A | 7.25 | 359 |
| Ik.12 | 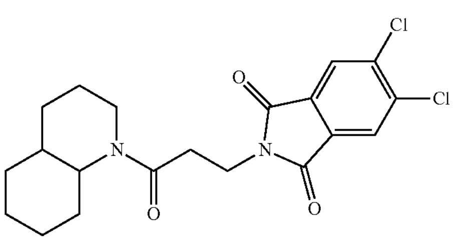 | 5,6-dichloro-2-[3-(octahydroquinolin-1-yl)-3-oxopropyl]isoindole-1,3-dione | A | 8.27 | 409, 411, 413 |

-continued

| Ex. | structure | name | method | tr (min) | m/z |
|---|---|---|---|---|---|
| Ik.13 | 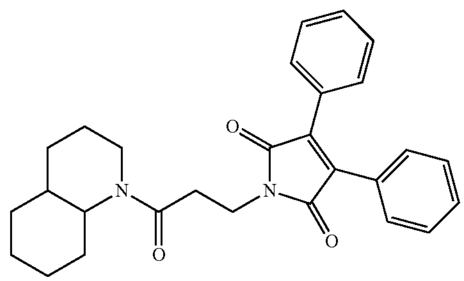 [SMILES: O=C1C(c2ccccc2)=C(c2ccccc2)C(=O)N1CCC(=O)N1CCCC2CCCCC21] | 1-[3-(octahydroquinolin-1-yl)-3-oxopropyl]-3,4-diphenylpyrrole-2,5-dione | A | 8.62 | 443 |
| Ik.14 | 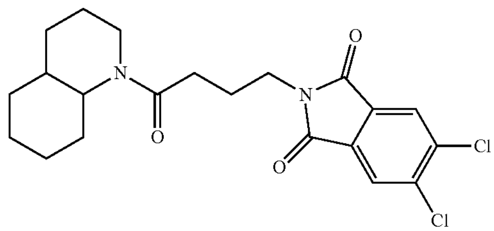 [SMILES: O=C1c2cc(Cl)c(Cl)cc2C(=O)N1CCCC(=O)N1CCCC2CCCCC21] | 5,6-dichloro-2-[4-(octahydroquinolin-1-yl)-4-oxobutyl]isoindole-1,3-dione | A | 8.43 | 423, 425, 427 |
| Ik.15 | 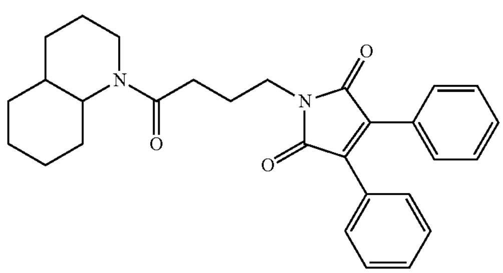 [SMILES: O=C1C(c2ccccc2)=C(c2ccccc2)C(=O)N1CCCC(=O)N1CCCC2CCCCC21] | 1-[4-(octahydroquinolin-1-yl)-4-oxobutyl]-3,4-diphenylpyrrole-2,5-dione | A | 8.75 | 457 |
| Ik.16 | RAC | (3aR,7aR)-2-[4-(octahydroquinolin-1-yl)-4-oxobutyl]hexahydroisoindole-1,3-dione | A | 7.04 | 361 |
| Ik.17 | RAC | (2R,6S)-4-[4-(octahydroquinolin-1-yl)-4-oxobutyl]-4-azatricyclo[5.2.2.0$^{(2,6)}$]undec-8-ene-3,5-dione | A | 7.14 | 385 |
| Ik.18 | 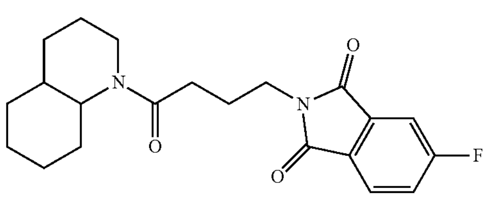 [SMILES: O=C1c2ccc(F)cc2C(=O)N1CCCC(=O)N1CCCC2CCCCC21] | 5-fluoro-2-[4-octahydroquinolin-1-yl)-4-oxobutyl]isoindole-1,3-dione | A | 7.38 | 373 |

-continued

| Ex. | structure | name | method | tr (min) | m/z |
|---|---|---|---|---|---|
| Ik.19 | 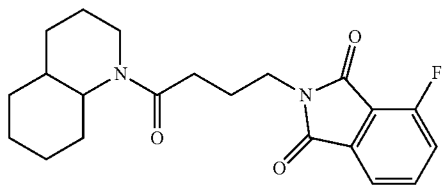 [SMILES: O=C1c2cccc(F)c2C(=O)N1CCCC(=O)N1CCCC2CCCCC21] | 4-fluoro-2-[4-(octahydroquinolin-1-yl)-4-oxobutyl]isoindole-1,3-dione | A | 7.19 | 373 |
| Ik.20 | RAC | (3aR,7aS)-2-[4-(octahydroquinolin-1-yl)-4-oxobutyl]hexahydroisoindole-1,3-dione | A | 7.13 | 361 |
| Ik.21 | 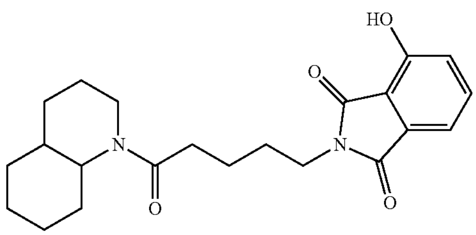 [SMILES: O=C1c2cccc(O)c2C(=O)N1CCCCC(=O)N1CCCC2CCCCC21] | 4-hydroxy-2-[5-(octahydroquinolin-1-yl)-5-oxopentyl]isoindole-1,3-dione | A | 6.64<br>6.69 | 385<br>385 |
| Ik.22 | RAC | (2R,6S)-4-[5-(octahydroquinolin-1-yl)-5-oxopentyl]-4-azatricyclo[5.2.2.0$^{(2,6)}$]undec-8-ene-3,5-dione | A | 7.32 | 399 |
| Ik.23 | 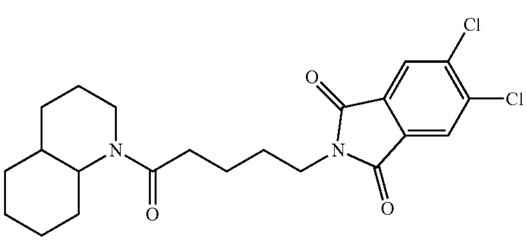 [SMILES: O=C1c2cc(Cl)c(Cl)cc2C(=O)N1CCCCC(=O)N1CCCC2CCCCC21] | 5,6-dichloro-2-[5-(octahydroquinolin-1-yl)-5-oxopentyl]isoindole-1,3-dione | A | 8.62 | 437,<br>439,<br>441 |
| Ik.24 | RAC | (3aS,7aR)-2-[5-(octahydroquinolin-1-yl)-5-oxopentyl]hexahydroisoindole-1,3-dione | A | 7.22 | 375 |

-continued

| Ex. | structure | name | method | tr (min) | m/z |
|---|---|---|---|---|---|
| Ik.25 | 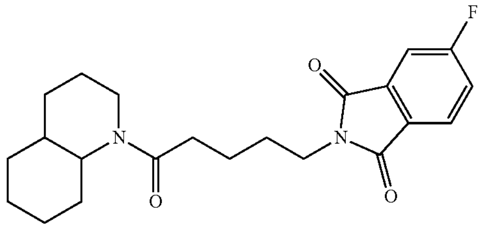 [SMILES: O=C1c2ccc(F)cc2C(=O)N1CCCCC(=O)N1CCCC2CCCCC21] | 5-fluoro-2-[5-(octahydroquinolin-1-yl)-5-oxopentyl]isoindole-1,3-dione | A | 7.61 | 387 |
| Ik.26 | 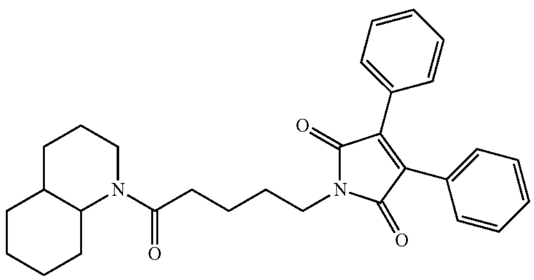 [SMILES: O=C1C(c2ccccc2)=C(c2ccccc2)C(=O)N1CCCCC(=O)N1CCCC2CCCCC21] | 1-[5-(octahydroquinolin-yl)-1-yl)-5-oxopentyl]-3,4-diphenylpyrrole-2,5-dione | A | 8.90 | 471 |
| Ik.27 | 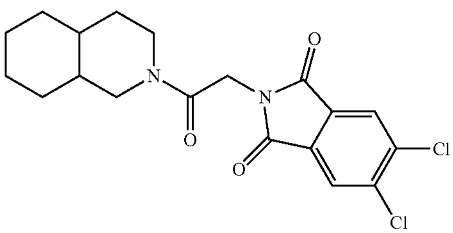 [SMILES: O=C(CN1C(=O)c2cc(Cl)c(Cl)cc2C1=O)N1CCC2CCCCC2C1] | 5,6-dichloro-2-[2-(octahydroisoquinolin-2-yl)-2-oxoethyl]isoindole-1,3-dione | A | 8.24 | 395, 397, 399 |
| Ik.28 | 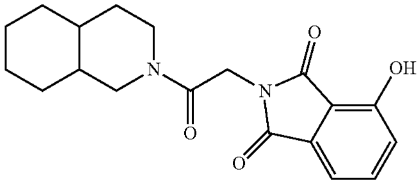 [SMILES: O=C(CN1C(=O)c2cccc(O)c2C1=O)N1CCC2CCCCC2C1] | 4-hydroxy-2-[2-(octahydroisoquinolin-2-yl)-2-oxoethyl]isoindole-1,3-dione | A | 6.45 | 343 |
| Ik.29 | RAC | (2R,6S)-4-[2-(octahydroisoquinolin-2-yl)-2-oxoethyl]-4-azatricyclo[5.2.2.0$^{(2,6)}$]undec-8-ene-3,5-dione | A | 7.02 | 357 |
| Ik.30 | 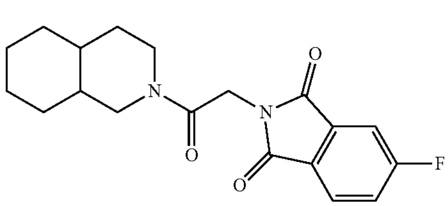 [SMILES: O=C(CN1C(=O)c2ccc(F)cc2C1=O)N1CCC2CCCCC2C1] | 5-fluoro-2-[2-(octahydroisoquinolin-2-yl)-2-oxoethyl]isoindole-1,3-dione | A | 7.14<br>7.31 | 345<br>345 |
| Ik.31 | 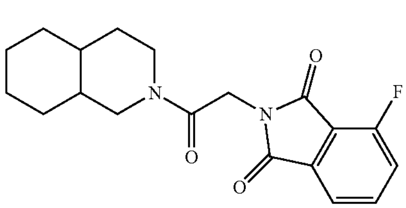 [SMILES: O=C(CN1C(=O)c2cccc(F)c2C1=O)N1CCC2CCCCC2C1] | 4-fluoro-2-[2-(octahydroisoquinolin-2-yl)-2-oxoethyl]isoindole-1,3-dione | A | 7.19 | 345 |

-continued

| Ex. | structure | name | method | tr (min) | m/z |
|---|---|---|---|---|---|
| Ik.32 | RAC | (3aR,7aS)-2-[2-(octahydroisoquinolin-2-yl)-2-oxoethyl]hexahydroisoindole-1,3-dione | A | 6.76<br>6.94 | 333<br>333 |
| Ik.33 | 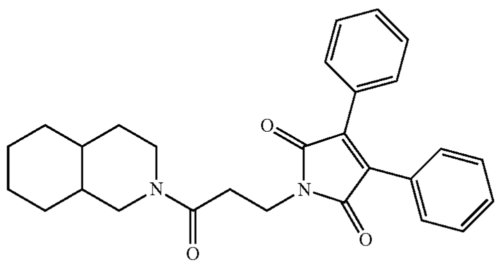 | 1-[3-(octahydroisoquinolin-2-yl)-3-oxopropyl]-3,4-diphenylpyrrole-2,5-dione | A | 8.61<br>8.73 | 443<br>443 |
| Ik.34 | RAC | (3aR,7aR)-2-[3-(octahydroisoquinolin-2-yl)-3-oxopropyl]hexahydroisoindole-1,3-dione | A | 6.89<br>7.07 | 347<br>347 |
| Ik.35 | 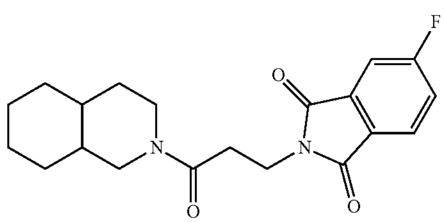 | 5-fluoro-2-[3-(octahydroisoquinolin-2-yl)-3-oxopropyl]isoindole-1,3-dione | A | 7.36 | 359 |
| Ik.36 | 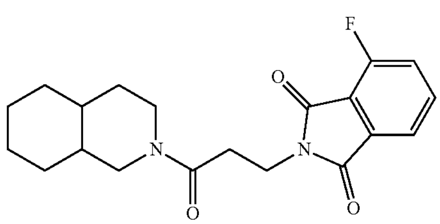 | 4-fluoro-2-[3-(octahydroisoquinolin-2-yl)-3-oxopropyl]isoindole-1,3-dione | A | 7.01<br>7.18 | 359<br>359 |
| Ik.37 | 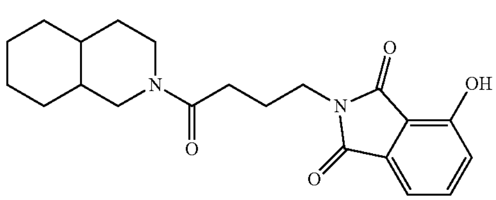 | 4-hydroxy-2-[4-(octahydroisoquinolin-2-yl)-4-oxobutyl]isoindole-1,3-dione | A | 6.45<br>6.61 | 371<br>371 |
| Ik.38 | RAC | (2R,6S)-4-[4-(octahydroisoquinolin-2-yl)-4-oxobutyl]-4-azatricyclo[5.2.2.0$^{(2,6)}$]undec-8-ene-3,5-dione | A | 7.14<br>7.32 | 385<br>385 |

-continued

| Ex. | structure | name | method | tr (min) | m/z |
|---|---|---|---|---|---|
| Ik.39 | 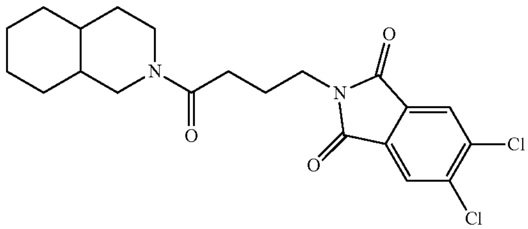 [SMILES: O=C(CCCN1C(=O)c2cc(Cl)c(Cl)cc2C1=O)N1CCC2CCCCC2C1] | 5,6-dichloro-2-[4-(octahydroisoquinolin-2-yl)-4-oxobutyl]isoindole-1,3-dione | A | 8.43<br>8.56 | 423,<br>425,<br>427<br>423,<br>425,<br>427 |
| Ik.40 | 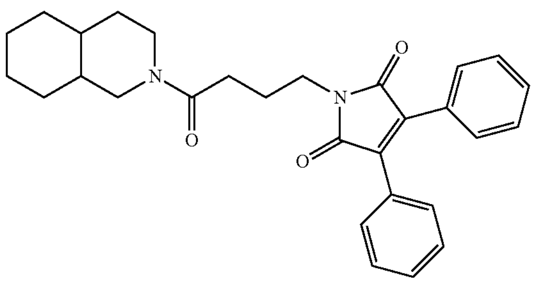 [SMILES: O=C(CCCN1C(=O)C(c2ccccc2)=C(c2ccccc2)C1=O)N1CCC2CCCCC2C1] | 1-[4-(octahydroisoquinolin-2-yl)-4-oxobutyl]-3,4-diphenylpyrrole-2,5-dione | A | 8.77<br>8.89 | 457<br>457 |
| Ik.41 | RAC | (3aS,7aR)-2-[4-(octahydroisoquinolin-2-yl)-4-oxobutyl]hexahydroisoindole-1,3-dione | A | 7.04<br>7.22 | 361<br>361 |
| Ik.42 | 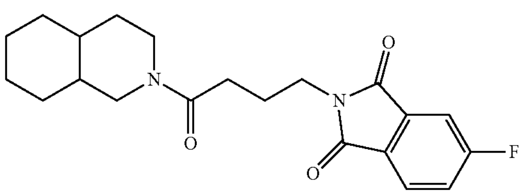 [SMILES: O=C(CCCN1C(=O)c2ccc(F)cc2C1=O)N1CCC2CCCCC2C1] | 5-fluoro-2-[4-(octahydroisoquinolin-2-yl)-4-oxobutyl]isoindole-1,3-dione | A | 7.39<br>7.55 | 373<br>373 |
| Ik.43 | 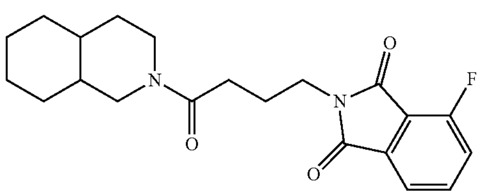 [SMILES: O=C(CCCN1C(=O)c2cccc(F)c2C1=O)N1CCC2CCCCC2C1] | 4-fluoro-2-[4-(octahydroisoquinolin-2-yl)-4-oxobutyl]isoindole-1,3-dione | A | 7.20<br>7.36 | 373<br>373 |
| Ik.44 | 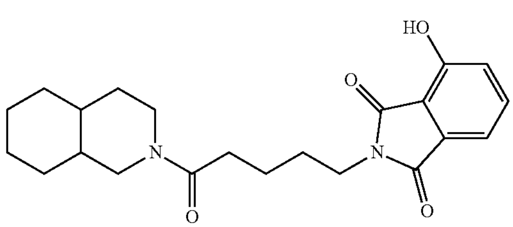 [SMILES: O=C(CCCCN1C(=O)c2cccc(O)c2C1=O)N1CCC2CCCCC2C1] | 4-hydroxy-2-[5-(octahydroisoquinolin-2-yl)-5-oxopentyl]isoindole-1,3-dione | A | 6.64<br>6.80 | 385<br>385 |

| Ex. | structure | name | method | tr (min) | m/z |
|---|---|---|---|---|---|
| Ik.45 | RAC | (2R,6S)-4-[5-(octahydroisoquinolin-2-yl)-5-oxopentyl]-4-azatricyclo[5.2.2.0$^{(2,6)}$]undec-8-ene-3,5-dione | A | 7.50 | 399 |
| Ik.46 | 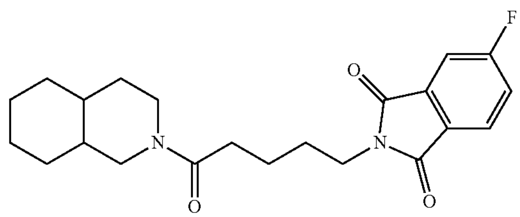 | 5-fluoro-2-[5-(octahydroisoquinolin-2-yl)-5-oxopentyl]isoindole-1,3-dione | A | 7.59<br>7.75 | 387<br>387 |
| Ik.47 | 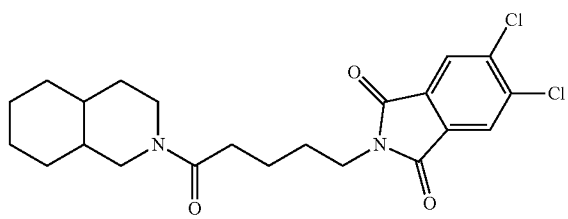 | 5,6-dichloro-2-[5-(octahydroisoquinolin-2-yl)-5-oxopentyl]isoindole-1,3-dione | A | 8.60<br>8.72 | 437,<br>439,<br>441<br>437,<br>439,<br>441 |

Example Ij.1

[3-(octahydroquinolin-1-yl)-3-oxopropyl]carbamic acid t-butylester

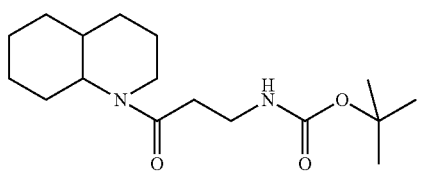 [SMILES: CC(C)(C)OC(=O)NCCC(=O)N1CCCC2CCCCC21]

0.12 mg (1 μmol) of 4-dimethylaminopyridine and 43 mg (0.2 mmol) of di-tertbutyl dicarbonate are added to a solution of 21 mg (0.1 mmol) of intermediate Vc.3 in 2 mL of DCM. The mixture is stirred for 18 h at rt. The solvent is evaporated and water and AcOEt are then added, the aqueous phase is separated and extracted again with AcOEt, the pooled organic phases are sequentially washed with 1N HCl and brine. The organic phase is dried over anhydrous Na$_2$SO$_4$, it is filtered and the solvent is evaporated under reduced pressure. The residue is purified by means of silica gel column chromatography, using a (20:1) mixture of DCM-MeOH as eluent, yielding 6.5 mg of a colorless paste identified as example Ij.1.
Method A: tr: 7.15 min; m/z: 311

Pharmacological Examples

Determination of the Inhibitory Activity of 11-Beta-HSD1 in the Microsomal Fraction of Transfected HEK293 Cells 99 μL of a reaction mixture which contained 80 nM [$^3$H]-cortisone, 1 mM NADPH and 40 μg/mL of the microsome preparations of HEK-293 cells stably transfected with the 11-beta-HSD1 clone, dissolved in assay buffer (50 mM HEPES, 100 mM KCl, 5 mM NaCl, 2 mM MgCl$_2$/100 mL H$_2$O) were added to a 96-well plate. The inhibitors to be analyzed were dissolved in 100% DMSO, and the final concentration in the reaction was 1%.

The reaction mixture was incubated for 2 hours at 37° C. under stirring. The total reaction volume per well was 100 μL. The stop solution (5 mg/mL ProteinA Spa bead, Superblock Blocking Buffer, 30 μM glycyrrhetinic acid, 1 μg/mL anti-cortisol monoclonal antibody) was simultaneously prepared, being incubated under stirring for two hours at rt and protected from light. Once the two hours lapsed, 50 μL of the stop solution were dispensed to each well in the reaction plate and was left to incubate for two hours at rt under stirring and protected from light. Once the second incubation ended, the plate was read in a 1450 Microbeta Tritalux (Wallac®) scintillation counter for 30 seconds per well.

Determination of the Inhibitory Activity of 11-Beta-HSD2 in the Microsomal Fraction of Transfected HEK293 Cells 59 μL of the reaction mixture were added to a 96-well plate. This contained 1 mM NAD$^+$ and 80 μg/mL of the microsome preparations of HEK-293 cells stably transfected with the 11-beta-HSD2 clone, dissolved in assay buffer (50 mM HEPES, 100 mM KCl, 5 mM NaCl, 2 mM MgCl$_2$/100 mL H$_2$O). The inhibitors to be analyzed were dissolved in 100% DMSO, and the final concentration in the reaction was 1%. The reaction mixture was pre-incubated for 30 minutes at 37° C. under stirring. 40 μL of the reaction substrate, 3.2 nM [$^3$H]-cortisol dissolved in assay buffer were added. It was incubated at 37° C. for two hours under stirring. The stop solution was simultaneously prepared, being incubated for two hours at rt and protected from light. After this time 50 μL of the stop solution were added to end the reaction, and it was incubated for two hours at rt under stirring and protected from light. The signal emitted by SPA heads-cortisol complex was measured in the 1450 Microbeta Tritalux (Wallac®) scintillation counter for 30 seconds per well. This case measures the binding to the substrate, and not to the product as in the assay for the type 1 isoenzyme.

The following table indicates the activity values of some compounds described in the examples expressed as percentage of inhibition at a 10 μM concentration.

| Example | % Inhibition (10 μM) | |
|---|---|---|
| | 11-beta-HSD1 | 11-beta-HSD2 |
| Ia.59 | 100 | 0 |
| Ia.61 | 93 | 0 |
| Ia.66 | 100 | 6 |
| Ib.8 | 100 | 5 |
| Ib.18 | 100 | 10 |
| Ib.80 | 100 | 13 |
| Ie.16 | 100 | 5 |
| Ib.8 | 100 | 0 |
| Id.6 | 100 | 0 |
| Id.12 | 100 | 0 |
| If.1 | 100 | 0 |
| Ik.25 | 100 | 6 |
| If.8 | 100 | 4 |

The invention claimed is:

1. A compound of formula (I)

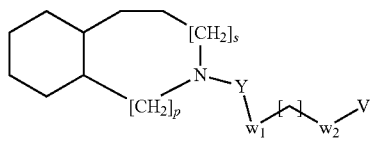

and pharmaceutically acceptable salts thereof, wherein:

s and p are an integer selected in an opposite manner between 0 and 1, such that when s is 1, p is 0 (to form a perhydroquinoline) and when s is 0, p is 1 (to form a perhydroisoquinoline), Y is a biradical selected from CO, CS and SO2, W1 and W2 is each independently a bond or a biradical selected from O, S and NR1, wherein R1 is selected from H, C1-4 alkyl and C3-10 cycloalkyl, n is an integer selected from 0, 1, 2, 3 and 4, V is a radical selected from the group consisting of —CO-T, —CS-T and —SO2-T, or a radical selected from the group consisting of:

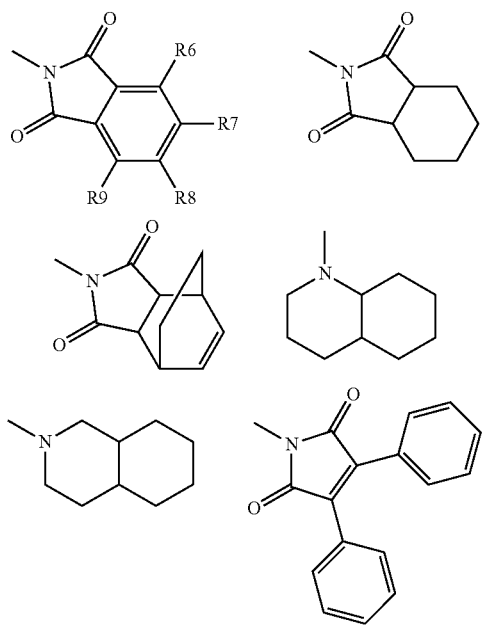

where T is a group selected from the group consisting of NR2R3, R2, OR2 and SR2; or a group selected from the group

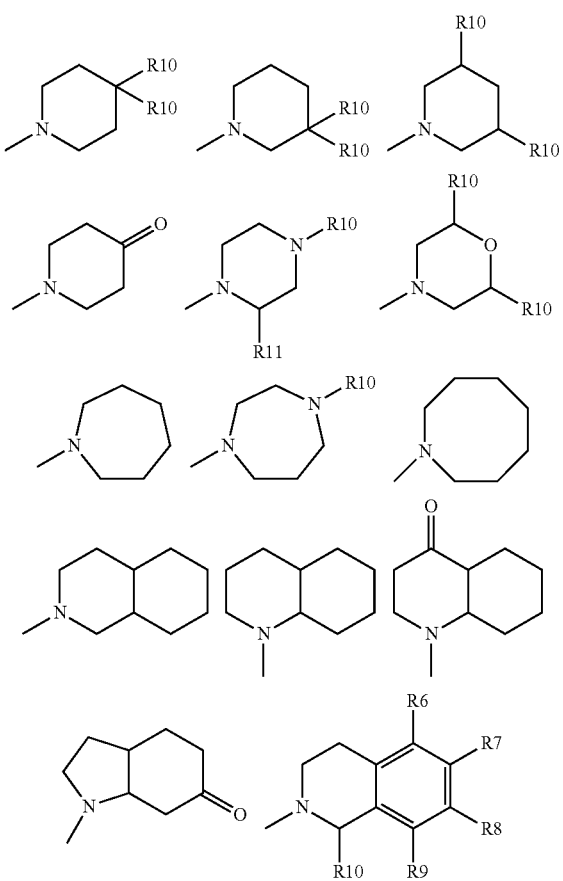

-continued

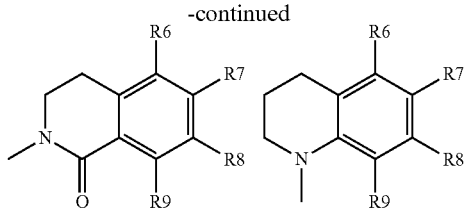

consisting of:
   wherein R2 and R3 is each independently H, COR4, SO2R4, C1-4 alkyl, aryl, benzyl, phenethyl, C2-4 alkenyl, C2-4 alkynyl, C3-10 cycloalkyl or a saturated, partially unsaturated or aromatic, 5 to 10 membered heterocycle, containing one or several heteroatoms elected from the group consisting of nitrogen, oxygen and sulfur,
   wherein when R2 or R3 is an alkyl, or an alkenyl these can be optionally substituted with one or several substituents independently selected from the group consisting of F, OR4, NR4R5, COOR4, CONR4R5, C3-10 cycloalkyl, aryl and heterocycle; and
   wherein when R2 or R3 is an aryl, a benzyl, a phenethyl, a cycloalkyl or a heterocycle, these can be optionally substituted with one or several substituents independently selected from the group consisting of NH2, F, Cl, CN, NO2, COOH, R4, COOR4, OR4, OCF3, SH, SR4, CONR4R5, SO2NR4R5, COR4, NR1COR4, OCOR4, SOR4, SO2R4 and heterocycle; and
   wherein when R2 or R3 is a cycloalkyl, this can be optionally substituted with one or several fused benzene rings, the benzene could be optionally substituted with one or several substituents independently selected from the group consisting of alkyl, alkoxide and halogen,
   wherein R4 and R5 is each independently selected from the group consisting of H, C1-4 alkyl, aryl, benzyl, phenethyl, C2-4 alkenyl, C2-4 alkynyl, C3-10 cycloalkyl and heterocycle, or optionally R4 and R5 can be bound to one another forming a 3 to 8 membered cycle,
   wherein R6, R7, R8 and R9 is each independently selected from the group consisting of H, OR4, F and Cl, and
   wherein R10 is independently selected from the group consisting of H, OH, F, C1-4 alkyl, COOR11, COR11, phenyl, benzyl, benzhydryl, C2-4 alkenyl, C2-4 alkynyl, C3-10 cycloalkyl and heterocycle, and wherein the alkyl, phenyl, benzyl, benzhydryl, cycloalkyl or heterocycle can be optionally substituted with one or several substituents independently selected from the group consisting of NH2, F, Cl, NO2, COOH, COOR4, OR4, CF3, SH, SR4, CONR4R5, SO2NR4R5, COR4, NR1COR4, OCOR4, SOR4, SO2R4 and C1-4 alkyl; and where R11 is selected from H, C1-4 alkyl and C3-10 cycloalkyl.

2. The compound according to claim 1, wherein Y is CO or SO2.

3. The compound according to claim 1, wherein W1 and W2 is each independently selected from the group consisting of a bond, S and NR1.

4. The compound according to claim 3, wherein R1 is H.

5. The compound according to claim 1, wherein V is —CO-T, —CS-T or -SO2-T.

6. The compound according to claim 1, wherein V is selected from the group consisting of:

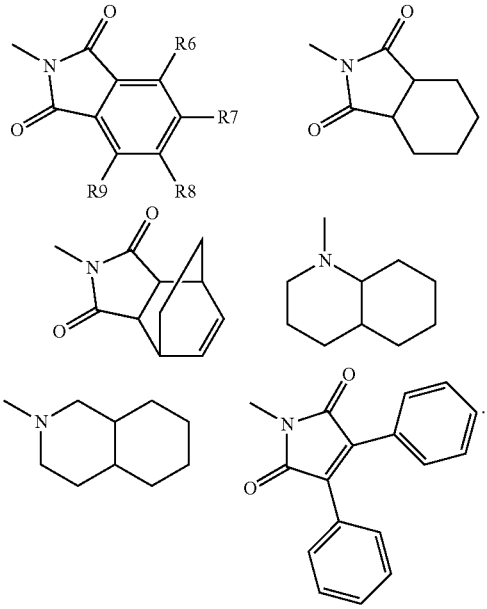

7. The compound according to claim 1, wherein T is NR2R3, R2, OR2 or SR2.

8. The compound according to claim 1, wherein R2 and R3 is each independently selected from the group consisting of H, COR4, SO2R4, C1-4 alkyl, phenyl, naphthyl, benzyl, phenethyl, C2-4 alkenyl, C3-10 cycloalkyl, and heterocycle, particularly, 2-furanyl, 2-thiophenyl, 2-(1-methylindole), quinoline, isoquinoline and 2-benzofuranyl.

9. The compound according to claim 8, wherein R2 and R3 is each independently selected from the group consisting of C1-4 alkyl and C2-4 alkenyl.

10. The compound according to claim 9, wherein R2 or R3 are optionally substituted with one or several substituents independently selected from the group consisting of F, OR4, NR4R5, COOR4, CONR4R5, phenyl, C3-10 cycloalkyl, hexenyl, naphthyl and heterocycle, particularly pyridine, 3-(1-methylindole), 3-thiophenyl and 2-furanyl.

11. The compound according to claim 8, wherein R2 and R3 is each independently selected from the group consisting of phenyl, benzyl, phenethyl and C3-10 cycloalkyl.

12. The compound according to claim 11, wherein R2 or R3 are optionally substituted with one or several substituents independently selected from the group consisting of F, Cl and OR4.

13. The compound according to claim 1, wherein R4 and R5 is each independently selected from the group consisting of C1--4 alkyl, benzyl, phenethyl and phenyl.

14. The compound according to claim 1, wherein T is selected from the group consisting of:

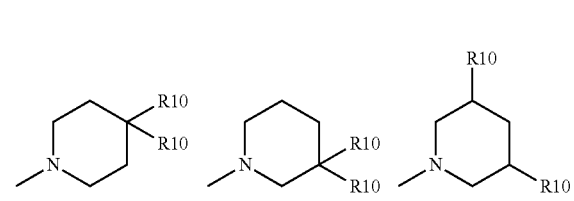

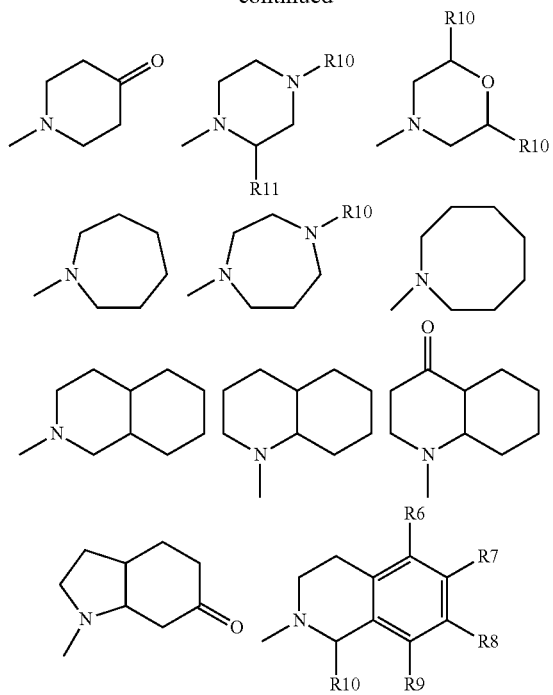

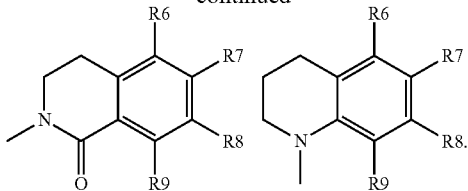

15. The compound according to claim 1, wherein R6, R7, R8 and R9 is each independently selected from H, OR4, F and Cl, and wherein R10 is independently selected from the group consisting of H, OH, F, C1-4 alkyl, COOR11, COR11, phenyl, benzyl and benzhydryl.

16. The compound according to claim 15, wherein R10 is phenyl, benzyl or benzhydryl.

17. The compound according to claim 16, wherein R10 is optionally substituted with one or several substituents, independently selected from the group consisting of F, OR4, CF3, COR4 and C1-4 alkyl.

18. The compound according to claim 1, wherein R11 is H or C3-10 cycloalkyl.

19. The compound according to claim 1, wherein s is 0 and p is 1.

20. The compound according to claim 1, wherein s is 1 and p is 0.

* * * * *